United States Patent
Brinker et al.

(10) Patent No.: US 11,344,629 B2
(45) Date of Patent: May 31, 2022

(54) ACTIVE TARGETING OF CELLS BY MONOSIZED PROTOCELLS

(71) Applicants: Charles Jeffrey Brinker, Albuquerque, NM (US); Kimberly Butler, Albuquerque, NM (US); Paul N. Durfee, Albuquerque, NM (US)

(72) Inventors: Charles Jeffrey Brinker, Albuquerque, NM (US); Kimberly Butler, Albuquerque, NM (US); Paul N. Durfee, Albuquerque, NM (US)

( * ) Notice: Subject to any disclaimer, the term of this patent is extended or adjusted under 35 U.S.C. 154(b) by 0 days.

(21) Appl. No.: 16/490,280

(22) PCT Filed: Mar. 1, 2018

(86) PCT No.: PCT/US2018/020496
§ 371 (c)(1),
(2) Date: Aug. 30, 2019

(87) PCT Pub. No.: WO2018/160865
PCT Pub. Date: Sep. 7, 2018

(65) Prior Publication Data
US 2020/0009264 A1 Jan. 9, 2020

Related U.S. Application Data

(60) Provisional application No. 62/465,582, filed on Mar. 1, 2017.

(51) Int. Cl.
*C12N 5/00* (2006.01)
*A61P 35/00* (2006.01)
(Continued)

(52) U.S. Cl.
CPC ...... *A61K 47/6915* (2017.08); *A61K 47/6913* (2017.08); *A61K 47/6923* (2017.08); *A61P 35/02* (2018.01); *C07K 16/2803* (2013.01); *C07K 16/3061* (2013.01); *A61K 2039/505* (2013.01); *C07K 2317/622* (2013.01); *C07K 2317/77* (2013.01)

(58) Field of Classification Search
None
See application file for complete search history.

(56) References Cited

U.S. PATENT DOCUMENTS

| 4,927,637 A | 5/1990 | Morano et al. |
| 5,057,296 A | 10/1991 | Beck |

(Continued)

FOREIGN PATENT DOCUMENTS

| EP | 1852393 A1 | 11/2007 |
| JP | 2009515520 A | 4/2009 |

(Continued)

OTHER PUBLICATIONS

Villegas et al., ACS Appl. Mater. Interfaces, 2015, vol. 7, pp. 24075-24081. (Year: 2015).*

(Continued)

*Primary Examiner* — Brian Gulledge
(74) *Attorney, Agent, or Firm* — Schwegman Lundberg & Woessner, P.A.

(57) ABSTRACT

In one aspect, the disclosure provides mesoporous silica nanoparticles (MSNPs), monodisperse populations of MSNPs and related protocells which exhibit cell binding specificity. For example, MSNPs and protocells of the disclosure may be used to target specific delivery of therapeutic agents to CD19 or EGFR expressing cancer cells, or target specific delivery of therapeutic agents to other cell types. Related protocells, pharmaceutical compositions and therapeutic and diagnostic methods are also provided.

20 Claims, 47 Drawing Sheets

(51) Int. Cl.
  *A61K 39/395* (2006.01)
  *A61K 47/69* (2017.01)
  *A61P 35/02* (2006.01)
  *C07K 16/28* (2006.01)
  *C07K 16/30* (2006.01)
  *A61K 39/00* (2006.01)

(56) References Cited

U.S. PATENT DOCUMENTS

| | | |
|---|---|---|
| 5,098,684 A | 3/1992 | Kresge et al. |
| 5,360,834 A | 11/1994 | Popall et al. |
| 5,689,574 A | 11/1997 | Heirich et al. |
| 5,789,230 A | 8/1998 | Cotten |
| 6,194,388 B1 | 2/2001 | Krieg et al. |
| 6,365,266 B1 | 4/2002 | MacDougall et al. |
| 6,387,453 B1 | 5/2002 | Brinker et al. |
| 6,808,867 B2 | 10/2004 | Doshi et al. |
| 6,913,832 B2 | 7/2005 | Fan et al. |
| 7,101,967 B2 | 9/2006 | Fischer et al. |
| 7,332,264 B2 | 2/2008 | Doshi et al. |
| 7,514,267 B1 | 4/2009 | Lopez et al. |
| 7,563,451 B2 | 7/2009 | Lin et al. |
| 8,268,962 B2 | 9/2012 | Heemskerk et al. |
| 8,374,816 B2 | 2/2013 | Vu |
| 8,734,816 B2 | 5/2014 | Liu et al. |
| 8,992,984 B1 | 3/2015 | Brinker et al. |
| 9,480,653 B2 | 11/2016 | Brinker et al. |
| 9,579,283 B2 | 2/2017 | Brinker et al. |
| 9,855,217 B2 | 1/2018 | Brinker et al. |
| 9,989,447 B1 | 6/2018 | Kaehr et al. |
| 10,022,327 B2 | 7/2018 | Brinker et al. |
| 10,465,189 B2 | 11/2019 | Venkatraman et al. |
| 2002/0147105 A1 | 10/2002 | Shamshoum et al. |
| 2004/0005352 A1 | 1/2004 | Lopez et al. |
| 2004/0258671 A1 | 12/2004 | Watkins |
| 2005/0239687 A1 | 10/2005 | Divita et al. |
| 2006/0154069 A1 | 7/2006 | Lin et al. |
| 2007/0224257 A1 | 9/2007 | Commander et al. |
| 2007/0287104 A1 | 12/2007 | Doshi et al. |
| 2008/0095852 A1 | 4/2008 | Kong et al. |
| 2008/0160313 A1 | 7/2008 | Lopez et al. |
| 2008/0213377 A1 | 9/2008 | Bhatia et al. |
| 2008/0241262 A1 | 10/2008 | Lee et al. |
| 2008/0241917 A1 | 10/2008 | Akita et al. |
| 2008/0286371 A1 | 11/2008 | Pacheco et al. |
| 2009/0054246 A1 | 2/2009 | Peabody et al. |
| 2009/0181090 A1* | 7/2009 | Dreis ............... A61K 9/1658 424/484 |
| 2009/0208563 A1 | 8/2009 | Watkins et al. |
| 2009/0305409 A1 | 12/2009 | Kogure et al. |
| 2010/0055167 A1 | 3/2010 | Zhang et al. |
| 2010/0152699 A1 | 6/2010 | Ferrari et al. |
| 2010/0166665 A1 | 7/2010 | Butts et al. |
| 2010/0168120 A1 | 7/2010 | Watterson et al. |
| 2010/0255103 A1 | 10/2010 | Liong et al. |
| 2011/0059156 A9 | 3/2011 | Mirkin et al. |
| 2011/0097819 A1 | 4/2011 | Groves et al. |
| 2011/0135571 A1 | 6/2011 | Lin et al. |
| 2011/0230372 A1 | 9/2011 | Willman et al. |
| 2011/0268791 A1 | 11/2011 | Liu et al. |
| 2011/0300186 A1 | 12/2011 | Hellstrom et al. |
| 2012/0207795 A1 | 8/2012 | Zink et al. |
| 2013/0115169 A1 | 5/2013 | Lahann et al. |
| 2013/0122054 A1 | 5/2013 | Harashima |
| 2013/0185823 A1 | 7/2013 | Kuang et al. |
| 2013/0197103 A1 | 8/2013 | Brown |
| 2014/0023700 A1* | 1/2014 | Knudsen ............... C07K 7/06 424/450 |
| 2014/0079774 A1 | 3/2014 | Brinker et al. |
| 2014/0141089 A1 | 5/2014 | Liang |
| 2014/0212479 A1 | 7/2014 | Zeinelden |
| 2014/0023421 A1 | 8/2014 | Lin et al. |
| 2014/0301951 A1 | 10/2014 | Liu et al. |
| 2015/0010475 A1 | 1/2015 | Brinker et al. |
| 2015/0125391 A1 | 5/2015 | Swami et al. |
| 2015/0164798 A1 | 6/2015 | Brinker et al. |
| 2015/0272885 A1 | 10/2015 | Ashley et al. |
| 2015/0320681 A1 | 11/2015 | Brinker et al. |
| 2016/0090603 A1 | 3/2016 | Carnes et al. |
| 2016/0106671 A1 | 4/2016 | Brinker et al. |
| 2016/0151482 A1 | 6/2016 | Carnes et al. |
| 2016/0193588 A1 | 7/2016 | Haynes |
| 2016/0287717 A1 | 10/2016 | Brinker |
| 2016/0338954 A1 | 11/2016 | Brinker |
| 2017/0165375 A1 | 6/2017 | Ashley et al. |
| 2017/0232115 A1 | 8/2017 | Ashley et al. |
| 2018/0028686 A1 | 2/2018 | Brinker et al. |
| 2018/0049984 A1 | 2/2018 | Brinker et al. |
| 2018/0105430 A1 | 4/2018 | Carnes et al. |
| 2018/0110831 A1 | 4/2018 | Brinker et al. |
| 2018/0344641 A1 | 12/2018 | Brinker et al. |
| 2019/0022235 A1 | 1/2019 | Durfee et al. |
| 2019/0091150 A1 | 3/2019 | Brinker et al. |
| 2019/0262469 A1 | 8/2019 | Brinker et al. |
| 2020/0197536 A1 | 6/2020 | Brinker et al. |
| 2020/0375912 A1 | 12/2020 | Serda et al. |
| 2020/0405650 A1 | 12/2020 | Noureddine et al. |
| 2021/0030675 A1 | 2/2021 | Brinker et al. |
| 2021/0315822 A1 | 10/2021 | Guo et al. |

FOREIGN PATENT DOCUMENTS

| | | |
|---|---|---|
| WO | WO-9747296 A2 | 12/1997 |
| WO | WO-0076556 A2 | 12/2000 |
| WO | WO-02066506 A2 | 8/2002 |
| WO | WO-03055469 A1 | 7/2003 |
| WO | WO-2004096140 A2 | 11/2004 |
| WO | WO-2005009602 A2 | 3/2005 |
| WO | WO-2005084710 A2 | 9/2005 |
| WO | WO-2007140618 A1 | 12/2007 |
| WO | WO-2009051837 A2 | 4/2009 |
| WO | WO-2010035304 A2 | 4/2010 |
| WO | WO-2010048572 A1 | 4/2010 |
| WO | WO-2010078569 A2 | 7/2010 |
| WO | WO-2011116219 A1 | 9/2011 |
| WO | WO-2011116226 A2 | 9/2011 |
| WO | WO-2011150264 A2 | 12/2011 |
| WO | WO-2012149376 A2 | 11/2012 |
| WO | WO-2013012891 A1 | 1/2013 |
| WO | WO-2013056132 A2 | 4/2013 |
| WO | WO-2013082612 A1 | 6/2013 |
| WO | WO-2013103614 A1 * | 7/2013 |
| WO | WO-2013103614 A1 | 7/2013 |
| WO | WO-2014093635 A1 | 6/2014 |
| WO | WO-2014165608 A1 | 10/2014 |
| WO | WO-2014165617 A1 | 10/2014 |
| WO | WO-2015042268 A1 * | 3/2015 ............. A61K 47/59 |
| WO | WO-2015042279 A1 | 3/2015 |
| WO | WO-2015095340 A1 | 6/2015 |
| WO | WO-2016145031 A1 | 9/2016 |
| WO | WO-2016145335 A1 | 9/2016 |
| WO | WO-2017041032 A1 | 3/2017 |
| WO | WO-2017041033 A1 | 3/2017 |
| WO | WO-2017120504 A1 | 7/2017 |
| WO | WO-2018000043 A1 | 1/2018 |
| WO | WO-2018160865 | 9/2018 |
| WO | WO-2018187287 A1 | 10/2018 |
| WO | WO-2019028387 A1 | 2/2019 |
| WO | WO-2019169152 A1 | 9/2019 |
| WO | WO-2020028342 A1 | 2/2020 |
| WO | WO-2020068798 A1 | 4/2020 |
| WO | WO-2020068806 A1 | 4/2020 |
| WO | WO-2020176716 A1 | 9/2020 |

OTHER PUBLICATIONS

"International Application Serial No. PCT/US2018/020496, International Search Report dated Jun. 14, 2018", 4 pgs.
"International Application Serial No. PCT/US2018/020496, Written Opinion dated Jun. 14, 2018", 4 pgs.
U.S. Appl. No. 09/838,153 U.S. Pat. No. 6,471,761, filed Apr. 20, 2001, Rapid Prototyping of Patterned Organic/Inorganic Functional Nanostructures.

(56) References Cited

OTHER PUBLICATIONS

U.S. Appl. No. 10/163,425 U.S. Pat. No. 6,913,832, filed Jun. 7, 2002, Prototyping of Patterned Functional Nanostructures.
U.S. Appl. No. 09/543,572, filed Apr. 5, 2000, Photo-Definable Self-Assembled Materials.
U.S. Appl. No. 10/100,108 U.S. Pat. No. 6,808,867, filed Mar. 19, 2002, Photo-Definable Self-Assembled Materials.
U.S. Appl. No. 10/373,565 U.S. Pat. No. 7,332,264, filed Feb. 26, 2003, Photo-Definable Self-Assembled Materials.
U.S. Appl. No. 09/389,085, filed Sep. 2, 1999, Low Frequency Feedback Speaker System.
U.S. Appl. No. 08/385,338, filed Feb. 8, 1995, Unidirectional Ring Laser Gyroscope.
U.S. Appl. No. 08/250,882 U.S. Pat. No. 5,438,585, filed May 31, 1994 Unstable Resonator Semiconductor Laser.
U.S. Appl. No. 16/500,349, filed Oct. 2, 2019, Porous Nanoparticle-Supported Lipid Bilayer Delivery of Transcriptional Gene Modulators.
U.S. Appl. No. 15/023,093, filed Mar. 18, 2016, Core and Surface Modification of Mesoporous Silica Nanoparticles to Achieve Cell Specific Targeting In Vivo.
U.S. Appl. No. 15/023,110 U.S. Pat. No. 9,855,217, filed Mar. 18, 2016, Toroidal Mesoporous Silica Nanoparticles (TMSNPS) and Related Protocells.
U.S. Appl. No. 15/858,923, filed Dec. 29, 2017, Toroidal Mesoporous Silica Nanoparticles (TMSNPS) and Related Protocells.
U.S. Appl. No. 14/350,674, filed May 20, 2014, Porous Nanoparticle-Supported Lipid Bilayers (Protocells) for Targeted Delivery Including Transdermal Delivery of Cargo and Methods Thereof.
U.S. Appl. No. 15/380,962, filed Dec. 15, 2016, Porous Nanoparticle-Supported Lipid Bilayers (Protocells) for Delivery Including Transdermal Delivery of Cargo and Methods Thereof.
U.S. Appl. No. 14/781,765, filed Nov. 23, 2015, Mesoporous Alum Nanoparticles as a Universal Platform for Antigen Adsorption, Presentation, and Delivery.
U.S. Appl. No. 12/909,572 U.S. Pat. No. 8,992,984, filed Oct. 21, 2010, Protocells and Their Use for Targeted Delivery of Multicomponent Cargos to Cancer Cells.
U.S. Appl. No. 14/627,739 U.S. Pat. No. 9,480,653, filed Feb. 20, 2015, Protocells and Their Use for Targeted Delivery of Multicomponent Cargos to Cancer Cells.
U.S. Appl. No. 14/797,487, filed Jul. 13, 2015 Protocells and Their Use for Targeted Delivery of Multicomponent Cargos to Cancer Cells.
U.S. Appl. No. 14/113,371 U.S. Pat. No. 9,579,283, filed Dec. 4, 2013, Porous Nanoparticle-Supported Lipid Bilayers (Protocells) for Targeted Delivery and Methods of Using Same.
U.S. Appl. No. 14/970,998 U.S. Pat. No. 10,022,327, filed Dec. 16, 2015, Porous Nanoparticle-Supported Lipid Bilayers (Protocells) for Targeted Delivery and Methods of Using Same.
U.S. Appl. No. 16/025,557, filed Jul. 2, 2018, Porous Nanoparticle-Supported Lipid Bilayers (Protocells) for Targeted Delivery and Methods of Using Same.
U.S. Appl. No. 14/781,817, filed Nov. 9, 2015, Antibiotic Protocells and Related Pharmaceutical Formulations and Methods of Treatment.
U.S. Appl. No. 15/474,800, filed Mar. 30, 2017, Protocells for Plasmid and RNP Delivery in the Treatment of Cancer and Other Disease States.
U.S. Appl. No. 15/474,810, filed Mar. 30, 2017, Carriers for Plasmid and RNP Delivery in the Treatment of Cancer and Other Disease States.
U.S. Appl. No. 14/369,741, filed Jun. 30, 2014, CRLF-2 Binding Peptides, Protocells and Viral-Like Particles Useful in the Treatment of Cancer, Including Acute Lymphoblastic Leukemia (All).
U.S. Appl. No. 15/788,634, filed Oct. 19, 2017, CRLF-2 Binding Peptides, Protocells and Viral-Like Particles Useful in the Treatment of Cancer, Including Acute Lymphoblastic Leukemia (All).
U.S. Appl. No. 13/143,164 U.S. Pat. No. 8,734,816, filed Jul. 1, 2011, Porous Nanoparticle Supported Lipid Bilayer Nanostructures.
U.S. Appl. No. 14/253,030, filed Apr. 15, 2014, Porous Nanoparticle Supported Lipid Nanostructures.
U.S. Appl. No. 15/557,368, filed Sep. 11, 2017, Generation of Mesoporous Materials Using Multiphase Surfactant Systems.
U.S. Appl. No. 12/903,577, filed Oct. 13, 2010, Protocells and Their Use for Pain Treatment.
U.S. Appl. No. 15/757,254, filed Mar. 2, 2018, Protocells to Treat Microbial Infection and for Synergistic Delivery.
U.S. Appl. No. 15/757,269, filed Mar. 2, 2018, Mesoporous Silica Nanoparticles and Supported Lipid Bi-Layer Nanoparticles for Biomedical Applications.
U.S. Appl. No. 16/828,137, filed Mar. 24, 2020, Mesoporous Silica Nanoparticles and Supported Lipid Bi-Layer Nanoparticles for Biomedical Applications.
U.S. Appl. No. 15/557,000, filed Sep. 8, 2017, CD 47 Containing Porous Nanoparticle Supported Lipid Bilayers (Protocells) Field of the Invention.
U.S. Appl. No. 16/068,235, filed Jul. 5, 2018, Osteotropic Nanoparticles for Prevention or Treatment of Bone Metastases.
U.S. Appl. No. 16/635,246, filed Jan. 30, 2020, Liposomal Coated Nanoparticles for Immunotherapy Applications.
U.S. Appl. No. 15/887,619, filed Feb. 2, 2018, Porous Nanoparticle-Supported Lipid Bilayers (Protocells) for Delivery Including Transdermal Delivery of Cargo and Methods Thereof.
U.S. Appl. No. 16/976,651, filed Aug. 28, 2020, Starry Mesoporous Silica Nanoparticles and Supported Lipid Bi-Layer Nanoparticles.
U.S. Appl. No. 17/264,452, filed Jan. 29, 2021, Biomimetic Rebuilding of Multifunctional Red Blood Cells.
U.S. Appl. No. 17/277,256, filed Mar. 17, 2021, Living Mammalian Cells Modified with Functional Modular Nanoparticles.
U.S. Appl. No. 17/277,260, filed Mar. 17, 2021, Armored Cells.
U.S. Appl. No. 17/434,363, filed Aug. 26, 2021, Modular Metal-Organic Polyhedra Superassembly Compositions.
"U.S. Appl. No. 12/903,577, Response filed Jul. 12, 2017 to Advisory Action dated Jul. 7, 2017", 7 pgs.
"U.S. Appl. No. 10/100,108, Non Final Office Action dated Jan. 22, 2004", 8 pgs.
"U.S. Appl. No. 10/100,108, Notice of Allowance dated Jul. 13, 2004", 10 pgs.
"U.S. Appl. No. 10/100,108, Response filed Apr. 21, 2004 to Non Final Office Action dated Jan. 22, 2004", 9 pgs.
"U.S. Appl. No. 10/163,425, Advisory Action dated Jul. 2, 2004".
"U.S. Appl. No. 10/163,425, Examiner Interview Summary filed Mar. 29, 2005", 9 pgs.
"U.S. Appl. No. 10/163,425, Final Office Action dated Mar. 31, 2004", 8 pgs.
"U.S. Appl. No. 10/163,425, Non Final Office Action dated Aug. 1, 2003", 10 pgs.
"U.S. Appl. No. 10/163,425, Non Final Office Action dated Sep. 22, 2004", 6 pgs.
"U.S. Appl. No. 10/163,425, Notice of Allowance dated Feb. 10, 2005", 8 pgs.
"U.S. Appl. No. 10/163,425, Response filed Jan. 2, 2004 to Non Final Office Action dated Aug. 1, 2003", 13 pgs.
"U.S. Appl. No. 10/163,425, Response filed May 28, 2004 to Final Office Action dated Mar. 31, 2004", 15 pgs.
"U.S. Appl. No. 10/163,425, Response filed Jul. 23, 2004 to Advisory Action dated Jul. 2, 2004", 15 pgs.
"U.S. Appl. No. 10/163,425, Response filed Dec. 22, 2004 to Non Final Office Action dated Sep. 22, 2004", 11 pgs.
"U.S. Appl. No. 10/373,565, Notice of Allowance dated Sep. 11, 2007", 4 pgs.
"U.S. Appl. No. 12/903,577, Advisory Action dated Mar. 20, 2012", 3 pgs.
"U.S. Appl. No. 12/903,577, Advisory Action dated Jun. 7, 2017", 2 pgs.
"U.S. Appl. No. 12/903,577, Final Office Action dated May 8, 2015", 19 pgs.
"U.S. Appl. No. 12/903,577, Final Office Action dated Nov. 30, 2011", 19 pgs.
"U.S. Appl. No. 12/903,577, Non Final Office Action dated Jun. 3, 2014", 16 pgs.

(56) References Cited

OTHER PUBLICATIONS

"U.S. Appl. No. 12/903,577, Non Final Office Action dated Jun. 30, 2011", 13 pgs.
"U.S. Appl. No. 12/903,577, Non Final Office Action dated Oct. 25, 2017", 16 pgs.
"U.S. Appl. No. 12/903,577, Notice of Non-Compliant Amendment dated Feb. 4, 2015", 5 pgs.
"U.S. Appl. No. 12/903,577, Response filed Jan. 20, 2016 to Final Office Action dated May 8, 2015", 7 pgs.
"U.S. Appl. No. 12/903,577, Response filed Feb. 26, 2015 to Notice of Non-Compliant Amendment dated Feb. 4, 2015", 5 pgs.
"U.S. Appl. No. 12/903,577, Response filed Mar. 9, 2012 to Final Office Action dated Nov. 30, 2011", 22 pgs.
"U.S. Appl. No. 12/903,577, Response filed Jun. 1, 2011 to Restriction Requirement dated May 13, 2011", 2 pgs.
"U.S. Appl. No. 12/903,577, Response filed Sep. 30, 2011 to Non Final Office Action dated Jun. 30, 2011", 9 pgs.
"U.S. Appl. No. 12/903,577, Response filed Dec. 3, 2014 to Non Final Office Action dated Jun. 3, 2014", 15 pgs.
"U.S. Appl. No. 12/903,577, Restriction Requirement dated May 13, 2011", 10 pgs.
"U.S. Appl. No. 13/143,164, 312 Amendment filed Mar. 27, 2014", 5 pgs.
"U.S. Appl. No. 13/143,164, Final Office Action dated Jun. 26, 2013", 14 pgs.
"U.S. Appl. No. 13/143,164, Non Final Office Action dated Jan. 11, 2013", 12 pgs.
"U.S. Appl. No. 13/143,164, Notice of Allowance dated Jan. 13, 2014", 7 pgs.
"U.S. Appl. No. 13/143,164, Response filed Apr. 10, 2013 to Non Final Office Action dated Jan. 11, 2013", 13 pgs.
"U.S. Appl. No. 13/143,164, Response filed Nov. 7, 2012 to Restriction Requirement dated Oct. 10, 2012", 4 pgs.
"U.S. Appl. No. 13/143,164, Response filed Nov. 26, 2013 to Final Office Action dated Jun. 26, 2013", 18 pgs.
"U.S. Appl. No. 13/143,164, Restriction Requirement dated Oct. 10, 2012", 11 pgs.
"U.S. Appl. No. 14/113,371, Examiner Interview Summary dated Mar. 25, 2016", 1 pg.
"U.S. Appl. No. 14/113,371, Final Office Action dated Feb. 1, 2016", 15 pgs.
"U.S. Appl. No. 14/113,371, Final Office Action dated Mar. 25, 2016", 13 pgs.
"U.S. Appl. No. 14/113,371, Non Final Office Action dated Jul. 13, 2015", 14 pgs.
"U.S. Appl. No. 14/113,371, Non Final Office Action dated Dec. 17, 2014", 15 pgs.
"U.S. Appl. No. 14/113,371, Notice of Allowability dated Jan. 31, 2017", 4 pgs.
"U.S. Appl. No. 14/113,371, Notice of Allowance dated Oct. 11, 2016", 9 pgs.
"U.S. Appl. No. 14/113,371, Preliminary Amendment filed Oct. 22, 2013", 14 pgs.
"U.S. Appl. No. 14/113,371, Response filed Apr. 16, 2015 to Non Final Office Action dated Dec. 17, 1", 23 pgs.
"U.S. Appl. No. 14/113,371, Response filed Aug. 25, 2016 to Final Office Action dated Mar. 25, 2016", 17 pgs.
"U.S. Appl. No. 14/113,371, Response filed Oct. 17, 2014 to Restriction Requirement dated Aug. 18, 2014", 19 pgs.
"U.S. Appl. No. 14/113,371, Response filed Nov. 4, 2015 to Non Final Office Action dated Jul. 13, 2015", 25 pgs.
"U.S. Appl. No. 14/113,371, Response filed Sep. 26, 2016 to Final Office Action dated Mar. 25, 2016", 16 pgs.
"U.S. Appl. No. 14/113,371, Restriction Requirement dated Aug. 18, 2014", 12 pgs.
"U.S. Appl. No. 14/253,030, Advisory Action dated Apr. 11, 2018", 25 pgs.
"U.S. Appl. No. 14/253,030, Advisory Action dated Sep. 5, 2017", 22 pgs.
"U.S. Appl. No. 14/253,030, Advisory Action dated Sep. 9, 2016", 16 pgs.
"U.S. Appl. No. 14/253,030, Declaration under 37 C.F.R 1.132 filed Mar. 27, 2018", 4 pgs.
"U.S. Appl. No. 14/253,030, Final Office Action dated May 11, 2016", 15 pgs.
"U.S. Appl. No. 14/253,030, Final Office Action dated Jun. 9, 2017", 19 pgs.
"U.S. Appl. No. 14/253,030, Final Office Action dated Dec. 1, 2017", 21 pgs.
"U.S. Appl. No. 14/253,030, Non Final Office Action dated Dec. 9, 2016", 19 pgs.
"U.S. Appl. No. 14/253,030, Non Final Office Action dated Dec. 10, 2015", 14 pgs.
"U.S. Appl. No. 14/253,030, Preliminary Amendment filed Jul. 1, 2015", 8 pgs.
"U.S. Appl. No. 14/253,030, Preliminary Amendment filed Dec. 9, 2014", 3 pgs.
"U.S. Appl. No. 14/253,030, Response filed Mar. 10, 2016 to Non Final Office Action dated Dec. 10, 2015", 11 pgs.
"U.S. Appl. No. 14/253,030, Response filed Aug. 11, 2016 to Final Office Action dated May 11, 2016", 9 pgs.
"U.S. Appl. No. 14/253,030, Response filed Oct. 10, 2017 to Advisory Action dated Sep. 5, 2017", 12 pgs.
"U.S. Appl. No. 14/253,030, Response filed Oct. 11, 2016 to Advisory Action dated Sep. 9, 2016", 9 pgs.
"U.S. Appl. No. 14/253,030, Response filed Nov. 2, 2015 to Restriction Requirement dated Oct. 6, 2015", 4 pgs.
"U.S. Appl. No. 14/253,030, Response filed Apr. 2, 2018 to Final Office Action dated Dec. 1, 2017", 10 pgs.
"U.S. Appl. No. 14/253,030, Response filed May 9, 2017 to Non-Final Office Action dated Dec. 9, 2016", 8 pgs.
"U.S. Appl. No. 14/253,030, Response filed Aug. 10, 2017 to Final Office Action dated Jun. 9, 2017", 12 pgs.
"U.S. Appl. No. 14/253,030, Restriction Requirement dated Sep. 17, 2015", 7 pgs.
"U.S. Appl. No. 14/253,030, Restriction Requirement dated Oct. 6, 2015", 7 pgs.
"U.S. Appl. No. 14/253,030, Supplemental Declaration under 37 C.F.R. 1.132 filed Aug. 7, 2017", 2 pgs.
"U.S. Appl. No. 14/350,674, Non Final Office Action dated Jun. 17, 2016", 19 pgs.
"U.S. Appl. No. 14/350,674, Response filed May 16, 2016 to Restriction Requirement dated Mar. 14, 2016", 10 pgs.
"U.S. Appl. No. 14/350,674, Restriction Requirement dated Mar. 14, 2016", 12 pgs.
"U.S. Appl. No. 14/369,741, Final Office Action dated Apr. 19, 2017", 10 pgs.
"U.S. Appl. No. 14/369,741, Non Final Office Action dated Aug. 22, 2016", 17 pgs.
"U.S. Appl. No. 14/369,741, Non Final Office Action dated Nov. 23, 2015", 11 pgs.
"U.S. Appl. No. 14/369,741, Preliminary Amendment filed Jun. 26, 2014", 16 pgs.
"U.S. Appl. No. 14/369,741, Response filed Mar. 23, 2016 to Non Final Office Action dated Nov. 23, 2015", 12 pgs.
"U.S. Appl. No. 14/369,741, Response filed Sep. 14, 2015 to Restriction Requirement dated May 14, 2015", 13 pgs.
"U.S. Appl. No. 14/369,741, Response filed Dec. 22, 2016 to Non-Final Office Action dated Aug. 22, 2016", 12 pgs.
"U.S. Appl. No. 14/369,741, Restriction Requirement dated May 14, 2015", 12 pgs.
"U.S. Appl. No. 14/627,739, Non Final Office Action dated Jan. 29, 2016", 4 pgs.
"U.S. Appl. No. 14/627,739, Notice of Allowance dated Jul. 6, 2016", 6 pgs.
"U.S. Appl. No. 14/627,739, Preliminary Amendment filed Feb. 20, 2015", 5 pgs.
"U.S. Appl. No. 14/627,739, Response filed Apr. 15, 2016 to Non Final Office Action dated Jan. 29, 2016", 6 pgs.
"U.S. Appl. No. 14/627,739, Response filed Nov. 5, 2015 to Restriction Requirement dated Aug. 6, 2015", 7 pgs.

(56) References Cited

OTHER PUBLICATIONS

"U.S. Appl. No. 14/627,739, Restriction Requirement dated Aug. 6, 2015", 5 pgs.
"U.S. Appl. No. 14/781,765, Advisory Action dated Jan. 29, 2019", 4 pgs.
"U.S. Appl. No. 14/781,765, Final Office Action dated Aug. 28, 2018", 9 pgs.
"U.S. Appl. No. 14/781,765, Non Final Office Action dated Feb. 15, 2018", 9 pgs.
"U.S. Appl. No. 14/781,765, Non Final Office Action dated Jul. 15, 2019", 7 pgs.
"U.S. Appl. No. 14/781,765, Response filed Jan. 21, 2019 to Final Office Action dated Aug. 28, 2018", 7 pgs.
"U.S. Appl. No. 14/781,765, Response filed Jun. 15, 2018 to Non Final Office Action dated Feb. 15, 2018", 6 pgs.
"U.S. Appl. No. 14/781,765, Response filed Jan. 24, 2018 to Restriction Requirement dated Aug. 24, 2017", 4 pgs.
"U.S. Appl. No. 14/781,765, Response filed Jan. 28, 2019 to Non-Final Office Action dated Aug. 28, 2018", 7 pgs.
"U.S. Appl. No. 14/781,765, Restriction Requirement dated Aug. 24, 2017", 6 pgs.
"U.S. Appl. No. 14/781,817, Preliminary Amendment filed Jan. 17, 2017", 5 pgs.
"U.S. Appl. No. 14/781,817, Restriction Requirement dated Oct. 31, 2018", 9 pgs.
"U.S. Appl. No. 14/781,817, Supplemental Preliminary Amendment field Aug. 8, 2017", 9 pgs.
"U.S. Appl. No. 14/781,817, Supplemental Preliminary Amendment filed Jun. 27, 2017", 9 pgs.
"U.S. Appl. No. 14/797,487, Non Final Office Action dated Jun. 14, 2017", 7 pgs.
"U.S. Appl. No. 14/797,487, Preliminary Amendment filed Jul. 24, 2015", 10 pgs.
"U.S. Appl. No. 14/797,487, Response filed Mar. 3, 2017 to Restriction Requirement dated Jan. 3, 2017", 10 pgs.
"U.S. Appl. No. 14/797,487, Restriction Requirement dated Jan. 3, 2017", 12 pgs.
"U.S. Appl. No. 14/970,998, Final Office Action dated Sep. 27, 2017", 13 pgs.
"U.S. Appl. No. 14/970,998, Non Final Office Action dated Apr. 6, 2017", 17 pgs.
"U.S. Appl. No. 14/970,998, Notice of Allowance dated Mar. 16, 2018", 9 pgs.
"U.S. Appl. No. 14/970,998, Preliminary Amendment filed Dec. 16, 2015", 3 pgs.
"U.S. Appl. No. 14/970,998, Preliminary Amendment filed Dec. 28, 2015", 13 pgs.
"U.S. Appl. No. 14/970,998, Response filed Feb. 27, 2018 to Final Office Action dated Sep. 27, 2017", 8 pgs.
"U.S. Appl. No. 14/970,998, Response filed Mar. 17, 2017 to Restriction Requirement dated Jan. 19, 2017", 8 pgs.
"U.S. Appl. No. 14/970,998, Response filed Aug. 7, 2017 to Non-Final Office Action dated Apr. 6, 2017", 13 pgs.
"U.S. Appl. No. 14/970,998, Restriction Requirement dated Jan. 19, 2017", 8 pgs.
"U.S. Appl. No. 15/023,093 Responsed filed Feb. 3, 2017 to Restriction Requirement dated Nov. 3, 2016", 12 pgs.
"U.S. Appl. No. 15/023,093, Non Final Office Action dated Apr. 11, 2017", 12 pgs.
"U.S. Appl. No. 15/023,093, Preliminary Amendment filed Mar. 18, 2016", 3 pgs.
"U.S. Appl. No. 15/023,093, Restriction Requirement dated Nov. 3, 2016", 10 pgs.
"U.S. Appl. No. 15/023,110, Corrected Notice of Allowance dated Sep. 5, 2017", 8 pgs.
"U.S. Appl. No. 15/023,110, Non Final Office Action dated Feb. 24, 2017", 10 pgs.
"U.S. Appl. No. 15/023,110, Notice of Allowance dated Aug. 21, 2017", 11 pgs.
"U.S. Appl. No. 15/023,110, Preliminary Amendment filed Mar. 18, 2016", 3 pgs.
"U.S. Appl. No. 15/023,110, Preliminary Amendment filed Jul. 5, 2016", 7 pgs.
"U.S. Appl. No. 15/023,110, Response filed Jul. 24, 2017 to Non-Final Office Action dated Feb. 24, 2017", 10 pgs.
"U.S. Appl. No. 15/380,962, Non Final Office Action dated Aug. 2, 2017", 20 pgs.
"U.S. Appl. No. 15/380,962, Preliminary Amendment filed Dec. 15, 2016", 3 pgs.
"U.S. Appl. No. 15/380,962, Response filed Jul. 19, 2017 to Restriction Requirement dated May 18, 2017", 9 pgs.
"U.S. Appl. No. 15/380,962, Restriction Requirement dated May 18, 2017", 9 pgs.
"U.S. Appl. No. 15/474,800, Final Office Action dated Mar. 8, 2019", 9 pgs.
"U.S. Appl. No. 15/474,800, Non Final Office Action dated Oct. 18, 2018", 8 pgs.
"U.S. Appl. No. 15/474,800, Preliminary Amendment filed Jul. 19, 2017", 12 pgs.
"U.S. Appl. No. 15/474,800, Preliminary Amendment filed Oct. 10, 2017", 4 pgs.
"U.S. Appl. No. 15/474,800, Response filed Jan. 18, 2019 t Non-Final Office Action dated Oct. 18, 2019", 11 pg.
"U.S. Appl. No. 15/474,800, Response filed Aug. 13, 2018 to Restriction Requirement dated Mar. 12, 2018", 11 pgs.
"U.S. Appl. No. 15/474,800, Restriction Requirement dated Mar. 12, 2018", 8 pgs.
"U.S. Appl. No. 15/474,810, Final Office Action dated Mar. 8, 2019", 10 pgs.
"U.S. Appl. No. 15/474,810, Non Final Office Action dated Sep. 20, 2018", 12 pgs.
"U.S. Appl. No. 15/474,810, Preliminary Amendment filed Jul. 18, 2017", 8 pgs.
"U.S. Appl. No. 15/474,810, Response filed Jan. 18, 2019 to Non-Final Office Action dated Sep. 20, 2018", 8 pgs.
"U.S. Appl. No. 15/474,810, Response filed Aug. 7, 2018 to Restriction Requirement dated Mar. 7, 2018", 8 pgs.
"U.S. Appl. No. 15/474,810, Restriction Requirement dated Mar. 7, 2018", 8 pgs.
"U.S. Appl. No. 15/474,810, Supplemental Preliminary Amendment filed Oct. 30, 2017", 4 pgs.
"U.S. Appl. No. 15/557,000, Preliminary Amendment filed Sep. 8, 2017", 7 pgs.
"U.S. Appl. No. 15/557,000, Restriction Requirement dated Mar. 11, 2019", 9 pgs.
"U.S. Appl. No. 15/557,368, Preliminary Amendment filed Sep. 11, 2017", 8 pgs.
"U.S. Appl. No. 15/557,368, Restriction Requirement dated Feb. 15, 2019", 8 pgs.
"U.S. Appl. No. 15/757,254, Preliminary Amendment filed Mar. 2, 2018", 11 pgs.
"U.S. Appl. No. 15/757,254, Restriction Requirement dated Sep. 16, 2019", 11 pgs.
"U.S. Appl. No. 15/757,269, Examiner Interview Summary dated Jun. 25, 2019", 5 pgs.
"U.S. Appl. No. 15/757,269, Final Office Action dated Oct. 25, 2019", 20 pgs.
"U.S. Appl. No. 15/757,269, Non Final Office Action dated Apr. 12, 2019", 30 pgs.
"U.S. Appl. No. 15/757,269, Non Final Office Action dated Dec. 4, 2018", 19 pgs.
"U.S. Appl. No. 15/757,269, Response filed Oct. 14, 2019 to Non-Final Office Action dated Apr. 12, 2019", 10 pgs.
"U.S. Appl. No. 15/757,269, Response filed Mar. 28, 2019 to Non-Final Office Action dated Dec. 4, 2018", 10 pgs.
"U.S. Appl. No. 16/025,557, Non Final Office Action dated Feb. 6, 2020", 8 pgs.
"U.S. Appl. No. 16/025,557, Preliminary Amendment filed Jul. 2, 2018", 10 pgs.
"U.S. Appl. No. 16/068,235, Examiner Interview Summary dated Apr. 5, 2021", 5 pgs.

(56) References Cited

OTHER PUBLICATIONS

"U.S. Appl. No. 16/068,235, Non Final Office Action dated May 13, 2020", 19 pgs.
"U.S. Appl. No. 16/068,235, Non Final Office Action dated Jun. 15, 2021", 27 pgs.
"U.S. Appl. No. 16/068,235, Non Final Office Action dated Aug. 25, 2020", 28 pgs.
"U.S. Appl. No. 16/068,235, Notice of Non-Compliant Amendment dated Apr. 6, 2021", 2 pgs.
"U.S. Appl. No. 16/068,235, Preliminary Amendment filed Jul. 5, 2018", 10 pgs.
"U.S. Appl. No. 16/068,235, Response filed Feb. 25, 2021 to Non Final Office Action dated Aug. 25, 2020", 13 pgs.
"U.S. Appl. No. 16/068,235, Response filed May 1, 2020 to Restriction Requirement dated Feb. 28, 2020", 9 pgs.
"U.S. Appl. No. 16/068,235, Response filed Jun. 7, 2021 to Notice of Non-Compliant Amendment dated Apr. 6, 2021", 1 pg.
"U.S. Appl. No. 16/068,235, Response filed Aug. 13, 2020 to Non Final Office Action dated May 13, 2020", 11 pgs.
"U.S. Appl. No. 16/068,235, Restriction Requirement dated Feb. 28, 2020", 10 pgs.
"U.S. Appl. No. 16/500,349, Preliminary Amendment filed Oct. 2, 2019", 7 pgs.
"U.S. Appl. No. 16/635,246. Preliminary Amendment filed Jan. 30, 2020", 7 pgs.
"U.S. Appl. No. 16/828,137, Non Final Office Action dated Jun. 15, 2021", 29 pgs.
"U.S. Appl. No. 16/828,137, Preliminary Amendment filed Mar. 24, 2020", 6 pgs.
"U.S. Appl. No. 16/828,137, Response filed Jun. 2, 2021 to Restriction Requirement dated Apr. 2, 2021", 6 pgs.
"U.S. Appl. No. 16/828,137, Restriction Requirement dated Apr. 2, 2021", 13 pgs.
"U.S. Appl. No. 16/976,651, Preliminary Amendment filed Aug. 28, 2020", 7 pgs.
"U.S. Appl. No. 17/264,452, Preliminary Amendment Filed Jan. 29, 2021", 6 pgs.
"U.S. Appl. No. 17/277,256, Preliminary Amendment filed Mar. 17, 2021", 7 pgs.
"U.S. Appl. No. 17/277,260, Preliminary Amendment filed Mar. 17, 2021", 7 pgs.
"U.S. Appl. No. 14/781,765, Preliminary Amendment filed Jul. 20, 2016", 6 pgs.
"U.S. Appl. No. 15/023,093, Preliminary Amendment filed Jun. 23, 2016", 11 pgs.
"U.S. Appl. No. 15/858,923, Preliminary Amendment filed Dec. 29, 2017", 7 pgs.
"Australian Application Serial No. 2012249474, First Examiner Report dated Jul. 20, 2016", 4 pgs.
"Australian Application Serial No. 2012323937, First Examiner Report dated Oct. 7, 2016", 5 pgs.
"Chinese Application Serial No. 201280031496.8, Decision on Rejection dated Jun. 7, 2016", (English Translation), 9 pgs.
"Chinese Application Serial No. 201280061866.2, Office Action dated Mar. 17, 2016", with English translation of claims, 23 pgs.
"European Application Serial No. 12776480.1, Extended European Search Report dated Oct. 9, 2014", 8 pgs.
"European Application Serial No. 12776480.1, Response filed May 5, 2015 to Office Action dated Oct. 28, 2014", 10 pgs.
"European Application Serial No. 12840155.1, Communication Pursuant to Article 94(3)EPC dated Nov. 24, 2016", 5 pgs.
"European Application Serial No. 12840155.1, Extended European Search Report dated May 28, 2015", 6 pgs.
"European Application Serial No. 14778464.9, Amendment filed Oct. 28, 2015", 18 pgs.
"European Application Serial No. 14778464.9, Extended European Search Report dated Oct. 21, 2016", 8 pgs.
"European Application Serial No. 14778464.9, Response filed May 13, 2016 to Communication pursuant to Rules 161(2) and 162 EPC dated Jan. 20, 2015", 17 pgs.
"European Application Serial No. 14779421.8, Extended European Search Report dated Oct. 13, 2016", 11 pgs.
"European Application Serial No. 14779421.8, Response filed May 12, 2016 to Communication pursuant to Rules 161(2) and 162 EPC dated Nov. 13, 2015", 21 pgs.
"European Application Serial No. 14845415.0, Response filed Nov. 2, 2016 to Communication pursuant to Rules 161(1) and 162 EPC dated May 2, 2016", 9 pgs.
"European Application Serial No. 14846653.5, Extended European Search Report dated Apr. 26, 2017", 9 pgs.
"European Application Serial No. 14846653.5, Response filed Nov. 2, 2016 to Communication pursuant to Rules 161(1) and 162 EPC dated May 2, 2016", 37 pgs.
"International Application Serial No. PCT/US2010/020096, International Preliminary Report on Patentability dated Jul. 14, 2011", 5 pgs.
"International Application Serial No. PCT/US2010/020096, International Search Report dated Sep. 17, 2010", 3 pgs.
"International Application Serial No. PCT/US2010/020096, Written Opinion dated Sep. 17, 2010", 3 pgs.
"International Application Serial No. PCT/US2012/035529, International Preliminary Report on Patentability dated Nov. 7, 2013", 8 pgs.
"International Application Serial No. PCT/US2012/035529, International Search Report dated Oct. 23, 2012", 5 pgs.
"International Application Serial No. PCT/US2012/035529, Written Opinion dated Oct. 23, 2012", 8 pgs.
"International Application Serial No. PCT/US2012/072297, International Preliminary Report on Patentability dated Jul. 10, 2014", 13 pgs.
"International Application Serial No. PCT/US2012/072297, International Search Report dated Jun. 2, 2013", 6 pgs.
"International Application Serial No. PCT/US2012/072297, Written Opinion dated Jun. 2, 2013", 11 pgs.
"International Application Serial No. PCT/US2014/032702, International Preliminary Report on Patentability dated Oct. 6, 2015", 10 pgs.
"International Application Serial No. PCT/US2014/032702, International Search Report dated Aug. 26, 2014", 5 pgs.
"International Application Serial No. PCT/US2014/032702, Written Opinion dated Aug. 26, 2014", 9 pgs.
"International Application Serial No. PCT/US2014/032711, International Preliminary Report on Patentability dated Oct. 6, 2015", 10 pgs.
"International Application Serial No. PCT/US2014/032711, International Search Report dated Aug. 5, 2014", 5 pgs.
"International Application Serial No. PCT/US2014/032711, Written Opinion dated Aug. 5, 2014", 9 pgs.
"International Application Serial No. PCT/US2014/056312, International Preliminary Report on Patentability dated Mar. 31, 2016", 10 pgs.
"International Application Serial No. PCT/US2014/056312, International Search Report dated Dec. 24, 2014", 5 pgs.
"International Application Serial No. PCT/US2014/056312, Written Opinion dated Dec. 24, 2014", 8 pgs.
"International Appiication Serial No. PCT/US2015/053244, International Preliminary Report an Patentability dated Apr. 13, 2017", 10 pgs.
"International Application Serial No. PCT/US2015/053244, International Search Report dated Feb. 4, 2016", 5 pgs.
"International Application Serial No. PCT/US2015/053244, Written Opinion dated Feb. 4, 2016", 8 pgs.
"International Application Serial No. PCT/US2016/021490, International Preliminary Report on Patentability dated Sep. 21, 2017", 7 pgs.
"International Application Serial No. PCT/US2016/021490, International Search Report dated Jun. 30, 2016", 4 pgs.
"International Application Serial No. PCT/US2016/021490, Written Opinion dated Jun. 30, 2016", 5 pgs.
"International Application Serial No. PCT/US2016/022056, International Preliminary Report on Patentability dated Sep. 21, 2017", 7 pgs.

(56) References Cited

OTHER PUBLICATIONS

"International Application Serial No. PCT/US2016/022056, International Search Report dated Jul. 7, 2016", 4 pgs.
"international Application Serial No. PCT/US2016/022056, Written Opinion dated Jul. 7, 2016", 5 pgs.
"International Application Serial No. PCT/US2016/050259, International Preliminary Report on Patentability dated Mar. 15, 2018", 10 pgs.
"International Application Serial No. PCT/US2016/050259, International Search Report dated Dec. 15, 2016", 4 pgs.
"International Application Serial No. PCT/US2016/050259, Written Opinion dated Dec. 15, 2016", 8 pgs.
"International Application Serial No. PCT/US2016/050260, International Preliminary Report on Patentability dated Mar. 15, 2018", 8 pgs.
"International Application Serial No. PCT/US2016/050260, International Search Report dated Dec. 22, 2016", 3 pgs.
"International Application Serial No. PCT/US2016/050260, Written Opinion dated Dec. 22, 2016", 6 pgs.
"International Application Serial No. PCT/US2017/012583, International Preliminary Report on Patentability dated Jul. 19, 2018", 7 pgs.
"International Application Serial No. PCT/US2017/012583, International Search Report dated Apr. 20, 2017", 3 pgs.
"International Application Serial No. PCT/US2017/012583, Written Opinion dated Apr. 20, 2017", 5 pgs.
"International Application Serial No. PCT/US2018/020496, International Preliminary Report on Patentability dated Sep. 12, 2019", 6 pgs.
"International Application Serial No. PCT/US2018/025830, International Preliminary Report on Patentability dated Oct. 17, 2019", 9 pgs.
"International Application Serial No. PCT/US2018/025830, International Search Report dated Aug. 2, 2018", 4 pgs.
"International Application Serial No. PCT/US2018/025830, Written Opinion dated Aug. 2, 2018", 7 pgs.
"International Application Serial No. PCT/US2018/045218, International Preliminary Report on Patentability dated Feb. 13, 2020", 7 pgs.
"International Application Serial No. PCT/US2018/045218, International Search Report dated Nov. 29, 2018", 3 pgs.
"International Application Serial No. PCT/US2018/045218, Written Opinion dated Nov. 29, 2018", 5 pgs.
"International Application Serial No. PCT/US2019/020084, International Preliminary Report on Patentability dated Sep. 10, 2020", 7 pgs.
"International Application Serial No. PCT/US2019/020084, International Search Report dated Jun. 6, 2019", 3 pgs.
"International Application Serial No. PCT/US2019/020084, Written Opinion dated Jun. 6, 2019", 5 pgs.
"International Application Serial No. PCT/US2019/044107, International Preliminary Report on Patentability dated Feb. 11, 2021", 6 pgs.
"International Application Serial No. PCT/US2019/044107, International Search Report dated Nov. 14, 2019", 2 pgs.
"International Application Serial No. PCT/US2019/044107, Written Opinion dated Nov. 14, 2019", 4 pgs.
"International Application Serial No. PCT/US2019/052658, International Preliminary Report on Patentability dated Apr. 1, 2021", 6 pgs.
"International Application Serial No. PCT/US2019/052658, International Search Report dated Mar. 12, 2020", 3 pgs.
"International Application Serial No. PCT/US2019/052658, Written Opinion dated Mar. 12, 2020", 4 pgs.
"International Application Serial No. PCT/US2019/052669, International Preliminary Report on Patentability dated Apr. 1, 2021", 7 pgs.
"International Application Serial No. PCT/US2019/052669, International Search Report dated Jan. 9, 2020", 3 pgs.
"International Application Serial No. PCT/US2019/052669, Written Opinion dated Jan. 9, 2020", 5 pgs.
"International Application Serial No. PCT/US2020/020066, International Preliminary Report on Patentability dated Sep. 10, 2021", 6 pgs.
"International Application Serial No. PCT/US2020/020066, International Search Report dated Jun. 25, 2020", 2 pgs.
"International Application Serial No. PCT/US2020/020066, Written Opinion dated Jun. 25, 2020", 4 pgs.
"Israel Application Serial No. 232025, Office Action dated May 1, 2016", 2 pgs.
"Japanese Application Serial No. 2014-508125, Office Action dated Feb. 15, 2016", with English translation of claims, 9 pgs.
"Japanese Application Serial No. 2014-508125, Written Amendment filed Apr. 27, 2015", with English translation, 29 pgs.
"Japanese Application Serial No. 2014-508125, Decision on Refusal dated Dec. 26, 2016", with English translation, 2 pgs.
"Japanese Application Serial No. 2014-535948, Office Action dated Jun. 27, 2016", with machine translation, 16 pgs.
"Mexican Application Serial No. MX/a/2014/004415, Office Action dated Apr. 19, 18", with machine translation, 6 pgs.
"New Zealand Application Serial No. 624962, First Examiner Report dated Feb. 9, 2016", 3 pgs.
"Russian Application Serial No. 2014119428, Office Action dated Apr. 15, 2016", 2 pgs.
"Russian Application Serial No. 2014119428, Office Action dated Apr. 21, 2017", With English Translation, 7 pgs.
"Singapore Application Serial No. 11201401499X, Office Action dated Apr. 19, 2016", 11 pgs.
"Singapore Application Serial No. 11201401499X, Written Opinion dated Oct. 5, 2015", 11 pgs.
Akazawa, Takashi, et al., "Development of a dendritic cell-targeting lipopeptide as an immunoadjuvant that inhibits tumor growth without inducina local inflammation", International Journal of Cancer, vol. 135, (2014), 2847-2856.
Ashley, et al., "(abstract) Development of a Virus-Like Particle that integrates Phage Display and Targeted delivery capabilities", MRS meeting, (2010), 1 pg.
Ashley, C E, et al., "Cell-Specific Delivery of Diverse Cargos by Bacteriophage MS2 Virus-like Particles", ACSNANO, 5(7), (2011), 1-26.
Ashley, C E, et al., "The targeted delivery of multicomponent cargos to cancer cells by nanoporous particle-supported lipid bilayers", Nature Materials, No. 5, vol. 10, (Apr. 17, 2011), 389-397.
Ashley, CE, et al., "Delivery of Small Interfering RNA by Peptide-Targeted Mesoporous Silica Nanoparticle-Supported Lipid Bilayers", ACS NANO, vol. 6 No. 3, (2012), 2174-2188.
Attard, George S, et al., "Liquid-crystalline phases as templates for the synthesis of mesoporous silica", Nature Publishing Group vol. 378, (Nov. 23, 1995), 3 pgs.
Aubin, R. A., et al., "Highly effective delivery of foreign DNA to adherent cells via polybrene/DMSO-assisted gene transfer", Methods Mol Biol., 62, (1997), 319-42.
Bao, et al., "Targeted Gene Therapy of Ovarian Cancer using an Ovarian-Specific Promoter", Gynecologic Oncology, 84, (2002), 228-34.
Beckett, D, et al., "Roles of Operator and Non-operator RNA Sequences in Bacteriophage R17 Capsid Assembly", J Mol Biol, 204, (1988), 939-947.
Benneti, GJ, et al., "A peripheral mononeuropathy in rat that produces disorders of pain sensation like those seen in man", Pain, (1988), 87-107.
Bennett, Gary, et al., "A peripheral mononeuropathy in rat that produces disorders of pain sensation like those seen in man.", Pain, 33, (1988), 87-107.
Beteck, Richard, "Chemical and biochemical modification of mesoporous silicon for in vivo analysis.", Master's thesis, University of Eastern Finland,, (2013), 8-9.
Brinker, C Jeffrey, et al., "Evaporation-Induced Self-Assembly: Nanostructures Made Easy", Advanced Materials, 11(7), (May 1999), 579-585.
Buranda, et al., "Langmuir", Langmuir, 19, (2003), 1654-1663.

(56) References Cited

OTHER PUBLICATIONS

Buranda, T, et al., "Biomimetic Molecular Assemblies on Glass and Mesoporous Silica Microbeads for Biotechnology. Langmuir", Langmuir, 19, (2003), 1654-1663.
Butler, Kimberly, et al., "Protocells: Modular Mesoporous Silica Nanoparticle-Supported Lipid Bilayers for Drug Delivery", Small 12, No. 16, (2016), 2173-2185.
Caldeira, J C, et al., "Stability and assembly in vitro of bacteriophage PP7 virus-like particles", Journal of Nanobiotechnology, 5, (2007), 1-13.
Carnes, E C, et al., "Confinement-induced quorum sensing of individual *Staphylococcus aureus* bacteria", Nature Chemical Biology, 6, (2010), 1-12.
Carnes, Eric C., et al., "Targeted Nanoporous Particle-Supported Lipid Bllayen for Treatment of Childhood Leukemia", (Jun. 2011), 1 pg.
Carroll, N J, et al., "Microparticles with Bimodal Nanoporosity Derived by Microemulsion Templating", Langmuir 25(23), (2009), 13540-13544.
Cartier, et al., "Utilization of synthetic peptides containing nuclear localization signals for nonviral gene transfer systems", Gene Therapy, 9, (2002), 157-67.
Chackerian, B, et al., "Peptide Epitope Identification by Affinity Selection on Bacteriophage MS2 Virus-Like Particles", J Mol Biol; 409, (2011), 1-18.
Chacur, M, et al., "A new model of sciatic inflammatory neuritis (SIN): induction of unilateral and bilateral mechanical allodynia following acute unilateral peri-sciatic immune activation in rats", Pain, 94, (2001), 231-244.
Chedid, Georgeset, et al., "Recent Trends in Covalent and Metal Organic Frameworks for Biomedical Applications", Nanomaterials (Basel), 8(11)., (Nov. 7, 2018), 27 pgs.
Cheng, WWK, et al., "Expression and purification of two anti-CD19 single chain Fv fragments for targeting of liposomes to CD19-expressing cells", Biochimica et Biophysica Acta, 1768, (2007), 21-29.
Citorik, R J, et al., "Sequence-specific antimicrobials using efficiently delivered RNA-guided nucleases", Nature biotechnology, (Sep. 21, 2014), 13 pgs.
Clemens, Daniel L., et al., "Targeted Intracellular Delivery of Antituberculosis Drugs to *Mycobacterium tuberculosis*-infected Macrophages via Functionalized Mesoporous Silica Nanoparticles", Antimicrobial Agents and Chemotherapy, (Feb. 2012), 2535-2545.
Cokol, M, et al., "Finding nuclear localization signals", EMBO Reports, 1(5), (2000), 1-17.
Crombez, Laurence, et al., "Targeting cyclin B1 through peptide-based delivery of siRNA prevents tumour growth", Nucleic Acids Res., vol. 37, No. 14, (2009), 4559-4569.
Dengler, Ellen C, et al., "Improvement of spinal non-viral IL-10 gene delivery by D-mannose as a transgene adjuvant to control chronic neuropathic pain", Journal of Neuroinflammation, (2014), 1-21.
Dengler, Ellen C., et al., "Mesoporous silica-supported lipid bilayers (protocells) for DAN cargo delivery to the spinal cord", Journal of Controlled Release 168, (2013), 209-224.
Dubertret, B, et al., "In Vivo Imaging of Quantum Dots Encapsulated in Phospholipid Micelles", Science, vol. 298, (Nov. 29, 2002), 1759-1762.
Epler, et al., "Nanopourous-Supported Lipid Bilayer Nanocarriers For Treatment Of Childhood Leukemia", Materials Research Society, Symposium LL: Biometic Engineering of Micro-and Nanoparticles; LL6.11, (2011), 32 pgs.
Epler, K, et al., "Delivery of Ricin Toxin A-Chain by Peptide-Targeted mesoporous Silica Nanoparticle Supported Lipid Bilayers.", Advanced Healthcare Materials, (2012), 348-353.
Fan, H, et al., "Rapid prototyping of patterned functional nanostructures", Nature, 405(6782), (May 4, 2000), 56-60.
Fang, Aiping, et al., "Template-Free Formation of Monodisperse Doughnut-Shaped Silica Microparitcles by Droplet-Based Microfluidics", Chem. Mater, (2011), 4660-4662 pgs.
Feng, Pingyun, et al., "Control of Pore Sizes in Mesoporous Silica Templated by Liquid Crystals in Block Copolymer-Cosurfactant-Water Systems", Langmuir, vol. 16, No. 12,, (Mar. 24, 2000), 7 pgs.
Fishkis, M, et al., "Abstracts: 'Self organization of short peptides and simple amphiphiles into membranes' and 'Encapsulation of polynucleotide/polypeptide systems by membranes', from Steps Towards the Formation of a Protocell: The Possible Role of Short Peptides", Orig Life Evol Biosph, vol. 37, (2007), 543-545.
Fishkis, Maya, "Steps Towards the Formation of a Protocell: The Possible Role of Short Peptides", Orig Live Evol Biosph 37, (2007), 537-553.
Gamal, M M, et al., "Skin delivery of oestradiol from lipid vesicles: importance of liposome structure", Int. J. Pharm., vol. 204, No. 1-2, (2000), 159-169.
Gariepy, et al., "Vectorial Delivery of Macromolecules Into Cells Using Peptide-Based Vehicles", TRENDS in Biotechnology vol. 19, (2001), 21-28.
Giacomo, Dacarro, et al., "Monolayers of Polyethilenimine on Flat Glass: A Versatile Platform for Cations Coordination and Nanoparticle Grafting in the Preparation of Antibacterial Surfaces", Dalton Trans. 41, 2456, (Jan. 5, 2012), 8 pgs.
Gordon, Alan N., et al., "Recurrent Epithelial Ovarian Carcinoma: A Randomized Phase III Study of Pegyiated Liposomal Doxorubicin Versus Topotecan", Journal of Clinical Oncology, 19(14), (2001), 3312-3322.
Harvey, R C, et al., "Rearrangement of CRLF2 is associated with mutation of JAK kinases, alteration of IKZF1, Hispanic/Latino ethnicity, and a poor outcome in pediatric, B-progenitor acute lymphoblastic leukemia", Blood, 115(26), 5312-5321.
Hatakeyama, "A pH-sensitive fusogenic peptide facilitates endosomal escape and greatly enhances the gene silencing of siRNA-containing nanoparticles in vitro and in vivo", Journal of Controlled Release, 139(2), (Oct. 15, 2009), 127-132.
Hicks, Randall W, et al., "Nanoparticle Assembly of Mesoporous A100H (Boehmite)", Chemistry of Materials, vol. 15, No. 1, (Jan. 1, 2003), 78-82.
Hildebrand, et al., "Nanoscale control of silica morphology and three-dimensional structure during diatom cell wall formation", Mater. Res. vol. 21, No. 10, (2006), 2689-2698.
Hooker, J M, et al., "Interior Surface Modification of Bacteriophage MS2", J Am Chem Soc, 126, (2004), 3718-3719.
Huo, Qisheng, et al., "Surfactant Control of Phases in the Synthesis of Mesoporous Silica-Based Materials", Chem. Mater. 1996, 8, (Feb. 15, 1996), 14 pgs.
Ikari, Kenichi, et al., "Structural Control of Mesoporous Silica Nanoparticles in a Binary Surfactant System", 5 pgs.
Iskandar, Ferry, et al., "Control of the morphology of nanostructured particles prepared by the spray drying of nanopartilce sol", Journal of Colloid and Interface Science 265, (2003), 296-303.
Israelachvili, J N, et al., "Physical principles of membrane organization", Quarterly Reviews of Biophysics, vol. 13(2),, (1980), 121-200.
Jain, P T, et al., "Enhancement of liposomal gene delivery in human breast cancer cells by dimethyl sulfoxide", (Mar. 1998), 609-611.
Jain, R. K, "Barriers to drug delivery in Solid Tumors", Scientific American,.271 (1), (Jul. 1994), 58-65.
Jewett, M C, et al., "Mimicking the *Escherichia coli* Cytoplasmic Environment Activates Long-Lived and Efficient Cell-Free Protein Synthesis", Wiley InterScience, [Online] Retrieved from the internet: <www.interscience.wiley.com DOI: 10.1002/bit.20026>, (2004), 19-26.
Jillavenkatesa, A, "Particle Size Characterization", National Institute of Standards and Technology, Special Publication 960-1, (2001), 1-167.
Jinping, Lai, et al., "Versatile Fluorescence Resonance Energy Transfer-Based Mesoporous Silica Nanoparticles for Real-Time Monitoring of Drug Release", ACS Nano, vol. 7, No. 3, (2013), 2741-2750.
Kaczanowska, Sabina, et al., "TLR agonists: our best frenemy in cancer immunotherapy", Journal of leukocyte Biology, 93(6), (2013), 847-863.

(56) References Cited

OTHER PUBLICATIONS

Kennedy, E M, et al., "Inactivation of the Human Papilloma virus E6 or E7 Gene in Cervical Carcinoma Cells by Using a Bacterial CRISPR/Cas RNA-Guided Endonuclease", Journal of Virology, (Aug. 6, 2014), 12 pgs.
Kim, D M, "A highly efficient cell-free protein synthesis system from *Excherichia coli*", Eur J Biochem, 239, (1996), 881-886.
Konermann, S, et al., "Genome-scale transcriptional activation by an engineered CRISPR-Cas9 complex", Nature, 2015, vol. 517, 583-588.
Kunkel, T. A., "Rapid and Efficient Site-Specific Mutagenesis Without Phenotypic Selection", Proc. Natl. Acad. Sci. USA, 82, (1985), 488-492.
Lacasse, E C, et al., "Nuclear localization signals overlap DNA- or RNA-binding domains in nucleic acid-binding proteins", Nucleic Acids Research, 23(10), (1995), 1647-1656.
Li, Z, et al., "Mesoporous Silica Nanoparticles in Biomedical Applications", Chemical Society Reviews 41, (2012), 2590-2605.
Lim, F, et al., "RNA recognition site of PP7 coat protein", Nucleic Acids Research, 30(19), (2002), 4138-4144.
Lingxiang, Wu, et al., "Synthesis of a Zwitterionic Silane and its Application in the Surface Modification of Silicon-Based Material Surfaces for Improved Hemocompatibility", ACS Applied Materials & Interfaces, vol. 2 No. 10, (2010), 2781-2788.
Liu, J, et al., "Electrostatically Mediated Liposome Fusion and Lipid Exchange with a Nanoparticle-Supported Bilayer for Control of Surface Charge, Drug Containment, and Delivery.", J Am Chem Soc, 131, (2009), 7567-7569.
Liu, Juewen, et al., "Porous Nanoparticle Supported Lipid Bilayers (Protocells) as Delivery Vehicles", J. Am. Chem. Soc., vol. 131, No. 4, (2009), 7 pgs.
Liu, Juewen, et al., "Silica nanoparticle supported lipid bilayers for gene delivery.", Chem Commun, (2009), 5100-5102.
Liu, Xiangsheng, et al., "Irinotecan Delivery by Lipid-Coated Mesoporous Silica Nanoparticles Shows Improved Efficacy and Safety over Liposomes for Pancreatic Cancer", ACS Nano 10, (2016), 2702-2715.
Lo, et al., "Hepatocellular Carcinoma Cell-Specific Peptide Ligand For Targeted Drug Delivery", Molecular Cancer Therapeutics 7(3), (2008), 579-589.
Lu, Weigang, et al., "Tuning the structure and function of metal-organic frameworks via linker design", Chemical Society Reviews, 43, (2014), 5561-5593.
Lu, Y, et al., "Aerosol-assisted self-assembly of mesostructured spherical nanoparticles", Nature, 398, (1999), 223-226.
Lu, Yunfeng, et al., "Continuous formation of supported cubic and hexagonal mesoporous films by sol-gel-dip-coating", Nature, 389(6649), (Sep. 25, 1997), 364-368.
Lu, Yunfeng, et al., "Evaporation-Induced Self-Assembly of Hybrid Bridged Silsesquioxane Film and Particulat Mesophases With Integral Organic Functionalitiy", Journal of the American Chemical Society, 122(22), (Jun. 1, 2000), 5258-5261.
Maghraby, EL, et al., "Interactions of surfactants (edge activators) and skin penetration enhancers with liposomes", Int. J. Pharm., vol. 276, No. 1-2, (2004), 143-161.
Mamaeva, Veronika, et al., "Mesoporous silica nanoparticles in medicine-Recent adva", Advanced Drug Delivery Reviews, Elsevier, Amsterdam, NL, vol. 65, No. 5, (Aug. 18, 2012), 689-702.
Mao, A, et al., "Deterministic encapsulation of single cells in thin tunable microgels for niche modeling and therapeutic delivery", Nat Mater 16, pp. 236-243, (2017), 21 pgs.
Matteo, Porotto, et al., "Synthetic protocells interact with viral nanomachinery and inactivate pathogenic human virus", PLOS One, val. 6, No. 3, (Mar. 1, 2011), 16874 pgs.
McDonald, Michael, "Functioning Nanostructures Self-Assemble Out of Ink", Posted May 8, 2000, http://www.amtexpo.com/nano/messages/255.html, (May 8, 2000), 3 pgs.

Meng, Huan, et al., "Co-delivery of an Optimal Drug/siRNA Combination Using Mesoporous Silica Nanoparticle to Overcome Drug Resistance in Breast Cancer In Vitro and In Vivo", ACS Nano., (2013), 1-21.
Meng, Huan, et al., "Two-Wave Nanotherapy To Target the Stroma and Optimize Gemcitabine Delivery To a Human Pancreatic Cancer Model in Mice", ACS Nano vol. 7 No. 11, (2013), 10048-10065.
Meng, Huan, et al., "Use of a Lipid-Coated Mesoporous Silica Nanoparticle Platform for Synergistic Gemcitabine and Paclitaxel Delivery to Human Pancreatic Cancer in Mice", ACS Nano, vol. 9, No. 4, (2015), 3540-3557.
Meng, Huan, et al., "Use of Size and a Co-polymer Design Feature to Improve the Biodistribution and the Enhanced Permeability and Retention Effect of Doxorubicin-loaded Mesoporous Silica Nanoparticles in a Murine Xenograft Tumor Model", ACS Nano, (2011), 32 pgs.
Midoux, P, et al., "Membrane Permeabilization and Efficient Gene Transfer by a Peptide Containing Several Histidines", Bioconjugate Chem, 9, (1998), 260-267.
Milligan, Ed, et al., "Pathological and protective roles of glia in chronic pain.", Nature Reviews Neuroscience, 10, (2009), 23-36.
Milligan, Ed, et al., "Thermal hyperalgesia and mechanical allodynia produced by intrathecal administration of the human immunodeficiency virus-1 (HIV-1) envelope glycoprotein, gp 120.", Brain Research, 861, (2000), 105-116.
Milligan, Erin, et al., "Intrathecal polymer-based interleukin-10 gene delivery for neuropathic pain", Neuron Glia Biology 2, (2007), 1-16.
Mohamed, Salma, et al., "(Abstract) Polymeric nano-micelles: versatile platform for targeted delivery in cancer", Ther. Deliv., vol. 5, No. 10, pp. 1101-1121, (Oct. 2014), 1 pg.
Moller, K, et al., "Highly efficient siRNA delivery from core-shell mesoporous silica nanoparticles with multifunctional polymer caps", Nanoscale, 8, (2016), 13 pgs.
Mollick, Samraj, et al., "(Abstract) Outer Surface Hydrophobic Shielding Strategy to Enhance the Chemical Stability of Metal-Organic Polyhedra", Angew Chem Int Ed Engl, vol. 58, No. 4, pp. 1041-1045, (Jan. 21, 2019), 1 pg.
Mornet, et al., "The Formation of Support Lipid Bilayers on Silica Nanoparticles Revealed by Cryoelectron Microscopy", NanoLetters 5(2), (2005), 281-285.
Mungall, Bruce, et al., "Inhibition of Henipavirus infection by RNA interference", Antiviral Res., vol. 80, No. 3, (2008), 324-331.
Nakamura, Takashi, et al., "Nanoparticulation of 3CG-CWS for application to bladder cancer therapy", Journal of Controlled Release vol. 176, (2014), 44-53.
Nekhotiaeva, Natalia, et al., "Inhibition of *Staphylococcus aureus* gene expression and growth using antisense peptide nucleic acids", Molecular Therapy, vol. 10, No. 4, 652-659.
Nikolic, M, et al., "Synthesis and characterization of mesoporous silica core-shell particles", Processing and Application of Ceramics, 4(2), (2010), 81-85.
Park, J, et al., "Cell-in-Shell Hybrids: Chemical Nanoencapsulation of Individual Cells", Acc. Chem. Res., 49(5), (2016), 792-800.
Pastan, I, et al., "Immunotoxin therapy of cancer.", Nature Reviews 6, (2006), 559-565.
Peabody, D S, "A Viral Platform for Chemical Modification and Multivalent Display", Journal of Nanobiotechnology, 1, (2003), 1-8.
Peabody, D S, et al., "Immunogenic Display of Diverse Peptides on Virus-like Particles of RNA Phage MS2", J Mol Biol, 380, (2008), 1-18.
Peabody, D S, "Translational Repression by Bacteriophage MS2 Coat Protein Expressed from a Plasmid", The Journal of Biological Chemistry; 265(10), (1990), 5684-5689.
Pickett, G G, et al., "Encapsidation of heterologous RNAs by bacteriophage MS2 coat protein", Nucleic Acids Research, 21(19), (1993), 4621-4626.
Pn, Durfee, et al., "Mesoporous Silica Nanoparticle-Supported Lipid Bilayers (Protocells) for Active Targeting and Delivery to Individual Leukemia Cells", ACS Nano, vol. 10, (2016), 8325-8345.

(56) References Cited

OTHER PUBLICATIONS

Porotto, M, et al., "Synthetic Protocelis Interact with Viral Nano machinery and Inactivate Pathogenic Human Virus", (2011), 1-9 pgs.

Prokop, Ales, "Intracellular Delivery Fundamentals and Applications", ISBN Springer, (2011), 1-867.

Rao, G.V. R, et al., "Monodisperse Mesoporous Silica Microspheres Formed by Evaporation-Induced Self Assembly of Surfactant Templates in Aerosols", Adv. Mater, 14. No. 18, (Sep. 16, 2002), 1301-1304.

Raskopf, et al., "siRNA Targeting Vegf Inhibits Hepatocellular Carcinoma Growth and Tumor Angiogenesis In Vivo", Journal of Heptaology 49, (2008), 977-984.

Ricco, R, et al., "Metal-Organic Frameworks for Cell and Virus Biology: A Perspective", ACS Nano, 12, (Jan. 8, 2018), 13-23.

Rocca, F D, et al., "Cell Composition of the Human Pulmonary Valve: A Comparative Study with the Aortic Valve—The VESALIO* Project", Ann Thorac Surg. 70, (2000), 1594-1600.

Rodriguez, et al., "Minimal Self Peptides That Inhibit Phagocytic Clearance and Enhance Delivery of Nano particles", (2013), 971-975 pgs.

Rodriguez, F, et al., "DNA Immunization: Ubiquitination of a Viral Protein Enhances Cytotoxic T-Lymphocyte Induction and Antiviral Protection but Abrogates Antibody Induction", Journal of Virology, vol. 7 No. 11, (Nov. 1997), 8497-8503.

Rosenholm, Jessica M, et al., "Towards multifunctional, targeted drug delivery systems using mesoporous silica nanoparticles-opportunities", NANOSCALE, val. 2, No. 10, (Jan. 1, 2010), 1870-1883.

Russell, R G, et al., "Bisphosphonates: An Update on Mechanisms of Action and How These Relate to Clinical Efficacy", Ann NY Acad Sci 1117, (2007), 209-257.

Ryther, RCC, et al., "siRNA therapeutics: big potential from small RNAs", Gene Therapy, vol. 12, (2005), 5-11.

Sanjana, N E, et al., "Improved vectors and genome-wide libraries for CRISPR screening", Nat Methods, (2014), 783-784.

Sapra P, Allen TM, et al., "Internalizing Antibodies are Necessary for Improved Therapeutic Efficacy of Antibody-targeted Liposomal Drugs.", Cancer Res 62, (2002), 7190-7194.

Schiller, Renate, et al., "Synthesis of Mesoporous Silica Particles and Capsules by Miniemulsion Technique", Chem. Mater. 2009, 21, (Sep. 23, 2009), 11 pgs.

Seo, Seog-Jin, et al., "Gene delivery techniques for adult stem cell-based regenerative therapy", Nanomedicine, vol. 8, No. 11,, (2013), 2 pgs.

Shiraishi, T., et al., "Photochemically enhanced cellular delivery of cell penetrating peptide-PNA conjugates.", FEBS Letters, 580(5), (2006), 1451-1456.

Shou-Cang, Shen, et al., "Mesoporous silica nanoparticle-functionalized poly(methylmethacrylate)-based bone cement for effective antibiotics delivery", Journal of Materials Science: Materials in Medicine, Kluwer Academic Publishers, BO,vol. 22, No. 10, (Jul. 24, 2011), 2283-2292.

Sloane, E, et al., "Chronic constriction injury induced pathological pain states are controlled long term via intrathecal administration of a non-viral vector (NW) encoding the anti-inflammatory cy1okine interleukin-10 (IL-10).", Second Joint Scientific Meeting of the American Pain Society and the Canadian Pain Society. Churchill Livingstone., (2004), p. 15.

Sloane, E, et al., "Immunological priming potentiates non-viral anti-inflammatory gene therapy treatment of neuropathic pain.", Gene Therapy, 16, (2009), 1210-1222.

Slowing, I I, et al., "(Abstract only) Mesoporous silica nanoparticles as Controlled release drug delivery and gene transfection carriers", Advanced Drug Delivery Reviews vol. 60., (2008), 1278-1288.

Smothers, J F, et al., "Affinity Selection from Biological Libraries", Science, 298, (2002), 621-622.

Soderquist, et al., "Microparticle-mediated delivery of interleukin-1 0 plasmid DNA for the treatment of neuropathic pain", Poster Abstract No. 206d, (May 2008), 2 pgs.

Soderquist, R., et al., "Release of Plasmid DNA-Encoding IL-10 from PLGA Microparticles Facilitates Long-Term Reversal of Neuropathic Pain Following a Single Intrathecal Administration.", Pharmaceutical Research, (2010), 841-854.

Sorensen, Malin, "Mesostructured particulate silica materials with tunable pore size", Doctoral Thesis at the Royal Institute of Technology. Stockholm, Sweden,, (2009), 19-21.

Stemmer, WPC, et al., "Single-step assembly of a gene and entire plasmid from large numbers of oligodeoxyribonucleotides", Gene,164, (1995), 49-53.

Suteewong, T, et al., "(Abstract) Synthesis and formation mechanism of aminated mesoporous silica nanoparticles", Chemistry of Materials, 24, (2012), 1 pg.

Suteewong, T, et al., "Highly aminated mesoporous silica nanoparticles with cubic pore structure", Journal of the American Chemical Society, 133(2), (2011), 172-175.

Takeuchi, S, "An Axisymmetric Flow-Focusing Microfluidic Device", Adv Mater, 17:8, (2005), 1067-1072.

Tarn, D, et al., "Mesoporous Silica Nanoparticle Nanocarriers: Biofunctionality and Biocompatibility.", Accounts of Chemical Research, (2013), 792-801.

Tatusova, T A, et al., "BLAST 2 Sequences, a new tool for comparing protein and nucleotide sequences", FEMS Microbiology Letters, 174, (1999), 247-250.

Tawfik, D S, et al., "Man-made cell-like compartments for molecular evolution", Nature Biotechnology; 16, (1998), 652-656.

Tejinder, Singh, et al., "The critical role of bisphosphonates to target bone cancer metastasis: an overview", Journal of Drug Targeting, vol. 23, (Sep. 9, 2014), 1-15.

Tianyi, Wang, et al., "Enhanced mucosal and systemic immune responses obtained by porous silica nanoparticles used as an oral vaccine adjuvant: Effect of silica architecture on immunological properties", International Journal of Pharmaceutics, vol. 436, No. 1-2, (Oct. 1, 2012), 351-358.

Torchilin, VP, et al., "Recent Advances ith Liposomes as Pharmaceutical Carriers.", Nature Reviews, vol. 4, (2005), 145-159.

Townson, Jason L, et al., "Re-examining the Size/Charge Paradigm: Differing in Vivo Characteristics of Size- and Charge-Matched Mesoporous Silica Nanoparticles", J Am Chem Soc 135(43), (Oct. 30, 2013), 4 pgs.

Tran, Chris, et al., "Development of a second-generation antiandrogen for treatment of advanced prostate cancer", Science 324(5928), (2009), 787-790.

Uhlenbeck, O C, "A coat for all sequences", Nature structural biology, 5(3), (1998), 174-176.

Videira, et al., "Lymphatic uptake of lipid nanoparticles following endotracheal administration", Journal of Microencapsulation: Micro and Nano Carriers, 23(8), (2006), 855-862.

Vingerhoeds, et al., "Immunoliposome-mediated targeting of doxorubicin to human ovarian carcinoma in vitro and in vivo", British Journal of Cancer, (1996), 1023-29.

Wang, G, "Bisphosphonate-decorated lipid nanoparticles designed as drug carriers for bone diseases", Journal of Biomedical Materials Research A, vol. 100A, (Dec. 30, 2011), 684-693.

Wang, L-S, et al., "Biofunctionalized Phospholipid-Capped Mesoporous Silica Nanoshuttles for Targeted Drug Delivery: Improved Water Suspensibility and Decreased", ACS Nano, vol. 4 No. 8, (2010), 4371-4379.

Wang, Qingmin, et al., "Improved Cellular Immune Response Elicited by a Ubiquitin-Fused DNA Vaccine Against *Mycobacterium tuberculosis*", DNA and Cell Biology, vol. 31, No. 4, (2012), 489-495.

Wani, Amit, et al., "Surface Functionalization of Mesoporous Silica Nanoparticles Controls Loading and Release Behavior of Mitoxantrone", Pharmaceutical Research, Kluwer Academic Publishers—Plenum Publishers, NL, vol. 29, No. 9, (May 4, 2012), 2407-2418.

Weis, K, "Importins and exportins: how to get in and out of the nucleus", TIBS, 23, (1998), 185-189.

Wenyi, Gu, et al., "Nanotechnology in the targeted drug delivery for bone diseases and bone regeneration", International Journal of Nanomedicine, vol. 8, (2013), 2305-2317.

(56) References Cited

OTHER PUBLICATIONS

Wu, M, et al., "Cell-specific Delivery of Bacteriophage-Encapsidated Ricin A Chain", Bioconjugate Chem, 6, (1992), 587-595.

Xia, Tian, et al., "Polyethyleneimine Coating Enhances the Cellular Uptake of Mesoporous Silica Nanoparticles and Allows Safe Delivery of siRNA and DNA Constructs", ACS Nano; 3(10), (Oct. 27, 2009), 25 pgs.

Yamamoto, Satoshi, et al., "Synthesis of Fe70Pd30 nanoparticles and their surface modification by zwitterionic linker", Materials Chemistry and Physics 234, (2019), 237-244.

I, Yazdi, et al., "Novel mesoporous silicon particles as an efficient sustained delivery system for antibiotics", NSTI-Nanotech 2010, [Online] Retrieved from the Internet: <https://www.researchgate.net/profile/Iman Yazdi/publication/290613308 Novel mesaporous silicon particles as an efficient sustained delivery system-for antibiotics/links>, (Jan. 1, 2010), 324-325.

Youn, W, et al., "(Abstract) Cytoprotective Encapsulation of Individual Jurkat T Cells within Durable TIO2 Shells for T-Cell Therapy", Angew. Chem. Int. Ed., 56(36), pp. 10702-10706, (2017), 1 pg.

Yu-Shen, Lin, et al., "Well-Ordered Mesoporous Silica Nanoparticles as Cell Markers", Chem. Mater, 17, (2005), 4570-4573.

Zapryanova, et al., "Toroidal Microporous Silica Gel", Journal of Materials Science 14, (1979), 1175-1178 pgs.

Zelphati, et al., "Mechanism of Oligonucleotide Release rom Cationic Liposomes", Proceedings of the National Academy of Sciences USA 93, (1996), 11493-98.

Zhang, Haiyuan, et al., "Differential Expression of Syndecan-1 Mediates Cationic Nanoparticle Toxicity in Undifferentiated versus Differentiated Normal Human Bronchial Epithelial Cells", ACS Nano, (2011), 1-29.

Zhang, Jing, et al., "Multifunctional Envelope-Type Mesoporous Silica Nanoparticles for Tumor-Triggered Targeting Drug Delivery", J. Am. Chem. Soc, 135 (13), (2013), 5068-5073.

Zhang, K, et al., "Facile Large-Scale Synthesis of Monodisperse Mesoporous Silica Nanospheres with Tunable Pore Structure", Journal of the American Chemical Society, (2013), 2427-2430.

Zhu, Kelong, et al., "Metal-Organic Frameworks with Mechanically Interlocked Pillars: Controlling Ring Dynamics in the Solid-State via a Reversible Phase Change", J Am Chem Soc. 136(20), (May 21, 2014), 7403-7409.

Zhu, Wei, et al., "Modular Metal-Organic Polyhedra Superassambly: From Molecular-Level Design to Targeted Drug Delivery", Adv. Mater., vol. 31, No. 12, 1806774, (Mar. 2019), 10 pgs.

"U.S. Appl. No. 16/068,235, Response filed Nov. 9, 2021 to Non Final Office Action dated Jun. 15, 2021", 12 pgs.

"U.S. Appl. No. 14/113,371, Amendment filed Sep. 23, 2016", 16 pgs.

"U.S. Appl. No. 14/113,371, 312 Amendment filed Dec. 21, 2016", 4 pgs.

"U.S. Appl. No. 14/350,674, Preliminary Amendment filed Jun. 4, 2015", 12 pgs.

"U.S. Appl. No. 17/434,363, Preliminary Amendment filed Aug. 26, 2021", 7 pgs.

"International Application Serial No. PCT US2014 056342, International Preliminary Report on Patentability dated Mar. 22, 2016", 9 pgs.

"International Application Serial No. PCT US2014 056342, International Search Report dated Dec. 23, 2014", 4 pgs.

"International Application Serial No. PCT US2014 056342, Written Opinion dated Dec. 23, 2014", 8 pgs.

"International Application Serial No. PCT US2012 060072, International Preliminary Report on Patentability dated Apr. 15, 2014", 10 pgs.

"International Application Serial No. PCT US2012 060072, International Search Report dated Mar. 28, 2013", 6 pgs.

"International Application Serial No. PCT US2012 060072, Written Opinion dated Mar. 28, 2013", 9 pgs.

Kim, E, "Iodine 125-labeled mesenchymal-epithelial transition factor binding peptide-click-cRGDyk heterodimer for glioma imaging", Cancer Science, vol. 102, No. 8, (2011), 1516-1521.

\* cited by examiner

A.

B.

20 μm

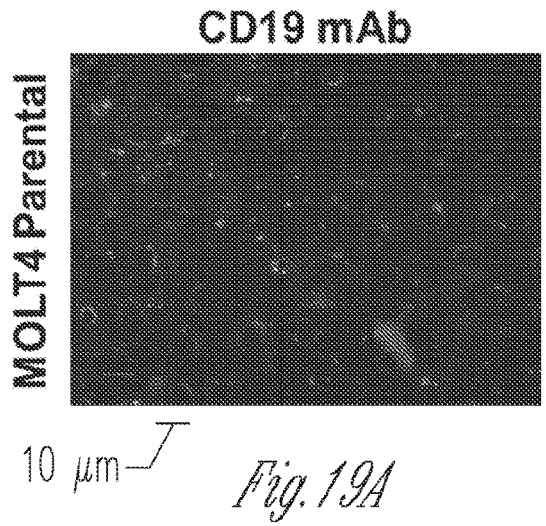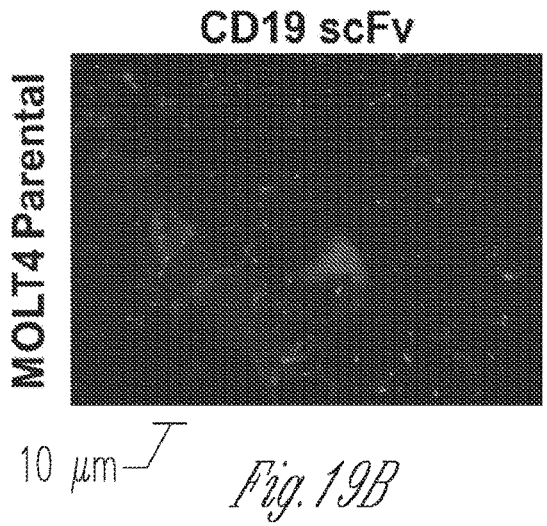
Fig. 19A  Fig. 19B
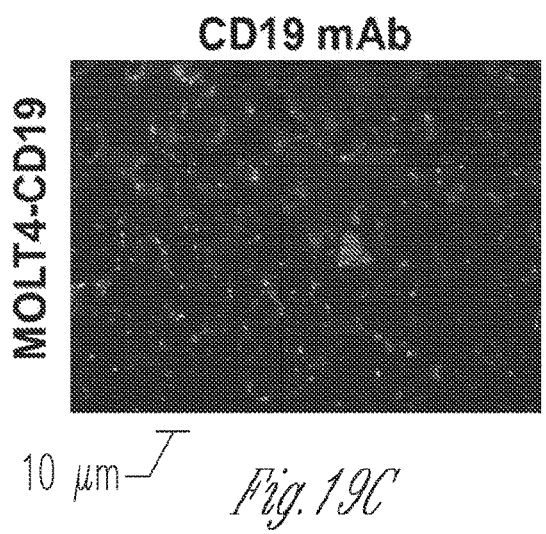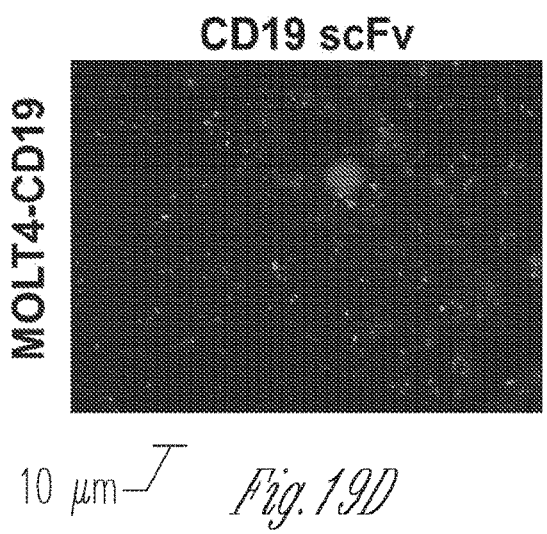
Fig. 19C  Fig. 19D
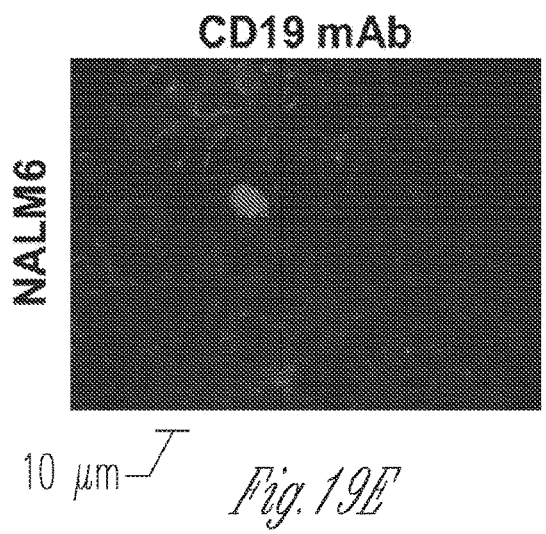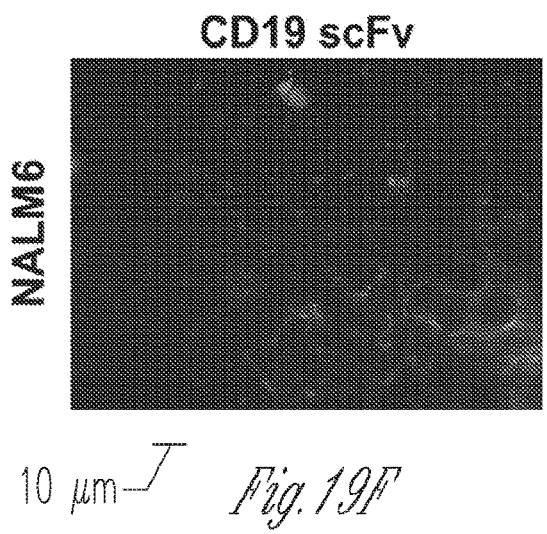
Fig. 19E  Fig. 19F

ACTIVE TARGETING OF CELLS BY MONOSIZED PROTOCELLS

CROSS-REFERENCE TO RELATED APPLICATIONS

This application is a U.S. National Stage Filing under 35 U.S.C. 371 from International Application No. PCT/US2018/020496, filed on Mar. 1, 2018, and published as WO 2018/160865 on Sep. 7, 2018, which application claims the benefit of the filing date of U.S. application Serial No. 62/465,582, filed on Mar. 1, 2017, the disclosures of which are incorporated by reference herein.

FIELD OF THE INVENTION

In one aspect, the disclosure provides mesoporous silica nanoparticles (MSNPs) and related protocells which exhibit single cell binding specificity to the substantial exclusion of non-targeted cells. For example, MSNPs and protocells of the disclosure may be used to target specific delivery of therapeutic agents to cancer cells or to specific blood vessel types (e.g., in the arterial, venous and/or capillary vessels or any combination of vessels). Related protocells, pharmaceutical compositions and therapeutic and diagnostic methods are also provided. Pharmaceutical compositions comprising MSNPs and protocells adapted for administration via intravenous, intramuscular, intraperitoneal, retro-orbital and subcutaneous injection routes and methods of administration, treatment and diagnostics utilizing these compositions are additional aspects of the present disclosure.

BACKGROUND

Nanoparticle (NP)/cell interactions, particularly in complex in vivo microenvironments, are regulated by an intricate spatiotemporal interplay of numerous biological and NP characteristics. Multiple NP physicochemical properties including, at the most basic level, material composition, size, shape, surface charge, and surface chemistry, have all been reported to play significant roles. However, the relative importance of these diverse NP physicochemical properties in regulating interactions with various biological systems remains incompletely understood. As such, achieving or avoiding cell-type specific interactions in vivo requires an improved understanding of the relative roles of these diverse NP properties, as well an ability to exert a high level of control over these properties during NP synthesis.

While the existing paradigm dictates that decreased size, neutral or negative zeta (.zeta.) potential, and extent of PEGylation are correlated with increased circulation time (i.e., reduced interaction with host cells), the manner in which these combined physicochemical properties conspire to direct in vivo cellular interactions has not been elucidated through careful systematic studies, and the nature of these interactions is likely to vary significantly by particle formulation and cell type. As amination of particles is commonly used in various particle modification schemes to enable labeling or targeting, enhance binding and internalization.

SUMMARY

The disclosure provides a population of protocells comprising a lipid bi- or multi-layer, monodisperse mesoporous silica nanoparticles (MSNPs), a cargo, and a targeting ligand, e.g., a CD19 targeting ligand, a EGFR targeting ligand or a motorneuron targeting ligand, wherein the MSNPs have a diameter ranging from about 1 nm to about 300 nm. In one embodiment, the monosized MSNPs have a polydispersity index of <0.1. In one embodiment, the protocells have a ratio of lipid to MSNP of about >1:1. In one embodiment, the protocells are in an aqueous composition having an ionic strength of >20 mM but less than about 500 mM, e.g., less than about 50, 100 or 200 mM. In one embodiment, the targeting ligand is an antibody. In one embodiment, the targeting ligand is an antibody fragment or a scFv. In one embodiment, the lipid bi- or multi-layer is PEGylated. In one embodiment, the lipid bi- or multilayer comprises: (a) at least one zwitterionic lipid selected from the group consisting of 1,2-dioleoyl-sn-glycero-3-phosphocholine (DOPC), 1,2-dioleoyl-sn-glycero-3-phosphoethanolamine (DOPE) and 1,2-di stearoyl-sn-glycero-3-phosphocholine (DSPC); and (b) optionally, one or more additional electrically S charged or neutral lipids selected from the group consisting of 1,2-dipalmitoyl-sn-glycero-3-phosphocholine (DPPC), dioleylglycero triethyleneglycyl iminodiacetic acid (DOIDA), distearylgtycerotdethyleneglycyl iminodiacetic acid (DSIDA), 1,2-dioleoyl-sn-glycero-3-[phosphorserine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino]lauroyl]-sn-Glyce-ro-3-Phosphocholine (18:1-12:0 NBD PC), 1-palmitoyl-2-(12-[(7-nitro-2-1,3-benzoxadiazol-4-yl)amino]lauroyl)-sn-gl-ycero-3-phosphocholine (16:0-12:0 NBD PC), cholesterol and mixtures/combinations thereof. In one embodiment, the MSNPs have an average diameter of less than about 200 nm. In one embodiment, the MSNPs have an average diameter of greater than about 20 nm. In one embodiment, the cargo comprises peptides, proteins, antibodies, nucleic acids, and drugs, e.g., drugs including but not limited to vincristine, daunorubicin, doxorubicin, cytarabine, L-asparaginase, PEG-L-asparaginase, etoposide, teniposide, 6-mercaptopurine, methotrexate, cyclophosphamide, predisone, dexamethasone, imatinib, dasatinib, nilotinib, ponatinib, nelarabine, rituximab, blinatumumab, or inotuzumab. In one embodiment, the lipid bi- or multi-layer comprises DSPC, cholesterol, and PEG-DSPC. In one embodiment, the amount of DSPC is about 45 mol % to about 80 mol %. In one embodiment, the amount of DSPC is about 50 mol % to about 78 mol %. In one embodiment, the amount of cholesterol is about 10 mol % to about 50 mol %. In one embodiment, the amount of cholesterol is about 17 mol % to about 25 mol %. In one embodiment, the amount of PEG-DSPC is about 1 mol % to about 3 mol %. In one embodiment, the amount of PEG DSPC is about 2 mol % to about 2.7 mol %. Also provided is a pharmaceutical composition comprising a population of the protocells in combination with a pharmaceutically acceptable carrier, additive and/or excipient. Further provded is a method of treating cancer, comprising administering to a subject having a CD19+ or EGFR+ cancer the pharmaceutical composition.

In one embodiment, a population of protocells comprising a lipid bi- or multi-layer, monodisperse mesoporous silica nanoparticles (MSNPs), a cargo, and a targeting ligand, e.g., a CD19 targeting ligand, an EGFR targeting ligand, or a motor neuron targeting ligand, wherein the MSNPs have a diameter ranging from about 1 nm to about 300 nm, is provided. In one embodiment, the protocells further comprise an enzyme that is directly or indirectly attached to the lipid layer. In one embodiment, the targeting ligand is directed attached to the lipid layer. In one embodiment, the targeting ligand is indirectly attached to the lipid layer. In one embodiment, the targeting ligand is a protein, e.g., an antibody. In one embodiment, the targeting ligand is an antibody fragment or a scFv. In one embodiment, the lipid bi- or multi-layer is PEGylated. In one embodiment, the lipid hi or multi-layer comprises a thiolated PEG containing moiety. In one embodiment, the cargo comprises a chemotherapeutic (anti-cancer) drug. In one embodiment, the lipid bi- or multi-layer comprises DSPC, cholesterol, PEG-DSPC, or a combination thereof. In one embodiment, the amount of DSPC is about 45 mol % to about 80 mol %. In one embodiment, the amount of DSPC is about 50 mol % to about 78 mol %. In one embodiment, the amount of cholesterol is about 10 mol % to about 50 mol %. In one embodiment, the amount of cholesterol is about 17 mol % to about 25 mol %. In one embodiment, the amount of PEG-DSPC is about 1 mol % to about 3 mol %. In one embodiment, the amount of PEG-DSPC is about 2 mol % to about 2.7 mol %. In one embodiment, the MSNPs have an average diameter of less than about 200 nm. In one embodiment, the MSNPs have an average diameter of greater than about 20 nm. In one embodiment, the CD19 targeting ligand comprises blinatumomab or a portion thereof, coltuxmiabravtasine or a portion thereof, MOR208 or a portion thereof, MEDI-551 or a portion thereof, denintuzumabmafodotin or a portion thereof, B4 or a portion thereof, DI-B4 or a portion thereof, taplitumomapaptox or a portion thereof, XmAb 5871 or a portion thereof, MDX-1342 or a portion thereof, or AFM 11 or a portion thereof. In one embodiment, the rnotorneuron targeting ligand is a subunit of cholera toxin or an inactivated cholera toxin. In one embodiment, the EGFR targeting ligand comprises cetuximab, panitumumab, IMC-225, CR62, ABX-EGF. necitumumab, EMD72000, matuzumab, zalutumumab, or nemotuzmumab, a fragment thereof, or a scFv thereof. In one embodiment, the protocell further comprises collagenase.

Also provided is a pharmaceutical composition comprising the population of protocells, in combination with a pharmaceutically acceptable carrier, additive and/or excipient. In one embodiment, the MSNPs have an average diameter ranging from about 100 nm to about 250 nm.

Further provided is a method of using the protocells, e.g., in a method of treating cancer. In one embodiment, the composition is intravenously administered. In one embodiment, the subject has ALL. In one embodiment, the targeting ligand is an antibody. In one embodiment, the cargo comprises vincristine, daunorubicin, doxorubicin, cytarabine, L-asparaginase, PEG-L-asparaginase, etoposide, teniposide, 6-mercaptopurine, methotrexate, cyclophosphamide, predisone, dexamethasone, imatinib, dasatinib, nilotinib, ponatinib, nelarabine, rituximab, blinatumumab, or inotuzumab. In one embodiment, the targeting ligand comprises blinatumomab or a portion thereof, coltuxmiabravtasine or a portion thereof, MOR208 or a portion thereof, MEDI-551 or a portion thereof, denintuzumabmafodotin or a portion thereof, B4 or a portion thereof, DI-B4 or a portion thereof, taplitumomapaptox or a portion thereof, XmAb 5871 or a portion thereof, MDX-1342 or a portion thereof, or AFM 11 or a portion thereof. In one embodiment, the targeting ligand comprises cetuximab, panitumumab, IMC-225. CR62, ABX-EGF. necitumumab, EMD72000, matuzumab, zalutumumab, or nemotuzmumab, a fragment htereof, or a scFv thereof. In one embodiment, the protocell further comprises collagenase.

Leukemia is a disseminated disease which makes active targeting advantageous to treat circulating cells. Active targeting is advantageous, but demands in vivo nanoparticle stability for prolonged circulation and binding to individual cells An effective targeted nanocarrier for leukemia includes one that is uniform and controllable particle size and shape, has high colloidal stability under physiological conditions, has minimal non-specific binding interactions, has high specificity for disease cells, has high capacity for and precise release of diverse therapeutic cargos, and has low cytotoxicity. As described herein, a targeting protocell to inhibit or treat CD19+ leukemias is provided. CD19 targeted protocells can selectively bind and deliver therapeutic cargo in vitro, flow and do not bind to endothelial cells in the vascularized CAM model, selectively bind and deliver fluorescent cargo to both cell lines and patient samples through the vasculature of the CAM system, circulate for prolonged periods in mice and can selectively targeted CD19 expressing leukemia cells in mice.

In vitro and in vivo behavior of the MSNPs illustrate the relative importance of charged molecule exposure and spatial arrangement versus zeta (zeta) potential and/or particle size as determinants of nonspecific binding and biodistribution. A uniform spatial distribution of charge presented within a PEG or PEG-like background for quaternary amines (e.g., PEG-NMe3+) confers both colloidal stability and protein corona neutrality, which in turn correlate with minimal nonspecific binding in vivo and prolonged circulation (and potentially opsonization neutrality), as evidenced by DLS. Such NP characteristics are expected to be ideal for maximizing the enhanced permeability and retention (EPR) effect or for binding and delivery to targeted circulating cells. In contrast, charge-matched PEG-PEI particles/interactions (e.g., amines having primary amines) displaying surface-exposed, branched amines, although colloidally stable, immediately form a protein corona and exhibit rapid nonspecific binding to endothelial and WBCs and arrest within the CAM. These characteristics are of potential interest for in vivo WBC and vascular labeling.

In one embodiment, the disclosure provides a population of optionally PEGylated, monodisperse mesoporous silica nanoparticles (MSNPs) that are aminated with a composition comprising a primary amine group and that exhibit a non-uniform surface charge distribution and colloidal stability, wherein the MSNPs have a diameter ranging from about 25 nm to about 300 nm and depending on route of administration of less than 50 about nm, less than about 30 nm, a pore size of between about 1 nm to about 200 nm, a surface area of between about 100-1,000 m$^2$/g, and a Zeta potential of between about −40 mV to about +40 mV (often greater than 0 mV to promote non-specific binding) and wherein upon administration in vivo, the MSNPs exhibit non-specific binding to white blood cells and arterial, venous and/or capillary vessels or combinations thereof. Core and surface modification of these MSNPs achieve vascular type specific arrest (i.e., in the arterial, venous or capillary bed) for delivery in vivo of cargo including imaging agents (e.g., rhodamine B isothiocynate) and/or therapeutic agents to endothelial cells.

"A composition comprising a primary amine group" or "primary amine-containing silane" is used to describe a silane compound containing a primary amine group which can be incorporated into MSNPs during production/formation and such compositions include, but are not limited to, a composition selected from the group consisting of trimethoxy-silylpropyl-modified polyethyleneimine (MW=1500-1800, PEI-silane), (3-aminopropyl)triethoxysilane, (3-Aminopropyl)trimethoxysilane, 3-Aminopropylmethyldiethoxysilane, 3-Aminopropyldimethylethoxysilane and mixtures thereof. In general, the amount of the primary amine containing silanes which are used to produce MSNPs in certain embodiments according to the present disclosure represent about 0.05% to about 25% (about 0.1% to about 20%, about 0.5% to about 15%, about 1% to about 10%, about 2.5% to about 7.5%, about 0.25% to about 5%, about 0.75% to about 15%) by weight of these monomers in combination with the silane monomers which are typically used to form MSNPs, which monomers will optionally include PEG-containing silane monomers as otherwise described herein.

In another embodiment, the disclosure provides a population of optionally PEGylated, monodisperse mesoporous silica nanoparticles (MSNPs) that are aminated with a composition that does not comprise a primary amine group (e.g., a quaternary amine, but such compositions may also include a tertiary amine and/or a secondary amine, depending on the desired zeta potential and the amount of non-specific binding to endothelial cells desired) and that exhibit a uniform surface charge distribution and colloidal stability, wherein the MSNPs have a diameter ranging from about 25 nm to about 300 nm (e.g., less than 50 nm or less than 30 nm, depending upon route of administration), a pore size of between about 1 nm to about 200 nm, a surface area of between about 100-1,000 m$^2$/g, and a Zeta potential (.zeta.) of between about −40 mV to about +40 mV (e.g., less than 0 mV in order to lessen/minimize non-specific binding to endothethilial cells/tissue and enhance distribution and residence times over a larger number of tissues and areas) and wherein upon administration in vivo, the MSNPs exhibit minimal non-specific binding and prolonged circulation. Core and surface modification of these MSNPs enable in vivo targeting of cargo including imaging agents (e.g., rhodamine B isothiocynate) and/or therapeutic agents to targets including (1) a cancer cell (2) kidney tissue (3) lung tissue (4) pancreatic tissue (5) a bacterium, or (6) a virus.

"A composition that does not comprise a primary amine group" includes, but is not limited to, a composition containing a quaternary amine selected from the group consisting of N-trimethoxysilylpropyl-N,N,N-trimethyl ammonium chloride (TMAC-silane, MW 258), and related silyl compounds which contain a quaternary amine group (a quaternary amine-modified silane compound). These compounds contain a quaternary amine group and a silyl group which can be used as silyl-containing monomers (in conjunction with other silyl monomers) to form MSNPs hereunder. These compounds are may be quaternary amine containing groups because they provide a uniform charge surface, especially in conjunction with PEG or PEG-like groups (often zwitterionic silyl groups), but may also include a compound containing a tertiary amine and/or a secondary amine (e.g., a tertiary amine modified silane or a secondary amine modified silane). Exemplary tertiary amine-modified silanes for use in the present disclosure include N$^1$-(3-Trimethoxylsilylpropyl)diethylenetriamine, among others, including 3-(trimethoxysilyl)propyl-di-n-octylmethyl-ammonium chloride; 3-(trimethosilyl)propyl-n-octyldimethyl-ammonium chloride; 3-(trimethoxysilyl)propyl-di-n-nonylmethyl-ammonium chloride; 3-(trimethoxysilyl)propyl-n-nonyldimethyl-ammonium chloride; 3-(trimethoxysilyl)propyl-di-decylmethyl-ammonium chloride; 3-(trimethoxysilyl)propyl-di-n-undecylmethyl-ammonium chloride; 3-(trimethoxysilyl)propyl-n-undecyldimethyl-ammonium chloride; 3-(trimethoxysilyl)propyl-di-n-dodecylmethyl-ammonium chloride; 3-(trimethoxysilyl)propyl-n-dodecyldimethyl-ammonium chloride; 3-(trimethoxysilyl)propyl-di-n-tridecyldimethyl-ammonium chloride; 3-(trimethoxysilyl)propyl-n-tridecyldimethyl-ammonium chloride; 3-(trimethoxysilyl)propyl-di-n-tetradecylmethyl-ammonium chloride; 3-(trimethoxysilyl)propyl-n-tetradecyldimethyl-ammonium chloride; 3-(triethoxysilyl)propyl-di-n-octylmethyl-ammonium chloride; 3-(triethoxysilyl)propyl-n-octyldimethyl-ammonium chloride; 3-(triethoxysilyl)propyl-di-n-nonylmethyl-ammonium chloride; 3(triethoxysilyl)propyl-n-nonyldimethyl-ammonium chloride; 3-(triethoxysilyl)propyl-di-n-decylmethyl-ammonium chloride; 3-(triethoxysilyl)propyl-n-decyldimethyl-ammonium chloride; 3-(triethoxysilyl)propyl-di-n-undecylmethyl-ammonium chloride; 3-(triethoxysilyl)propyl-n-undecyldimethyl-ammonium chloride; 3-(triethoxysilyl)propyl-di-n-dodecylmethyl-ammonium chloride; 3-(triethoxysilyl)propyl-n-dodecyldimethyl-ammonium chloride; 3-(triethoxysilyl)propyl-di-n-tridecylmethyl-ammonium chloride; 3-(triethoxysilyl)propyl-n-tridecyldimethyl-ammonium chloride; 3-(triethoxysilyl)propyl-di-n-tetradecylmethyl-ammonium chloride; 3-(triethoxysilyl)propyl-n-tetradecyldimethyl-ammonium chloride; 3-(tripropoxysilyl)propyl-di-n-octylmethyl-ammonium chloride; 3-(tripropoxysilyl)propyl-n-octyldimethyl-ammonium chloride; 3-(tripropoxysilyl)propyl-di-n-nonylmethyl-ammonium chloride; 3-(tripropoxysilyl)propyl-n-nonyldimethyl-ammonium chloride; 3-(triproposilyl)propyl-di-n-decylmethyl-ammonium chloride; 3-(tripropoxysilyl)propyl-n-decyldimethyl-ammonium chloride; 3-(tripropoxysilyl)propyl-di-n-undecylmethyl-ammonium chloride; 3-(tripropoxysilyl)propyl-n-undecyldimethyl-ammonium chloride; 3-(tripropoxysilyl)propyl-di-n-dodecylmethyl-ammonium chloride; 3-(tripropoxysilyl)propyl-n-dodecyldimethyl-ammonium chloride; 3-(tripropoxysilyl)propyl-di-n-tridecylmethyl-ammonium chloride; 3-(tripropoxysilyl)propyl-n-tridecyldimethyl-ammonium chloride; 3-(tripropoxysilyl)propyl-di-n-tetradecylmethyl-ammonium chloride; 3-(tripropoxysilyl)propyl-n-tetradecyldimethyl-ammonium chloride; 3-(tributoxysilyl)propyl-di-n-octylmethyl-ammonium chloride; 3-(tributoxysilyl)propyl-n-octyldimethyl-ammonium chloride; 3-(tributoxysilyl)propyl-di-n-nonylmethyl-ammonium chloride; 3-(tributoxysilyl)propyl-n-nonyldimethyl-ammonium chloride; 3-(tributoxysilyl)propyl-di-n-decylmethyl-ammonium chloride; 3-(tributoxysilyl)propyl-n-decyldimethyl-ammonium chloride; 3-(tributoxysilyl)propyl-di-n-undecylmethyl-ammonium chloride; 3-(tributoxysilyl)propyl-n-undecyldimethyl-ammonium chloride; 3-(tributoxysilyl)propyl-di-n-dodecylmethyl-ammonium chloride; 3-(tributoxysilyl)propyl-n-dodecyldimethyl-ammonium chloride; 3-(tributoxysilyl)propyl-di-n-tridecylmethyl-ammonium chloride; 3-(tributoxysilyl)propyl-n-tridecyldimethyl-ammonium chloride; 3-(tributoxysilyl)propyl-di-n-tetradecylmethyl-ammonium chloride; 3-(tributoxysilyl)propyl-n-tetradecyldimethyl-ammonium chloride and mixtures thereof. Exemplary secondary amine-modified silanes (e.g., diamines which may contain both primary and secondary amines) for use in the present disclosure include N-[3-(Trimethoxysilyl)propyl]ethylenediamine, N-2-(Aminoethyl)-3-aminopropylmethyldimethosilane, N-(2-Aminoethyl)-3-aminoisobutyldimethylmethoxysilane, N-(6-Aminohexyl)aminopropyltrimethoxysilance and mixtures thereof. In general, the amount of the quaternary amine-containing silanes which optionally are used to produce MSNPs according to the present disclosure represent about about 0.05% to about 25% (about 0.1% to about 20%, about 0.5% to about 15%, about 1% to about 10%, about 2.5% to about 7.5%, about 0.25% to about 5%, about 0.75% to about 15%) by weight of these monomers in combination with the silane monomers which are typically used to form MSNPs. Of course secondary and tertiary amine-containing silanes may also be used within the same general weight range to effect binding non-specific binding characteristics which fall somewhere between the primary amines (high non-specific binding) and the quaternary amines (very low non-specific binding).

The size, charge, charge exposure and PEGylation of the MSNPs and protocells described herein can be controlled such that specifically tuned particles can be controllably deposited within certain tissue types (e.g., in the arterial, venous and/or capillary vessels or any combination of vessels). To enhance binding specificity, the MSNPs may be combined with targeting peptide or ligand. We have determined that an increasing cationic charge results in more localized binding to vasculature, whereas a less cationic, neutral or anionic charge results in broader in vivo dispersal.

The disclosure includes protocells in which the novel MSNPs described herein are encapsulated within a lipid bi- or multi-layer.

By modifying MSNPs core (size, shape, mass) and surface properties, we can alter in vivo biodistribution by changing the proportion of particles arrested in different types of vasculature (e.g., capillary versus arterial or venous system). This control over the particles allows for physiochemical targeting of specific vasculature (and thereby tissues) and can be further modified to incorporate single cell type specific binding in the vasculature. (The term "binding" as used herein includes MSNPs and/or protocell binding to bacteria in vivo.)

The in vitro and in vivo behavior of the MSNPs described and claimed herein illustrate the relative importance of charged molecule exposure and spatial arrangement versus Zeta (.zeta.) potential and/or particle size as determinants of nonspecific binding and biodistribution. A uniform spatial distribution of charge presented within a PEG background for PEG-NMe3+ confers both colloidal stability and protein corona neutrality, which in turn correlate with minimal nonspecific binding in vivo and prolonged circulation (and potentially opsonization neutrality), as evidenced by DLS. Such NP characteristics are expected to be ideal for maximizing the enhanced permeability and retention (EPR) effect or for binding and delivery to targeted, including circulating cells. In contrast, charge-matched PEG-PEI particles displaying surface-exposed, primary amines, including branched amines, although colloidally stable, immediately form a protein corona and exhibit rapid nonspecific binding to endothelial and WBCs and arrest within the CAM.

In still other embodiments, the disclosure includes methods of treatment and diagnostic methods which use the MSNPs and protocells described herein to treat and/or diagnose a variety of disorders, including cancers, bacterial and viral infections, vascular disorders and inflammatory diseases and disorders as otherwise described herein.

The present disclosure also relates to the discovery that MSNPs and protocells which are monodisperse and in one embodiment are less than 50 nm in average diameter, often 30 nm or less in diameter (in many instances MSNPs and protocells which are less than 25 nm in diameter, especially for subcutaneous administration) can be used to effectively deliver cargo therefrom (especially therapeutic agents) after administration to a patient or subject by intravenous, intramuscular, intraperitoneal, retro-orbital and subcutaneous injection routes. In a particular embodiment, compositions according to the present disclosure which are administered pursuant to the present disclosure, and in particular subcutaneously which have not been modified with an amine or if modified, modified with a quaternary amine pursuant to the present disclosure, are shown to have excellent biodistribution after administration, in contrast to compositions wherein the protocells are larger in diameter (e.g., above about 30-50 nm in diameter) and which contain primary, and to a lesser extent, secondary and tertiary amines. Accordingly, the present disclosure may be used effectively for administering agents which have not been traditionally administered to patients for therapeutic and or diagnostic purposes by intravenous, intramuscular, intraperitoneal, retro-orbital and subcutaneous injection routes in a much more efficient manner and wadditionally, the present compositions and methods may be formulated for numerous therapeutic agents, including drugs, nucleic acids and polypeptides, among others and/or diagnostic agents which may have exhibited poor biodistribution/bioavailability before the advent of the present disclosure.

The rpesent disclosure also provides for non-ligand targeting of MSNPs. As disclosed hereinbelow, monosized MSNs with differing surface chemistries, e.g., protected uniform quaternary amines versus exposed primary amines, can provide for different biodistribution. For example, these different surface chemistries plus PEG trimethylsilyl modified MSNs alter the biodistribution, e.g., depending on the surface modification PEI (primary amine), QA (quaternary amine) or trimethylsilyl (TMS) the MSNs show differing efficiencies of remaining in circulation versus accumulation in the liver and spleen. In addition, there is a size dependence of the MSNPs on biodistribution. In one embodiment, the MSNs are modified with TMS or PEG-TMS and have a diameter of from about 10 to about 40 nm, about 15 to about 30 nm, about 20 to about 30 nm, about 70 to about 100 nm, or about 120 to about 160 nm. In one embodiment, the MSNs are modified with QA or PEG-QA and have a diameter of from about 30 to about 70 nm, about 40 to about 60 nm, about 45 to about 55 nm, about 70 to about 100nm, or about 120 to about 160 nm. In one embodiment, the MSNs are modified with PEI or PEG PEI and have a diameter of from about 30 to about 70 nm, about 40 to about 60 nm, about 45 to about 55 nm, about 70 to about 100 nm, or about 120 to about 160 nm.

These and other aspects of the disclosure are described further in the Detailed Description.

BRIEF DESCRIPTION OF THE FIGURES

FIGS. 19A-F. Intravital fluorescent microscopy images acquired ex ovo in the CAM model reveal stable circulation of CD19 targeted antibody- and scFv-modified protocells (red) avoiding MOLT4 cells and binding to CD19 positive cells MOLT4-CD19 and NALM6 (blue) in circulation at 4 hours.

DETAILED DESCRIPTION

Figure 1:
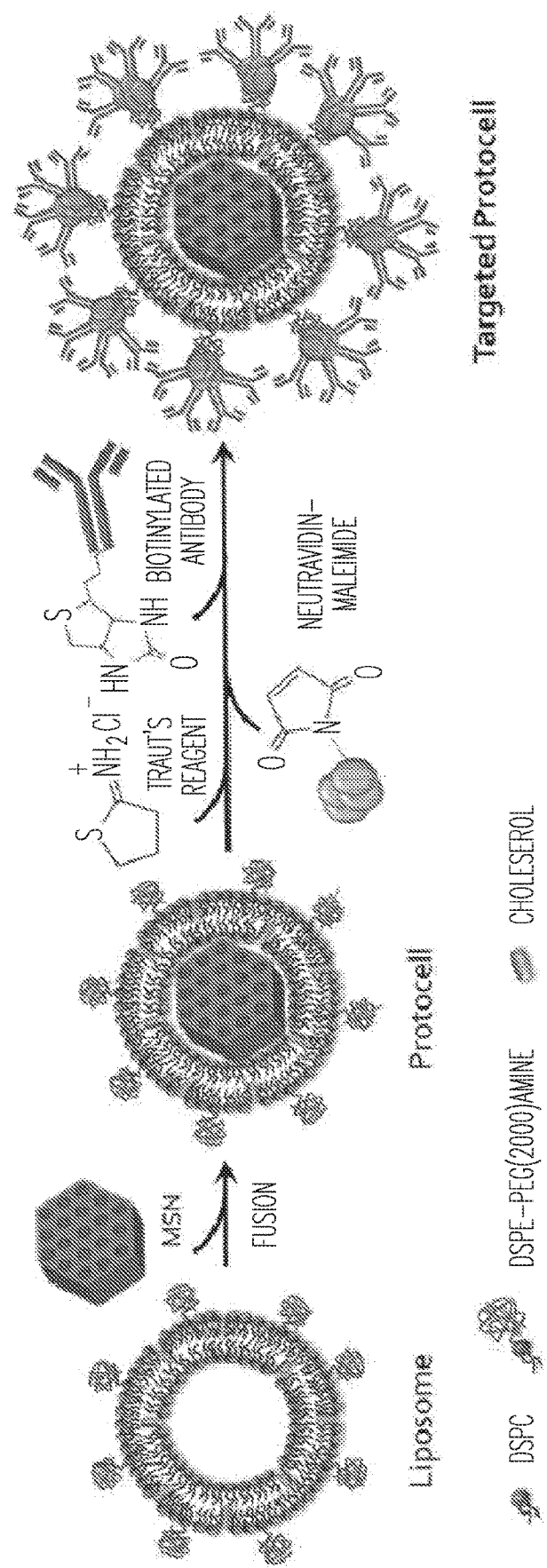
FIG. 1. Schematic of targeted protocells. MSN core has a high surface area, stabilizes lipid bilayer, can control size and shape, and tunable pore geometry. Lipid bilayer has enhanced stability in physiological buffer, increases biocompatibility, allows for targeting modifications, and decreases immunogenicity.

The following terms shall be used throughout the specification to describe the present disclosure. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the methods and materials are now described.

It must be noted that as used herein and in the appended claims, the singular forms "a" "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal or a human, to whom treatment, including prophylactic treatment (prophylaxis), with the compounds or compositions according to the present disclosure is provided. For treatment of those infections, conditions or disease states which are specific for a specific animal such as a human patient, the term patient refers to that specific animal. In most instances, the patient or subject of the present disclosure is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "compound" is used herein to describe any specific compound or bioactive agent disclosed herein, including any and all stereoisomers (including diastereomers), individual optical isomers (enantiomers) or racemic mixtures, pharmaceutically acceptable salts (including alternative pharmaceutically acceptable salts when a pharmaceutically acceptable salt is disclosed) and prodrug forms. The term compound herein refers to stable compounds. Within its use in context, the term compound may refer to a single compound or a mixture of compounds as otherwise described herein. One or more bioactive agent (any agent which produces an intended biological, including pharmacological effect) may be included in MSNPs according to the present disclosure to provide pharmaceutical compositions hereunder.

The term "mesoporous silica nanoparticles" (MSNPs) is used to describe nanoparticles according to the present disclosure which are modified to target specific cells (in many instances, cancer cells) in vivo for diagnostic and/or therapeutic purposes.

A nanoparticle may have a variety of shapes and cross-sectional geometries that may depend, in part, upon the process used to produce the particles. In one embodiment, a nanoparticle may have a shape that is a sphere, a rod, a tube, a flake, a fiber, a plate, a wire, a cube, or a whisker. A nanoparticle may include particles having two or more of the aforementioned shapes. In one embodiment, a cross-sectional geometry of the particle may be one or more of circular, ellipsoidal, triangular, rectangular, or polygonal. In one embodiment, a nanoparticle may consist essentially of non-spherical particles. For example, such particles may have the form of ellipsoids, which may have all three principal axes of differing lengths, or may be oblate or prelate ellipsoids of revolution. Non-spherical nanoparticles alternatively may be laminar in form, wherein laminar refers to particles in which the maximum dimension along one axis is substantially less than the maximum dimension along each of the other two axes. Non-spherical nanoparticles may also have the shape of frusta of pyramids or cones, or of elongated rods. In one embodiment, the nanoparticles may be irregular in shape. In one embodiment, a plurality of nanoparticles may consist essentially of spherical nanoparticles.

The phrase "effective average particle size" as used herein to describe a multiparticulate (e.g., a porous nanoparticulate) means that at least 50% of the particles therein are of a specified size. Accordingly, "effective average particle size of less than about 2,000 nm in diameter" means that at least 50% of the particles therein are less than about 2000 nm in diameter. In certain embodiments, nanoparticulates have an effective average particle size of less than about 2,000 nm (i.e., 2 microns), less than about 1,900 nm, less than about 1,800 nm, less than about 1,700 nm, less than about 1,600 nm, less than about 1,500 nm, less than about 1,400 nm, less than about 1,300 nm, less than about 1,200 nm, less than about 1,100 nm, less than about 1,000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods. In certain aspects of the present disclosure, where administration via intravenous, intramuscular, intraperitoneal, retro-orbital and subcutaneous injection routes produces long residence times (on the order of at least 12 hours to 2 weeks or more) and greater biodistribution and/or bioavailability, the MSNPs and protocells are monodisperse and generally no greater than about 50 nm in average diameter, often less than about 30 nm in average diameter, as otherwise described herein. The term "$D_{50}$" refers to the particle size below which 50% of the particles in a multiparticulate fall. Similarly, the term "$D_{90}$" refers to the particle size below which 90% of the particles in a multiparticulate fall.

The MSNP size distribution depends on the application, but is principally monodisperse (e.g., a uniform sized population varying no more than about 5-20% in diameter, as otherwise described herein). The term "monodisperse" is used as a standard definition established by the National Institute of Standards and Technology (NIST) (Particle Size Characterization, Special Publication 960-1, January 2001) to describe a distribution of particle size within a population of particles, in this case nanoparticles, which particle distribution may be considered monodisperse if at least 90% of the distribution lies within 5% of the median size. See Takeuchi, et al., Advanced Materials, 2005, 17, No. 8, 1067-1072.

In certain embodiments, mesoporous silica nanoparticles can range, e.g., from around 1 nm to around 500 nm in size, including all integers and ranges there between. The size is measured as the longest axis of the particle. In various embodiments, the particles are from around 5 nm to around 500 nm and from around 10 nm to around 100 nm in size. The mesoporous silica nanoparticles have a porous structure. The pores can be from around 0.5 nm to about 25 nm in diameter, often about 1 to around 20 nm in diameter, including all integers and ranges there between. In one embodiment, the pores are from around 1 to around 10 nm in diameter. In one embodiment, around 90% of the pores are from around 1 to around 20 nm in diameter. In another embodiment, around 95% of the pores are around 1 to around 20 nm in diameter.

In certain embodiments, MSNPs according to the present disclosure are monodisperse and range in size from about 25 nm to about 300 nm; exhibit stability (colloidal stability); have single cell binding specification to the substantial exclusion of non-targeted cells; are neutral or cationic for specific targeting (e.g., cationic); are optionally modified with agents such as PEI, NMe3+, dye, crosslinker, ligands (ligands provide neutral charge); and optionally, are used in combination with a cargo to be delivered to a targeted cell.

In certain alternative embodiments, the MSNPs are monodisperse and range in size from about 25 nm to about 300 nm. The sizes used may include 50 nm (+/−10 nm) and 150 nm (+/−15 nm), within a narrow monodisperse range, but may be more narrow in range. A broad range of particles is not used because such a population is difficult to control and to target specifically.

In certain alternative embodiments, the present disclosure are directed to MSNPs and for example, protocells of a particular size (diameter) ranging from about 0.5 to about 30 nm, about 1 nm to about 30 nm, often about 5 nm to about 25 nm (e.g., less than about 25 nm), often about 10 to about 20 nm, for administration via intravenous, intramuscular, intraperitoneal, retro-orbital and subcutaneous injection routes. These MSNPs and/or protocells are often monodisperse and provide colloidally stable compositions. These compositions can be used to target tissues in a patient or subject because of enhanced biodistribution,/bioavailability of these compositions, and optionally, specific cells, with a wide variety of therapeutic and/or diagnostic agents which exhibit varying release rates at the site of activity. As noted in the present application, MSNPs and protocells may have a charged surface (zeto potential) which ranges from about −40 EV to +40 EV. MSNPs and protocells according to the present disclosure may exhibit varied surface charges as a consequence of the componentry used to create the MSNPs. A typical MSNP based upon silica (without amine modification) exhibits a negatively charged surface having a zeta potential often within the range of about −10 EV to about −40 EV. A negative surface charge, or alternatively, a positive surface charge which is presented through use of quaternary amines for MSNPs and protocells pursuant to the present disclosure are consistent with these particles being less interactive with vascular/endothelial tissue and providing greater distribution to and high residence times in tissue after administration. A positively charged MSNP exhibits a zeta potential of about +10 EV to about +40 EV. A positive surface charge for MSNPs and protocells pursuant to the present disclosure, especially from primary amines, and to a less extent secondary and tertiary amines, are consistent with these particles being more interactive with vascular tissue and providing limited distribution principally to vascular tissue after administration. It is noted that when secondary and tertiary amines, as opposed to primary amines, are used to provide a more positively charged surface, whether the actual surface charge is negative or positive, these may exhibit non-specific binding to vascular tissue (endothelial tissue), but the effect is substantially less (muted) than the effect is for primary amines. Of course, using mixtures of amines may be used to influence both the surface charge (zeta potential) as well as the non-specific binding of the nanoparticles to vascular tissue along a continuum from very little, if any binding (quaternary amines) to some binding (tertiary and secondary amines) to specific targeting of endothelial cells utilizing primary amines.

The term "uniform surface" is used to describe a surface which contains a uniform surface charge. Uniform surfaces occur for MSNPs (e.g., PEgylated) which contain quaternary amines such as the charge is consistently projected on the whole surface of the MSNP without appreciable patches or gaps in the surface charge. A "non-uniform surface" describes a surface of an MSNP which contains patches of charge which are distinguishable from the broader portions of the surface. In the case of MSNPs which are modified with primary amines, the overall surface may be neutral or charged, but the primary amine creates a patch of more positive charge with protruding protonated amines characterizing the patches on the surface of the MSNPs. The surface of the MSNPs, including protocells according to the present disclosure may be measured and/or identified using cryo-TEM and TEM analysis, among others. These analyses look at the characteristics of the binding of a metal with high electron density—often a heavy metal such as gold, silver, iron and the like—to produce a 3-dimensional spatial arrangement on the nanoparticle. Uniform surfaces tend to be consistent and uniform in their surface charge, whereas non-uniform surfaces tend to have areas of concentrated charge in a patchwork that can often be random.

The term "PEGylated" in its principal use refers to an MSNP which has been produced using PEG-containing silanes or zwitterionic group-containing silanes to form the MSNP. In general, the amount of the PEG-containing silanes and/or zwitterionic-containing silanes which optionally are used to produce MSNPs according to the present disclosure represent about 0.05% to about 50% (about 0.1% to about 35%, about 0.5% to about 25%, about 1% to about 20%, about 2.5% to about 30%, about 0.25% to about 10%, about 0.75% to about 15%) by weight of these monomers in combination with the silane monomers which are typically used to form MSNPs. A PEG-containing silane is any silane which contains a PEG as one of the substituents and the remaining groups can facilitate the silane reacting with other silanes to produce MSNPs according to the present disclosure. PEG-containing silanes and/or zwitterionic-containing silanes which may be used in the present disclosure to create PEGylated MSNPs include 2-[methoxy(polyethyleneoxy)propyl]trimethoxysilane (containing varying molecular weights of PEG ranging from about 100 to 10,000 average molecule weight, often about 200 to 5,000 average molecular weight, about 1,000-2,500 average molecular weight, about 1500-2000 average molecular weight) and 3-([Dimethoxyl(3-trimethoxysilyl)propyl]arnmonio)propane-1-sulfonate and mixtures thereof, among others. The term "PEGylated" may also refer to lipid bilayers which contain a portion of lipids which are PEGylated (from about 0.02% up to about 50%, about 0.1% to about 35%, about 0.5% to about 25%, about 1% to about 15%, about 0.5% to about 7.5%, about 1% to about 12.5% by weight of the lipids used to form the lipid bilayer or multilayer). These lipids often are amine-containing lipids (e.g., DOPE and DPPE) which are conjugated or derivatized to contain a PEG group (having an average molecule weight ranging from about 100 to 10,000, about 200 to 5,000, about 1,000-5,000, including 1,000, 2000, 3000 and 3400) and combined with other lipids to form the bilayer/multilayer which encapsulates the MSNP.

The term "non-specific binding" refers to the binding which occurs between a charged surface of the MSNPs according to the present disclosure and endothelial tissue pursuant to the present disclosure because the interaction between the particles and the tissue surface are based non-specifically upon the interactions of charges on the particles and the tissue surface rather than a ligand-ligand interaction. In the case of "specific binding" the interaction between the particle and a target is based upon a specific ligand-ligand interaction. It is noted that when a particle exhibits low non-specific binding, that particle may exhibit very little binding (i.e., little specific or non-specific binding) or more specific binding (greater ligand-ligand interaction) depending upon the context of its use.

The terms "targeting ligand" and "targeting active species" are used to describe a compound or moiety (e.g., an antigen) which is complexed or covalently bonded to the surface of a MSNPs and/or protocells according to the present disclosure which binds to a moiety on the surface of a cell to be targeted so that the MSNPs and/or protocells may selectively bind to the surface of the targeted cell and deposit their contents into the cell. The targeting active species for use in the present disclosure may be a targeting peptide as otherwise described herein, a polypeptide including an antibody or antibody fragment, an aptamer, or a carbohydrate, among other species which bind to a targeted cell.

Ligands which may be used to target cells include peptides, affibodies and antibodies (including monoclonal and/or polyclonal antibodies). In certain embodiments, targeting ligands selected from the group consisting of Fc gamma from human IgG (which binds to Fcgamma receptors on macrophages and dendritic cells), human complement C3 (which binds to CR1 on macrophages and dendritic cells), ephrin B2 (which binds to EphB4 receptors on alveolar type II epithelial cells), and the SP94 peptide (which binds to unknown receptor(s) on hepatocyte-derived cells). Other targeting peptides known in the art may also be used.

The charge of the nanoparticle is controlled based on what is to be accomplished (via PEI, NMe3+, dye, crosslinker, ligands, etc.), but for targeting vascular tissue the charge may be cationic. In the case of enhanced biodistribution, the charge may be anionic, but may be cationic provided that the charge occurs principally from the inclusion of quaternary amines. Charge also changes throughout the process of formation. Initially, in certain embodiments the targeted particles are cationic and are often delivered as cationically charged nanoparticles, however post modification with ligands they are closer to neutral. The ligands which find use in the present disclosure include peptides, affibodies and antibodies, among others. These ligands are site specific and are useful for targeting specific cells which express peptides to which the ligand may bind selectively to targeted cells.

MSNPs pursuant to the present disclosure may be used to deliver cargo to a targeted cell, including, for example, cargo component selected from the group consisting of a polynucleotide such as DNA, including double stranded linear DNA or a plasmid DNA, RNA, including small interfering RNA, small hairpin RNA, microRNA, a drug (in particular, an anticancer drug such as a chemotherapeutic agent), an imaging agent, or a mixture thereof.

In protocells of the disclosure, a PEGylated lipid bi- or multilayer encapsulates a population of MSNPs as described herein and comprises (1) an optionally-thiolated PEG (2) at least one lipid and, optionally (3) at least one targeting ligand which is conjugated to the outer surface of the lipid bi- or multilayer and which is specific against one or more receptors of white blood cells and arterial, venous and/or capillary vessels or combinations thereof, or which is specific against one or more receptors of targets a cancer cell, a bacterium, or a virus.

Protocells of the disclosure are highly flexible and modular. High concentrations of physiochemically-disparate molecules can be loaded into the protocells and their therapeutic and/or diagnostic agent release rates can be optimized without altering the protocell's size, size distribution, stability, or synthesis strategy. Properties of the supported lipid bi- or multilayer and mesoporous silica nanoparticle core can also be modulated independently, thereby optimizing properties as surface charge, colloidal stability, and targeting specificity independently from overall size, type of cargo(s), loading capacity, and release rate.

The terms "treat", "treating", and "treatment", are used synonymously to refer to any action providing a benefit to a patient at risk for or afflicted with a disease, including improvement in the condition through lessening, inhibition, suppression or elimination of at least one symptom, delay in progression of the disease, delay in or inhibition of the likelihood of the onset of the disease, etc. In the case of viral infections, these terms also apply to viral infections and include, in certain embodiments the eradication or elimination (as provided by limits of diagnostics) of the virus which is the causative agent of the infection. Treatment can also be used to provide prevention (prophylaxis/reducing the likelihood) of a disease state occurring, but the present disclosure contemplates a distinction between the treatment of a disease state and/or condition and the prevention (prophylaxis/reducing the likelihood) that a disease state or condition will occur, within the context of such treatment/prevention.

The term "pharmaceutically acceptable" as used herein means that the compound or composition is suitable for administration to a subject, including a human patient, to achieve the treatments described herein, without unduly deleterious side effects in light of the severity of the disease and necessity of the treatment.

Treatment, as used herein, may encompass prophylactic and/or therapeutic treatment depending on context, principally of cancer, but also of other disease states. Compounds according to the present disclosure can, for example, be administered prophylactically to a mammal in advance of the occurrence of disease to reduce the likelihood of that disease. Prophylactic administration is effective to reduce or decrease the likelihood of the subsequent occurrence of disease in the mammal, or decrease the severity of disease (inhibition) that subsequently occurs, especially including metastasis of cancer. Alternatively, compounds according to the present disclosure can, for example, be administered therapeutically to a mammal that is already afflicted by disease. In one embodiment of therapeutic administration, administration of the present compounds is effective to eliminate the disease and produce a remission or substantially eliminate the likelihood of metastasis of a cancer. Administration of the compounds according to the present disclosure is effective to decrease the severity of the disease or lengthen the lifespan of the mammal so afflicted, as in the case of cancer, or inhibit or even eliminate the causative agent of the disease, as in the case of human immunodeficiency virus (HIV I or II), hepatitis B virus (HBV) and/or Antibiotic MSNPs and protocells of the disclosure can contain one or more antibiotics, e.g., "Antibiotics" include, but are not limited to, compositions selected from the group consisting of Gentamicin, Kanamycin, Neomycin, Netilmicin, Tobramycin, Paromomycin, Spectinomycin, Geldanamycin, Herbimycin, Rifaximin, Streptomycin, Ertapenem, Doripenem, Imipenem/Cilastatin, Meropenem, Cefadroxil, Cefazolin, Cephalothin, Cephalexin, Cefaclor, Cefamandole, Cefoxitin, Cefprozil, Cefuroxime, Cefixime, Cefdinir, Cefditoren, Cefoperazone Cefotaxime, Cefpodoxime, Ceftazadime, Ceftibuten, Ceftizoxime Ceftriaxone, Cefepime, Ceftaroline fosamil, Ceftobiprole, Teicoplanin, Vancomycin, Telavancin, Daptomycin, Oritavancin, WAP-8294A, Azithromycin, Clarithromycin, Dirithromycin, Erythromycin, Roxithromycin, Telithromycin, Spiramycin, Clindamycin, Lincomycin, Aztreonam, Furazolidone, Nitrofurantoin, Oxazolidonones, Linezolid, Posizolid, Radezolid, Torezolid, Amoxicillin, Ampicillin, Azlocillin, Carbenicillin, Cloxacillin Dicloxacillin, Flucloxacillin, Mezlocillin, Methicillin, Nafcillin, Oxacillin, Penicillin G, Penicillin V, Piperacillin, Temocillin, Ticarcillin, Arnoxicilliniclavulanate, Ampicillin/sulbactam, Piperacillin/tazobactam, Ticarcillin/clavulanate, Bacitracin, Colistin, Polyrnyxin B, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Mafenide, Sulfacetamide, Sulfadiazine, Sulfadimethoxine, Sulfamethizole, Sulfamethoxazole, Sulfasalazine, Sulfisoxazole, Trimethoprim-Sulfamethoxazole, Sulfonamidochrysoidine, Demeclocycline, Doxycycline, Vibramycin Minocycline, Tigecycline, Oxytetracycline, Tetracycline, Clofazimine, Capreomycin, Cycloserine, Ethambutol, Rifampicin, Rifabutin, Rifapentine, Arsphenamine, Chloramphenicol, Fosfomycin, Fusidic acid, Metronidazole, Mupirocin, Platensimycin, Quinupristin/Dalfopristin, Thiamphenicol, Tigecycline and Tinidazole and combinations thereof.

The term "neoplasia" refers to the uncontrolled and progressive multiplication of tumor cells, under conditions that would not elicit, or would cause cessation of, multiplication of normal cells. Neoplasia results in a "neoplasm," which is defined herein to mean any new and abnormal growth, particularly a new growth of tissue, in which the growth of cells is uncontrolled and progressive. Thus, neoplasia includes "cancer," which herein refers to a proliferation of tumor cells having the unique trait of loss of normal controls, resulting in unregulated growth, lack of differentiation, local tissue invasion, and/or metastasis.

As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. Examples of neoplasms or neoplasias from which the target cell of the present disclosure may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, $17^{th}$ ed. (Whitehouse Station, N.J.: Merck Research Laboratories, 1999) 973-74, 976, 986, 988, 991.

The term "anticancer agent" or "additional anticancer agent" (depending on the context of its use) shall mean chemotherapeutic agents such as an agent selected from the group consisting of microtubule-stabilizing agents, microtubule-disruptor agents, alkylating agents, antimetabolites, epidophyllotoxins, antineoplastic enzymes, topoisomerase inhibitors, inhibitors of cell cycle progression, and platinum coordination complexes. These may be selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]-benzoyl]-, disodium salt, heptahydrate, camptothecin, PEG-labeled irinotecan, tamoxifen, toremifene citrate, anastrazole, exemestane,letrozole, DES(diethylstilbestrol), estradiol, estrogen, conjugated estrogen, bevacizumab, IMC-1C11, CHIR-258,); 3-[5-(methylsulfonylpiperadinemethyl)-indolyl]-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [$C_{59}H_{84}N_{18}Oi_4$-($C_2H_4O_2$)x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, Ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezirnib, paclitaxel, crernophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-9,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

MSNPs and protocells of the disclosure also can comprise anti-cancer agents selected from the group consisting of doxorubicin-loaded liposomes that are functionalized by polyethylene glycol (PEG), antimetabolites, inhibitors of topoisomerase I and II, alkylating agents and microtubule inhibitors, adriamycin aldesleukin; alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemcitabine, gemtuzumab ozogamicin; goserelin acetate; hydroxyurea; Ibritumomab Tiuxetan; idarubicin; Ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); uracil mustard; valrubicin; vattorcitabine (monoval LDC); vinblastine; vinorelbine; zoledronate; and mixtures thereof.

In certain embodiments, MSNPs and protocells of the disclosure comprise anti-cancer drugs selected from the group consisting of doxorubicin, melphalan, bevacizumab, dactinomycin, cyclophosphamide, doxorubicin liposomal, amifostine, etoposide, gemcitabine, altretamine, topotecan, cyclophosphamide, paditaxel, carboplatin, cisplatin, and taxol.

MSNPs and protocells of the disclosure can include one or more antiviral agents to treat viral infections, especially including HIV infections, HBV infections and/or HCV infections. Exemplary anti-HIV agents include, for example, nucleoside reverse transcriptase inhibitors (NRTI), non-nucloeoside reverse transcriptase inhibitors (NNRTI), protease inhibitors, fusion inhibitors, among others, exemplary compounds of which may include, for example, 3TC (Lamivudine), AZT (Zidovudine), (−)-FTC, ddl (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development. Exemplary anti-HBV agents include, for example, hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof. Anti-HCV agents include, for example, interferon, pegylated intergeron, ribavirin, NM 283, VX-950 (telaprevir), SCH 50304, TMC435, VX-500, BX-813, SCHSO3034, R1626. ITMN-191 (R7227), R7128, PF-868554, 11033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9 Agonist, PHX1766, SP-30 and mixtures thereof.

The above compounds/bioactive agents may also be included in MSNPs, including protocells, having average diameters which are less than about 50 nm, or less than 30 nm for formulating compositions adapted for intravenous, intramuscular, intraperitoneal, retro-orbital and subcutaneous injection routes. In certain embodiments, subcutaneous routes of administration are used for administering bioactive agents including vaccines (immunogenic compositions), opiates, hormones (epinephrine, growth hormone, insulin, etc.), synthetic steroidal agents, fertility agents, contraceptive agents and antibodies, especially including therapeutic monoclonal antibodies. Additional specific bioactive agents which may be administered favorably by subcutaneous routes according to the present disclosure include, for example, alfentanil, cyclizine, dexamethasone, diamorphine, glycopyrronium, haloperidol, hydromorphine, hyoscine butylbromide, hyoscine hydrobromide, ketamine, ketorolac, levomepromazine, metoclopramide, midazolam, morphine (morphine sulfate), octreotide, oxycodone and pharmaceutically acceptable salts and/or alternative salts.

Typically the MSNPs and protocells according to the present disclosure are loaded with cargo to a capacity up to about 50 weight % or more (from about 0.01% to about 50%, about 0.02% to about 40%, about 0.2 to about 35%, about 0.5% to about 25%, about 1% to about 25%, about 1.5% to about 15%, about 0.1% to about 10%, about 0.01% to about 5%): defined as (cargo weight/weight of loaded protocell).times.100. The optimal loading of cargo is often about 0.01 to 10% but this depends on the drug or drug combination which is incorporated as cargo into the MSNPs. This is generally expressed in µM per $10^{10}$ particles where we have values ranging from 2000-100 µM per $10^{10}$ particles. MSNPs according to the present disclosure may exhibit release of cargo at pH about 5.5, which is that of the endosome, but are stable at physiological pH of 7 or higher (7.4).

The surface area of the internal space for loading is the pore volume whose optimal value ranges from about 1.1 to 0.5 cubic centimeters per gram (ccig). Note that in the MSNPs according to one embodiment of the present disclosure, the surface area is mainly internal as opposed to the external geometric surface area of the nanoparticle.

The term "lipid" is used to describe the components which are used to form lipid bi- or multilayers on the surface of the nanoparticles which are used in the present disclosure. Various embodiments provide nanostructures which are constructed from nanoparticles which support a lipid bilayer(s). In embodiments according to the present disclosure, the nanostructures may include, for example, a core-shell structure including a porous particle core surrounded by a shell of lipid bilayer(s). The nanostructure, e.g., a porous alum nanostructure as described above, supports the lipid bilayer membrane structure.

The lipid bi- or multilayer supported on the porous particle according to one embodiment of the present disclosure has a lower melting transition temperature, i.e., is more fluid than a lipid bi- or multilayer supported on a non-porous support or the lipid bi- or multilayer in a liposome. This is sometimes important in achieving high affinity binding of immunogenic peptides or targeting ligands at low peptide densities, as it is the bilayer fluidity that allows lateral diffusion and recruitment of peptides by target cell surface receptors. One embodiment provides for peptides to cluster, which facilitates binding to a complementary target.

In the present disclosure, the lipid bi- or multilayer may vary significantly in composition. Ordinarily, any lipid or polymer which may be used in liposomes may also be used in MSNPs according to the present disclosure. Lipids are as otherwise described herein.

In embodiments according to the disclosure, the lipid bi- or multilayer of the protocells can provide biocompatibility and can be modified to possess targeting species including, for example, antigens, targeting peptides, fusogenic peptides, antibodies, aptamers, and PEG (polyethylene glycol) to allow, for example, further stability of the protocells and/or a targeted delivery into a cell to maximize an immunogenic response. PEG, when included in lipid bilayers (using PEGylated lipids), can vary widely in molecular weight (although PEG ranging from about 10 to about 100 units of ethylene glycol, about 15 to about 50 units, about 15 to about 20 units, about 15 to about 25 units, about 16 to about 18 units, etc, may be used) and the PEG component which is generally conjugated to a phospholipid through an amine group comprises about 1% to about 20%, e.g., about 5% to about 15%, about 10% by weight of the lipids which are included in the lipid bi- or multilayer.

Numerous lipids which are used in liposome delivery systems may be used to form the lipid bi- or multilayer on nanoparticles to provide MSNPS according to the present disclosure. Virtually any lipid which is used to form a liposome may be used in the lipid bi- or multilayer which surrounds the nanoparticles to form MSNPS according to an embodiment of the present disclosure. Lipids for use in the present disclosure include, for example, 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino]lauroyl]-sn-Glyce-ro-3-Phosphocholine (18:1-12:0 NBD PC), 1-palmitoyl-2-(12-[(7-nitro-2-1,3-benzoxadiazol-4-yl)amino]lauroyl)-sn-gl-ycero-3-phosphocholine (16:0-12:0 NBD PC), cholesterol and mixtures/combinations thereof. Cholesterol, not technically a lipid, but presented as a lipid for purposes of an embodiment of the present disclosure given the fact that cholesterol may be an important component of the lipid bilayer of protocells according to an embodiment of the disclosure. Often cholesterol is incorporated into lipid bilayers of protocells in order to enhance structural integrity of the bilayer. These lipids are all readily available commercially from Avanti Polar Lipids, Inc. (Alabaster, Ala., USA). DOPE and DPPE are particularly useful for conjugating (through an appropriate crosslinker) peptides, polypeptides, including immunogenic peptides, proteins and antibodies, RNA and DNA through the amine group on the lipid.

MSNPs and protocells of the disclosure can be PEGylated with a variety of polyethylene glycol-containing compositions. PEG molecules can have a variety of lengths and molecular weights and include, but are not limited to, PEG 200, PEG 1000, PEG 1500, PEG 4600, PEG 10,000, PEG-peptide conjugates or combinations thereof. Example 3 herein describes the use of 2-[methoxy(polyethyleneoxy)-propyl]trimethoxysilane (MW 550-750, 9-12 EO, PEG-silane) for MSNP PEGylation. Typically, pegylation occurs by using a silyl agent containing a PEG groups (PEG-silane) which is added to the silane mixture in synthesizing MSNPs according to the present disclosure. Alternatively, a reactive amine group on the surface of the MSNPs may be functionalized by reacting the amine with a PEG containing group to form a PEG group on the amine.

The term "reporter" is used to describe an imaging agent or moiety which is incorporated into the phospholipid bilayer or cargo of MANPS according to an embodiment of the present disclosure and provides a signal which can be measured. The moiety may provide a fluorescent signal or may be a radioisotope which allows radiation detection, among others. Exemplary fluorescent labels for use in MSNPs and protocells (e.g., via conjugation or adsorption to the lipid bi- or multilayer or silica core, although these labels may also be incorporated into cargo elements such as DNA, RNA, polypeptides and small molecules which are delivered to cells by the protocells) include Hoechst 33342 (350/461), 4',6-diamidino-2-phenylindole (DAPI, 356/451), Alexa Fluor® 405 carboxylic acid, succinimidyl ester (401/421), CellTracker™. Violet BMQC (415/516), CellTracker™ Green CMFDA (492/517), calcein (495/515), Alexa Fluor® 488 conjugate of annexin V (495/519), Alexa Fluor® 488 goat anti-mouse IgG (H+L) (495/519), Click-iT® AHA Alexa Fluor® 488 Protein Synthesis HCS Assay (495/519), LIVE/DEAD® Fixable Green Dead Cell Stain Kit (495/519), SYTOX®. Green nucleic acid stain (504/523), MitoSOX™ Red mitochondrial superoxide indicator (510/580). Alexa Fluor® 532 carboxylic acid, succinimidyl ester (532/554), pHrodoTmsuccinimidyl ester (558/576), CellTracker™ Red CMTPX (577/602), Texas Red® 1,2-dihexadecanoyl-sn-glycero-3-phosphoethanolamine (Texas Red® DHPE, 583/608), Alexa Fluor® 647 hydrazide (649/666), Alexa Fluor® 647 carboxylic acid, succinimidyl ester (650/668), Ulysis™ Alexa Fluor® 647 Nucleic Acid Labeling Kit (650/670) and Alexa Fluor® 647 conjugate of annexin V (650/665). Moities which enhance the fluorescent signal or slow the fluorescent fading may also be incorporated and include SlowFade.RTM. Gold antifade reagent (with and without DAPI) and Image-iT® FX signal enhancer. All of these are well known in the art.

Additional reporters include polypeptide reporters which may be expressed by plasmids (such as histone-packaged supercoiled DNA plasmids) and include polypeptide reporters such as fluorescent green protein and fluorescent red protein. Reporters pursuant to the present disclosure are utilized principally in diagnostic applications including diagnosing the existence or progression of cancer (cancer tissue) in a patient and or the progress of therapy in a patient or subject.

Pharmaceutical compositions according to the present disclosure comprise an effective population of MSNPs and/or protocells as otherwise described herein formulated to effect an intended result (e.g., immunogenic result, therapeutic result and/or diagnostic analysis, including the monitoring of therapy) formulated in combination with a pharmaceutically acceptable carrier, additive or excipient. The MSNPs and/or protocells within the population of the composition may be the same or different depending upon the desired result to be obtained. Pharmaceutical compositions according to the present disclosure may also comprise an addition bioactive agent or drug, such as an antibiotic or antiviral agent.

Generally, dosages and routes of administration of the compound are determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g., orally, transdermally, perineurally or parenterally, that is, by intravenous, subcutaneous, intraperitoneal, intrathecal or intramuscular injection, among others, including buccal, rectal and transdermal administration. Subjects contemplated for treatment according to the method of the disclosure include humans, companion animals, laboratory animals, and the like. The disclosure contemplates immediate and/or sustained/controlled release compositions, including compositions which comprise both immediate and sustained release formulations. This is particularly true when different populations of MSNPs and/or protocells are used in the pharmaceutical compositions or when additional bioactive agent(s) are used in combination with one or more populations of protocells as otherwise described herein.

In certain formulation embodiments of the disclosure include protocells comprised of mesoporous silica nanoparticulates (MSNPs) that (a) are loaded with one or more pharmaceutically-active agents and (b) that are encapsulated by and that support a lipid bilayer, and wherein the protocell has an average diameter of between about 1 nm to about 50 nm, e.g., between about 1 nm to about 30 nm, about 5 nm to about 25 nm, often 10 nm to about 25 nm, about 10 to about 20 nm. It has unexpectedly been discovered that the administration of protocells comprising therapeutic and/or diagnostic agents via intravenous, intramuscular, intraperitoneal, retro-orbital and especially subcutaneous routes of administration at the average diameters indicated above provide enhanced biodistribution, enhanced bioavailability and increased residence time (often at least 12-24 hours to several days up to a week or in certain cases, two weeks to a month or even longer), of these protocells compared to protocells with average diameters which are in excess of 50 nm, often greater than about 100 nm or more (e.g., 200-300 nm). Accordingly, the present compositions and methods of treatment and diagnosis in these routes of administration are greatly facilitated compared to compositions which contain protocells of larger diameters. Compositions according to the present disclosure may be used to administer cargo as otherwise described herein to a patient or subject through intravenous, intramuscular, intraperitoneal, retro-orbital and subcutaneous routes of administration, with unexpected biodistribution, bioavailability and residence times far exceeding compositions utilizing nanoparticles with average diameters in excess of 50-100 nm or greater (200-250 nm).

Formulations containing the compounds according to the present disclosure may take the form of liquid, solid, semisolid or lyophilized powder forms, such as, for example, solutions, suspensions, emulsions, sustained-release formulations, tablets, capsules, powders, suppositories, creams, ointments, lotions, aerosols, patches or the like, e.g., in unit dosage forms suitable for simple administration of precise dosages.

Pharmaceutical compositions according to the present disclosure typically include a conventional pharmaceutical carrier or excipient and may additionally include other medicinal agents, carriers, adjuvants, additives and the like.

In some embodiments, the composition is about 0.1% to about 85%, about 0.5% to about 75% by weight of a compound or compounds of the disclosure, with the remainder consisting essentially of suitable pharmaceutical excipients.

An injectable composition for parenteral administration (e.g., intravenous, intramuscular or intrathecal) will typically contain the compound in a suitable i.v. solution, such as sterile physiological salt solution. The composition may also be formulated as a suspension in an aqueous emulsion. Liquid compositions can be prepared by dissolving or dispersing the population of MSNPs and/or protoells (about 0.5% to about 20% by weight or more), and optional pharmaceutical adjuvants, in a carrier, such as, for example, aqueous saline, aqueous dextrose, glycerol, or ethanol, to form a solution or suspension. For use in an oral liquid preparation, the composition may be prepared as a solution, suspension, emulsion, or syrup, being supplied either in liquid form or a dried form suitable for hydration in water or normal saline.

For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g., an excipient such as a saccharide or cellulose preparation, a binder such as starch paste or methyl cellulose, a filler, a disintegrator, and other additives typically used in the manufacture of medical preparations.

Methods for preparing such dosage forms are known or is apparent to those skilled in the art, for example, see Remington's Pharmaceutical Sciences (17th Ed., Mack Pub. Co., 1985). The composition to be administered will contain a quantity of the selected compound in a pharmaceutically effective amount for therapeutic use in a biological system, including a patient or subject according to the present disclosure.

Methods of treating patients or subjects in need for a particular disease state or infection comprise administration an effective amount of a pharmaceutical composition comprising therapeutic MSNPs and/or protocells and optionally at east one additional bioactive (e.g., antiviral) agent according to the present disclosure.

Diagnostic methods according to the present disclosure comprise administering to a patient in need an effective amount of a population of diagnostic MSNPs and/or protocells (e.g., MSNPs and/or protocells which comprise a target species, such as a targeting peptide which binds selectively to cancer cells and a reporter component to indicate the binding of the protocells whereupon the binding of protocells to cells as evidenced by the reporter component (moiety) will enable a diagnosis of the existence of a disease state in the patient.

An alternative of the diagnostic method of the present disclosure can be used to monitor the therapy of a disease state in a patient, the method comprising administering an effective population of diagnostic MSNPs and/or protocells (e.g., MSNPs and/or protocells which comprise a target species, such as a targeting peptide which binds selectively to target cells and a reporter component to indicate the binding of the protocells to cancer cells if the cancer cells are present) to a patient or subject prior to treatment, determining the level of binding of diagnostic protocells to target cells in said patient and during and/or after therapy, determining the level of binding of diagnostic protocells to target cells in said patient, whereupon the difference in binding before the start of therapy in the patient and during and/or after therapy will evidence the effectiveness of therapy in the patient, including whether the patient has completed therapy or whether the disease state has been inhibited or eliminated.

The present disclosure also is directed to a process or processes for preparing the MSNPs according to the present disclosure.

In one embodiment, the disclosure is directed to a process for making a population of optionally PEGylated, monodisperse mesoporous silica nanoparticles (MSNPs) that exhibit a relatively non-uniform surface charge distribution and colloidal stability and that have a diameter ranging from about 25 nm to about 300 nm (or from about 25 nm to about 200 nm, or from about 25 nm to about 100 nm, or from about 25 nm to about 95, 90, 85, 80, 75, 70, 65, 60, 55, 50, 45, 40, 35 or 30 nm (e.g., less than 50 nm, or less than 30, 25, 20, 15 or 10 nm)), a pore size of between about 1 nm to about 200 nm or between about 50, 40, 30, 25, 20, 15, 10, 9, 8, 7, 6, 5, 4, 3, 2 or 1 nm, a surface area of between about 100-1,000 m.sup.2/g, and a Zeta potential (.zeta.) of between about −40 mV to about +40 mV (e.g., greater than 0 mV) and that, upon administration in vivo, exhibit non-specific binding to white blood cells and arterial, venous and/or capillary vessels or combinations thereof, the process comprising:

(a) (1) preparing a mesoporous silica colloidal solution comprising: (1) a solvent solution comprising: (i) an alkoxysilane selected from the group consisting of tetramethylortho silicate (TMOS), tetraethylortho silicate (TEOS), tetrakis(2-hydroxyethyl)ortho silicate (THEOS), methyldiethoxysilane (MDES), 3-(glycidoxypropyl)triethoxysilane (GPTMS), 3-(trimethyoxysilyl)propylacrylate (TMSPA), N-(3-triethoxysilylpropyl)pynole (TESPP), vinyltriethyoxysilane (VTES), methacryloxypropyltriethoxysilane (TESPM), diglycerylsilane (DGS), methyltriethosilane (MTMOS), trimethylmethoxysilane (TMMS), ethyltriethoxysilane (TEES), n-propyltriethoxysilane (TSPS), n-butyltriethyoxysilane (TEBS), 3-aminopropyltriethoxysilane (APTS), 2-(2,4-dinitrophenylamino)propyltriethoxysilane, mercaptopropyltriethoxysilane (TEPMS), 2-(3-aminoethylamino)propyltriethosilane, isocyanatopropyltriethoxysilane, hydroxyl-terminated polydimethylsiloxane, triethoxysilyl-terminated polydimethylsiloxane, methyltriethoxysilane (MTES), and triethosilyl-terminated poly(oxypropylene) (ii) a solvent (iii) optionally, a reporter, and (2) a surfactant which is selected from the group consisting of polyvinyl alcohol (PVA), dioctyl sodium sulfosuccinate, methyl cellulose, polysorbates, cetyltrimethylammonium bromide (CTAB), dodecylamine (DDA), 1,2-di-O-octadecenyl-3-trimethylammonium propane (DOTMA), and 1,2-Dioleoyl-3-trimethylammonium-propane (DOTAP) and which is heated to a temperature of between about 30° C. to about 60° C., or from about 35° C. to about 55° C., or at about 45° C., 46° C., 47° C., 48° C., 49° C., 50° C., 51° C., 52° C., 53° C. or 54° C., e.g., at about 50° C.; (b) including in said mesoporous silica colloidal solution a composition comprising a primary amine group and, optionally, a PEG-silane compound to produce a nanoparticle containing amine groups; and (c) hydrothermally treating the aminated nanoparticles produced in step (b) by heating the nanoparticles at a temperature of between about 100° C. to about 150° C. (e.g., about between about 110° C. to about 140° C., e.g., between about 115° C. to about 135° C., e.g., at about 120° C.) to yield the optionally PEGylated, monodisperse mesoporous silica nanoparticles (MSNPs); wherein the process can be one pot or in steps.

In the above process, (a) the alkoxysilane may be 3-aminopropyltriethoxysilane (APTS), the solvent may be N,N-dimethyl formamide (DMF) and the reporter may be rhodamine B isothiocynate (RITC); and the composition comprising a primary amine group is trimethoxysilylpropyl modified polyethyleneimine (50% in isopropanol, M.W. 1500-1800, PEI-silane) and the PEG-silane compound is methoxy(polyethyleneoxy)propyl]trimethoxysilane (Mw 550-750, 9-12 EO, PEG-silane).

In an alternative embodiment, the present disclosure is directed to a process for making a population of optionally PEGylated, monodisperse mesoporous silica nanoparticles (MSNPs) that exhibit a relatively uniform surface charge distribution and colloidal stability and that have a diameter ranging from about 25 nm to about 300 nm (or from about 25 nm to about 200 nm, or from about 25 nm to about 100 nm, or from about 25 nm to about 95, 90, 85, 80, 75, 70, 65, 60, 55, 50, 45, 40, 35 or 30 nm (e.g., less than 50 nm, such as less than 30, 25, 20, 15 or 10 nm)), a pore size of between about 1 nm to about 200 nm or between about 50, 40, 30, 25, 20, 15, 10, 9, 8, 7, 6, 5, 4, 3, 2 or 1 nm, a surface area of between about 100-1,000 m$^2$/g, and a Zeta potential (.zeta.) of between about −40 mV to about +40 mV (e.g., less than 0 mV) and that, upon administration in vivo, exhibit minimal non-specific binding and prolonged circulation, the process comprising:

(a) (1) preparing a mesoporous silica colloidal solution comprising: (1) a solvent solution comprising: (i) an alkoxysilane selected from the group consisting of tetramethylortho silicate (TMOS), tetraethylortho silicate (TEOS), tetrakis(2-hydroxyethyl)ortho silicate (THEOS), methyldiethoxysilane (MDES), 3-(glycidoxypropyl)triethoxysilane (GPTMS), 3-(trimethyoxysilyl)propylacrylate (TMSPA), N-(3-triethoxysilylpropyl)pyrrole (TESPP), vinyltriethyoxysilane (VTES), methacryloxypropyltriethoxysilane (TESPM), diglycerylsilane (DGS), methyltriethoxysilane (MTMOS), trimethylmethoxysilane (TMMS), ethyftriethoxysilane (TEES), n-propyltriethoxysilane (TSPS), n-butyltriethyoxysilane (TEBS), 3-aminopropyltriethoxysilane (APTS), dinitrophenylamino)propyltriethoxysilane, mercaptopropyltriethoxysilane (TEPMS), 2-(3-aminoethylamino)propyltriethoxysilane, isocyanatopropyltriethoxysilane, hydroxyl-terminated polydimethylsiloxane, triethoxysilyl-terminated polydimethylsiloxane, methyltriethoxysilane (MTES), and triethoxysilyl-terminated poly(oxypropylene) (ii) a solvent (iii) optionally, a reporter, and (2) a surfactant which is selected from the group consisting of polyvinyl alcohol (PVA), dioctyl sodium sulfosuccinate, methyl cellulose, polysorbates, cetyltrimethylammonium bromide (CTAB), dodecylamine (DDA), 1,2-di-O-octadecenyl-3-trimethylammonium propane (DOTMA), and 1,2-Dioleoyl-3-trimethylammonium-propane (DOTAP) and which is heated to a temperature of between about 30° C. to about 60° C., or from about 35° C. to about 55° C., or at about 45° C., 46° C., 47° C., 48° C., 49° C., 50° C., 51° C., 52° C., 53° C. or 54° C., e.g., at about 50° C.; (b) including in the mesoporous silica colloidal solution (i) a composition that does not comprise a primary amine group and, optionally, (ii) a PEG-silane compound to produce a nanoparticle containing amine groups (e.g., quaternary, but also secondary and/or tertiary amine) which are not primary amine groups; and (c) hydrothermally treating the nanoparticles produced in step (b) by heating the nanoparticles at a temperature of between about 100° C. to about 150° C. (e.g., about between about 110° C. to about 140° C., such as between about 115° C. to about 135° C., or at about 120°, to yield the optionally PEGylated, monodisperse mesoporous silica nanoparticles (MSNPs); wherein the process can be one pot or in steps.

In the above process, (a) the alkoxysilane is 3-aminopropyltriethoxysilane (APTS), the solvent is N,N-dimethyl formamide (DMF) and the reporter is rhodamine B isothiocynate (RITC); and (b) the composition that does not comprise a primary amine group is N-trimethoxysilylpropyl-N,N,N-trimethyl ammonium chloride (50% in methanol, TMAC-silane) and the PEG-silane compound is methoxy(polyethyleneoxy)propyl]trimethoxysilane (Mw 550-750, 9-12 EO, PEG-silane).

Additional embodiments are directed to MSNPs and/or populations of MSNPs which are produced by the above methods.

In accordance with the present disclosure there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL.

The invention is described further in the following non-limiting examples.

EXAMPLE 1

Active Targeting of Circulating Tumor Cells by Monosized Protocells

Many cancer nanotherapeutics currently under development, as well as those currently in use in the clinical setting, rely upon passive mechanisms to treat tumors or circulating cancer cells. For example, the enhanced permeability and retention (EPR) effect leads to passive accumulation of the nanotherapeutic in the tumor microenvironment which allows killing of tumor cells. However, the EPR effect has limited to no efficacy against circulating tumor cells present in leukemia or in metastatic cancer. Alternatively, encapsulation of therapeutic agents within a nanocarrier, such as a liposome, leads to slower release into the blood stream versus bolus drug injection and therefore enhanced therapeutic efficacy of the nanocarrier versus free drug. However, the slow release does not prevent nonspecific killing of healthy cells which is a major source of toxicity in chemotherapy. By utilizing active targeting of monosized protocells we can target circulating tumor cells and provide specific cell killing while sparing healthy cells.

The protocell platform, which consists of a mesoporous silica nanoparticle (MSNP) core wrapped in a supported lipid bilayer (SLB), can be utilized to specifically deliver therapeutic cargo to circulating tumor cells, such as leukemia, while sparing nontargeted cells. The modular nature of the protocell allows customization of each part to facilitate delivery of a wide variety of cargo. The high pore volume of the MSNP core allows loading of large amounts of drugs within the protocell. The use of the monosized MSNP allows specific size control to enhance circulation and reduce uptake by the mononuclear phagocyte system, a major source of nanoparticle removal from circulation and non-specific uptake. The use of the monosized MSNP allows selection of the most appropriate size particle for the delivery to individual cells such as those in the bone marrow in leukemia. The MSNP can be modified in charge or surface chemistry to facilitate loading of diverse cargo based on the structure of the cargo. The use of the SLB allows the addition of specific targeting moieties, such as: antibodies, peptides, affibodies, single chain variable fragments (scFv), fragment antibodies (Fab) and small molecule targeting agents. The SLB further seals in the cargo and prevents premature leakage of cargo. The formulation of the SLB can be modified to enhance protection cargo and control release of cargo based on the specific cargo selected.

Figure 2:
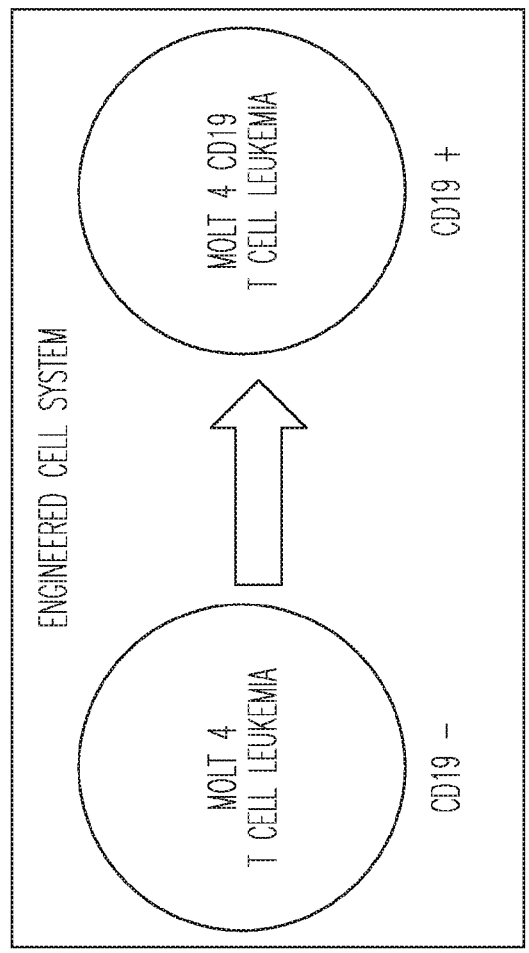
FIG. 2. Schematic of a leukemia cell specific targeting system. CD19 is a B cell surface protein that is expressed throughout B cell development and is expressed on nearly all B cell malignancies.
Figure 3:
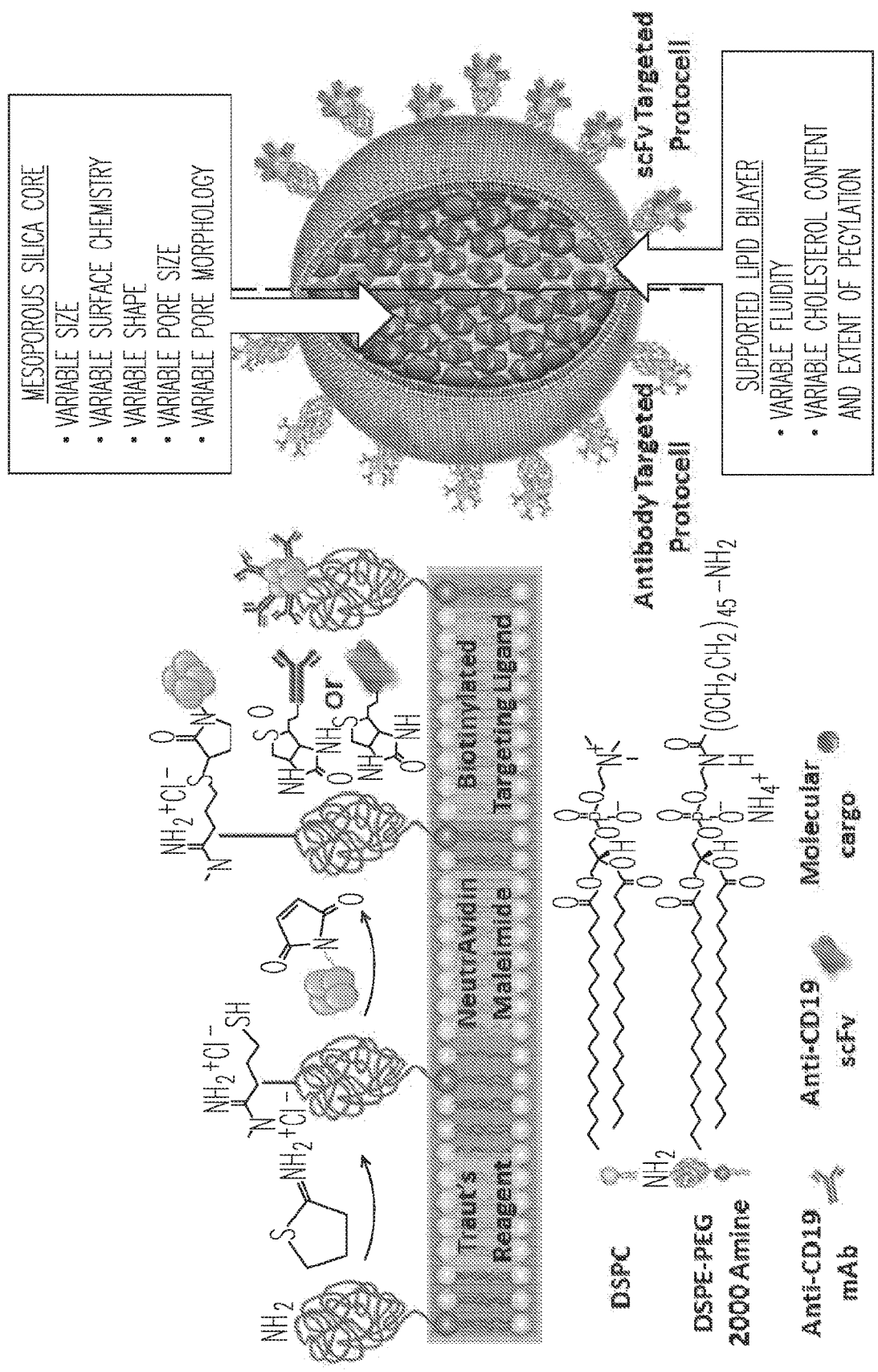
FIG. 3. Exemplary conjugation of taregeting moieties to lipid. After protocell formation, an exemplary targeting moiety, e.g., CD19 antibodies of scFvs are added to the surface. The MSN can vary in size, surface chemistry, shape, pore size and pore geometry. The supported lipid bilayer provides for variations in fluidity and in some embodiment, variable cholesterol content and/or variable PEGylation.

As an example of specific targeting of protocells to a disseminated disease, protocells for treatment of leukemia were developed that were targeted to the cell surface marker CD19. CD19 expression is limited to B-cells and therefore a therapeutic target for acute lyphoblastic leukemia (ALL). As shown in FIG. 2, monosized protocells modified with anti-CD19 antibodies bind only to cells the express CD19 and bind in a time dependent manner. Anti-CD19 targeted protocells internalize into CD19 expressing cells but not into cells which do not express CD19 (FIG. 3). Internalization is necessary for specific cargo delivery.

Figure 4A:
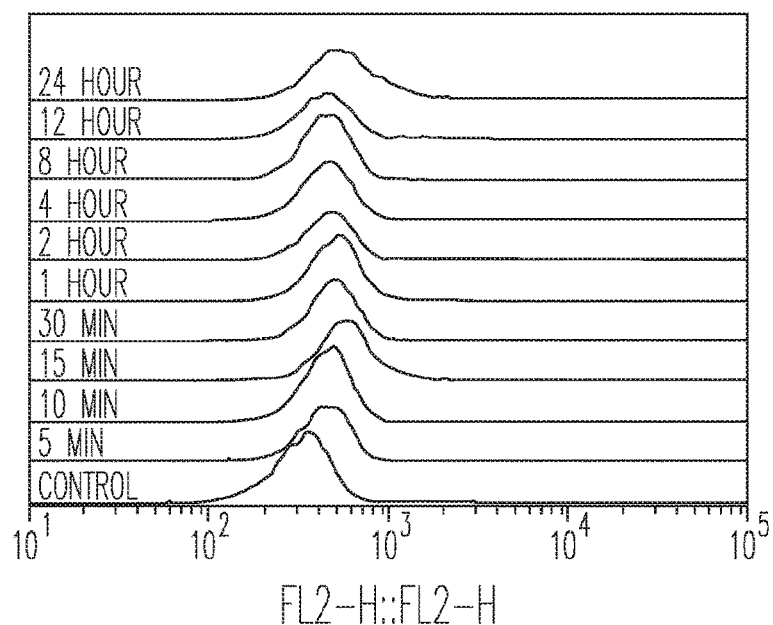
FIGS. 4A-C. Molt-4 parental cells, which do not express CD19, and Molt-4 cells engineered to express CD19 (Molt4-CD19) were incubated with protocells bearing anti-CD19 antibodies and a fluorescent MSNP core. Samples were collected at various time points and assessed for protocell binding by flow cytometry. The anti-CD19 protocells do not bind to the Molt-4 parental cells which do not express CD19. The anti-CD19 protocells bind specifically and in a time dependent manner to Molt-4 CD19 cells.
Figure 4B:
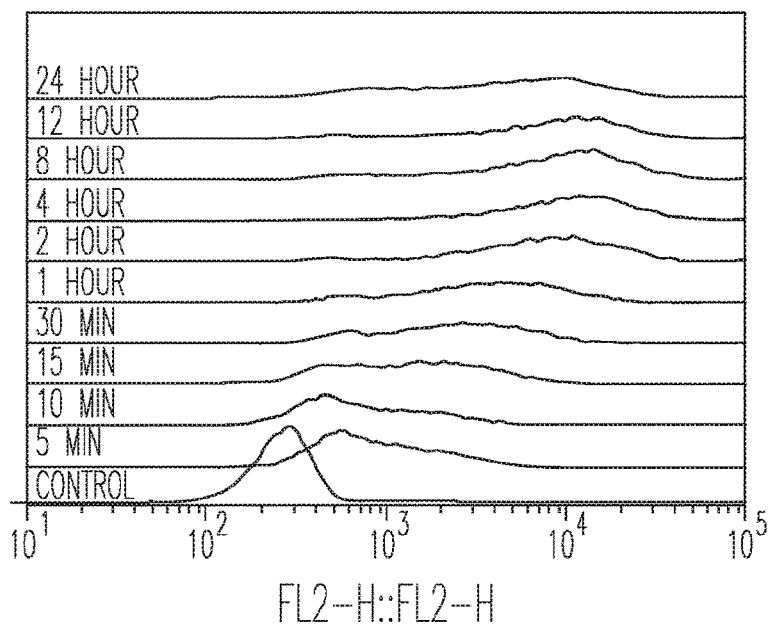
Figure 4C:
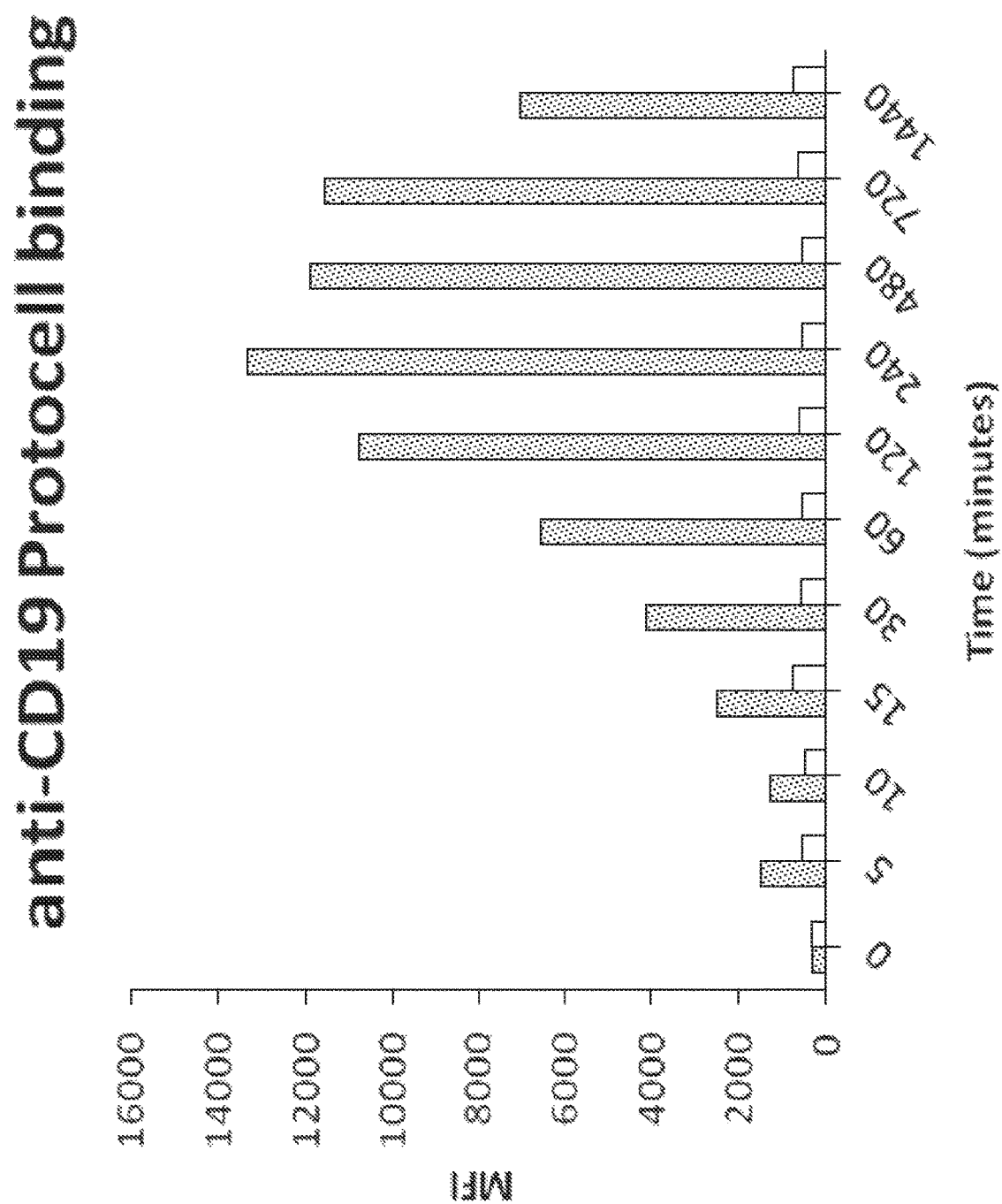

Protocells can be targeted to cells using different targeting moieties. For example, specific binding can be achieved with both antibodies and scFvs to CD19 (FIG. 4). Protocells that do not have targeting moieties present on the surface do not bind to cells.

Figure 5:
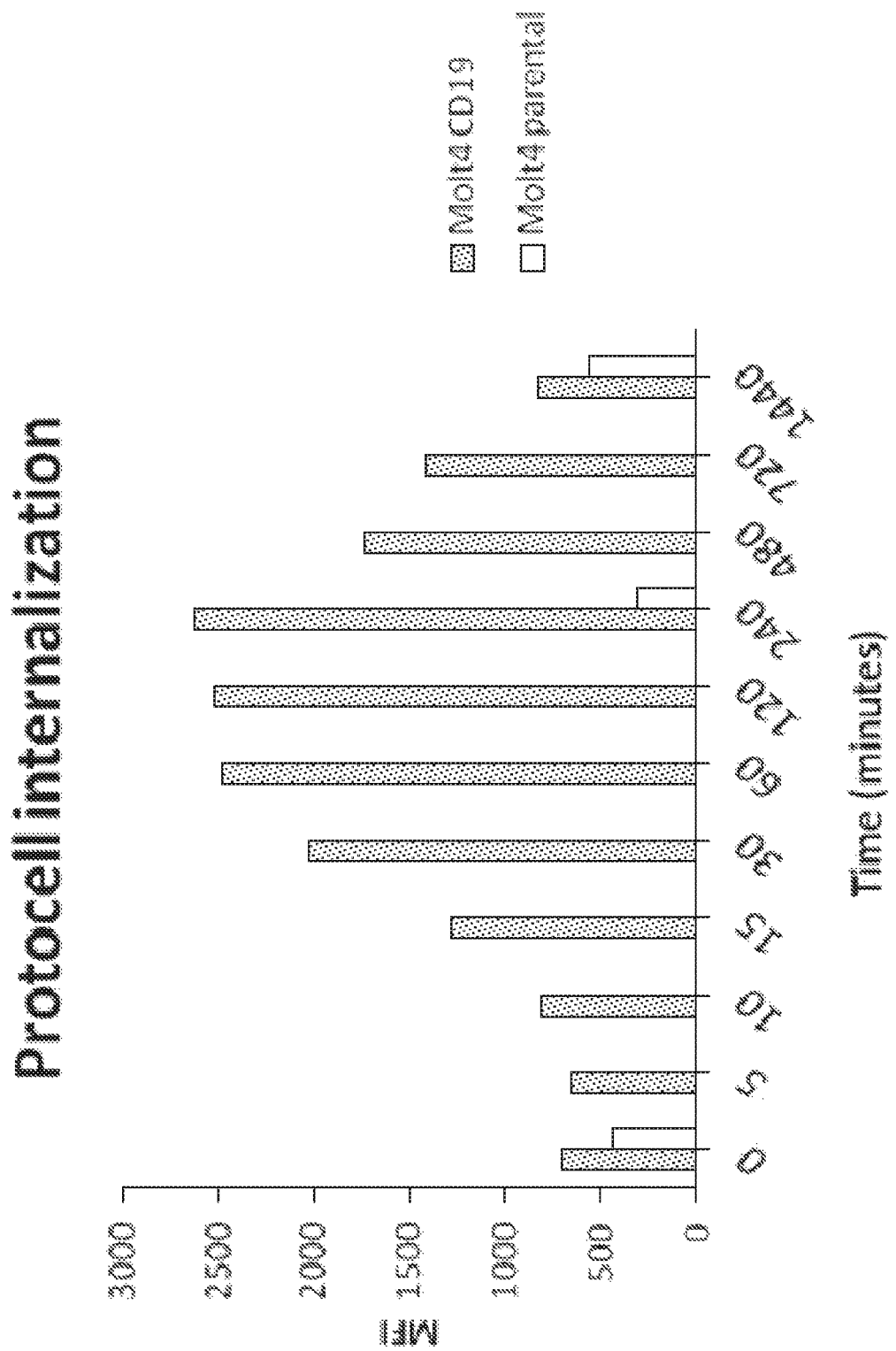
FIG. 5. Protocells surface modified with antibodies to CD19 internalize only into cells which express CD19. Protocells were incubated at 4° C. for 1 hour to allow binding but prevent internalization. The samples were then washed and warmed to 37° C. to allow internalization and samples were collected a various time points from 5 minutes to 24 hours. Samples were then stripped of surface receptors using a mild acid solution. Internalization was assessed by flow cytometry and confirmed by microscopy. The protocell binding control demonstrates that binding was present prior to increasing the temperature to 37° C.

Protocells targeted to cells using different targeting moieties can specifically deliver cargo (FIG. 5). For example, cargo can be delivered to cells using either antibodies or scFvs to CD19.

Figure 6:
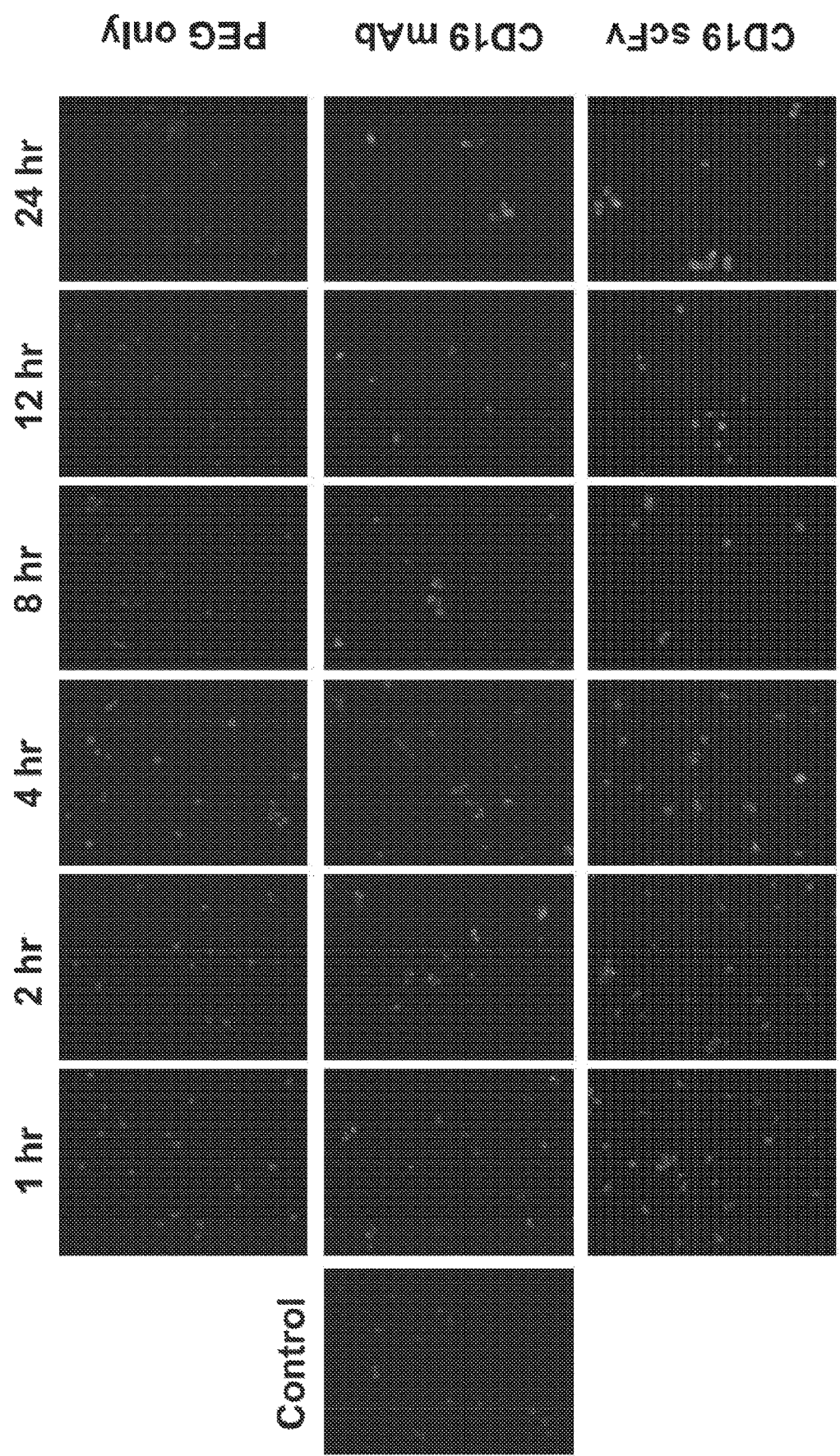
FIG. 6. Protocells bind specifically to cells when targeted with either CD19 scFvs or antibodies and do not bind to cells if targeting moieties are not present. Protocells (red) either non-targeted (PEG only) or targeted by scFvs or antibodies to CD19 were incubated with cells (blue) for times from 1-24 hours. Binding was accessed by microscopy.
Figure 7:
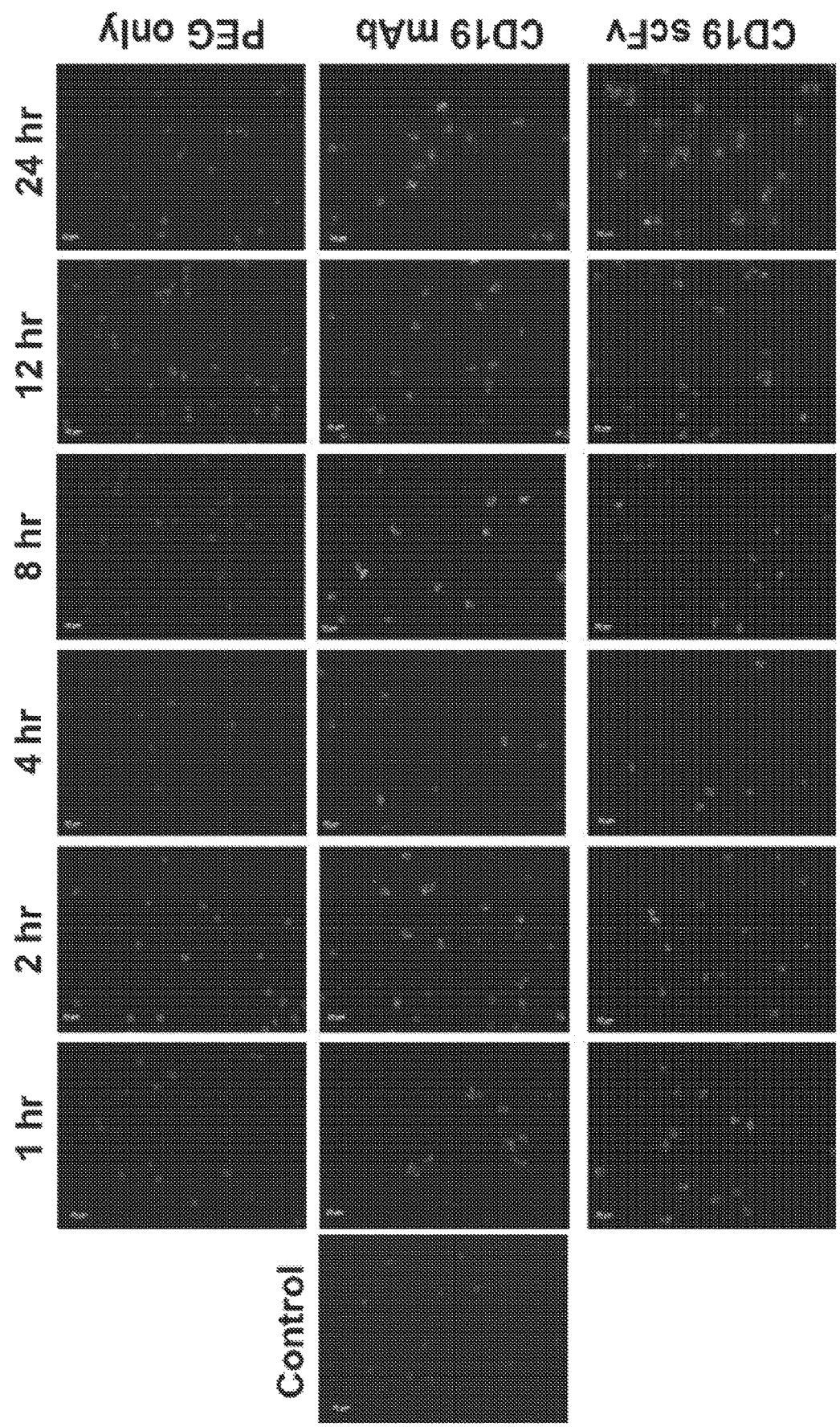
FIG. 7. Protocells deliver cargo specifically to cells when targeted with either CD19 scFvs or antibodies and do not deliver cargo to cells if targeting moieties are not present. Protocells (red) loaded with a fluorescent cargo (green) and either non-targeted (PEG only) or targeted by scFvs or antibodies to CD19 were incubated with cells (blue) for times from 1-24 hours. Cargo delivery was accessed by microscopy.

Targeted protocells bind only to cells which express their target within a vascular system (FIG. 6). Protocells targeted with different targeting moieties can specifically bind to target cells within a vascular system (FIGS. 7). Protocells targeted with different targeting moieties can specifically bind to target cells within a vascular system.

Figure 8:
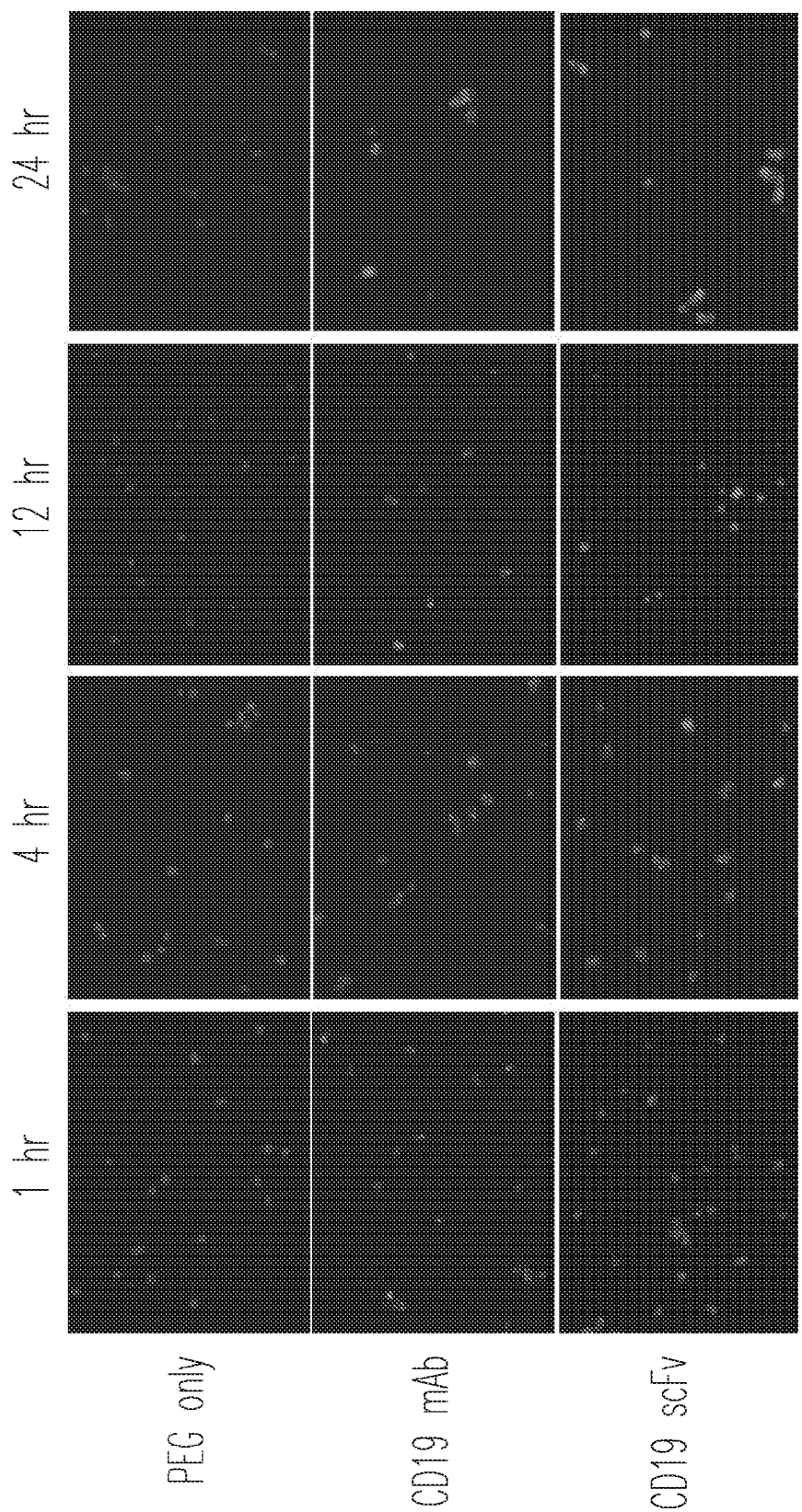
FIG. 8. Binding of anti-CD-19 protocells targeted by scFv or antibody to MOLT-4 CD19 cells. CD19 antibody and scFv targeted protocells (red) sthow strong binding by 60 minutes to CD19 expressing cells (blue).
Figure 9:
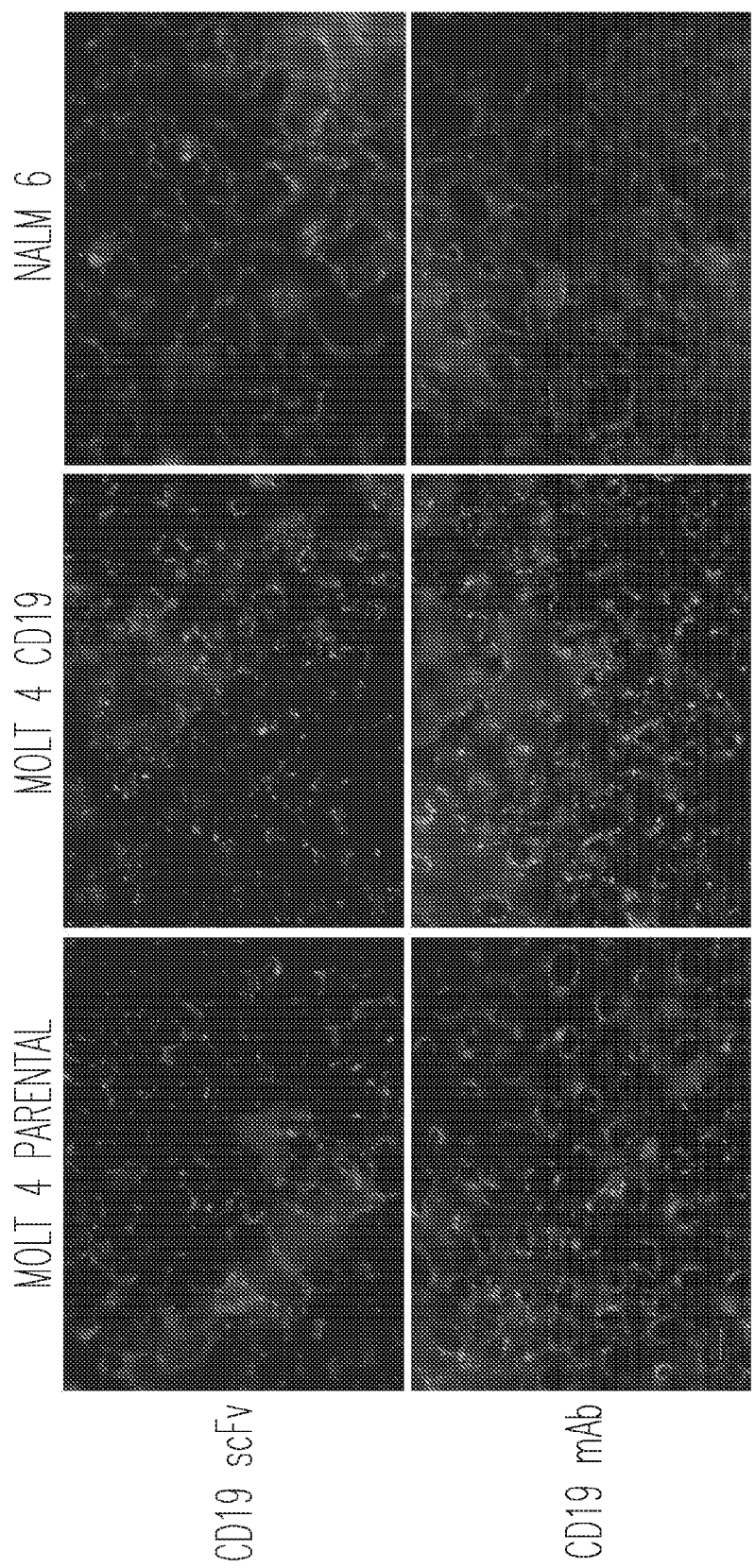
FIG. 9. Leukemia cells (blue) with engineered CD19 expression (Molt-4 CD19) or natural CD19 expression (Nalm 6) and without (Molt-4) CD19 expression were injected into the vascular system (purple) of the Chicken Chorioallantoic membrane (CAM). Protocells modified with anti-CD19 antibodies or scFvs (red) were then injected into the CAM, Protocells targeted with both antibodies and scFvs were able to successfully find and bind to CD19 expressing cells of both engineered and natural origin within the vascular system. Protocells targeted with either antibodies or scFvs not bind to non-CD19 expressing cells.
Figure 10A:
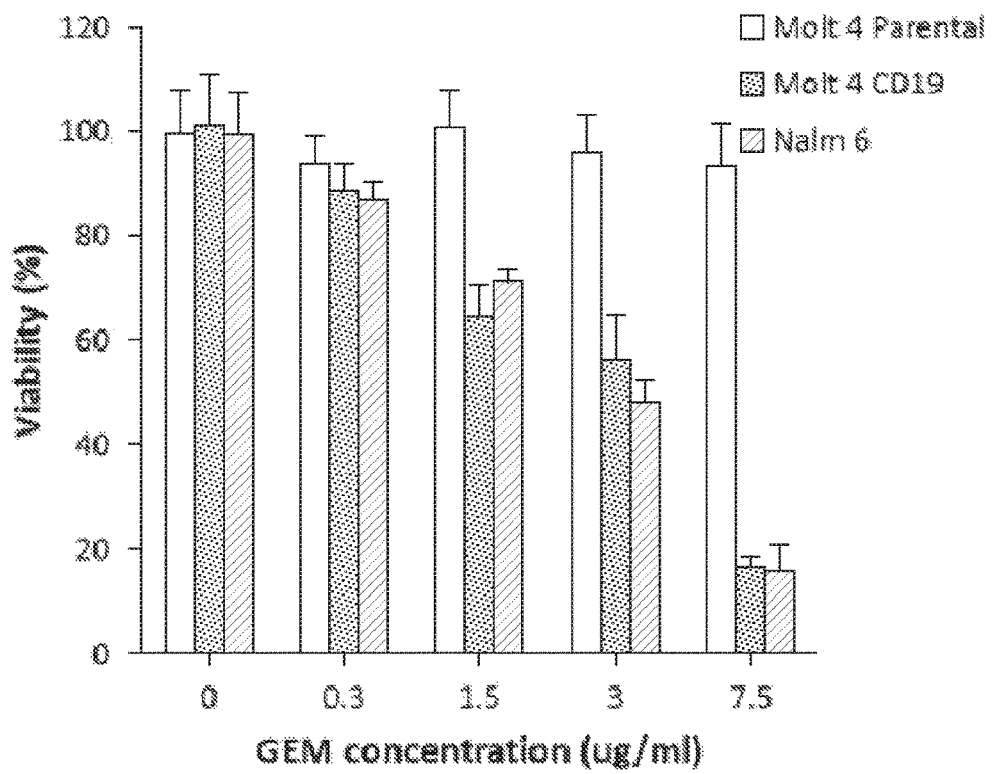
FIGS. 10A-B. Protocells targeted to CD19 delivered the cytotoxic drugs Gemcitabine (left) and Cytarabine (right) loaded (15.5±0.7 wt %) to cells expressing CD19 both naturally (Nalm6) and engineered (Molt-4 CD19). Cytarabine dosage=0 µg/mL, 0.3 µg/mL, 1.6 µg/mL, 3.2 µg/mL, and 7.75 µg/mL. Delivery of drug cargo resulted in death of the targeted cells. The targeted protocells did not deliver cytotoxic cargo to cells which did not express CD19 (Molt-4 Parental), resulting in cell survival.
Figure 10B:
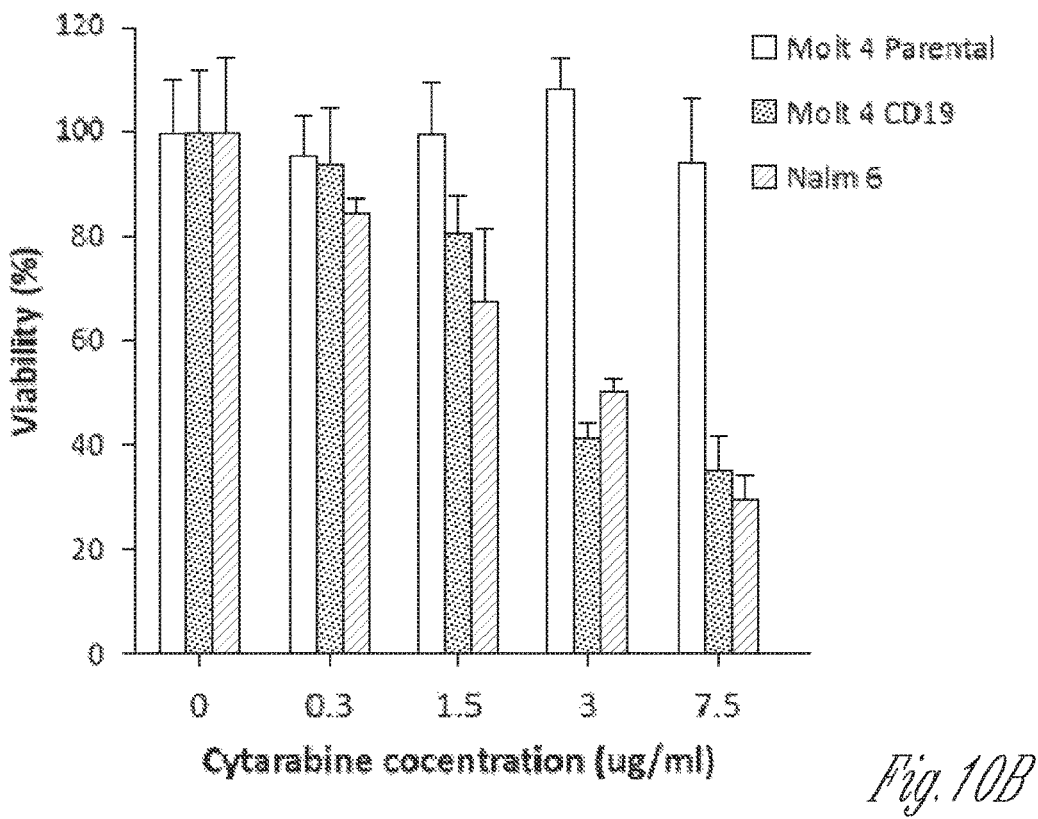
Figure 11A:
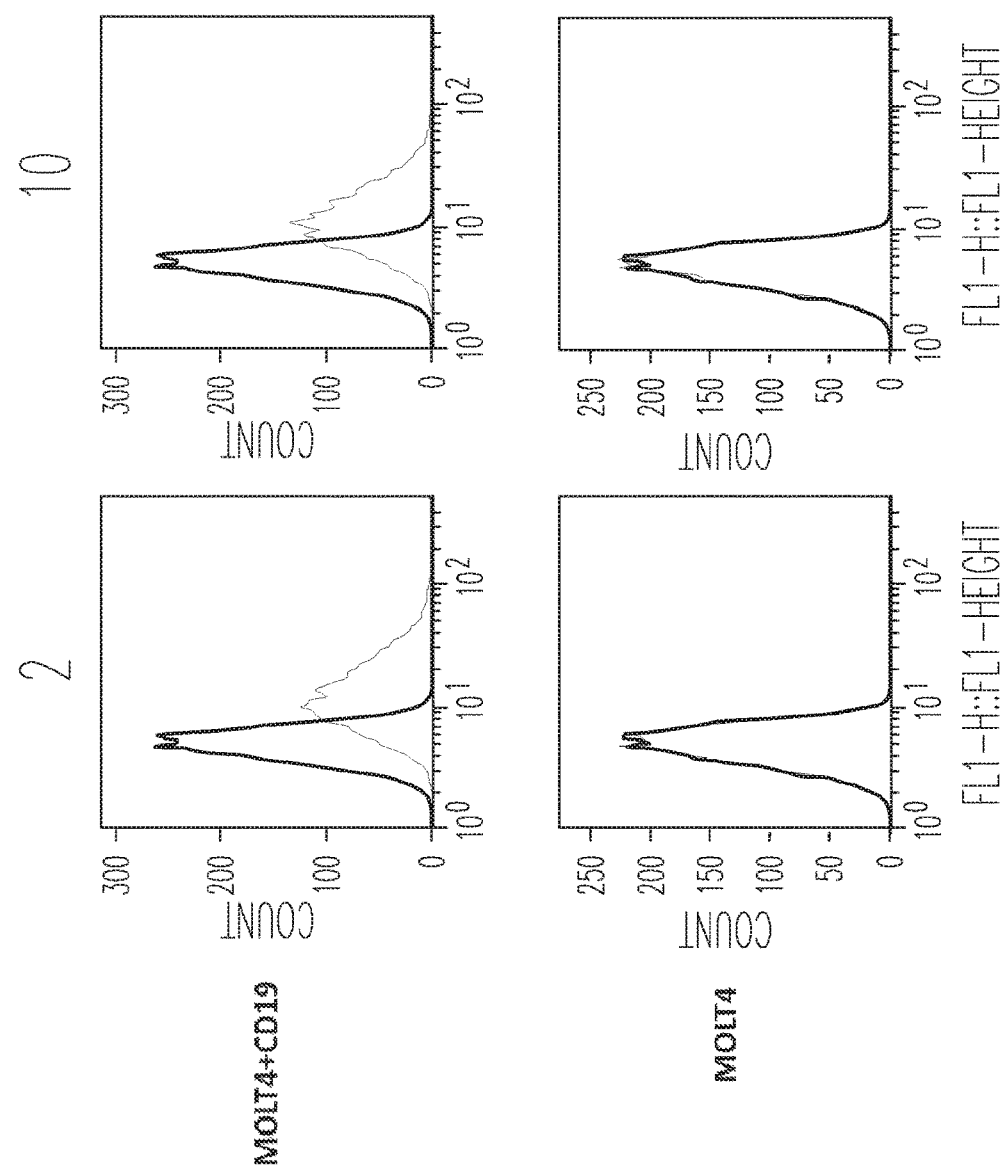
FIGS. 11A-D. A) Different formulations of protocells were prepared that varied with regard to Traut's modification (of liposome or protocell), subjection to extrusion and/or cysteine passivation. B-D) Results for different preparations.
Figure 11B:
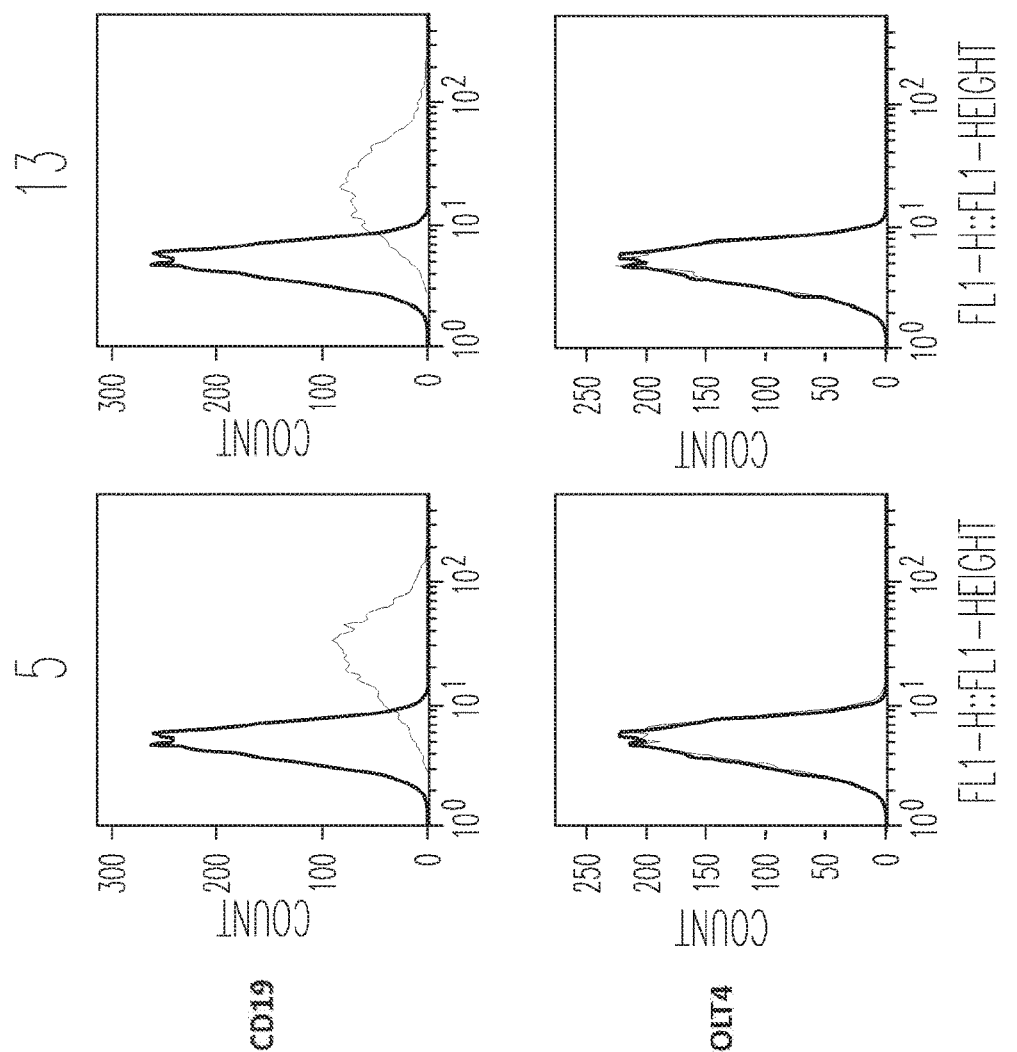
Figure 11C:
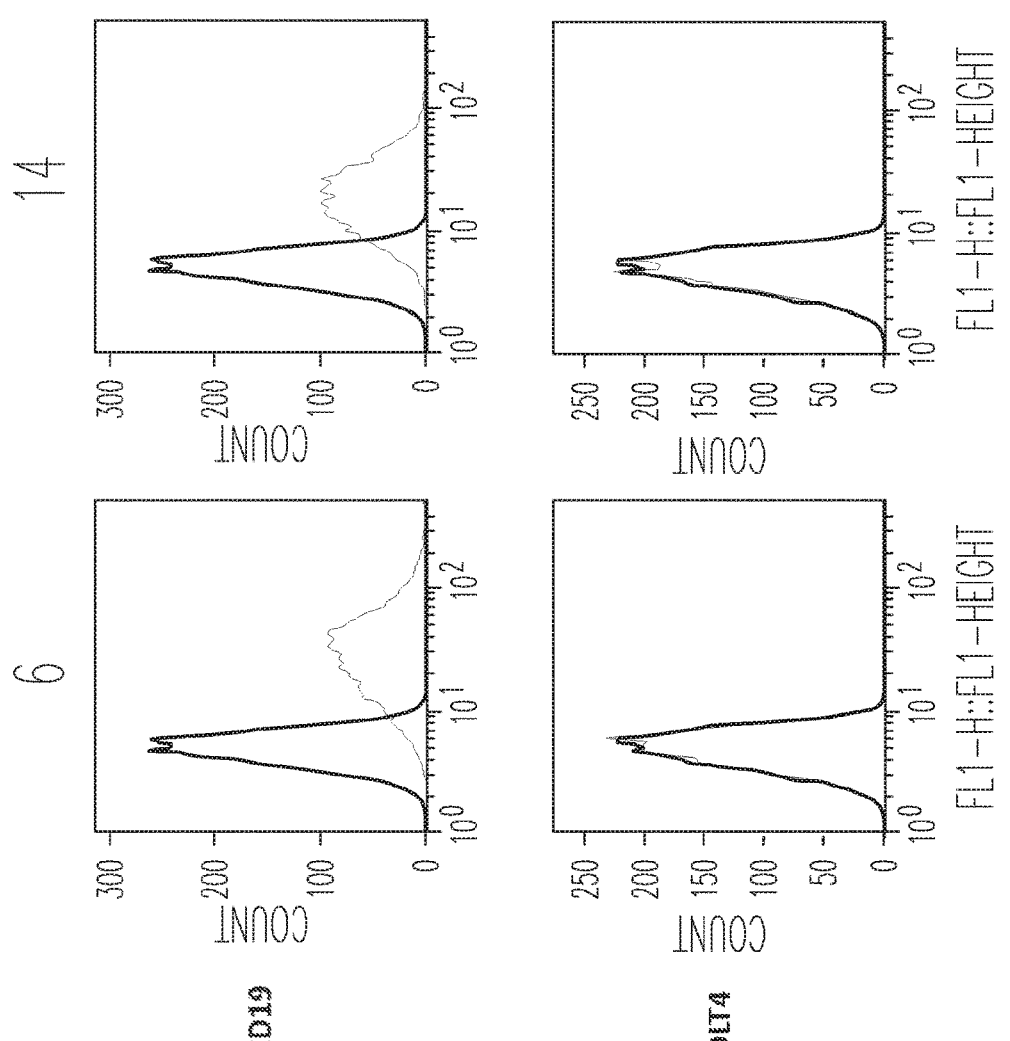
Figure 11D:
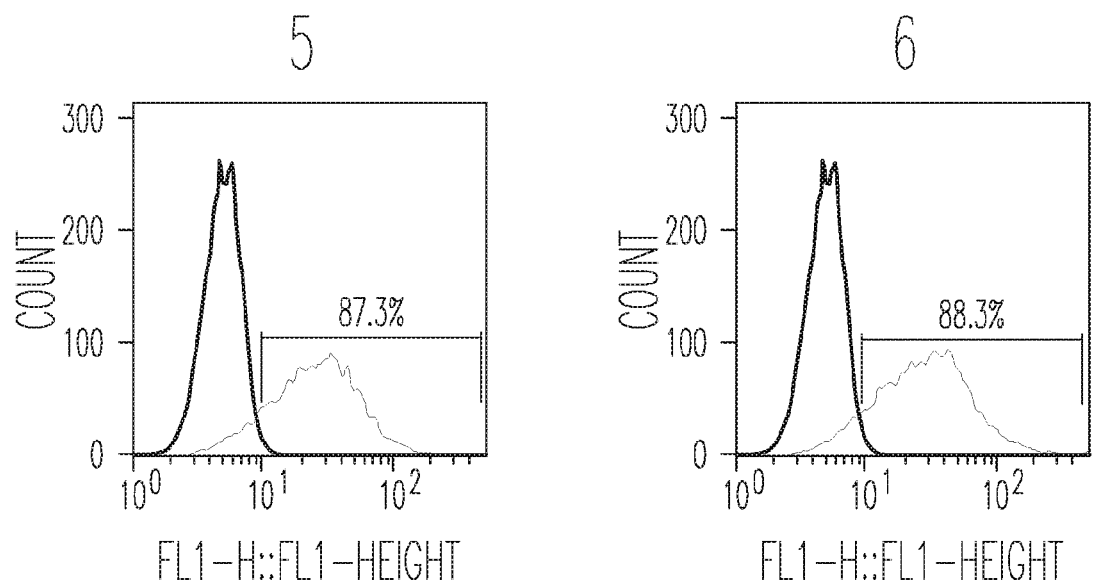
Figure 12A:
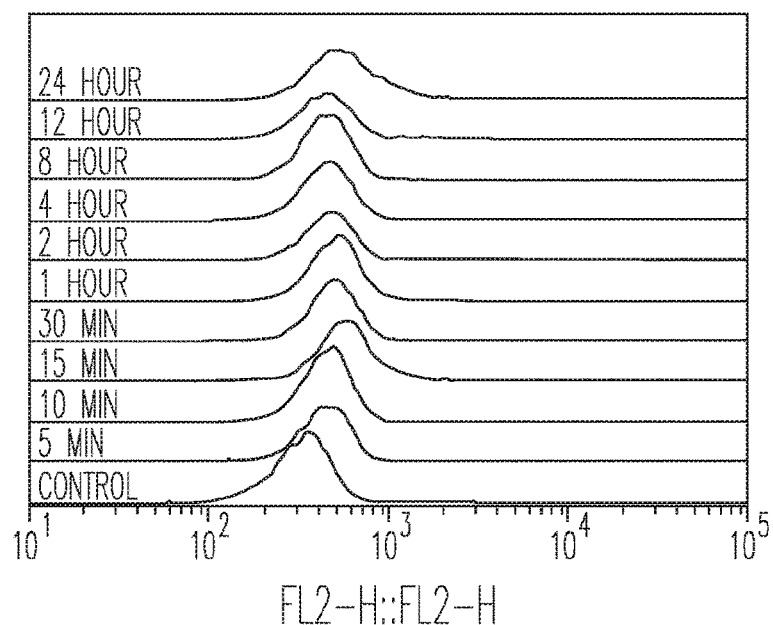
FIGS. 12A-C. Flow cytometry analysis of A) parental MOLT4 and B) MOLT4-CD19 cells incubated with red fluorescent CD19 targeted protocells at multiple time points. This data illustrates rapid specific in vitro protocell binding to MOLT4-CD19 in as little as 5 minutes in complete medium, and maximal protocell accumulation after 240 minutes. C) Mean fluorescence intensity graph of protocell bind further illustrates CD19-targeted protocell specificity.
Figure 12B:
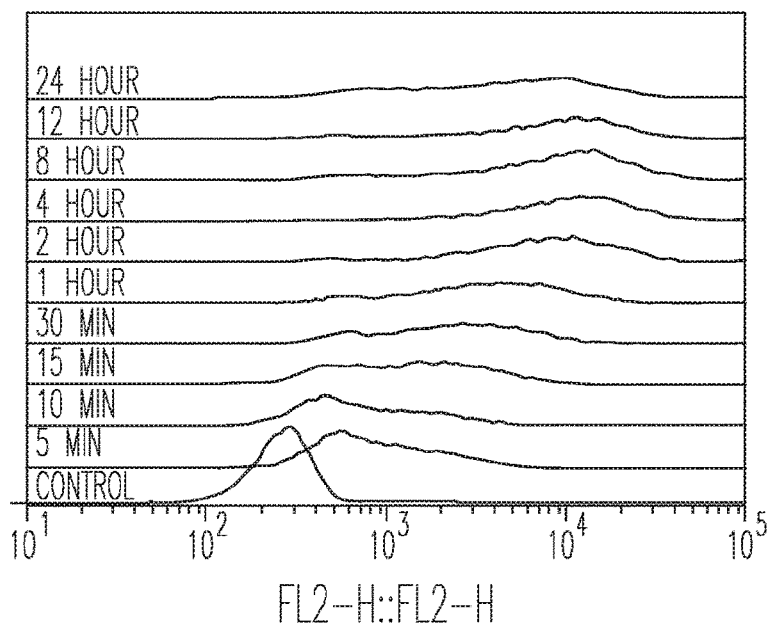
Figure 12C:
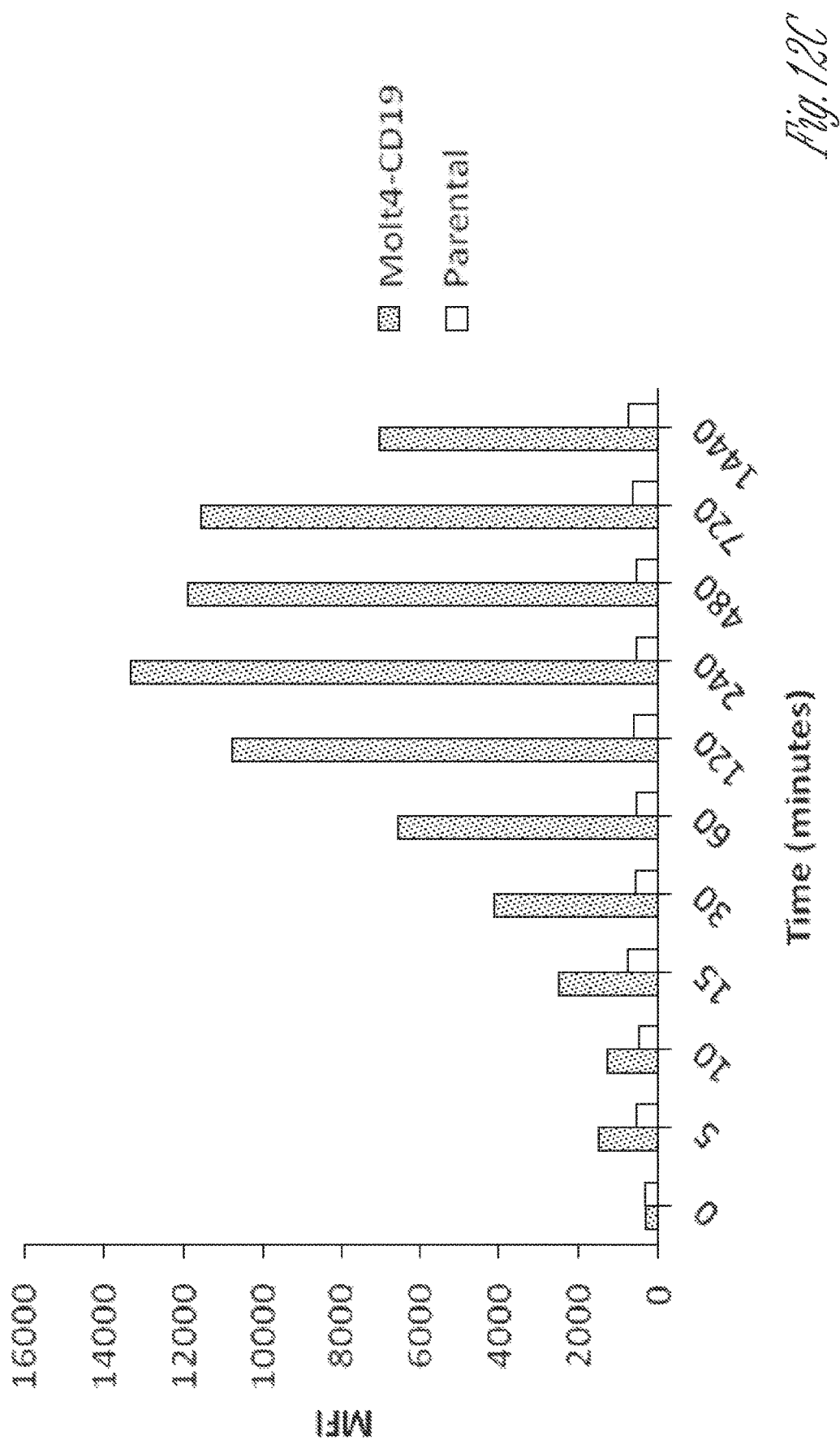
Figure 13:
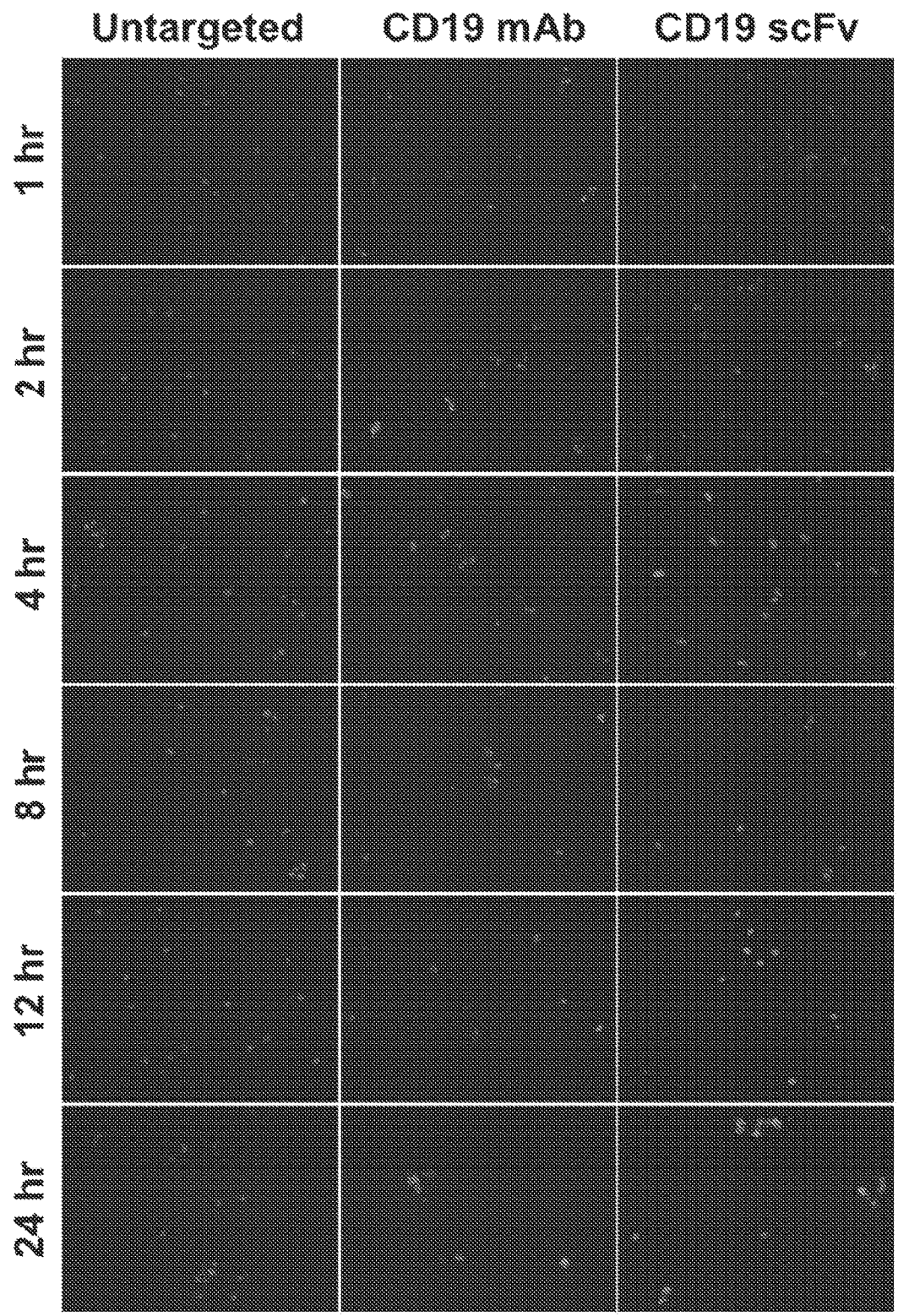
FIG. 13. Fluorescent microscopy analysis of MOLT4-CD19 cells incubated with either CD19 untargeted, antibody-targeted, or scFv-targeted protocells at multiple time points, fixed and stained (blue—cells, red—protocells). These data illustrate rapid in vitro protocell binding in complete medium with a high degree of specificity.

Protocells targeted with different targeting moieties can deliver cargo to their target cells within a vascular system (FIGS. 8-9). Protocells actively targeted to cell surface markers can specifically deliver cytotoxic cargos to cells which express the surface marker (FIG. 10).

EXAMPLE 2

Test conditions
  Cells 250,000 cells/mL+10 µg/mL Protocells in complete media
  1 hour incubation at 37° C. on nutator
  Washed in complete media, added CMFDA live cell stain
  Wash 2 more times in complete media and imaged cells on slide.
  Results are shown in FIG. 11.

EXAMPLE 3

Tested preparations
  Liposome formulations
  DSPC/Cholesterol/DSPE-PEG-NH2
    Standard (mol % 50/48/2)
  Traut's modification (NH2 to SH)
  Liposomes modified Protocells modified
Extrusion
+/−
Cysteine Passivation
+/−
Protocells 2 and 10
50/48/2
Traut's modified Protocell
Extrusion
No cysteine 2
Cysteine 10
Protocells 5 and 13
77.5/20/2.5
Traut's modified Protocell 5
Traut's modified Liposome 13
No Extrusion
No cysteine 5
Cysteine 13
Protocells 6 and 14
77.5/20/2.5
Traut's modified Protocell 6
Traut's modified Liposome 14
No Extrusion
No cysteine 6
Cysteine 14

Cysteine does not appear to significantly influence the non-specific binding. DSPC/Cholesterol/DSPE-PEG-NH2 (77.5/20/2.5) is a liposome formulation with better properties.

Extrusion is a limiting step. There is not a significant difference between 5 and 6, therefore extrusion can be omitted (See % shift in histograms).

About 100 nm MSNPs (DLS in $H_2O$) were sunthesized that were modified with FITC and DyLight 755 dyes. In one embodiment, 10% wt antibody to MSNP may be employed, up to 7 mg of antibody,

EXAMPLE 4

After confirmation that the targeting strategy was not influenced by the type of cell line used, the ease of switching cell-targets was investigated, in an effort to engineer a disease agnostic nanocarrier platform. To achieve this goal, as a model system, a human T cell leukemia cell line (MOLT4) that was engineered to express the CD19 receptor (MOLT4-CD19) was selected and protocell interactions with MOLT4-CD19 cells were compared to the parental (CD19-negative) cell line so as to have a matched negative control for the experiments. In addition, binding on a native CD19 expressing human B cell precursor leukemia (NALM6) was tested.

NeutrAvidin/biotin targeting chemistry was used as well as amine functionalized SLB, however, Biotin Anti-Human CD19 Antibody (Biolegend, CA) or custom synthesized Biotin Anti-CD19 single chain variable fragment (scFv) (GenScript, NJ) was substituted in place of the Biotin Anti-EGFR Antibody. To examine targeting specificity, protocell interactions with MOLT4 parental cell line controls, MOLT4-CD19, and NALM6 cell lines were compared.

Figure 14:
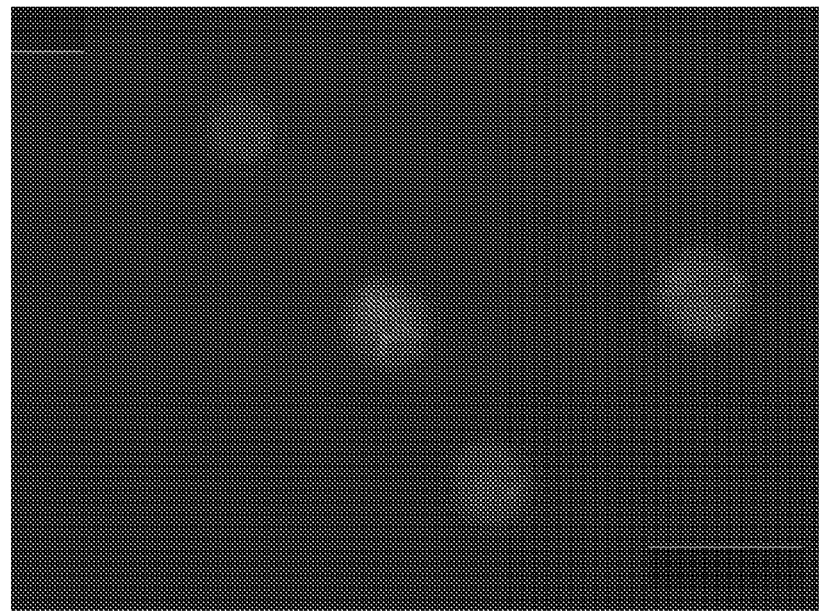
FIG. 14. A) Fluorescent microscopy shows absent CD19-targeted protocell (red) interactions with parental MOLT4 cell line after 1-hour incubation (blue CMFDA live cell stain—false colored blue), while B) targeted protocells (red) exhibit a high degree of binding to MOLT4-CD19 cell line.
Figure 14:
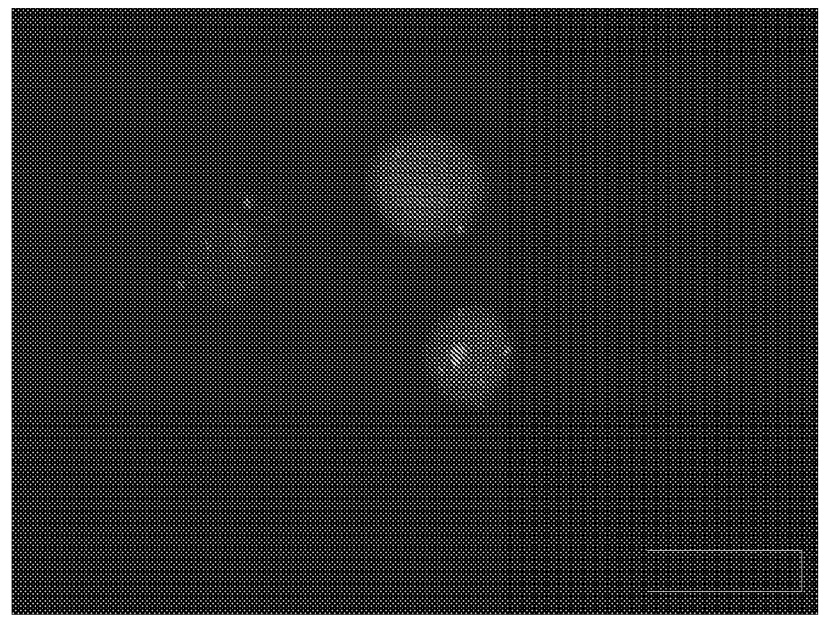
Figure 15A:
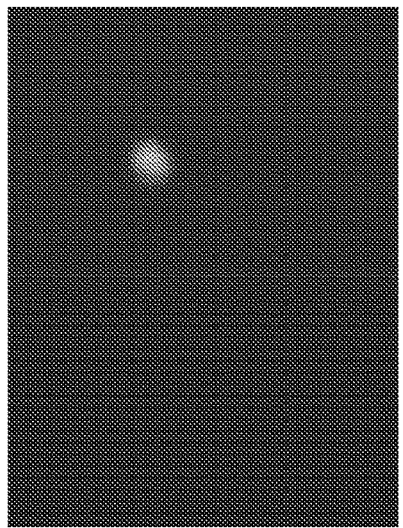
FIGS. 15A-D. A) Fluorescent microscopy shows absent untargeted protocell (red) interactions with NALM6 cell line (green) after 1-hour incubation 20× magnification, B) 63× magnification, while C) CD19-targeted protocells (red) exhibit a high degree of binding to NALM6 cell line at 20× magnification and D) 63× magnification.
Figure 15B:
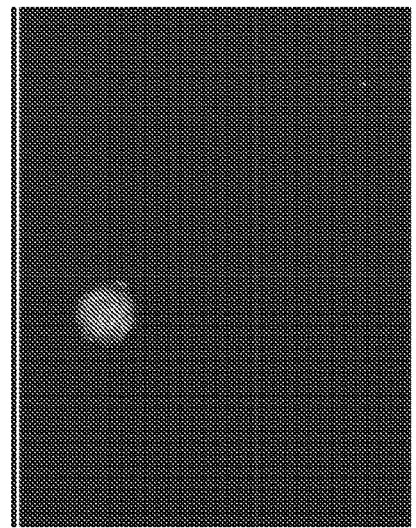
Figure 15C:
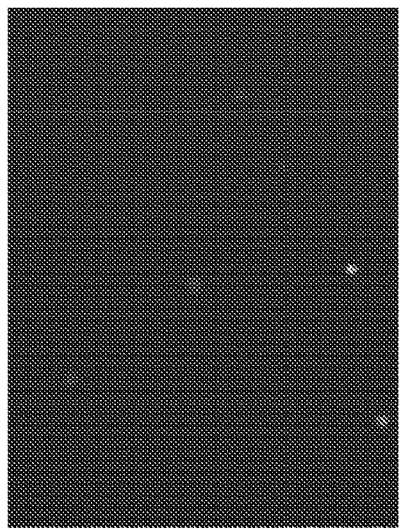
Figure 15D:
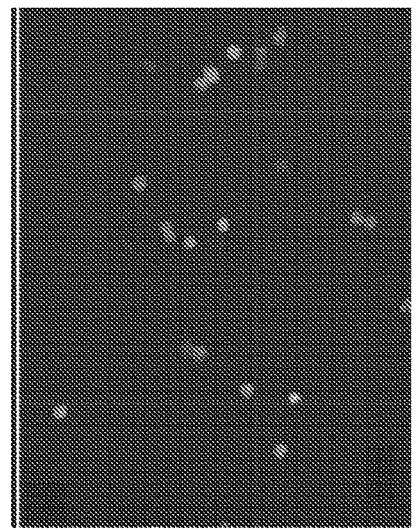
Figure 16:
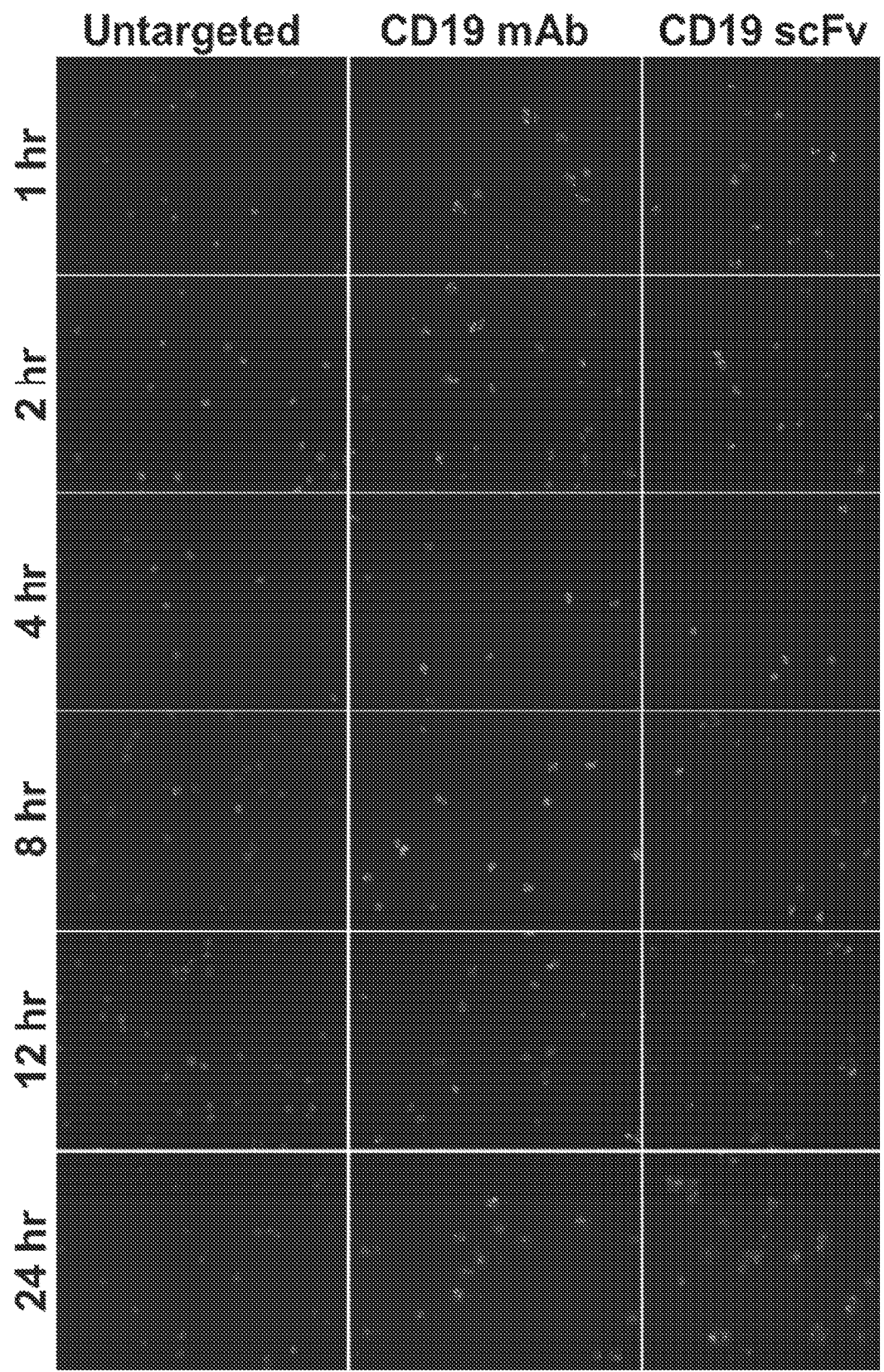
FIG. 16. Fluorescent microscopy analysis of MOLT4-CD19 cells incubated with either CD19 untargeted, antibody-targeted, or scFv-targeted protocells at multiple time points, fixed and stained (blue—cells, red—protocells, green-YO-PRO-1). Protocell binding was observed at 1 hour in complete medium with cargo release occurring between 8 and 24 hours.

To assess the kinetics of CD19-targeted protocell binding, either anti-CD19 antibody-labelled protocells or anti-CD19-scFv-labelled protocells were incubated with MOLT4 parental and MOLT4-CD19 cells for various time points in vitro Detectable binding of the antibody-labelled protocells was observed within 5 minutes and maximal binding at 240 minutes of incubation in complete media under normal cell culture conditions as assessed by flow cytometry. By fluorescence microscopy, comparable cell-specific binding in vitro of both antibody- and scFv-labelled protocells was observed (FIG. 14). Similar to the non-specific binding profile, protocell binding was not observed in the MOLT4 parental cell line (FIG. 15). Cell-specific targeting was observed using antibody-labelled protocells incubated with NALM6 cells for 1 hour in complete media, under normal cell culture conditions (FIG. 16). Therefore, in vitro targeted binding in multiple cell lines, with multiple targeting ligands was demonstrated.

Figure 17:
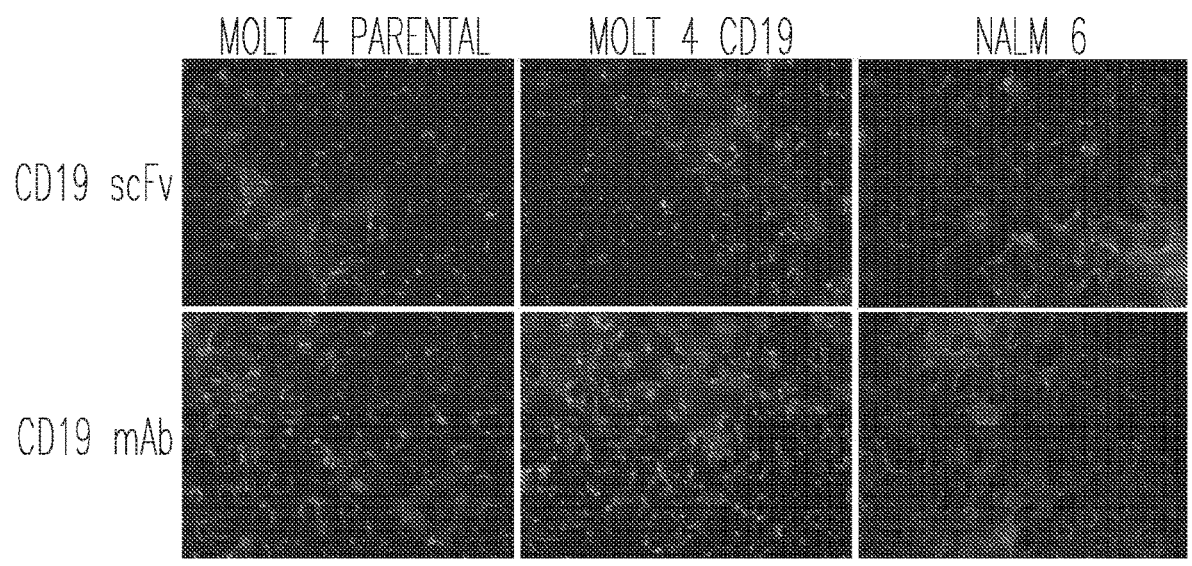
FIG. 17. Anti-CD19 mAb and scFv targeted protocells exhibit specific binding to CD19 expressing cells in the CAM vascular model at 4 hours post injection.

Next, untargeted, antibody-labelled, and scFv-labelled protocells were loaded with YO-PRO®-1 and targeting and delivery evaluated in vitro by incubating with MOLT4-CD19 cells at multiple time-points. Next, protocells were incubated with MOLT4-CD19 cells in complete media under normal cell culture conditions for 1 hour, 2 hours, 4 hours, 8 hours, 12 hours, and 24 hours, then fixed and imaged the cells. No binding, nor cargo delivery was observed in the untargeted protocell control. CD19 target-specific delivery of the membrane impermeable cargo, YO-PRO®-1, was observed after 8 hours of incubation, with more significant cargo release at 12 hours (FIG. 17).

Figure 18:
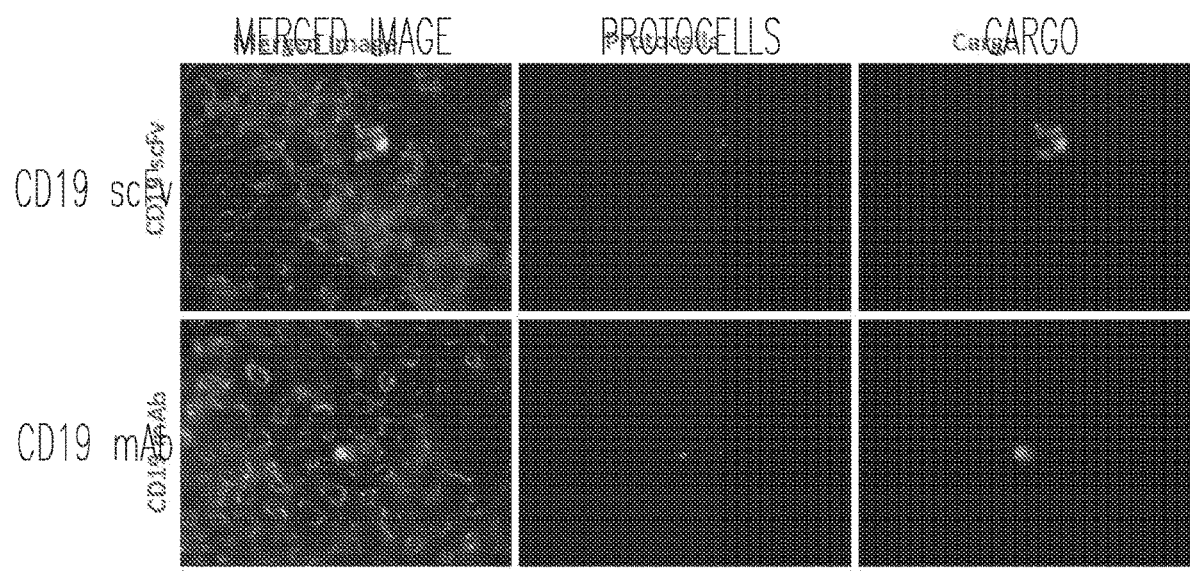
FIG. 18. Anti-CD19 mAb and scFv targeted protocells deliver cell imperant molecule (YOPRO) to Naml6 cells in the CAM vascular model after 20 hours.

Following the steps described previously, the targeted binding characteristics of the CD19-targeted protocell binding were evaluated using real-time intravital imaging in the ex ovo CAM model. Blue fluorescent labelled MOLT4, MOLT4-CD19, or NALM6 cells were injected into the CAM and allowed to arrest in the capillary bed about 30 minutes). Next, either antibody- or scFv-labelled CD19-targeted protocells were injected into the CAM and protocell flow and binding dynamics imaged after 4 hours in circulation. Protocells were observed to flow in the blood stream but not interacting with the parental MOLT4 cells (FIGS. 18A and B), however, significant binding to the MOLT4-CD19 cells was detected (FIGS. 18C and D) and NALM6 cells (FIGS. 18E and F) in the CAM.

Next, protocell targeted cell specific killing, in vitro was assessed, GEM was used as a cytotoxic agent. MOLT4, MOLT4-CD19, and NALM6 cells were incubated with increasing concentrations of CD19-targeted GEM-loaded protocells in complete media under normal cell culture conditions. Similar to EGFR-targeted GEM delivery, a CD19-target specific decrease in cell viability correlating to an increase in CD19-targeted protocell concentration was detected in both antibody- and scFv-labelled systems (FIG. 5.19). Since GEM had been verified as being responsible for the cell killing as opposed to the protocell itself, the effect of the unloaded-protocell on MOLT4, MOLT4-CD19, and NALM6 cell lines was not measured.

Figure 20:
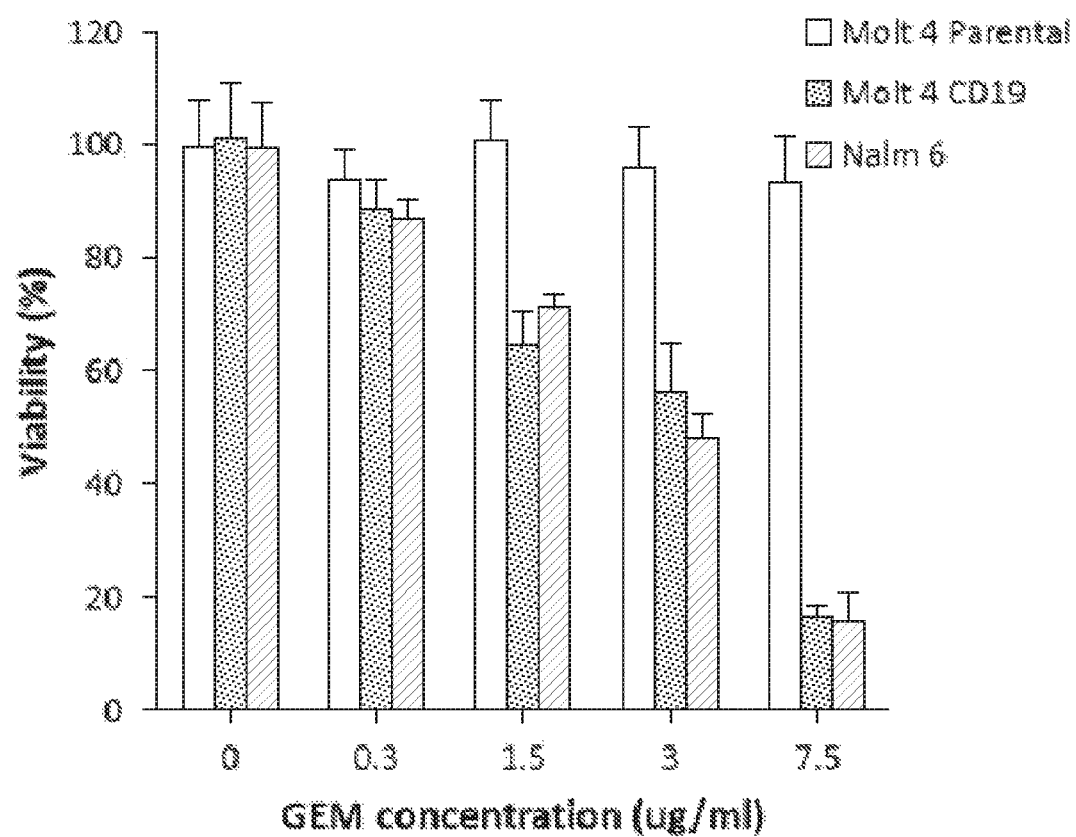
FIG. 20. Maintained viability of CD19 negative MOLT4 cells and decrease in viability of MOLT4-CD19 and NALM6 cells with increasing concentration of GEM loaded CD19-targeted protocells. Viability was assessed at 48 hours. Viability data r highlights target specific delivery of cytotoxic cargo using the monosized protocell platform. Data represents mean±SD, n=3.
Figure 21:
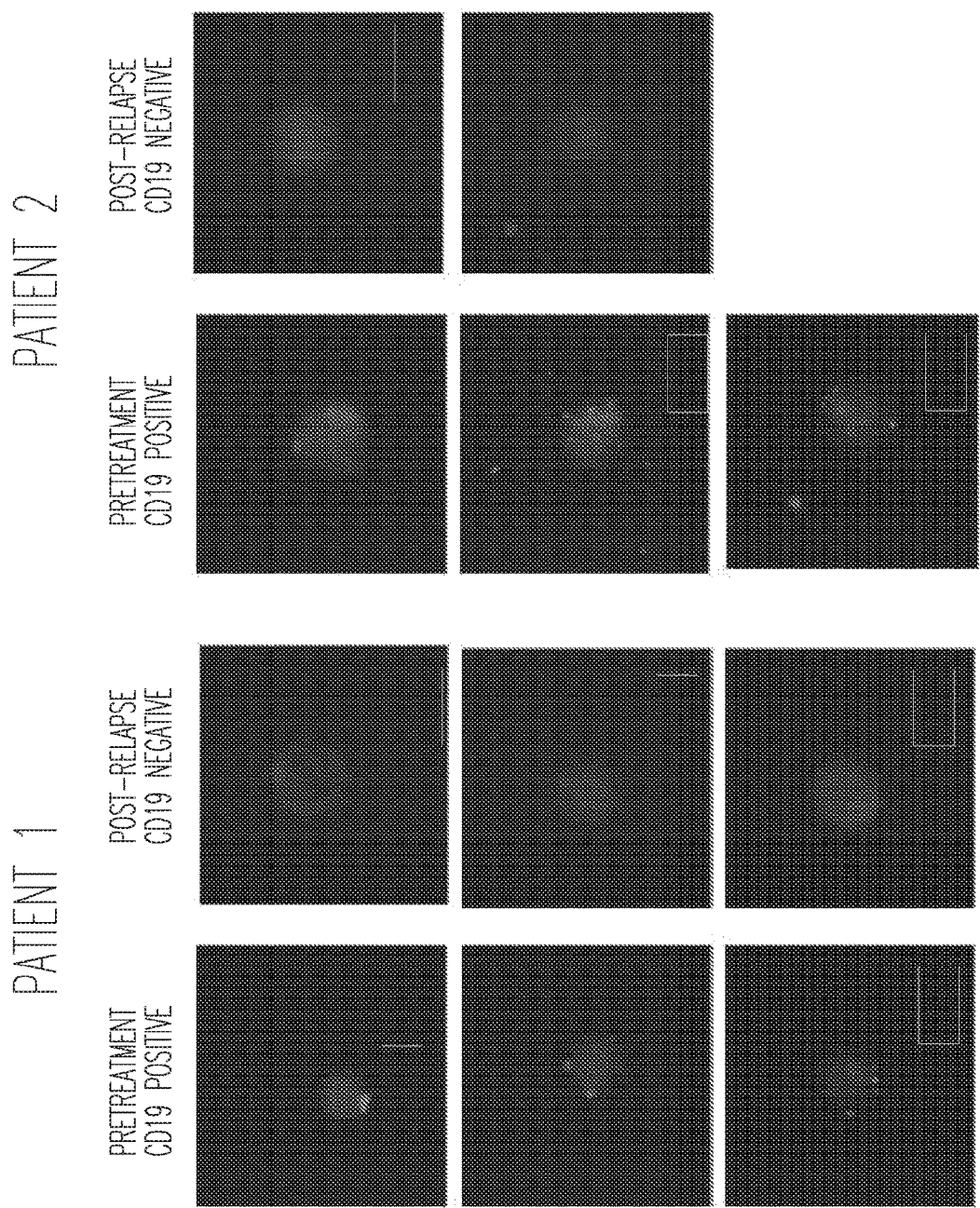
FIG. 21. Selective binding of protcells to patient leukemia samples which express CD19.
Figure 22B:
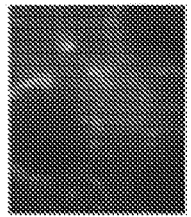
FIGS. 22A-D. Targeted binding of anti-CD19 protocells to primary patient leukemia samples expressing CD19.
Figure 22C:
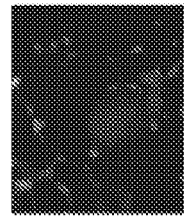
Figure 22D:
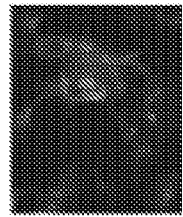
Figure 22A:
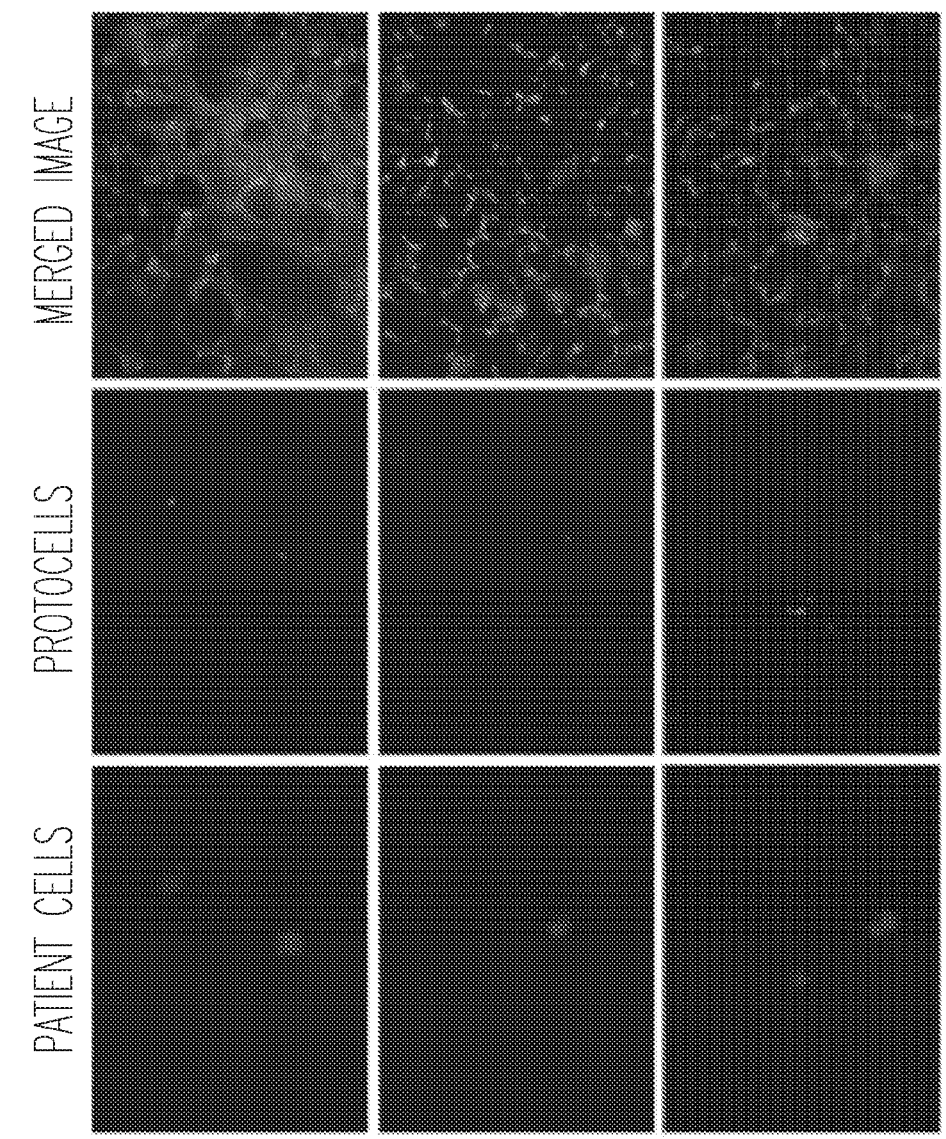
Figure 23B:
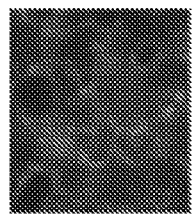
FIGS. 23A-D. Anti-CD19 protocells are unable to target primary patient leukemia samples which do not express CD19.
Figure 23C:
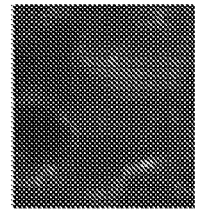
Figure 23D:
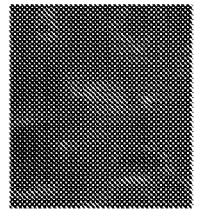
Figure 23A:
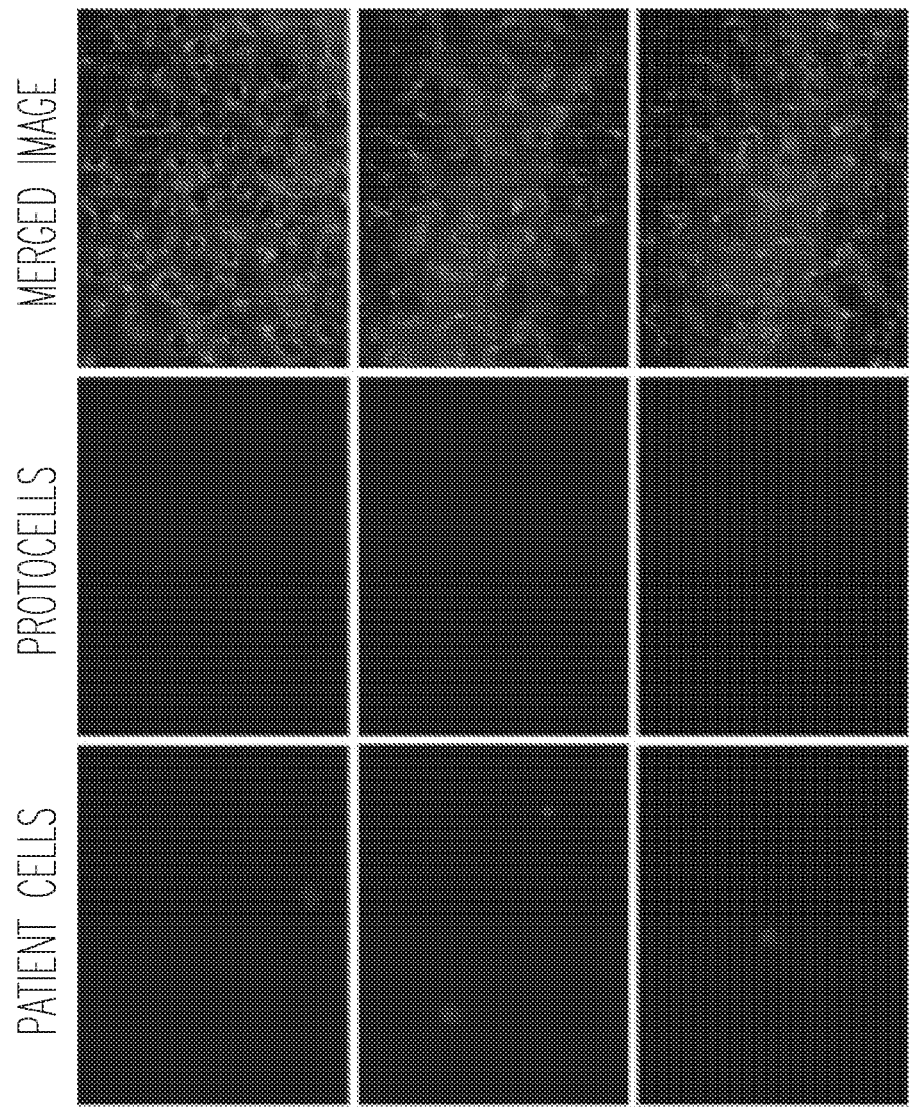
Figure 24:
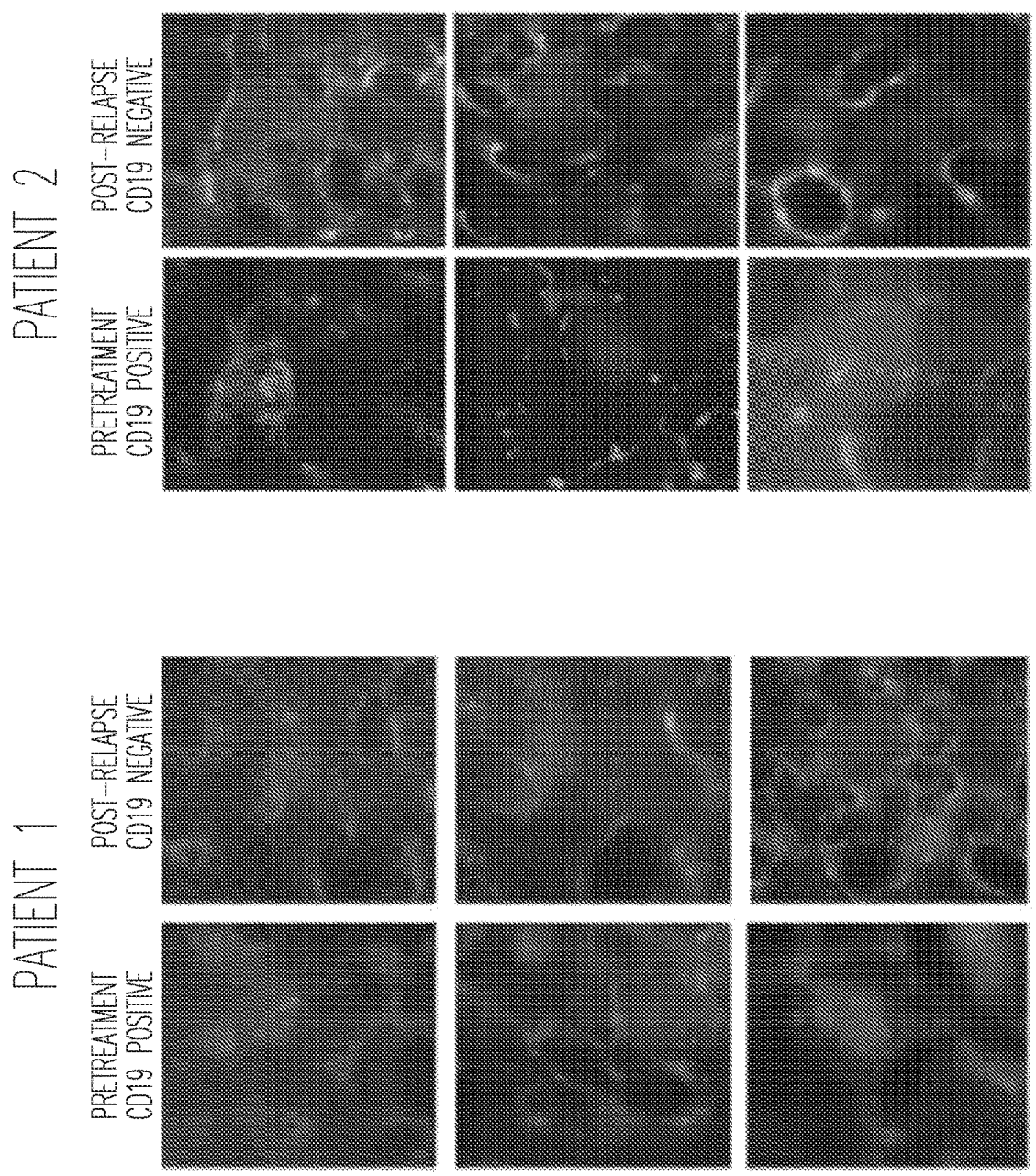
FIG. 24. CD19 antibody targeted protocells show selective binding of patient samples that express CD19.
Figure 25B:
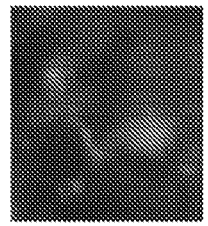
FIGS. 25A-D. A-C) CD19 antibody targeted protocells show deliver of cargo to patient samples that express CD19. D) Zoomed images.
Figure 25C:
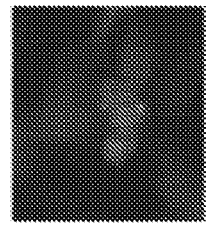
Figure 25D:
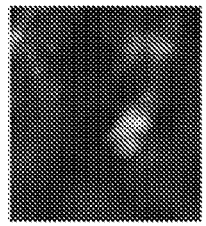
Figure 25A:
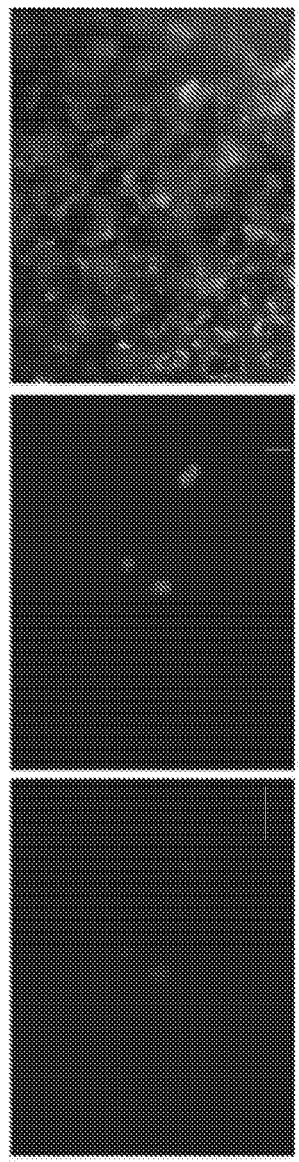
Figure 25A:
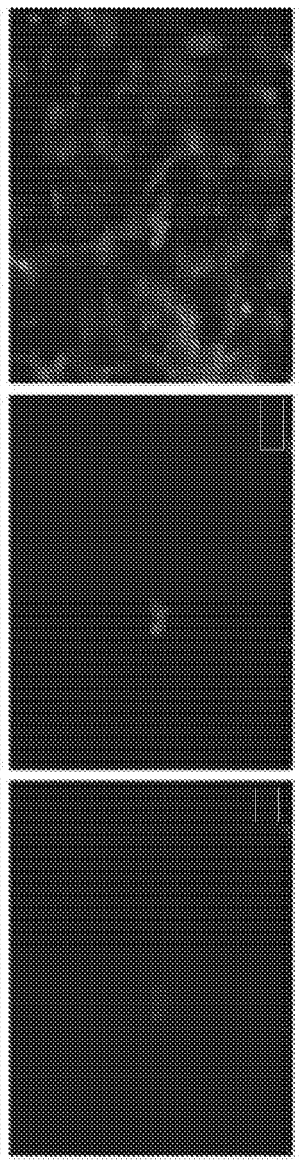
Figure 25A:
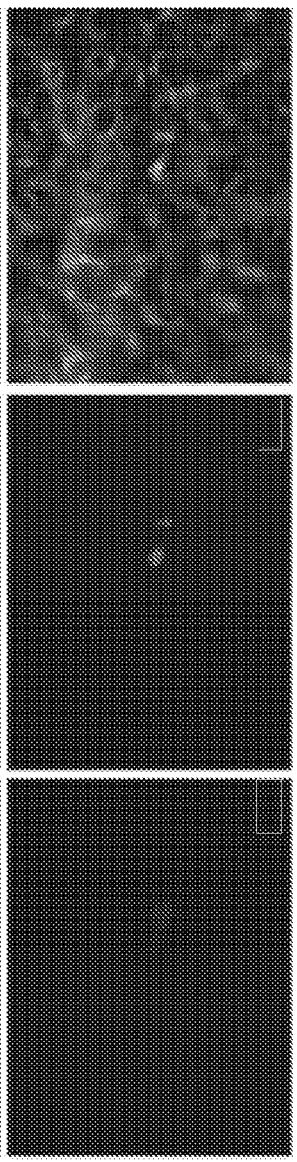
Figure 26:
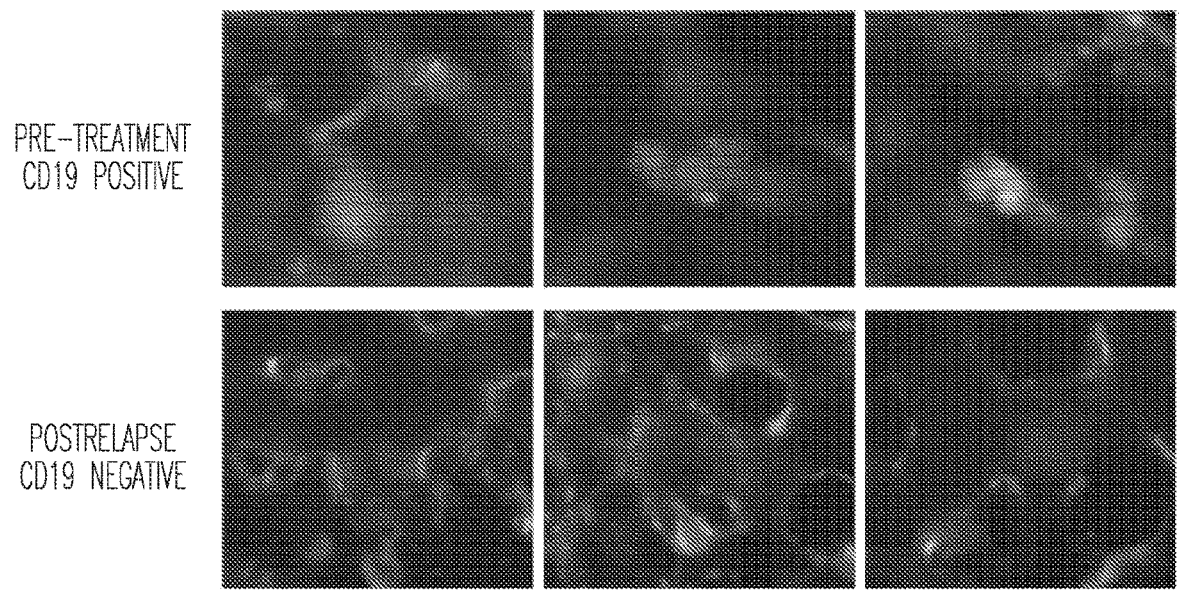
FIG. 26. Anti-CD19 protocells are able to deliver fluorescent cargo (drug mimic) to primary patient cells within the CAM system after 30 hours.
Figure 27:
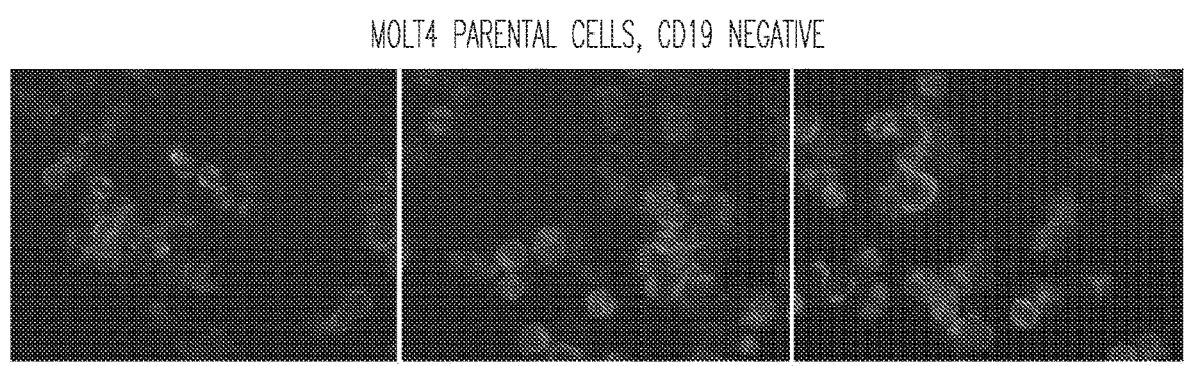
FIG. 27. Anti-CD19 protocells are able to selectively deliver fluorescent cargo (drug mimic) to cells.
Figure 27:
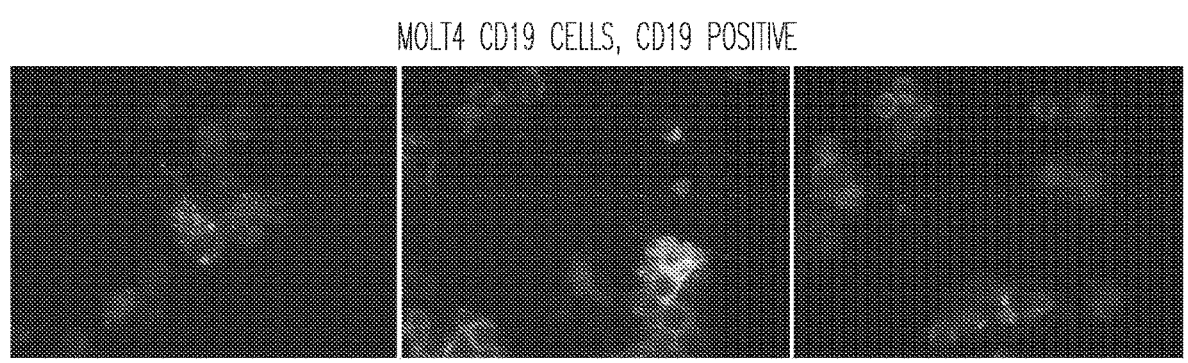

Next, protocells with YO-PRO®-1 were evaluated for targeting and delivery in an ex ovo system. CAM was injected with fluorescent labelled MOLT4-CD19 cells, then 30 minutes later, YO-PRO®-1 loaded antibody- or scFv-labelled CD19-targeted protocells were injected. Intravital imaging of a lectin vascular stain was used to provide contrast in the blood vessels. Intravital fluorescent imaging of binding, internalization, and cargo release were taken at 30 hours (MOLT4-CD19) and 20 hours (NALM6) post ex ovo injection. After 30 hours, YO-PRO®-1 was observed to be dispersed throughout MOLT4-CD19 cells (FIG. 20) and 20 hours with NALM6 cells (FIG. 21), similar to the EGFR-targeted cargo release in the CAM. The differences in cargo release between the two cell lines may be due to the artificial expression of CD19 on the MOLT4 cell line, since NALM6 has native CD19 expression, it is likely to possess a more complete CD19-mediated internalization system, therefore more rapid internalization and cargo release.

These results demonstrate the "plug-and-play" simplicity of target modification to the protocell platform, and further support the advantages of the SLB to prevent non-specific cell interactions that are paramount to a disease agnostic drug-delivery nanocarrier platform.

EXAMPLE 5

The high density of the extracellular matrix in tumors is an important obstacle to nanocarriers for reaching deep tumor regions and has severely limited the efficacy of nanomedicines for cancer treatment. The administration of proteolityc enzymes prior to nanoparticles or direct attachment of proteolytic enzymes to the nanocarrier surface have been proposed in order to enhance their penetration, but the low in vivo stability of these macromolecules compromises their efficacy at long term. Herein, we have designed a multifunctional nanocarrier able to transport cytotoxic drugs to deep areas of solid tumors and once there, to be engulfed by tumoral cells causing their destruction. This system is based on a mesoporous silica nanocarrier encapsulated within a supported lipid bilayer (SLB). The SLB avoids premature release of the housed drug while providing high colloidal stability and an easy to functionalize surface. The tumor penetrating properties are provided by attachment of engineered polymeric nanocapsules to the SLB that contain collagenase and release it by controlled hydrolysis. These proteolytic enzymes digest the extracellular matrix facilitating the diffusion of the nanocarrier through the tissue. Additionally, the nanocarrier SLB was conjugated with a cancer-specific antibody to achieve cell-specific binding, internalization, and drug delivery. The present system has shown excellent antitumoral efficacy, being able to cause significant tumoral cell destruction in deep zones of 3D tumoral tissues, whereas the system without collagenase nanocapsules, used as a control, scarcely produced any effect. This multifunctional design provides enhanced therapeutic efficacy of the transported drug as a consequence of its more homogeneous distribution throughout the malignancy.

Introduction

Despite the huge research efforts carried out in the last decades, cancer continues to be one of the leading causes of mortality in the World. Cancer cannot be considered as one simple disease. There are many different types of cancer depending on the type of malignant cell and the affected organ and therefore, each of them present their own set of particular features and therapeutic challenges. Moreover, even within the same tumor type, it usually coexists in several tumoral cell lines with different genetic alterations which respond differently to the common administered therapeutic agents. When is not possible to remove the tumoral mass by surgery, the common treatment involves the administration of high energy radiation (radiotherapy) and/or the use of potent cytotoxic compounds (chemotherapy) in order to destroy actively dividing cells, as is the case of tumoral ones. However, the lack of selectivity of these therapies provokes the appearance of severe systemic toxicity on surrounding healthy tissues compromising not only the efficacy of the therapy but also the patient's life or quality of life. Since Maeda and Matsumura's discovery in 1986 of passive accumulation of nanoparticles within tumoral masses, the use of nanoparticles as drug carriers has been extensively studied in oncology. This phenomenon, referred to as the Enhanced Permeation and Retention effect (EPR), is caused by the unique blood vessel architecture present in solid tumors that presents pores with diameters up to a few hundred nanometers. Thus, when nanoparticles reach the tumoral area, they are extravasated into the tumor passing through these pores, whereas they cannot cross the healthy vessel walls. The discovery of the EPR effect triggered the development of a multitude of nanocarriers with the aim to deliver the cytotoxic compounds directly to the diseased zone, without affecting the rest of the healthy tissues. These nanocarriers have been engineered to possess remarkable properties such as stimuli-responsive drug release, invisibility to the immune system or the capacity to specifically bind to tumoral cells or even the most dangerous tumoral stem cells. However, the clinical application of these nanocarriers is still far from being a reality. A recent meta-study has concluded that on average over the past ten years only 0.7% of the administered nanocarrier dose accumulates in the tumoral area, which could explain the low effectiveness of the nanotherapies observed in clinical trials. One common problem to all nanomedicines is the lack of penetration within the tumoral tissue. The extracellular matrix of tumoral tissues is usually denser than common due to the higher presence of collagen which severely limits the penetration of nanocarriers. Thus, the extravasated nanomedicine accumulates mainly in the periphery of the tumor causing local effects without affecting the tumor core and remaining easily removed by intravasation. The intratumoral administration of proteolytic enzymes such as collagenase or hyaluronidase prior to nanoparticle injection has been proposed in order to enhance the particle penetration. These proteolytic enzymes have also been anchored on the nanocarrier surface showing improved outcomes. Recently, Villegas et al. have reported the use of pH-responsive polymeric nanocapsules which contain collagenase for enhancing the particle penetration in 3D tumoral tissue models while at the same time protecting the action of the proteolytic enzyme. In addition to achieving higher penetration within the tumoral mass, an efficient nanocarrier should be able to fulfill other features such as the ability to selectively bind to target tumoral cell within a myriad of different cell populations and have the capacity to keep retained the transported therapeutic payload until it reaches the intracellular space of the malignant cell.

Herein, the synthesis and evaluation of a novel multifunctional nanodevice able to penetrate deeply within a solid tumoral mass while retaining a transported cytotoxic compound and finally, be internalized selectively by the tumoral cells causing their destruction, is reported. This nanodevice is composed of a mesoporous silica nanoparticle (MSN) core capable of loading high amounts of drugs due to its very high specific area and accessible interior pore volume. The MSN external surface is encapsulated within a supported lipid bilayer conjugated with proteolytic NPs, targeting ligands, and PEG in a nanocarrier construct referred to as protocell.

The protocell SLB serves to protect and retain cargo within the MSN until pH triggered release within acidified endosomal environments. It also confers unique properties to the system such as high colloidal stability, low immunogenicity and long circulation times within the blood stream. The SLB of the protocell was decorated with pH-responsive collagenase nanocapsules for enhancing tissue penetration and with EGFR-antibodies, able to selectively bind to cells that overexpress epidermal growth factor receptors (EGFR), in order to increase the internalization of the protocell into tumoral cells. The capacity of this novel multifunctional protocell to recognize EGFR-positive tumoral cells which are deeply located within a solid tumoral mass was tested employing an in vitro 3D cell culture model, showing significantly improved penetration, internalization and destruction capacity of the malignant cells relative to protocells prepared without collagenase nanocapsules.

Material and Methods

Materials

Rhodamine B isothiocyanate (RBITC) (Sigma Aldrich); Ethanol (Dismadel); (3-aminopropyl)triethoxysilane (APTES) (ABCR); Hexadecyltrimethylammonium bromide (CTAB) (Sigma Aldrich); ammonium hydroxide (NH4OH, 28-30%) (Fluka); Tetraethyl orthosilicate (TEOS) (Aldrich); Ammonium nitrate (Sigma Aldrich); 1,3-distearoyl-sn-glycero-3-phosphocholine (DPSC) (Avanti Lipids); 1,2-distearoyl-sn-glycero-3-phosphoethanolamine-N-[amino(polyethylene glycol)-2000] (ammonium salt) (DSPE-PEG (2000)-NH2) (Avanti Lipids); 1,2-distearoyl-sn-glycero-3-phosphoethanolamine-N-[carboxy(polyethyleneglycol)-2000] (ammonium salt) (DSPE-PEG(2000)-COOH) (Avanti Lipids); Cholesterol (Avanti Lipids); Traut's reagent (Aldrich); Maleimide activated netrAvidin (thermo Scientific); biotinlyated EGFR antibody (Abcam); Collagenase Type I (Life Technologies); Acrylamide (Fluka); 2-Aminoethyl methacrylate hydrochloride (Sigma Aldrich); Ethylene glycol dimethacrylate (Sigma Aldrich); Ammonium persulfate (Sigma Aldrich); N,N,N',N'-Tetramethylethylenediamine (Sigma Aldrich); Amicon®Ultra-2mL Centrifugal Filters Ultracef®-10K (Millipore); N-(3-Dimethylaminopropyl)-N'-ethylcarbodiimide hydrochloride (Sigma Aldrich); N-Hydroxysuccidimide, (Sigma Aldrich); EnChek®Gelatinase/Collagenase Assay Kit (Life Technologies); 10×PBS Buffer pH=7.4 (Ambion); Dulbecco's modified eagle's medium (Sigma Aldrich); Rat tail collagen (type I) First Link (UK) Ltd; Bovine serum Albumin (BSA) (Sigma); Paraformaldehyde; Atto488 phalloidine (Sigma Aldrich); Triton® X-100 (Aldrich®); DAPI (Sigma®); Topotecan; Alamar blue (Invitrogen).

Instrumental Section

The hydrodynamic size of mesoporous nanoparticles and protein capsules was measured by means of a Zetasizer Nano ZS (Malvern Instruments) equipped with a 633 nm "red" laser. Transmission Electron Microscopy (TEM) was performed with a JEOL JEM 3000 instrument operated at 300 kV and equipped with a CCD camera. Sample preparation was performed by dispersing specimens in distilled water and subsequent deposition onto carbon coated copper grids. A solution of 1% of phosphotungstic acid (PTA) pH 7.0 was employed as staining agent in order to visualize the protein capsules alone and attached to the mesoporous surface. Fluorescence was measured with Synergy 4, power supply for Biotek Laboratory Instrument 100-240VAC, 50/60 Hz, 250 W. Confocal microscopy was performed using an Olympus FV1200 (Electron Microscopy Centre, UCM).

Synthesis of Mesoporous Silica Nanoparticles (MSN)

In order to prepare dye-labeled mesoporous silica nanoparticles, 1.5 mg of Rhodamine B isothiocyanate (RBITC) was dissolved in 1 mL of ethanol and 1.5 µL of (3-aminopropyl)triethoxysilane (APTES) and the solution RBITC-APTES was keep at room temperature under magnetic stirring for 2 h. 0290 g of Hexadecyltrimethylammonium bromide (CTAB) was dissolved in 150 g of ammonium hydroxide 0.32 M and the solution was incubated at 50° C. under magnetic stirring for 1 h in a 200 mL beaker sealed with parafilm. Then 3 mL of 0.88 M Tetraethyl orthosilicate (TEOS) in ethanol and RBITC-APTES were added to the surfactant solution after adjusting the stirring speed to 650 rpm. The mixture was incubated at 50° C. under magnetic stirring for 1 h without parafilm, then the solution was aged at 50° C. overnight under static conditions. The next day, the particles were subjected to a hydrothermal treatment at 70° C. for 20 h before being collected by centrifugation and washed three times with water and ethanol. The surfactant was removed by washing the particles in 500 mL of a solution of 95% ethanol, 5% water, and 10 g $NH_4NO_3$ $mL^{-1}$ at 80° C. during 3 h with reflux and under stirring. The nanoparticles were washed with ethanol and were finally stored in pure ethanol.

Vesicle Preparation

The lipids and cholesterol were solubilized in choloroform and were stored at −20° C. To prepare vesicles, the corresponding lipids were mixed at mol 9/0 ratios: DSPC/Chol/DSPE-PEG(2000)-$NH_2$/DSPE-PEG(2000)-COOH=65/20/2/13 and 48/20/2/30. The lipids were dried under vacuum to remove the organic solvent and obtain lipid films. Lipid films were rehydrated in 1×PBS and bath sonicated for 1 h to form vesicles. In order to prepare monosized vesicles, the vesicles were extruded using a 0.05 µm polycarbonate filter membrane for at least 21 times.

Synthesis of Protocells (PC-COOH13 and PC-COOH30)

MSNs were transferred to water at (2.5 mg/mL) from the ethanolic suspension by centrifugation (15000 rpm, 10 min) and resuspension in water. To each batch of MSNs, a suspension of vesicles, $8 \cdot 10^{-6}$ mol in 1×PBS with 13% or 30% of carboxylic groups, was added, The mixtures were sonicated for 20 s and excess vesicles were removed by centrifugation (15000 rpm, 10 min). The pelleted protocells were redispersed in PBS(1×) by sonication; this process was repeated two times. Finally, the protocells were stored in 1 mL of PBS (2.5 mg/mL).

Synthesis of Collagenase Capsule ($Col_{nc}$). Firstly, the reaction buffer $NaHCO_3$ (0.01 M, pH 8.5) was deoxygenated by freeze-vacuum-$N_2$ cycles. Then, Collagenase ($3.1 \times 10^{-5}$ mmol) was dissolved in the freshly deoxygenated buffer. In another vial, 0.035 mmol of acrylamide (AA), 0.026 mmol of 2-aminoethyl metacrylate hydrochloride (Am), and 0.01 mmol of ethylene glycol dimetacrylate (EG) were dissolved in 1 mL of deoxygenated buffer and the monomers solution was added to the protein solution. This mixture was stirred at 300 rpm for 10 min under nitrogen atmosphere at room temperature. Then, 0.013 mmol of ammonium persulfate and 0.002 mmol of N,N,N',N'-tetramethyl ethylenediamine (TMDA) dissolved in 1 mL of the deoxygenated buffer were added. The solution was stirred at 300 rpm for 90 min at room temperature under inert atmosphere. Next, the encapsulated enzyme was purified by centrifugal separation with 10 KDa cut-off filters (AMICON Ultra-2 mL 10 KDa) and washed three times with $NaHCO_3$ buffer (0.01 M pH 8.5). The capsules of collagenase were preserved at 4° C.

Protocell Modification with Anti-EGFR and $Col_{nc}$

Conversion of $NH_2$ groups into SH groups, 125 µL of 250 mM Traut's reagent in PBS was added to the protocells. The reaction was kept for 2 h under stirring at room temperature. After this time, the excess of Traut's reagent was removed via centrifugation (15000 rpm, 10 min) and the pellet of protocells was resuspended in PBS. This step was repeated twice. Finally, the thiol-functionalized protocells were stored in 1 mL of PBS (2.5 mg·$mL^{-1}$)

Attachment of NeutrAvidin: 0.5 mL of (1 mg·$mL^{-1}$ in water) maleimide-functionalized NeutrAvidin protein was added to 1 mL (2.5 mg·$mL^{-1}$) of thiol-functionalized protocells. The reaction was incubated under stirring at room temperature during 12 hours. After this time, the excess of maleimide-functionalized NeutrAvidin was removed via centrifugation (15000 rpm, 10 min) and the protocells pellet was resuspended in 1×PBS. This step was carried out twice. PC-NeutrAvidin were stored in 1 mL of 1×PBS (2.5 mg·mL$^{-1}$) at 4° C.

Synthesis of Col$_{nc}$-PC: the carboxylic groups of PC-NeutrAvidin (0.6 mL of 2.5 mg·mL$^{-1}$ in NaHCO$_3$ buffer (0.01 M, pH 8.5)) were activated by adding 2.5 mg of N-(3-(Dimethylamino)-propyl)-N'-ethylcarbodiimide hydrochloride (EDC) and 2.5 mg of N-Hydroxysuccidimide (NHS). In order to maintain the basic conditions, 2.5 mg of Na HCO$_3$ was added to the mixture. The sample was placed in an orbital stirrer at 400 rpm during 10 min. After this time, 4 mg of collagenase nanocapsules were added and the mixture was stirred during 4 h. Col-PC-NeutrAvidin were collected by centrifugation and washed three times with PBS. Col-PC-NeutrAvidin were stored at 4° C.

Synthesis of Col$_{nc}$-PC-Anti-EGFR: 25 μg of biotinlyated Anti-EGFR were mixed with 250 μg of PC-NeutrAvidin or Col$_{nc}$-PC-NeutrAvidin Protocells, respectively, during 1 h at room temperature. After this time, protocells were isolated by centrifugation (15000 rpm, 10 min) and they were redispersed in 250 μL of PBS(1×) yielding PC-Anti-EGFR or Col$_{nc}$-PC-Anti-EGFR, respectively.

Cell culture and targeting studies in 2D. Protocell selective uptake was evaluated in a 2D cell culture model by flow cytometry. For this study, 20,000 A549 cells·cm$^{-2}$ were seeded into each well of a 24-well plate. The cells were incubated with 80 μg of the corresponding protocell (PC-NetrAvidin or PC-Anti-EGFR) during 24 h at 37° C. at 5% CO$_2$ atmospheric concentration. Then, the cells were washed two times with PBS(1×) in order to remove the non-internalized protocells and then, the cells were treated with trypsin and the percentage of cells that engulfed fluorescently-labelled protocells was measured by flow cytometry, Enzymatic Activity Measurements. The enzymatic activity of all samples were evaluated following the protocol of the EnChekGelatinase/Collagenase Assay Kit.

Preparation of 3D tumoral tissue models based on A549-seeded collagen gels. For this study 20,000 A549 cells·cm$^{-2}$ were seeded in a 24-well plate. 0.5 mL of complete media was added to each well, and the cells were cultured at 37° C. at 5% CO$_2$ atmospheric concentration for 24 h. Then, the collagen gel with A549 cells embedded into the collagen matrix was directly prepared in contact with the cell monolayer. For this purpose, 5.32 mL of rat tail collagen type I (3 mg·mL$^{-1}$) and 15.48 mL of complete medium (Dulbecco's modified eagle's medium complemented with 10% of FBS) were mixed at 0° C. Then, 100 μL of sodium hydroxide was added in order to obtain a mixture with neutral pH. 5 mL of FBS, 5 mL of complete medium and 5 mL of a solution of cells of concentration A549 1.7×10$^6$ cell·mL$^{-1}$ were added to the neutral collagen solution, keeping the temperature at 0° C. The mixture was pipetted into 24 well plates (0.25 mL per well) and incubated at 37° C. at 5% CO$_2$ atmospheric concentration for 1 day, in order to promote gel formation. Then, 250 μL of complete medium was added in each well and the gel was incubated at 37° C. at 5% CO$_2$ atmospheric concentration overnight. These gels were used for the further experiments 2 days after gel formation.

Study of penetration and cell internalization in A549-seeded collagen gels. To study the penetration of nanocarriers in 3D tumoral tissue models, 80 μL of suspended PC-Anti-EGFR and Col$_{nc}$-PC-Anti-EGFR (1 mg·mL$^{-1}$) were respectively added on top of each gel. These samples were incubated at 37° C. at 5% CO$_2$ atmospheric concentration during 24 h. Then, the supernatant was removed and the gel was washed twice with PBS. Then, 0.5 mL of a solution 4% paraformaldehyde and 1% sucrose in PBS was added to each well, and were incubated for 20 min. After this time, the wells were washed two times with PBS 1× and 0.5 mL of a solution of 0.5% triton X-100 in PBS was added and the wells were incubated during 5 min at room temperature in order to permeate the cell membrane. Then, the wells were washed with PBS and incubated for 20 min at 37° C. with a solution of BSA 1% in PBS. After this step, BSA was removed and 0.5 mL of a solution of 30 μL of ATT0488 phallloidine solution (1 mg ml$^{-1}$ in methanol) in 1 mL of BSA19/0, was added. The wells were incubated for 40 min, and washed two times with PBS(1×). Then, 0.5 mL of one solution of DAPI in PBS (0.1 μg/mL) was added and the wells were incubated during 15 min at room temperature. Finally, the excess of DAPI was removed washing two times with PBS(1×). The samples were ready for observation by fluorescent confocal microscopy.

Topotecan Loading 1 mL of ethanolic suspension of MSN (2.5 mg·ml$^{-1}$) was washed two times with water and finally was resuspended in 0.5 ml of an aqueous solution of topotecan (5 mg·ml$^{-1}$) during 12 hours. The excess of topotecan was removed by centrifugation (15000 rpm, 10 min) and two washing steps in H$_2$O. The amount of topotecan loaded within MSNs was determined by the difference in fluorescence in the initial cargo solution and the resulting supernatant. These topotecan-loaded MSNs were employed for the drug-loaded protocell following the method described above.

Cell Viability Studies.

The cytotoxic capacity of these multifunctional protocells were evaluated using the same 3D tumoral tissue model mentioned above. Briefly, 80 μL of each drug-loaded protocell (1 mg·mL$^{-1}$) was added on the top of 3D gels embedded with A549 cells. These gels were incubated at 37° C. at 5% CO$_2$ atmospheric concentration during 24 h. The supernatant was removed and the gel was washed two times with PBS(1'). Then, 0.5 mL of Alamar Blue solution (10%) in cell culture medium was added to each well and the gels were incubated at 37° C. at 5% CO$_2$ atmospheric concentration during 1 h. Finally, the fluorescence of supernatant was measured using $\lambda_{exc}$=570 nm and $\lambda_{em}$=585 nm using a microplate reader.

Results

Synthesis of Protocells

Figure 28A:
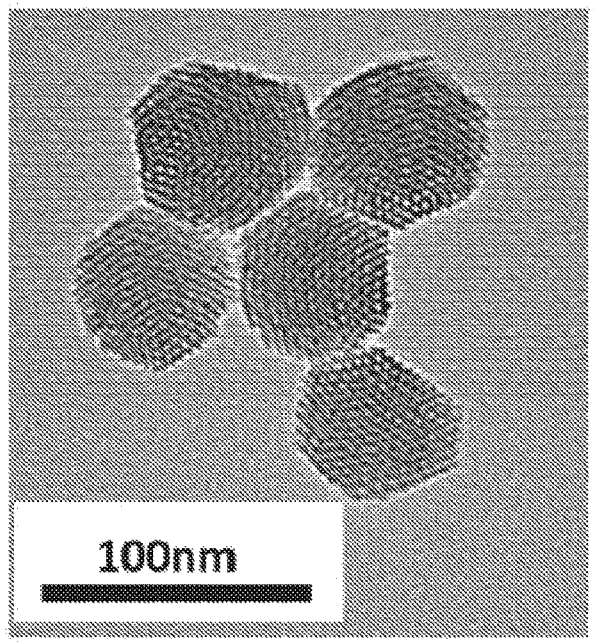
FIGS. 28A-D. TEM images of A) MSN, B) PC-COOH13, C) $Col_{nc}$ and D) PC-COOH13-$Col_{nc}$.

The protocell MSN core was designed with hexagonally arranged cylindrical pores of diameter 3-4-nm, which represents the optimal size for loading therapeutic agents based on small molecules, as is the case for many conventional cytotoxic compounds employed in antitumoral chemotherapy. MSNs were synthesized following a modified Stöber method reported elsewhere, yielding monodisperse nanoparticles with an average diameter centered around 100 nm according to dynamic light scattering (DLS) measurements and transmission electron microscopy (TEM) (FIG. 28A). MSNs were covalently labeled with rhodamine b throughout the silica matrix to enable fluorescence imaging.

Figure 29A:
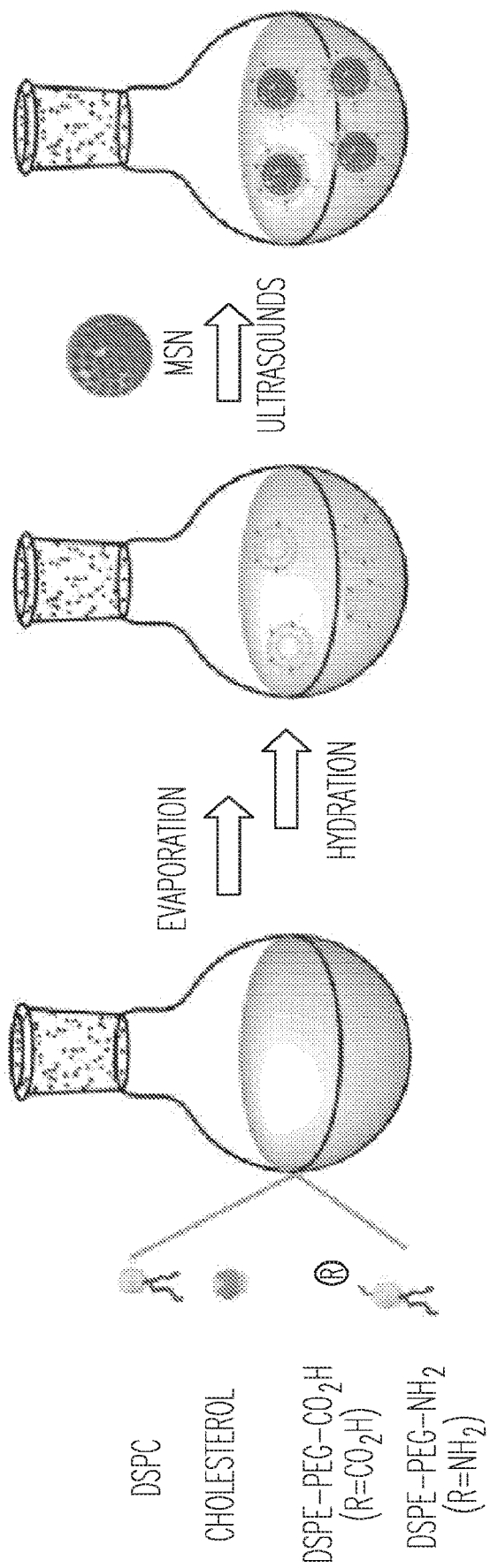
FIG. 29A. Synthetic pathway for the production of protocells.

MSNs were encapsulated within SLBs formed by fusion of zwitterionic lipid-based vesicles (FIG. 29A). The zwitterionic lipid, 1,3-distearoyl-sn-glycero-3-phosphocholine (DSPC) was chosen as main lipid component and cholesterol was added for controlling the fluidity of the SLB. In order to provide anchoring points for the further introduction of targeting moieties and collagenase nanocapsules, the functional PEGylated lipids, 1,2-distearoyl-sn-glycero-3-phosphoethanolamine-N-[carboxy(polyethylene glycol)-2000] (DSPE-PEG(2000)-COOH) providing a functional carboxylic group and 1,2-distearoyl-sn-glycero-3-phosphoethanolamine-N-[amino(polyethylene glycol)-2000]

(DSPE-PEG(2000)-NH$_2$), providing a functional amine, were also employed in the vesicle formulation. Here the polyethylene glycol chain (2000 Da) intercalated between the phospholipid head group and the respective functional group serves to enhance the colloidal stability of the resulting vesicle, as well as the protocells once formed. Moreover, it is well-established that the presence of PEG chains on the particle surface improves the circulation time of the nanocarriers within the blood stream. These polymeric chains hamper the adsorption of the immune proteins (opsonins) responsible of labeling foreign bodies for macrophage capture. Vesicles were synthesized following the thin-film hydration or 'Bangham' method.[2] This method is based on the dissolution of the phospholipids in an organic phase followed by solvent evaporation to obtain a lipid film. After that, the film is hydrated in a salt-rich aqueous medium under strong sonication which results in the vesicle formation. Two batches of vesicles were synthesized maintaining a fixed molar ratio of cholesterol to DSPE-PEG(2000)-NH$_2$ (20:2) and varying the molar ratio of DSPC and DSPE-PEG (2000)-COOH (65:13) and (48:30), respectively. The percentage of introduced amino groups was kept constant at 2%, because this percentage is sufficient for the antibody attachment as previously reported. Thus, the two batches present different concentrations of carboxylic groups in order to determine the effect of the concentration of collagenase nanocapsules on penetration. Both vesicle batches were extruded to yield a monodisperse size distribution centered at 100 nm according to DLS measurements.

Figure 28B:
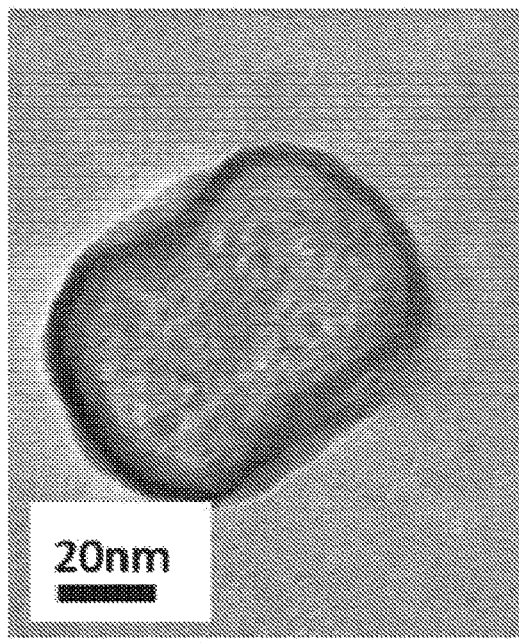

Two batches of protocells were prepared by incubating an aqueous suspension of MSN with vesicles of the respective formulation under strong sonication for 20 seconds in phosphate buffer saline (PBS). Excess vesicles not fused to the silica surface were removed via centrifugation. Both protocell batches (PC-COOH13 and PC-COOH30, respectively) showed monodisperse sizes centered around 175 nm according to the DLS measurements. The presence of the lipid bilayer on MSN surface was confirmed by TEM employing phosphotungstic acid (PTA) as a staining agent (FIG. 28B). The thickness of the supported lipid bilayer was measured to be 4.7 nm on both batches (n=_), which is in agreement with the values reported in the literature for 'protocell' systems.

Synthesis of Collagenase Nanocapsules (Col$_{nc}$)

Figure 29B:
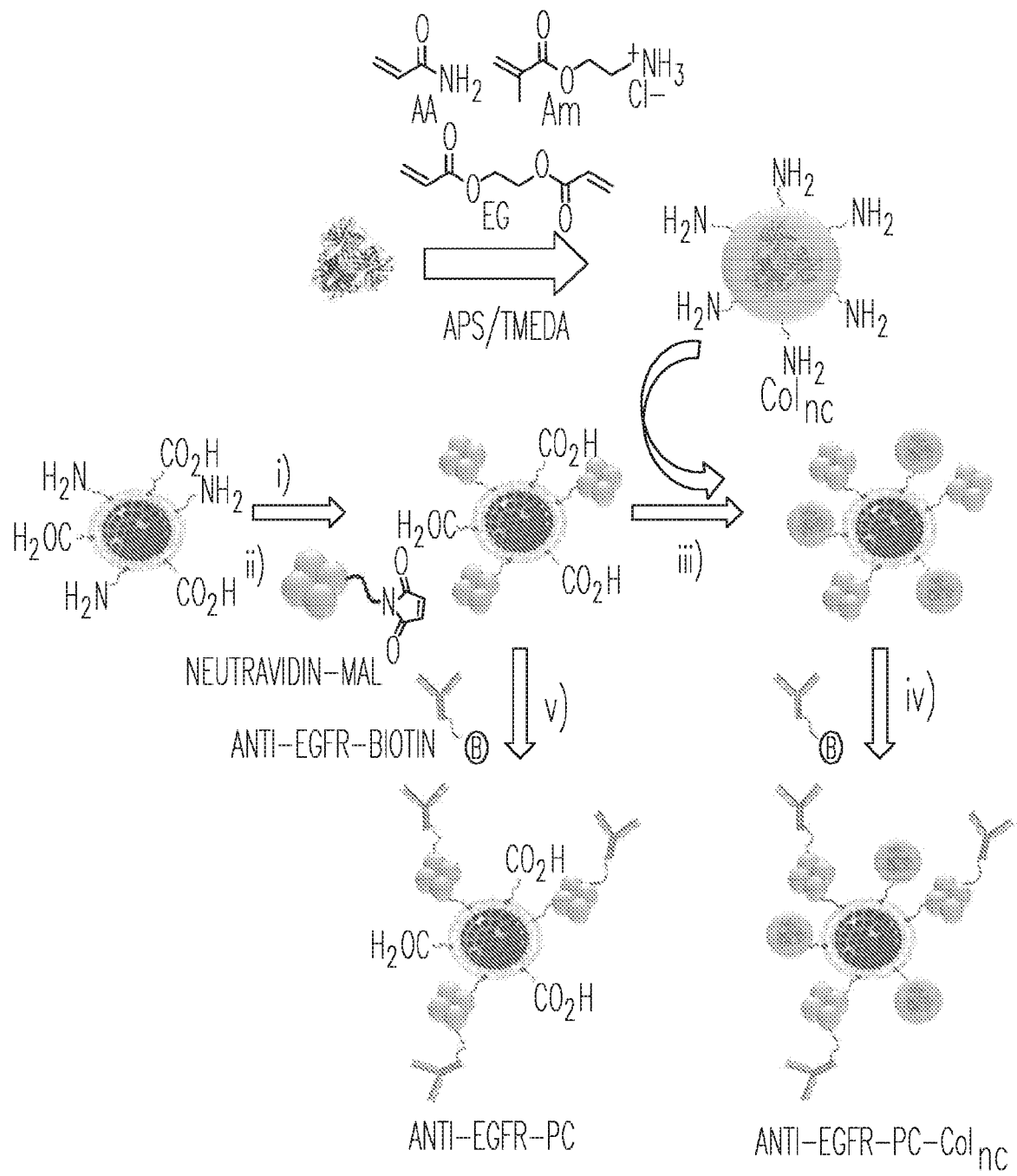
FIG. 29B. Synthesis of $Col_{nc}$ (upper scheme) and attachment pathway of $Col_{nc}$ and Anti-EGFR-biotin on PC surface (down scheme).

As was mentioned in the introduction, tumor penetration is one of the most important challenges facing the field of nanomedicine. The diffusion of nanometric objects in a fluid is understood by the Stokes-Einstein equation (D=KT/6πηr) which indicates that the diffusion rate (D) is inversely proportional to the particle radius (r) and also to the viscosity of the media (η). Therefore, the diffusion of nanometric objects is clearly reduced by increasing particle size and the viscosity of the media. Many solid tumors exhibit overproduction of collagen, which accumulates within the extracellular matrix (ECM) and greatly impedes particle diffusion through the inner tumoral core. The intratumoral injection of proteolytic enzymes able to destroy these collagen accumulations partially alleviates this problem, but due to the labile nature of these enzymes, it is necessary to administer several dosages of them in order to achieve significant results. The use of polymeric nanocapsules which contain enzymes encapsulated within an organic shell in order to preserve their catalytic function in the presence of aggressive agents such as temperature or other proteolytic enzymes has been reported. Recently, collagenase has been encapsulated within pH-sensitive polymeric nanocapsules which were designed to release the housed enzyme when the pH drops to the mild acidic conditions usually present in many tumoral tissues.[16] Following the same methodology, collagenase polymeric nanocapsules were formed by a radical polymerization method which employs acrylamide (AA), as a structural monomer, 2-aminoethylmethacrylate (Am) as a monomer that provides the amino groups required for the further attachment to the protocell surface, and Ethyleglycol dimethacrylate (EG) as a pH-degradable cross-linker (FIG. 29B). In this process, a monomer,/protein molar ratio of 1:2025 and AA:Am:EG ratio (7:6:2) were employed.

Figure 28C:
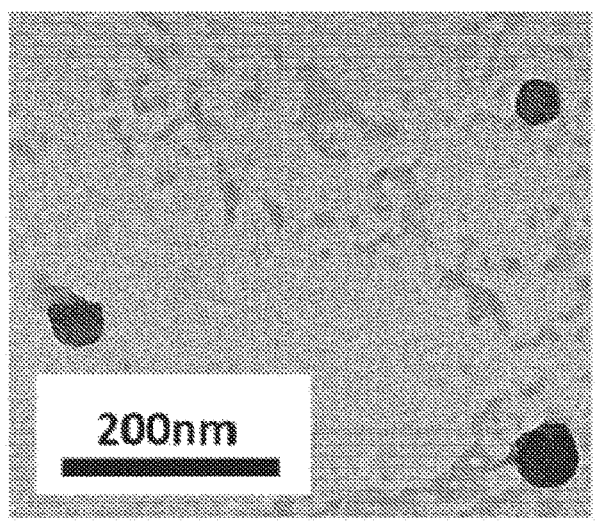
Figure 28D:
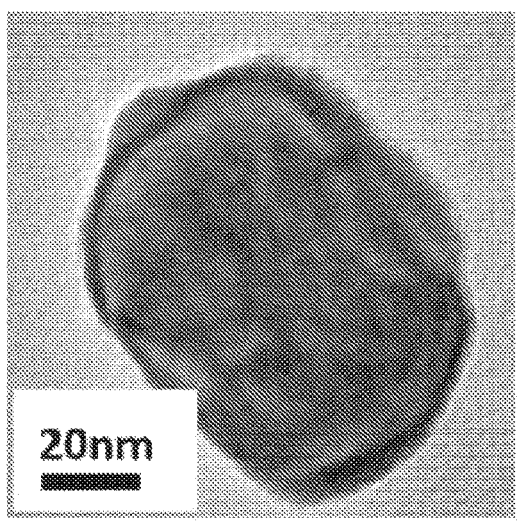

The resulting nanocapsules were characterized by DLS measurements and TEM showing an average diameter of about 50 nm and a round-shaped morphology (FIG. 28C). The employed polymer composition was selected in order to exhibit degradation by progressive hydrolysis during 24 hours, which can be accelerated in the mild-acidic conditions present in the tumor environment. The capsule degradation at physiological pH was monitored by following the hydrodynamic diameter variation over time. It was observed that the collagenase nanocapsules of 50-nm in hydrodynamic diameter, were progressively degraded until they reached a size of about 7 nm and the protein is completely released after 24 hours. The encapsulated collagenase retained its catalytic activity as was previously reported.[1]

Protocell Decoration: Anchoring of Anti-EGFR and Collagenase Nanocapsules.

In order to confer selectivity against tumoral cells, the nanoparticle surface should be decorated with targeting moieties capable of being specifically recognized by cell membrane receptors overexpressed mainly by the cancerous cells. Anti-EGFR was selected as targeting group due to the common overexpression of EGFR in many tumoral cell lines, as is the case of A549 lung tumor cells, selected in this work as cellular tumoral model. The anchoring of anti-EGFR and collagenase nanocapsules was carried out following a synthetic process which involves several steps (FIG. 29B).

The first step (i) was the conversion of the amino groups present on the protocell surface into thiol groups by the reaction with 2-iminothiolane hydrochloride (Traut's reagent). Then, these thiol groups were employed for anchoring the maleimide-neutravidin moieties (ii). Thus, the protocells were ready for the antibody introduction employing biotinylated-Anti-EGFR (iv or v). Due to the sensitive nature of antibodies, collagenase nanocapsules were anchored (iii) prior to the introduction of antibody in order to preserve as much as possible the recognition capacity of this macromolecule. As was mentioned above, two protocell batches displaying different percentages of carboxylic groups were synthesized (PC-COOH13 and PC-COOH30) in order to find the optimal composition, which allows a higher collagenase nanocapsule attachment. Collagenase nanocapsules were anchored on both batches of protocells, using the well-known carbodiimide chemistry (iii). The presence of collagenase nanocapsules was confirmed measuring the enzymatic activity of the PC-COOH13-Col$_{nc}$ and PC-COOH30-Col$_{nc}$ respectively, using the EnChekGelatinase/Collagenase Assay Kit and protocol. Both samples exhibited similar enzymatic activity and therefore, an increase in the amount of carboxylic groups on the PC surface did not improve the Cal$_{nc}$ attachment presumably due to steric considerations. Additionally, the colloidal stability of PC-COOH13-Col$_{nc}$ was significantly higher than PC-COOH30-Col$_{nc}$, and DLS showed that the particles remain well suspended in PBS for more than 15 days. For these reasons, PC-COOH13-Col$_{nc}$ was selected as the best system for the further attachment of Anti-EGFR, which was carried out through the formation of biotin-neutravidin bridge (steps iv and v).

2D In Vitro Evaluation of Protocell Targeting Capacity

Figure 30:
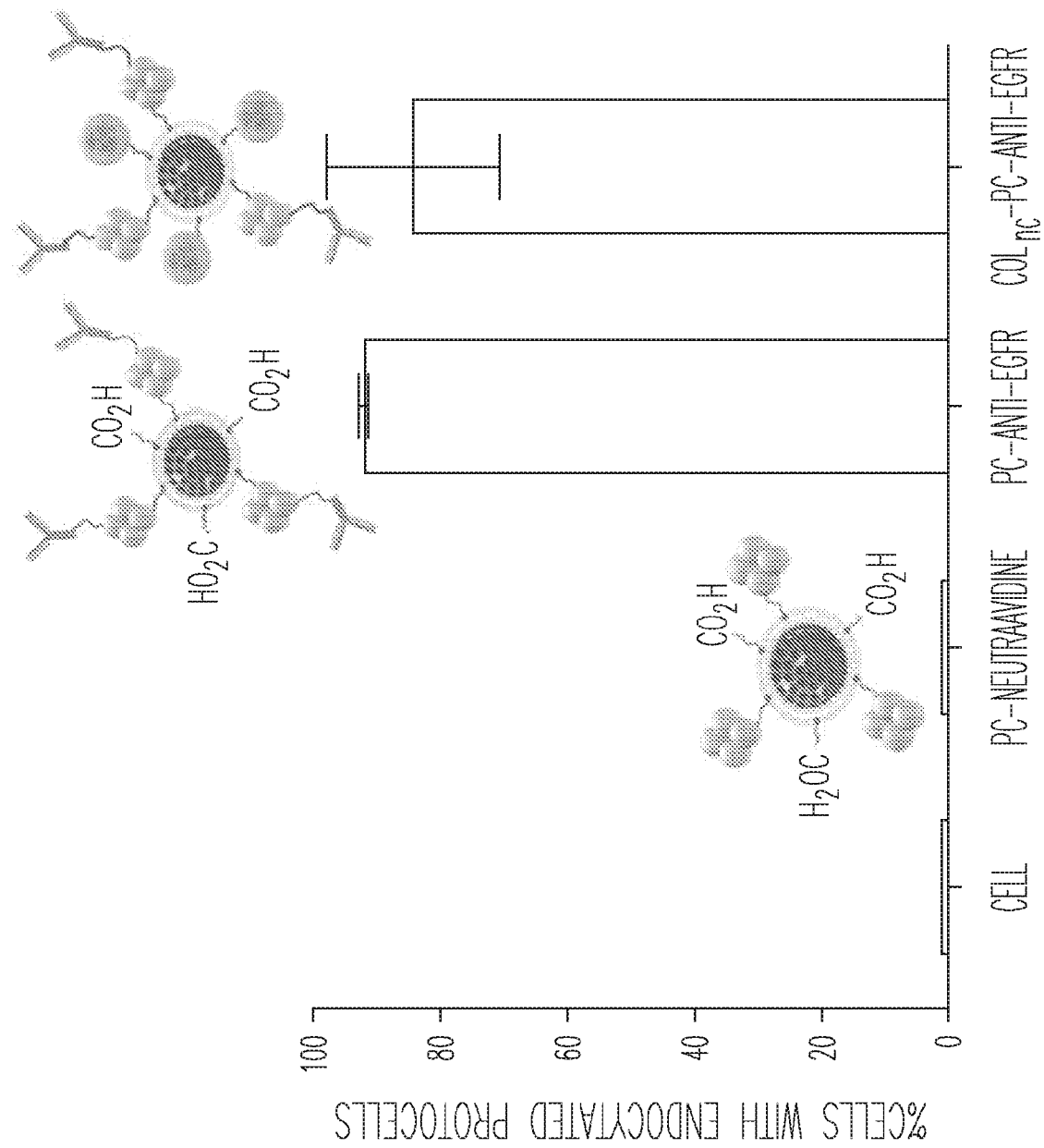
FIG. 30. Cellular uptake of protocell with and without anti-EGFR and $Col_{nc}$. Samples were performed in triplicate.

As described above, Anti-EGFR was anchored on the protocell surface for improving the particle uptake within tumoral cells. The capacity of these systems to selectively bind to tumoral cells was tested employing 2D cultures of A549 lung cancer cells, because these cells overexpress EGFR on their surface. A549 cancer cells were exposed during 24 hours to a fixed concentration of protocells (80 µg/ml) with and without antibody modification. After this time, the cells were gently washed with PBS in order to remove all non-internalized particles. Then the percentage of cells that had internalized protocells was determined by flow cytometry thanks to the presence of rhodamine b covalently labeled within the silica matrix of the protocells (FIG. 30).

The results confirmed the pertinence of the functionalization with the antibody because only 2% of the tumoral cells engulfed the protocells that did not present the antibody on their surface, whereas this value rose to over 90% when the antibody was present. Additionally, the binding affinity of $Col_{nc}$-PC-Anti-EGFR protocells was compared to protocells decorated with 15% of PEG chains, which have demonstrated excellent colloidal stability and which block the carboxylic acid and amino groups as is the case for protocells decorated with antibodies and collagenase nanocapsules. Again, the observed particle uptake is extremely low, lower than 2%, corroborating that the improvement in the particle uptake in the case of $Col_{nc}$-PC-Anti-EGFR was exclusively due to the presence of the antibody.

Evaluation of Penetration Capacity in 3D Tumoral Tissue

Figure 31:
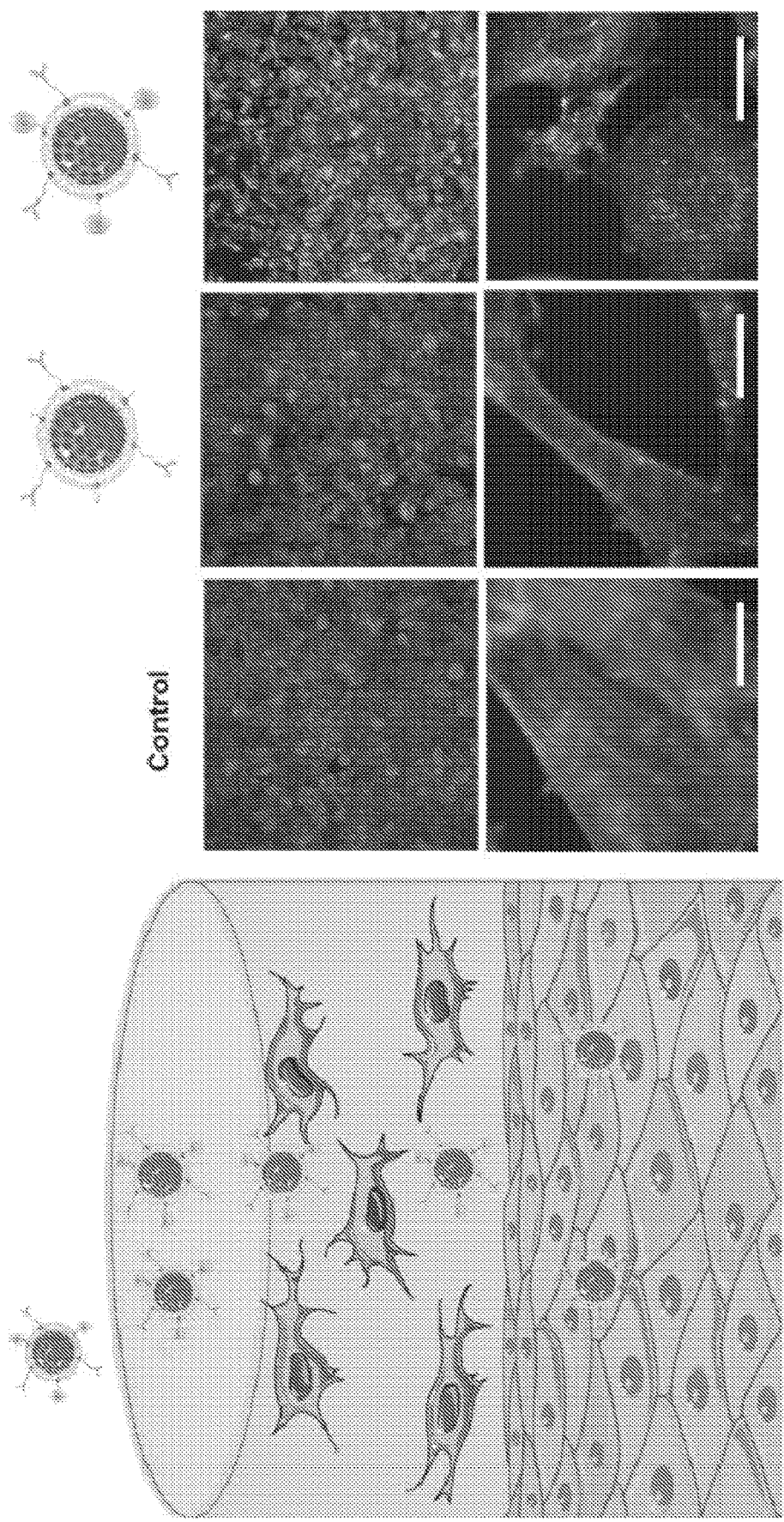
FIG. 31. Penetration and internalization capacity evaluation of PC-Anti-EGFR and $Col_{nc}$-PC-Anti-EGFR nanodevices, employing 3D tumoral tissue models. Cell nuclei are stained in blue, actin filaments were stained in green and protocells were labeled in red (white bars correspond to 25 μm).

In order to evaluate the penetration capacity of this multifunctional protocell, a 3D tissue model which mimics the existing conditions in a solid tumoral mass was prepared. This model was based on the use of a 3D collagen gel containing embedded tumoral cells. This model exhibits similar consistency and rheological properties as a real tissue and therefore can be employed as a simple substitute of a complex in vivo microenvironment. The model consisted of a monolayer of A549 cells on which a 200-µm thick 3D collagen gel embedded with A549 cells was grown (FIG. 31).

The gel mimics the ECM of the tumor and acts as barrier hindering the diffusion of protocells to the A549 monolayer. Thus to test the effectiveness of the collagenase nanocapsules in tumor penetration, suspensions of fluorescently-labelled AB-targeted protocells (80 µg/mL) prepared with or without the collagenase nanocapsules, were carefully placed on the top of the gel. After 24 h of incubation, the gels were gentley washed with PBS in order to remove the protocells unable to penetrate within the collagen matrix. The capacity to reach the bottom cell monolayer was tested in each case by fluorescence confocal microscopy. The cell nuclei were stained with DAPI (blue) and, with the aim to assess whether targeted protocells were truly internalized, actin filaments were stained with green phalloidine. The confocal images show that only protocells decorated with nanocapsules were able to reach the bottom layer, as can be observed by the existence of perinuclear red dots which correspond to the rhodamine b labelled MSN cores f the protocells. This result confirms the capacity of $Col_{nc}$-PC-Anti-EGFR to overcome the collagen barrier and reach deep layers of the tissue model. In addition, these protocells were found within the tumoral cell cytosol, which confirms the enhanced internalization of these protocells inside malignant cells. On the contrary, PC-Anti-EGFR were not able to overcome the collagen barrier being removed in the washing step, as can be observed by the absence of red dots in the bottom layer.

Figure 32:
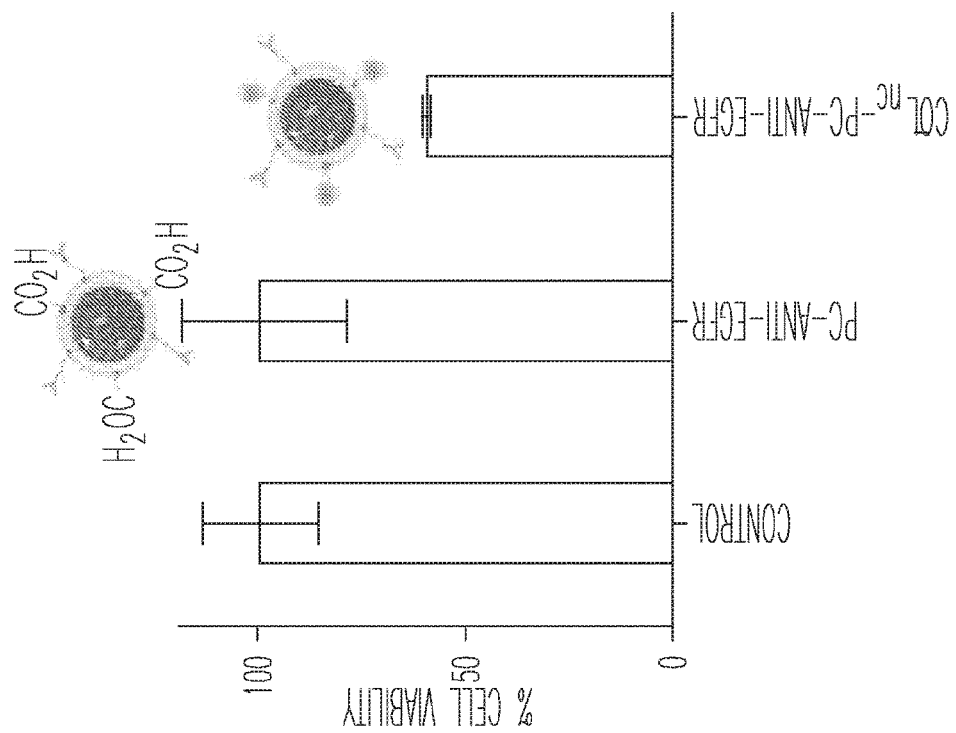
FIG. 32. Cytotoxic capacity of protocells in 3D tumoral tissue model after 24 hours of incubation (n=3, p<0.05).
Figure 32:
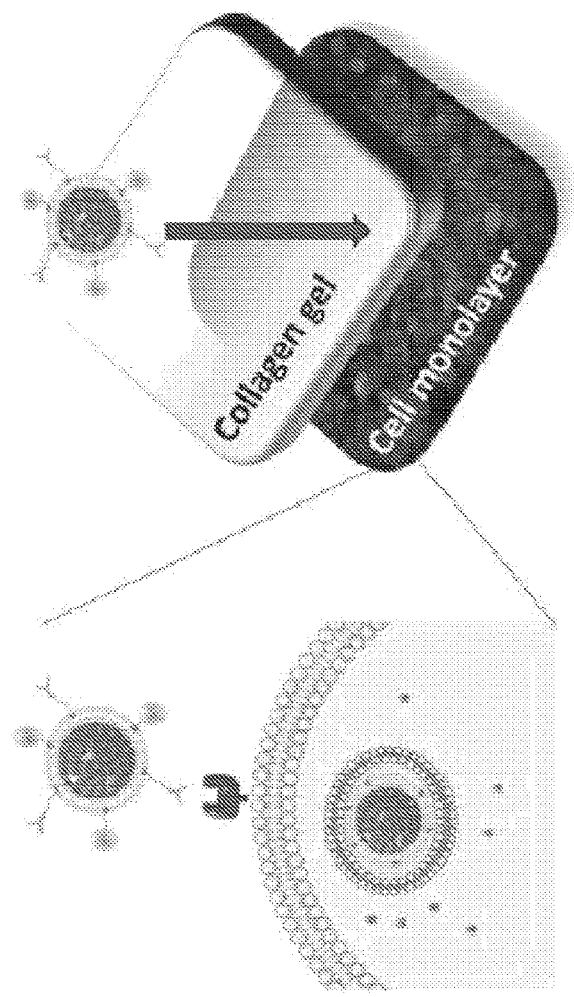

Evaluation of Cytotoxic Capacity of Drug-Loaded Protocells in 3D Tumoral Tissue Model Having established the ability of $Col_{nc}$-PC-Anti-EGFR-modified protocells to reach deep areas within a 3D tumoral model and once there, to be selectively internalized by tumoral cells, the ability of the system to transport and deliver cytotoxic drugs capable of inducing cell death was studied. Topotecan presents a potent antitumoral effect but it suffers significant instability in the blood stream, losing its activity in a few hours. For this reason, repeated dosages are required in order to maintain its concentration in blood, which induces the apparition of severe side effects. It is reported that the encapsulation of topotecan within a nanocarrier improves its therapeutic efficacy. For these facts, TOP has been selected as drug model for this system. $Col_{nc}$-PC-Anti-EGFR were loaded prior to the formation of the protocell by incubating the silica core for 24 hours in an aqueous solution of topotecan (3 mg·mL$^{-1}$). The load capacity of the protocells was determined by differences in fluorescence between the topotecan solution, before and after the loading, yielding 0.6% (w:w) of loading. A suspension of topotecan-loaded $Col_{nc}$-PC-Anti-EGFR-modified protocells were deposited on the surface of 3D tumoral tissue model. PC-Anti-EGFR loaded with the same amount of topotecan was employed as a control in order to evaluate the cytotoxic capacity of protocells which did not possess a penetration capacity. After 24 and 48 hours of incubation time, cell viability was evaluated by the Alamar blue viability assay. At 24 hours, the results showed that topotecan-loaded $Col_{nc}$-PC-Anti-EGFR-modified protocells induced around 40% cell mortality, whereas the system prepared without collagenase nanocapsules had negligible cytotoxicity. After 48 hours, the cytotoxicity observed in the case of topotecan-loaded Col-PC-Anti-EGFR protocells increased to 60% and that of PC-Anti-EGFR protocells increased to 20% (FIG. 32). These results confirmed that the higher penetration capacity of collagenase nanocapsules results in significant improvements in the therapeutic efficacy of the cytotoxic compounds transported by these multifunctional protocells.

Conclusions

Herein, a multifunctional tumor penetrating nanocarrier capable of selective delivery of antitumoral drugs to deep tumoral layers has been described. This nanocarrier is composed of a mesoporous silica nanoparticle core loaded with topotecan and encapsulated within a supported lipid bilayer to form a 'protocell'. The SLB of the protocell construct was modified with collagenase containing nanocapsules that serve to digest the highly dense tumoral extracellular matrix and enable protocell penetration. The collagenase nanocapsules were designed to yield an accelerated collagenase release within the tumoral area while at the same time protecting their catalytic activity until the system reaches the target tissue. The protocell SLB was also modified with an EGFR antibody in order to achieve selective internalization within tumoral cells. The ability of the of the system to penetrate within dense matrix, be selectively engulfed by tumoral cells and deliver cytotoxic anticancer drugs was confirmed employing a 3D tumoral tissue model which mimics the conditions present in real diseased tissues. The collagenase nanocapsule-modified protocell has proven its ability to overcome one of the main problems of current nanomedicines, which is their scarce penetration. The application of this strategy could pave the way for the design of smarter nanomedicines able to achieve more homogeneous drug distribution within solid tumors, which would result an important advance to their clinical applications.

EXAMPLE 6

The prospects of nanoparticle (NP)-based drug delivery and imaging have been hindered by insufficient understanding of the effects of NP physicochemical properties on their in vivo disposition. Using stable, monosized, radiolabeled mesoporous silica nanoparticles (MSNs), an integrated SPECT/CT imaging and mathematical modeling approach was used to understand the relationship between NP physicochemical properties and their biodistribution and clearance kinetics, under intravenous or intraperitoneal routes of administration, in healthy rats. Simple master equations were developed in closed-form to accurately represent the time-dependent concentration of MSNs in different regions of the body and obtain functional relationships for predictive purpose to support rational design of nanomedicine. Analyses revealed that an incremental increase in particle size between about 32 and about 142 nm results in a monotonic but non-linear decline in systemic bioavailability of MSNs, as observed from the radioactivity washout in heart, irrespective of route of administration ($AUC_{0-24\ h} = \lambda \cdot size^{-1}$). Correspondingly, this effect is accompanied by increased accumulation of MSNs in liver and spleen ($AUC_{0-24\ h}^{i.v.} = \lambda \cdot size$; $AUC_{0-24\ h}^{i.p.} = \lambda \cdot size^{0.5}$). Further, cationic MSNs with surface exposed amines are shorter lived in systemic circulation, compared to MSNs of identical size and charge but with shielded surface amines, due to rapid sequestration of the former into liver and spleen. However, the latter MSNs show greater hepatobiliary and urinary excretion than former and also than their size-matched neutral counterparts. Overall, the results indicate that about 32 nm sized neutral MSNs can be promising candidates for delivery to tumors via the EPR effect or to circulating, disseminated cells due to their avoidance of uptake by the mononuclear phagocytic system organs, liver and spleen, which serve as sinks for NPs, and their low excretion rates resulting in comparatively prolonged systemic residence.

Introduction

The implementation of nanotechnology in medicine promises to advance drug delivery and diagnostic imaging (Lin et al., 2010). Nanoparticle (NP)-based drug delivery and imaging systems (nanocarriers) have the potential to package and protect cargos that are too toxic, fragile, insoluble, or unstable to deliver as free drugs or imaging agents. Nanocarriers can be engineered to package combined therapeutic and diagnostic cargos (so-called theranostics) and equipped with a variety of triggering mechanisms to release cargo on demand according to intra- or extracellular environmental cues. Further, it is possible to engineer the nanocarrier size, shape, and surface chemistry to enhance circulation times and direct the biodistribution of the drug or imaging agent within the organism by 'passive' targeting, e.g., by the enhanced permeability and retention (EPR) effect (Lin et al., 2011), wherein NPs accumulate in the tumor microenvironment due to its leaky vasculature characterized by about 200-2000 nm diameter fenestrations. Finally, by surface modification of the nanocarrier with targeting ligands that bind to receptors/antigens over-expressed on the cells of interest, it is possible to achieve precise administration of therapeutic cargos to specific/personalized cells or tissues via 'active' targeting, while sparing collateral damage to healthy cells and potentially overcoming multiple drug resistance (Townson et al., 2013) mechanisms.

Whereas the potential of nanocarriers as effective drug delivery vehicles and imaging agents has been established extensively in vitro, NP-based delivery has achieved only moderate success in clinical translation, especially for therapeutic nanomedicines (Lin et al., 2010; Pimlott et al., 2011). According to a comprehensive review surveying the literature from the past 10 years, the in vivo tumor delivery efficiency of nanocarriers, which has relied primarily upon the EPR effect, has averaged around only 0.7% of the injected dose ((Durfee et al., 2016). This has been attributed to uncontrolled, non-specific interactions of NPs with the immune and microanatomical components of non-tumor sites, particularly the mononuclear phagocytic system (MPS) organs, liver, spleen, and bone marrow, that serve as 'sinks' for preferential NP accumulation (Durfee et al., 2016). This is highly problematic as clinical translation of nanotherapeutics demands a custom, reproducible disposition (biodistribution and clearance) profile of NPs needed to achieve the requirements of efficacy and safety. For instance, the U.S. Food and Drug Administration (FDA) guidelines require that diagnostic agents be completely cleared from the body in a reasonable timeframe (Braet et al., 2002). In contrast, it is particularly desirable to have prolonged systemic circulation of chemotherapy-loaded NPs for maximal exposure to tumor tissue and accumulation by the EPR effect (Alexis et al., 2008). Literature stipulates that a hydrodynamic size of <5.5 nm and a positive zeta potential promote rapid renal clearance of NPs, which is ideal for diagnostic applications (Bract et al., 2002; Sarin et al., 2010), but also that solid NPs exceeding 6 nm in diameter cannot be renally cleared, now showed to be untrue (see below). For therapeutic applications, e.g. cancer nanotherapy, polymeric coatings, like polyethylene glycol (PEG) that serve to reduce serum protein adsorption (opsonization) on the NP surface, are proclaimed to enhance the longevity of NPs in circulation, ideal for increased exposure to the tumor (Alexis et al., 2008; Satchel) et al., 2009) but so far the tumor targeting efficiency of largely PEGylated NPs has been modest and highly variable (Durfee et al., 2016).

It is hypothesized that the deficiencies of NP therapeutics and the confusion in the literature as to their efficiencies and behaviors are largely attributable to insufficient control of NP synthesis and the lack of in vivo colloidal stability, which have led to inconsistent biodistribution and therefore have prevented the establishment of definitive structure-activity relationships. So far, based on the ten year survey of NP delivery to solid tumors previously cited, several trends have been observed with respect to NP physicochemical properties: inorganic NPs have higher delivery efficiencies than organic NPs, NPs smaller than 100-nm in hydrodynamic diameter have higher delivery efficiencies than larger particles, nearly neutrally charged NPs (defined as having zeta-potentials −10 to +10 mV) have higher delivery efficiencies than more positively or negatively charged particles, and rod-shaped particles are more efficient than spherical or plate-like particles. These trends presumably reflect the in vivo stabilities of the NPs, differential uptake by the MPS, and differences in renal clearance, however this survey did not establish unambiguously the stability or size polydispersity of the NPs nor their biodistribution, and there appeared to be no systematic studies to isolate the effects of size or charge or surface chemistry for NPs of comparable composition and shape. Previous biodistribution studies have shown that NP physicochemical properties, primarily size, charge, and surface polymeric coatings (Choi et al., 2007; Bertrand et al., 2014; Sou et al., 2011; Zhang et al, 2016) along with routes of administration (Tsui et al., 2016; Yu et al;., 2012; Bateman) are critical in governing the disposition kinetics of NPs, but again systematic studies are often lacking. Noteworthy in this regard, we have recently demonstrated for NPs of identical size and charge, that the spatial arrangement and accessibility of charged molecules on the NP surface (surface chemistry) is another critical, but to date unrecognized, factor governing biological behavior of NPs (Gabreilson et al., 2004).

Herein to establish quantitative NP structure-activity relationships in vivo, single photon emission computed tomography integrated with computed tomography (SPECT/CT) imaging (Toutain et al., 2004) of $^{111}$In radio-labeled, mono-sized, mesoporous silica NPs (MSNs) was employed to determine biodistribution in healthy rats. By systematically varying MSN isolated physicochemical variables in the therapeutically relevant size range, 25-150 nm (corresponding to physical diameter determined by TEM), the effect of size, zeta potential, and surface chemistry on in vivo disposition of hydrodynamically stable, non-targeted MSNs administered via intravenous (i.v.) or intraperitoneal (i.p.) injection was examined. The selection of MSNs as the NP of choice for the current investigation is based on their biocompatibility, high cargo-loading capacity, ability to undergo surface functionalization, and precise synthesis control that allows for selection of particle size, shape, and pore size, making MSNs ideal candidates for drug-delivery systems (More, 1978; Guide, 1998). SPECT/CT imaging was employed to determine the disposition kinetics of MSNs within ten regions of interest (ROI) in the rat. Then a parsimonious, semi-mechanistic mathematical model was developed to describe the macroscopic concentration-time behavior of MSNs in individual ROIs and estimate relevant pharmacokinetic (PK) parameters. The results allowed the formulation of significant correlations between particle physicochemical properties and PK parameters, thus enabling quantitative comparison of the disposition behavior of MSNs necessary to advance their status toward clinical use. An interplay between physiological and NP physicochemical variables governs the in vivo behavior of NPs, and this study furthers our understanding of this interaction.

Methods

To study the effect of particle size, PEG-TMS-coated MSNs of four different nominal sizes (25 nm, 50 nm, 90 nm, and 150 nm) were administered i.v., and three different nominal sizes (25 nm, 50 nm, and 150 nm) were administered i.p. The i.v. and i.p. groups were also compared to investigate the effect of route of administration. To study the effect of zeta potential, size- and surface chemistry-matched MSNs (TMS50 and QA50) were compared. Here, surface chemistry refers to the spatial arrangement and relative exposure of surface amines, rather than the chemical identity of surface ligands. To study the effect of surface chemistry, size- and zeta potential-matched particles (QA50 and PEI50) were analyzed. Bolus tail vein or i.p. injection of particles conjugated with radioactive Indium-111 ($^{111}$In) was given to healthy female rats, followed by whole-body SPECT/CT imaging of animals longitudinally over 24 hours. Regions of interest analysis was performed on reconstructed SPECT/CT images to obtain dose normalized radioactivity concentration time-course data. Semi-mechanistic modeling and pharmacokinetic (PK) analysis were then performed to understand the effect of physicochemical properties and routes of administration on MSN disposition kinetics.

Nanoparticle Synthesis and Characterization

The synthesis of colloidally stable PEGylated MSNs with various sizes and different surface chemistries was based on published methods (Lin et al., 2010; Lin et al., 2011; Townson et al., 2013). To enable detection by SPECT, monodisperse MSNs were covalently-coupled to diethylene triamine pentaacetic acid (DTPA) through isothiocyanate and amine reactions to enable binding of $^{111}$In, a gamma emitting radioisotope with a radioactive half-life of 2.8 days[4]. First, 7.5 mg of S-2-(4-isothiocyanatobenzyl)-diethylenetriamine pentaacetic acid (p-SCN-Bn-DTPA, Macrocyclics, Pano, Tex.), 3.75 µL of 3-aminopropyltriethoxysilane (APTES, Sigma Aldrich, St. Louis, Mo.), and 15 µL of trimethylamine (Sigma Aldrich, St. Louis, Mo.) were mixed in 1 mL of anhydrous ethanol under continuous agitation for 18 h. Then, 0.29 g of cationic surfactant, n-cetyltrimethylammonium bromide (CTAB, Sigma Aldrich, St. Louis, Mo.) was dissolved in 150 mL of ammonium hydroxide ($NH_4OH$, Sigma Aldrich, St. Louis, Mo.) solution and heated to 50° C. After 1 h, dilute tetraethyl orthosilicate (TEOS, Sigma Aldrich, St. Louis, Mo.) solution (prepared in ethanol) and APTES/p-SCN-Bn-DTPA mixture solution were added simultaneously to the CTAB containing ammonium hydroxide solution. After an additional 1 h of continuous stirring, 2-methoxypolyethyleneoxy-propyltrimethoxysilane (PEG-silane, Gelest, Morrisville, Pa.) was added to the solution and the mixture was stirred for 30 min., then a secondary silane (trimethylchlorosilane, TMS, Sigma Aldrich, St. Louis, Mo. or trimethoxysilylpropyl modified polyethyleneimine, 50% in isopropanol, MW 1500-1800, PEI-silane, Gelest, Morrisville, Pa. or N-trimethoxysilylpropyl-N,N,N-trimethyl ammonium chloride, 50% in methanol, TMAC-silane), was added. Stirring was stopped after an additional 30 min., and solution was stored at 50° C. for 20 h. Solutions were then sealed and stored at 90° C. for 24 h for hydrothermal treatment. Next, we followed a procedure for CTAB extraction described previously in the literatures. Prior to use, MSNs were transferred to DI water at a concentration of 10 mg/mL. The detailed conditions and amounts of chemical reagents used in the preparation of PEG-TMS, PEG-PEI, and PEG-QA modified MSNs are described in Table 1.

To load $^{111}$In$^{3+}$ to MSNs, $InCl_3$ solution (Inidiclor, GE Healthcare, Arlington Heights, Ill.) was incubated with the DTPA-modified PEG/TMS, PEG/PEI, or PEG/QA NPs, using 15 mCi of In-111 per 10 mg particles, for 30 min. at room temperature in 500 mM Sodium Citrate Buffer. Unbound $^{111}$In was removed by centrifugation at 21,000×g for 60 min., followed by resuspension in 1 mL of 1×PBS at 10 mg/mL. No loss of radioactivity from the MSNs was observed following 2 subsequent washes.

The purified PEGylated MSNs were characterized by transmission electron microscopy (TEM), dynamic light scattering (DLS), and zeta potential prior in vivo injections. TEM images were acquired with JEOL 2010 (200 kV voltage, Tokyo, Japan) equipped with a Gatan Orius digital camera system (Warrendale, Pa.). Hydrodynamic size and zeta potential analyses (Table 1) were performed on a Malvern Zetasizer Nano-ZS equipped with a He—Ne laser (633 nm) and Non-Invasive Backscatter optics (NIBS). All samples for DLS or zeta potential measurements were suspended in either PBS or 10 mM NaCl at 200 µg/mL. Measurements were acquired at 25° C. in triplicate. The Z-average diameter and number particle size distribution was used for all reported hydrodynamic size measurements. The zeta potential for each sample was obtained from monomodal analysis measurements. All reported values correspond to the average of at least three independent samples.

Animal Study Design, SPECT/CT Imaging, and Quantification

All procedures involving rats were conducted in accordance with the National Institutes of Health regulations concerning the care and use of experimental animals. This study was approved by the University of New Mexico Health Sciences Center Institutional Animal Care and Use Committee (protocol #13-101096-HSC) and the USAMRMC Animal Care and Use Review Office (protocol #CB-2013-29.03).

Healthy female Fischer 344 rats (approx. 150 g each) were used in these studies. Each rat was administered 1 mg of particles, suspended in 200 μL of 0.5×PBS and labeled with approximately 1 mCi of $^{111}$In by either tail vein (i.v.) or i.p. injection. Four groups (N=4 rats per group) were administered PEG-TMS-coated particles of different nominal sizes (25, 50, 90, or 150 nm) by tail vein injection. Two additional groups (N=4 rats per group) received 50 nm particles i.v. coated with PEG-PEI or PEG-QA, respectively. Further, three additional groups were administered 1 mg of PEG-TMS particles of different nominal sizes (25, 50, or 150 nm) by i.p. injection (N=3 rats per group, except TMS150, where N=4 rats per group).

SPECT/CT imaging was conducted at the Keck-UNM Small Animal Imaging Resource using a dual-modality NanoSPECT/CT® Small Animal In Vivo Imager (Bioscan, Inc., Washington, D.C.). For each subject, the $^{111}$In biodistribution was imaged longitudinally at three-time points (30 min., 5 h (6 h instead for TMS150 (i.v.) group), and 24 h), post-injection with the rat maintained under isoflurane anesthesia on a heated bed (37° C.) during imaging. The CT acquisition (approx. 5 min. duration) was completed using 180 projections with a pitch of 1.5. Helical SPECT acquisition included 32 projections and varying time per projection resulting in an acquisition time of 15-30 min. per time point. Immediately after the 24 h imaging time point, each rat was euthanized and tissues were harvested and fixed in 10% formaldehyde for future analysis by microscopy.

The SPECT/CT image data were exported to VivoQuant 2.00 software (inviCRO, LLC, Boston, Mass.) for image reconstruction, display, and analysis. Camera calibration and reconstructions were performed using both In-111 gamma energy windows (0.1713 and 0.2454 MeV). Co-registered CT and SPECT axial images were reconstructed with a 176×176 matrix, 0.4 mm in-plane resolution, and a slice thickness of 0.4 mm. The number of slices for each whole-body image was approximately 450. Tissue segmentation and ROI analysis were performed by inviCRO, LLC. ROIs corresponding to the whole body, brain, liver, kidneys, spleen, heart, lungs, lymph nodes, bladder, abdominal aorta, bone (knee joint), and muscles were selected according to the following procedure: except for muscle and bone ROIs, which were generated manually, ROIs were generated using inviCRO's Multi Atlas Segmentation Tool. First, fixed volume ROIs were placed manually for 10 CTs, and used as a reference library for 10 additional scans. The final reference library included all 20 CTs. The reference CTs were registered to each new data set using both affine and deformable registration. The reference ROI had the same transform applied to it, resulting in 20 representations of possible ROI locations. Finally, using the best 5 registrations, a probability map of each ROI was created and thresholded to generate a final ROI of the correct volume. At each time point, ROIs were quantitatively analyzed to determine the dose normalized concentration of radiolabeled NPs (expressed as percent of injected dose per gram tissue, % IID/g) based on the total activity detected in the ROI, the ROI volume, and the tissue density.

Mathematical Modeling and Pharmacokinetic Analysis

The radioactivity observed in SPECT images has two origins: 1) radioactivity from NPs circulating through the vasculature of organs, and 2) radioactivity from NPs sequestered in the extravascular space of organs (due to the activity of NP 'traps', discussed in introduction). The former NPs are still bioavailable for delivery to a potential target site, but the latter are not unless the organ they are sequestered in is the target organ. The extent of NP sequestration in the extravascular space of an organ may be dependent on the density of traps in the organ's microvasculature. We were able to classify the organs in the body according to high or low density of the most relevant physiological traps (phagocytes, fenestrae, interendothelial gaps). Large blood vessels (e.g. the aorta) as well as capillaries in the muscles (including the heart), lungs, and brain have continuous endothelium, and thus lack fenestrations large enough to allow NP escape from circulation[89]. Kidney glomerular capillaries have fenestrations with a diameter of ~60 nm[8,10], but with a physiological limit of about 5.5 nm for renal clearance. Spleen and liver have capillaries (sinusoids) with discontinuous endothelium having pore sizes of about 5 μm and an about 180 nm, respectively. Similarly, the neovasculature of tumors has marked inter-endothelial gaps ranging between 200-2000 nm in diameter, leading to the enhanced permeability and retention (EPR) effect. Furthermore, among the phagocytes of MPS organs, Kupffer cells of the liver, macrophages of the spleen, and macrophages of the bone marrow have access to circulating blood, and are thus considered the prime culprits in removing NPs from circulation. However, in other organs, such as the lungs, where the alveolar macrophages exist on the air-side of the blood-air barrier, the contribution of phagocytes in removing NPs from blood is negligible.

In a nutshell, ROIs that are 'almost' devoid of traps (aorta, heart, lungs, brain, muscles) act as 'source-like' organs. It is assumed that the radioactivity from such ROIs is the result of NPs traveling through the vasculature of these organs without getting permanently trapped into the extravascular space. They represent the blood pool through which NPs travel without being taken up into the interstitium, remaining bioavailable for delivery to the 'sink' organs, i.e. organs enriched in traps, including, liver, spleen, kidneys, lymph nodes, and tumor (if any). In contrast, NPs in the 'sink-like' organs can passively accumulate overtime in the extravascular space, and may additionally be metabolized/excreted, leading to a permanent loss of bioavailable NPs.

An organ i receives an influx of NPs from the major feeding artery. Based on the characteristics of NPs and organ anatomy and physiology at the microvascular scale, NPs traverse through the vasculature of organ while forming transient or permanent associations with intravascular traps. The untrapped fraction of incoming particles is free to leave organ and rejoin the venous blood. These interactions at the microvascular scale thus govern the global biodistribution profile of NPs. Given the nature of data in the current study, we do not model NP interactions at microscopic scale, but only phenomenologically describe the observed macroscopic concentration-time behavior of NPs using a parsimonious model.

Assuming the influx and efflux process of NPs both follow a first order kinetics, we thus obtain the following differential equation describing the rate of change of concentration $C_i$ (units, % ID/g) of NPs in organ i:

$$\frac{dC_i}{dt} = k_{in,i} \cdot C_{b,i} - k_{out,i} \cdot C_i \quad (S1)$$

where $k_{in,i}$ and $k_{out,i}$ are the first-order uptake and elimination rate constants, respectively (units, $h^{-1}$); and $C_{b,i}$ is the concentration of NPs in the local arterial blood supply of organ i, which changes at a rate assumed to be governed by a first order distribution process:

$$C_{b,i}(t) = C_0 \cdot e^{-k_{in,i} \cdot t} \quad (S2)$$

where $C_0$ is the local systemic concentration of particles at t=0. The integrated form of Eq. (S1), solved for initial condition $C_i(0)=0$ is:

$$C_i(t) = A \cdot (e^{-k_{out,i} \cdot t} - e^{-k_{in,i} \cdot t}) \quad (S3)$$

where the macro-constant $$A = \frac{k_{in,i} \cdot C_0}{k_{in,i} - k_{out,i}},$$

is the intercept or pack-extrapolated elimination phase of double-exponential concentration-time curve of an ROI. This equation resembles the Bateman function for oral absorption of free drugs. Based on empirical evidence from the quantified SPECT/CT images, equation (S3) was further adapted to model the behavior of individual source-like and sink-like ROIs, under i.v. or i.p. conditions of MSN administration.

Following i.p. delivery, for all source-organs and lymph nodes (sink-like organ), an obvious uptake phase followed by an elimination phase is observed; thus, we fit equation (S3) in its canonical form to the concentration-time data. However, for the remaining sink-like organs following i.p. delivery, an apparent elimination phase was not seen within the duration of study, thus assuming $k_{out,i} \cong 0$, equation (S3) becomes:

$$C_i(t) = A \cdot (1 - e^{-k_{in,i} \cdot t}) \quad (S4)$$

Further, fitting equation (S3) to the source-like organs in i.v. case, we found that $k_{in} \gg k_{out}$, and as a result, the second exponential term in equation (S3) becomes insignificant, reducing the equation for source-like ROIs to:

$$C_i(t) = A \cdot e^{-k_{out,i} \cdot t} \quad (S5)$$

And, in the case of sink-like organs following i.v. injection, equation (S3) employed to model the empirical behavior of MSNs in liver, and equation (S4) in spleen, based on whether elimination is seen in the data. For the activity observed in urinary bladder, we use the cumulative amount (cumulative % ID), instead of concentration, of NPs to describe the renal excretion behavior of NPs. Concentration is largely irrelevant in the context of accumulation of NPs in bladder, because the volume of urine being produced will strongly influence the concentration but not the amount of NPs being excreted. In the case of the urinary bladder ROI for both i.v. and i.p. cases, we use an adaptation of equation (S4):

$$U(t) = U_t \cdot (1 - e^{-k_u \cdot t}) \quad (S6)$$

where U is the cumulative amount of MSNs in urinary bladder at time t (units % ID); $k_u$ is the first order urinary excretion rate constant (units $h^{-1}$); and $U_t$ is the total amount of MSNs excreted via urine.

To estimate model parameters and correlate them to the physiological and physicochemical underpinnings of the observed in vivo behavior of MSNs, non-linear regression analyses of the semi-mechanistic models (equations (S3, S4, S5, and S6)) to concentration (or, cumulative amount)-time data of individual ROIs were performed. Further, traditional PK analysis was perfomed by employing the concentration-time data of the heart ROI as a substitute for plasma concentration-time-course data. This substitution assumes that radioactivity from the heart ROI is purely due to NPs in the blood pool of the heart, and not in the extravascular tissue space (based on our previous discussion of the heart being a source organ). Based on the nature of concentration-time curves of MSNs in the heart, we applied a one-compartment PK model's (same as equations (1 or S5) for i.v. delivery, and equation (S3) for i.p. delivery), and determined PK parameters: i) area under the curve from 0-24 hours ($AUC_{0-24\,h}$), ii) uptake rate constant ($k_{in}$), iii) elimination rate constant ($k_{out}$), and iv) half-life ($t_{1/2}$). $AUC_{0-24\,h}$ represents the systemic bioavailability of NPs and is the definite integral of NP concentration-time in plasma (head, in this study), determined analytically, $k_{out}$ is the slope of the terminal phase on a semi-log plot between $C_{heart}$ and t, and represents the fraction of NPs eliminated from plasma per unit time. $t_{1/2}$ is the time required for NP concentration to reduce to half, and for a one-compartment model, $t_{1/2}$[18,19] is obtained as:

$$t_{1/2} = \ln(2)/k_{out} \quad (S7)$$

Further, model parameters for all the other ROIs were estimated to understand the effect of MSN characteristics and route of administration on organ exposure to MSNs, and their uptake and elimination behaviors.

Statistical Analysis

For in vivo studies, four animals per group were used. One subject from the TMS25 (i.p.) group and one subject from the TMS50 (i.p.) group were excluded from analysis due to subject motion and a misplaced injection, respectively, resulting in N=3 for these groups, Experimental results are presented as mean±standard deviation (SD), One-way ANOVA and Tukey's honest significant difference procedures were performed to evaluate differences in model parameters across groups. Unpaired-sample t-test was also performed for relevant pairwise comparisons. The levenberg-Marquardt' algorithm[20] was used to perform non-linear regression analysis to the observed data. All analyses were performed in MATLAB R2015b.

TABLE 1

Synthesis conditions of colloidally stable MSNs.

| Samples | NH$_4$OH concentration (M) | 0.88M ethanolic TEOS* (mL) | PEG-silane (μL) | TMS (μL) | PEI-silane (μL) | TMAC*-silane (μL) |
|---|---|---|---|---|---|---|
| TMS25 | 0.125 | 2.0 | 320 | 46.4 | 0 | 0 |
| TMS50 | 0.250 | 2.5 | 400 | 58.0 | 0 | 0 |
| TMS90 | 0.375 | 3.0 | 480 | 69.6 | 0 | 0 |
| TMS150 | 0.500 | 3.0 | 430 | 69.6 | 0 | 0 |
| PEI50 | 0.250 | 2.5 | 400 | 0 | 20 | 0 |
| QA50 | 0.250 | 2.5 | 400 | 0 | 0 | 250 |

Figure 33:
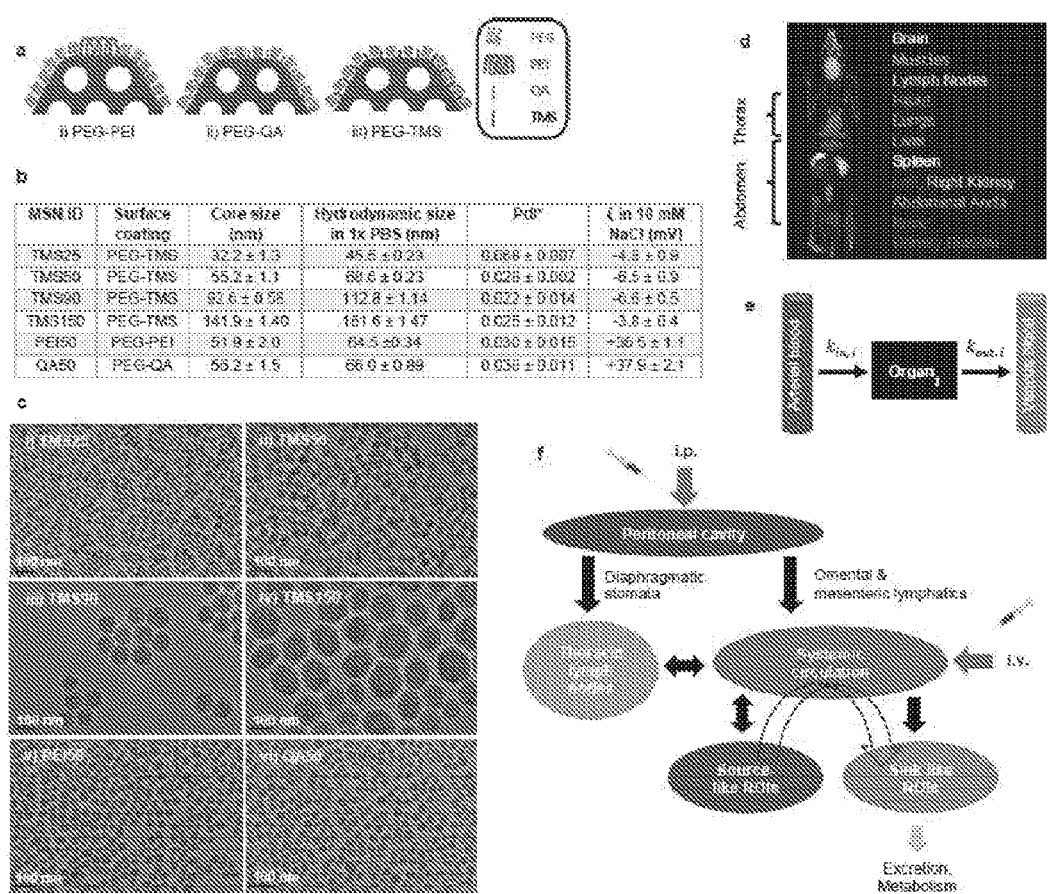
FIGS. 33A-F. Characterization of MSNs, SPECT/CT imaging, and semi-mechanistic modeling. A) Schematic representation of surface chemistries of the three types of MSNs used in the study. The bulky polyethylenimine (PEI) group in PEG-PEI-coated MSNs (i) is exposed beyond the PEG layer, unlike the smaller quaternary amine (QA) and trimethylsilane (TMS) groups in PEG-QA- (ii) and PEG-TMS- (iii) coated MSNs, respectively, which remain obstructed by PEG molecules. PEI and QA groups provide a strongly positive zeta potential ($\zeta$) to MSNs, while TMS makes them neutral. B) Table shows details of MSN characterization (size, *Pdl: polydispersity index, and Each MSN is identified by the type of surface coating (PEI, QA, or TMS) and nominal diameter (25, 50, 90, or 150) in nm. Data represents mean±SD, n=3. Hydrodynamic stability of MSNs overtime is shown in FIG. 38. Representative TEM images of all MSNs used in the study. Scale bars, 100 nm. D) Regions of interest (ROIs) generated using inviCRO's Multi Atlas Segmentation Tool to perform quantification of whole-body radioactivity concentration. E) A schematic of the underlying modeling hypothesis depicts an organ i that receives influx of NPs from its major feeding artery, and after passing through the vasculature of organ i, NPs exit into venous blood. Assuming the influx and efflux processes to both follow first order kinetics with rate constants $k_{in,i}$ and $k_{out,i}$, respectively, a double-exponential function (equation (1)) was obtained to describe the concentration-time course of NPs in individual ROIs. F) A schematic of the whole-body framework to understand the disposition of NPs. I.p, administration, unlike i.v. injection, is associated with absorption of NPs from the peritoneal cavity into systemic circulation through bowel lymphatics, causing accumulation of NPs in thoracic lymph nodes. Once in the systemic circulation through either route of injection, NPs are distributed across all organs in the body in proportionality to organ blood flow rates. Once inside the organ microvasculature, NPs encounter mechanisms (referred to here as 'traps') like fenestrations, endothelial cells, and phagocytes that sequester NPs form circulation, either into cells or into the interstitial space. Based on the low or high density of traps in an organ, the organs can be classified as 'source-like' and 'sink-like', respectively. Source-like organs do not sequester NPs due to a lack of traps; in contrast, generally the sink-like organs entrap NPs because of being enriched with traps, unless the physicochemical properties of NPs are unfavorable for entrapment. By allowing NPs to pass through their vasculature without sequestration, source-like organs thus become a secondary source of NPs for the sink-like organs (as depicted through the dotted black arrow), which eventually dispose of the particles through excretory and metabolic pathways. Generally, source-like organs will have a higher $k_{out,i}$ than sink-like organs, due to lesser sequestration of NPs in the former.
Figure 38:
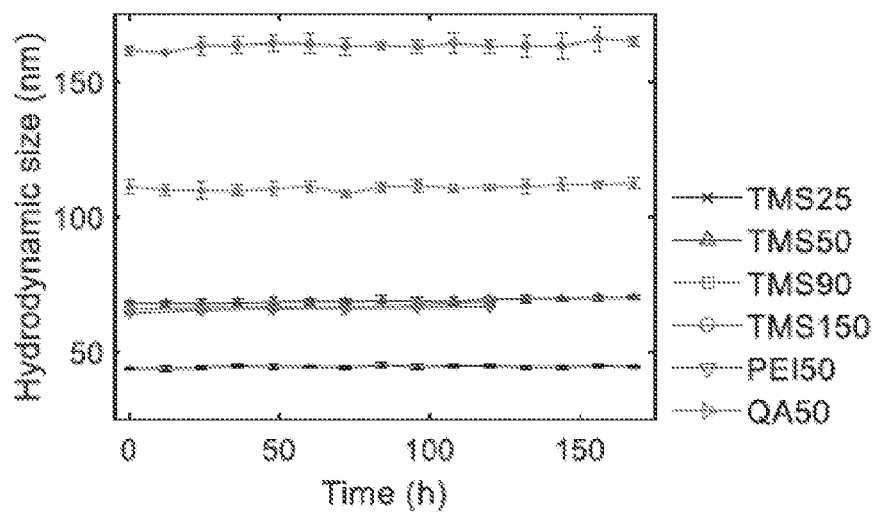
FIG. 38. Hydrodynamic stability of MSNs, Time-dependent stability of MSNs in 1× PBS at 25° C. over a period of five to seven days. Data represents mean±SD, n=3.

*TEOS: tetraethyl orthosilicate, *TMAC: N-trimethoxysilyipropyl-N,N,N-trimethyl ammonium chloride Synthesis and Characterization of MSNs The establishment of NP structure-activity relationships in vivo demands consummate control of NP particle size, shape, surface chemistry, and stability. Here, to avoid confounding effects of particle size polydispersity and hydrodynamic instability (which have obscured the role of particle size in previous studies), well characterized, monosized (defined as hydrodynamic size polydispersity index (PdI)<0.1), PEGylated MSNs that exhibited long-term stability in physiologically relevant media were used. $^{111}$In-labelled MSNs with three different surface chemistries were synthesized with nominal diameter 50 nm: 1) PEG-polyethylenimine (PEG-PEI), 2) PEG-quaternary amine (PEG-QA), and 3) PEG-trimethylsilane (PEG-TMS). Additionally, PEG-TMS MSNs were synthesized with nominal sizes: 25, 90, and 150 nm. The MSN core diameter was determined by TEM and the hydrodynamic diameter and PdI were determined by dynamic light scattering (DLS) (FIG. 33). Hydrodynamic diameter was consistently between 10 and 20 nm larger than the core TEM measurement, consistent with previous observations. MSNs showed excellent hydrodynamic stability in 1×PBS over five to seven days (FIG. 38) where hydrodynamic diameter varied by less than 4.5%. Surface charge of the particles was determined by measurement of the zeta potential ($\zeta$). PEG-TMS-modified particles were nearly neutrally charged ($\zeta$=−4 to −7 mV), while PEG-PEI- and PEG-QA-modified particles were strongly positively charged with nearly identical zeta potentials ($\zeta$=+37 to +38 mV) (FIG. 33B), In fact, PEI- and QA-modified MSNs are essentially indistinguishable according to the standard determinants of biodistribution (core size, hydrodynamic size, shape, and zeta potential), however, as we will show, they differ greatly in disposition (see below) due to differing distributions and exposures of surface amines (see schematic FIG. 33A), consistent with previous observations of their ex ovo behaviors within a highly vascularized chorioallantoic membrane model.

SPECT/CT Imaging

Advancements in small-animal imaging techniques have enabled whole-body, three-dimensional, dynamic imaging in rodents to quantify biodistribution of radiolabeled xenobiotics in the presence of an anatomical reference. These techniques provide the ability to study spatiotemporal evolution of whole-body biodistribution non-invasively within the same animal, presenting a significant advantage over blood sampling and organ resection. Cargo-less, gamma-ray emitting $^{111}$In labeled MSNs were injected i.v. or i.p, into healthy female Fischer 344 rats, and conducted SPECT/CT imaging over 24 hours to obtain the longitudinal biodistribution and clearance of MSNs. Reconstructed SPECT/CT images were then quantified to obtain dose normalized radioactivity concentration of MSNs (percent of injected dose per gram of tissue (% ID/g)) in ten ROIs (see FIGS. 33 and 34). The longer radioactive half-life of [111]In (about 2.8 days), over other commonly used SPECT radionuclides like [99m]Tc (half-life, 6 hours) and positron emission tomography (PET) radionuclides, makes $^{111}$In-based SPECT ideal for biodistribution studies spread over longer time periods.

Semi-Mechanistic Mathematical Modeling

Different from prior work on modeling free drug (Pascal et al., 2013; Koay et al., 2014; Frieboes et al., 2015; Cristini et al, 2017; Edgerton et al., 2011) and targeted nanocarrier delivery to tumors (Pascal et al., 2013; Wang et al., 2016; Hosoya et al., 2016), a parsimonious, semi-mechanistic model was used to S describe the macroscopic concentration-time behavior of MSNs in individual 'black box-like' ROIs and estimate relevant PK parameters. NPs traversing the organ microvasculature encounter three critical microscopic mechanisms that work to remove NPs from circulation: i) opsonization by plasma proteins (Monopoli et al., 2012) which label the NPs as foreign invaders for targeted phagocytosis (Walkley et al., 2012), ii) binding of NPs to vascular endothelial surfaces, which may lead to cellular internalization (Serda et al., 2009) and iii) fenestrated capillaries and sinusoids allowing extravasation[2] of NPs into tissue interstitia or directing excretion (Croissant et al., 2017). These microscopic mechanisms, referred to here as nanoparticle 'traps', are not distributed uniformly across the body, but rather are localized in higher densities in the MPS organs, and thus drive the macroscopic disposition profile of NPs. The present model is based on the hypothesis that superposition of two opposing first order processes of influx and efflux of NPs, through the vasculature of an ROI, can explain the observed concentration-time course of NPs in the given ROI (see FIG. 33E). The resulting equation, similar to the Bateman function[38] for oral absorption of free drugs, governing the concentration $C_i$ (units, % ID/g) of MSNs in individual ROIs is (see Methods in SI for details):

$$C_i(t) = A \cdot (e^{-k_{out,i} \cdot t} - r^{-k_{in,i} \cdot t}) \tag{1}$$

where $$A = \frac{k_{in,i} \cdot C_0}{k_{in,i} - k_{out,i}},$$

is a macro-constant representing the intercept of back-extrapolated elimination phase of double-exponential concentration-time curve of an ROI, $k_{in,i}$ and $k_{out,i}$ are the first-order uptake and elimination rate constants, respectively (units, h$^{-1}$), and $C_0$ is the concentration of NPs in arterial blood at t=0. Based on the present data and the premise that a differential density of traps exists across the body, ROIs can be classified as i) source-like and ii) sink-like, where source-like ROIs tend not to sequester NPs into their interstitial space, whereas sink-like ROIs tend to accumulate NPs in the interstitium (see FIG. 1f and Methods for details). The generalized equation (1) is thus adapted for the two classes of ROIs to fit the concentration-time profile of MSNs and thus quantify in vivo disposition (see Methods for details on modifications of equation (1)). To test equation (1) and its modifications, we perform nonlinear regression of the model to concentration-time data of individual ROIs.

Generalized Biodistribution of MSNs

Figure 34:
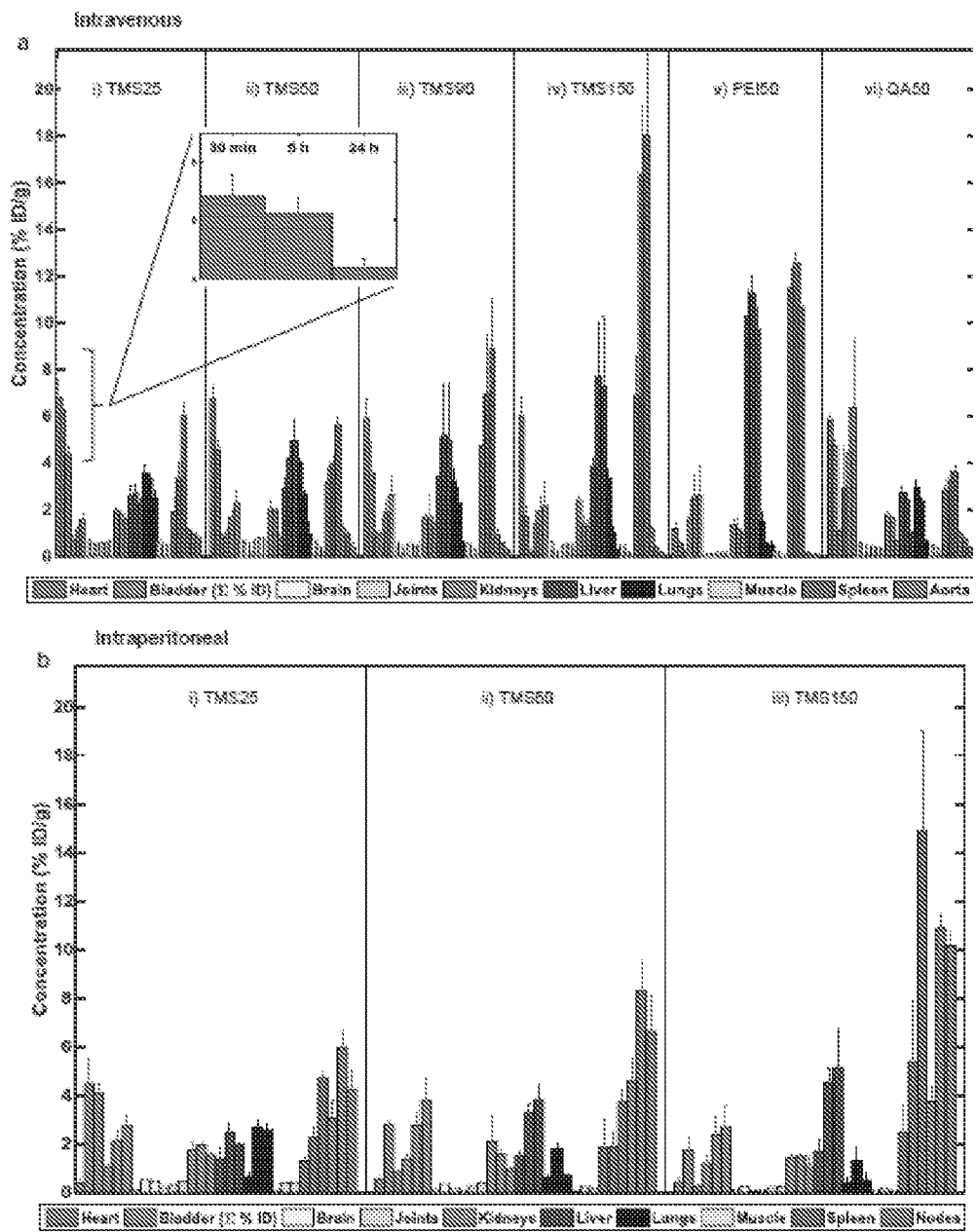
FIGS. 34A-B. Whole-body quantitative biodistribution of MSNs. Bar plots of mean concentration-time data for various ROIs following a, i.v. and b, i.p. injection of MSNs. For each MSN-type, concentration (% ID/g) of MSNs in ten ROIs is shown at 30 min, 5 h (6 h for TMS 150 (i.v.)), and 24 h, represented by three adjacent bars of same color (see inset in a). Data represents mean±SD, n=4 (except TMS50 (i.p.) and TMS25 (i.p,), where n=3). Note: Data for urinary bladder ROI is presented as cumulative amount (Σ% ID) and not as concentration.

From representative SPECT/CT images and their quantification in FIG. 34, the generalized biodistribution behavior of MSNs can be understood and thus infer similarities and differences between groups. As seen following i.v, injection at the 30-minute time point, an almost identical concentration is observed across all groups in the thoracic region (heart and lungs). The exception however is PEI50 (FIGS. 34a-v), where a much weaker signal is observed in the thorax. As confirmed through one-way ANOVA and Tukey's test on the quantified concentration-time data of heart (FIG. 34a), a significant difference is not observed between groups at 30 minutes (P>0.05), except with PEI50. Overtime, however, the concentration in the thorax tends to decline at different rates, suggesting that the organs in the thorax tend not to accumulate MSNs into their interstitium, and NPs are cleared from the blood pool of thoracic organs in a particle-type dependent fashion. This justifies the classification of heart and lungs as source-like organs. In contrast, the concentration in the abdomen (spleen and liver) tends to rise to a maximum followed by a slow or zero decline within 24 hours post injection; note that this behavior is also particle-type dependent (see FIG. 34a). The rise of MSN concentration in MPS organs up to prolonged periods of time suggests that MSNs tend to accumulate over time in the interstitium of these organs, hence a very small wash-out is observed within 24 hours, justifying these organs to be classified as sink-like organs. The literature shows that overtime the spleen and liver gradually clear of the MSN load through hepatobiliary route of elimination and not recirculation into blood (Kumar et al., 2010: Him et al., 2011; Souris et al., 2010; Fu et al., 2013). Further, PEI50 MSNs (FIGS. 34a-v) that exhibit the lowest concentration in heart and lungs at 30 minutes among all groups, accordingly exhibit the highest accumulation in liver and spleen at 30 minutes, indicating a rapid hepatic and splenic uptake of PEI50 MSNs from blood. As seen in FIG. 34a, the behavior of kidneys and urinary bladder appears to be consistent across groups, except for QA50 (FIGS. 34a-vi), where the bladder shows significantly larger cumulative amounts overtime than other groups. Also, QA50 shows radioactivity in the large intestine at the 5 h and 24 h time points, unlike other MSNs. Thus, because of the greater urinary and fecal excretion, QA50 shows one of the lowest accumulations in spleen and liver among other MSNs (see FIG. 34a). Finally, other ROIs, including abdominal aorta, brain, joints, and muscles exhibit only trivial concentrations (<1.5% ID/g) across groups. Their behavior, except joints, resembles that of source-like ROIs, i.e., a particle-type dependent, exponential decline in concentration over time (see FIG. 34a).

Next, i.p. injection of PEG-TMS coated MSNs shows a punctate biodistribution pattern throughout the abdomen at the initial time point of 30 minutes that maps the abdominal lymph circulatory network (Parungo et al., 2007), with mediastinal lymph nodes in thorax (see ROI map FIG. 33d) being an important site of radioactivity. This initial phase represents the absorption of MSNs from the peritoneal cavity into blood (Parungo et al., 2007; Mactier et al., 1987). Over time, however the distribution pattern starts to resemble that of the corresponding i.v. cases for the three particle-types, meaning that the MSNs have entered the systemic circulation. This behavior demonstrates the in vivo stability of the MSNs with respect to non-specific binding in lymph nodes. Having entered the circulatory system, i.p.-injected MSNs ultimately exhibit a mass transfer phenomenon similar to the one following i.v. administration, namely transfer of MSNs overtime from source-like organs (e.g., heart and lungs) to sink-like organs (e.g., liver and spleen), and finally excretion (as depicted in FIG. 33f). The kinetics of these processes are however particle-type dependent and in the subsequent sections we will unravel the effects of MSN physicochemical properties on the kinetics of MSN disposition in blood, visceral organs, and excretion.

Systemic Kinetics

Figure 35:
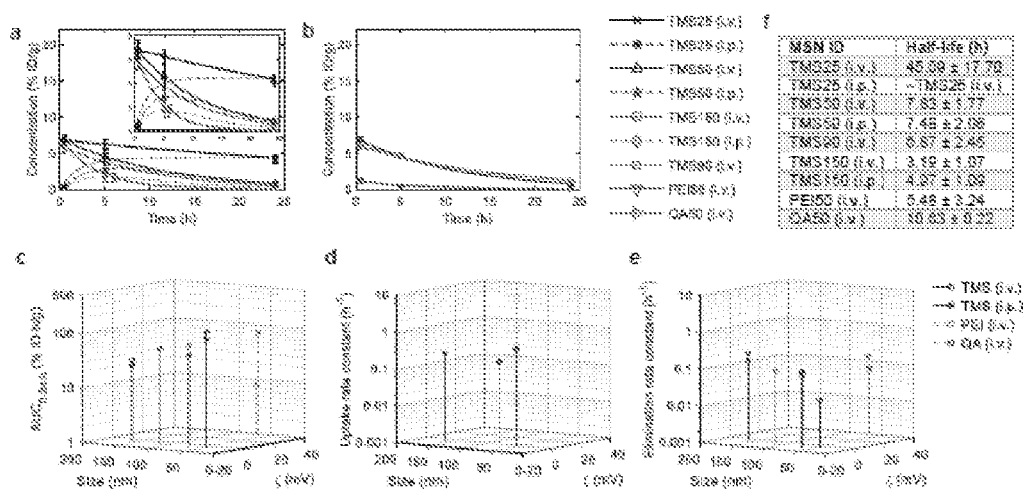
FIGS. 35A-F. Systemic kinetics. A-B) One compartment PK model (equation (S5) for i.v. and equation (1) for i.p.) was fit to the concentration-time data for different MSNs in the heart ROI ($R^2 > 0.93$. Fitted concentration-time curves demonstrate the effect of MSN size and route of administration for TMS-modified MSNs (A) and surface chemistry and zeta potential for 50 nm diameter MSNs modified with TMS, QA, or PEI (B). The inset in (A) is a rescaled version of the figure for a clearer view. Solid lines, i.v. cases; dotted lines, i.p. cases. C-E) 3-D stem plots show area under the concentration-time curves ($AUC_{0-24\,h}$) (c) and model parameter estimates ((D) uptake rate constant, $k_{in}$, and (E) elimination rate constant, $k_{out}$), obtained for different MSNs from a,b, in multiparameter space. f. Table shows values of estimated half-lives ($t_{1/2}$) for different MSNs. Data represents mean±SD, n=4 (except TMS50 (i.p.) and TMS25 (i.p.), where n=3). Note: for TMS25 (i.p.), $t_{1/2}$ is not available because an elimination phase was absent in its concentration-time profile within the timeframe of study (see dotted black curve in A).

SPECT-derived radioactivity concentration-time data of the heart ROI was used as a substitute for plasma concentration-time data (assuming that MSNs in the heart were in circulation) to understand systemic kinetics of MSNs and estimate relevant PK parameters; see FIGS. 34 and 35a,b. Since the concentrations of different MSNs seems to vary in mono- or bi-exponential fashion, we fit a one-compartment PK model[46] (a monoexponential equation (S5) for i.v. and a double-exponential equation (1) for i.p.) to the concentration-time data. As seen in FIGS. 35a,b, nonlinear regression of the one-compartment PK model produced best fits with $R^2 > 0.93$. Fitted concentration-time curves demonstrate the effect of MSN size and route of administration (FIG. 35a) and surface chemistry and zeta potential (FIG. 4b) on systemic kinetics of MSNs. Normalizing the predicted concentration over time (C(t)) of individual MSNs by their own predicted concentration maxima ($C_{max}$) allows a direct comparison of different groups. Then the estimated area under the curves $AUC_{0-24\,h}$), uptake and elimination rate constants ($k_{in}$ and $k_{out}$), and half-lives ($t_{1/2}$) of individual curves wre determined from FIG. 35a,b.

As seen in FIG. 35c, $AUC_{0-24\,h}$ decreases monotonically with an increase in particle size in the studied size range of ~32 nm to ~142 nm, irrespective of the route of delivery, governed by the mathematical relation: $AUC_{0-24\,h} = \lambda \cdot size^{-1}$, where $\lambda$ is a numerical coefficient. Further, the elimination rate constant ($k_{out}$) increases (and thus $t_{1/2}$ decreases) with an increase in size (see FIGS. 35e,f); however, one-way ANOVA reveals no significant difference in the uptake rate constant ($k_{in}$) values across i.p. administered cases (P>0.05) (see FIG. 35d). This suggests that absorption of NPs from peritoneal cavity in the studied size range is independent of particle size (Hirano et al., 1985) and that the systemic bioavailability through either route of administration is primarily a function of the $k_{out}$ parameter. Published hemodynamic studies (Carboni et al., 2014; Gentile et al., 2008; Muller et al., 2014) show that smaller particles tend to have smaller margination probabilities in blood capillaries, in addition to being shielded by erythrocytes, thus escaping near-wall accumulation, resulting in reduced extravasation through fenestrations and reduced internalization by endothelium or near-wall phagocytes (Lee et al., 2013). Thus, greater protection from the traps in microvasculature yields a higher systemic bioavailability for smaller sized particles, The absolute bioavailability (Gabrielsson et al., 2001) (ratio of dose normalized $AUC_{0-24\,h}$ of i.p. to $AUC_{0-24\,h}$ of i.v.) of i.p. administered TMS25, TMS50, and TMS150 MSNs is 72.8%, 66.6%, and 79.6%, respectively, assuming that the i.v. injected MSNs are 100% bioavailable. This parameter quantifies the incomplete absorption of MSNs from the peritoneal cavity into blood. It is however important to note that $t_{1/2}$ is not significantly different (P>0.05) between corresponding MSNs injected through the i.v. and i.p. route (see FIG. 35f), indicating that upon entering the blood stream MSNs behave independent of their route of administration, which again highlights their in vivo stability necessary for clinical translation.

Next looking at the effect of surface chemistry in FIGS. 35b,c,e,f, PEI50 with surface exposed amines has an about nine-fold lesser $AUC_{0-24\,h}$ (P<0,0001) and half the $t_{1/2}$ (P<0.05) of size- and zeta potential-matched QA50 with obstructed surface amines. These results are consistent with a previously published report (Townsone t al., 2013), where it was demonstrated the difference in cellular and tissue interactions of PEG-PEI and PEG-QA coated MSNs in vitro and ex ovo in the highly vascularized chicken chorioallantoic membrane model which recapitulates the diverging-converging capillary vasculature associated with sink organs like liver and spleen. It was shown that PEI50 rapidly binds to serum proteins and endothelial cells in comparison to QA50. The subtle difference in surface chemistry arguably alters the vulnerability of PEI50 MSNs to phagocytosis because of increased opsonization and hence reduced systemic residence, and is consistent with previous studies of the effects of surface chemistry on protein corona[52,53].

Interestingly, no significant effect of zeta potential was observed on the $AUC_{0-24\,h}$ of size- and surface chemistry-matched, but differently charged TMS50 and QA50 particles (P>0.05) (see FIG. 35c), although the positively charged QA50 has a slightly lesser $k_{out}$ (hence slightly greater $t_{1/2}$) than neutral TMS50 (P<0.05) (see FIG. 35e,f). The washout of TMS50 from thorax is accompanied by increased concentration of MSNs in the liver and spleen, but that of QA50 is accompanied primarily by excretion into large intestine and urinary bladder. This indicates that the positively charged particles tend to be excreted out faster than their neutral counterparts, which tend to be sequestered in liver and spleen longer (Souris et al., 2010) but without much difference in the systemic exposure of the two particles.

Individual-Organ Kinetics

ROIs in the body are theoretically classified as source-like and sink-like, which becomes more evident as we consider the kinetic behavior of MSNs in individual ROIs. Because of source-like ROIs, namely lungs, abdominal aorta, muscles, and brain, being deficient in traps, MSNs do not sequester into their interstitium, rather only traverse through the blood pool of these ROIs. Hence a monoexponential decay function (equation (S5)) explains the concentration-time course of MSNs through such ROIs, producing best fits with $R^2 > 0.89$, except PEI50 (i.v.) in lungs and brain (see FIGS. 36a,d). MSNs demonstrate synchronous behavior across all source-like ROIs, which in turn closely resembles their behavior to the heart ROI (substitute for plasma) (FIGS. 35a,b). A change in the heart concentration of MSNs is reflected by a similar change in source-like ROIs, as is also evident from similarity in the $k_{out}$ values of MSNs across ROIs (ANOVA, P>0.05, except PEI50 (P=0.03) (FIG. 35e). This is strongly suggestive of a coupling between the heart and source-like ROIs; heuristically, the underlying reason lies in the similar microanatomy of these ROIs. As seen in the ROI-to-heart concentration ratios (FIG. 36g), source-like ROIs have an almost constant ratio over time, which corroborates the coupling of source-like ROIs to the head. Also, the mathematical relation $AUC_{0-24\ h} = \lambda \cdot size^{-1}$ holds true for all source-like ROIs as well. All the above suggest that the effect of MSN physicochemical properties and routes of administration on MSN disposition kinetics in source-like ROIs is similar to that on systemic kinetics. The concentration levels however do vary across ROIs because of differences in organ perfusion (see FIG. 34).

As anticipated, the sink-like ROIs (i.e., liver, spleen, and thoracic lymph nodes) behave differently than the heart and source-like ROIs. MSN concentrations in these ROIs rise over time followed by slow or no decline in concentration within 24 hours, indicating the presence of traps causing MSN accumulation overtime into the interstitium or into resident macrophages (see FIGS. 36b,c,e,f). As a result in FIGS. 36b,c,e,f and S7a equation (1) or its adaptation, equation (S4), is fit to MSN concentration-time data in sink-like ROIs, with $R^2 > 0.81$, except TMS50 (i.p.) in spleen.

Figure 36:
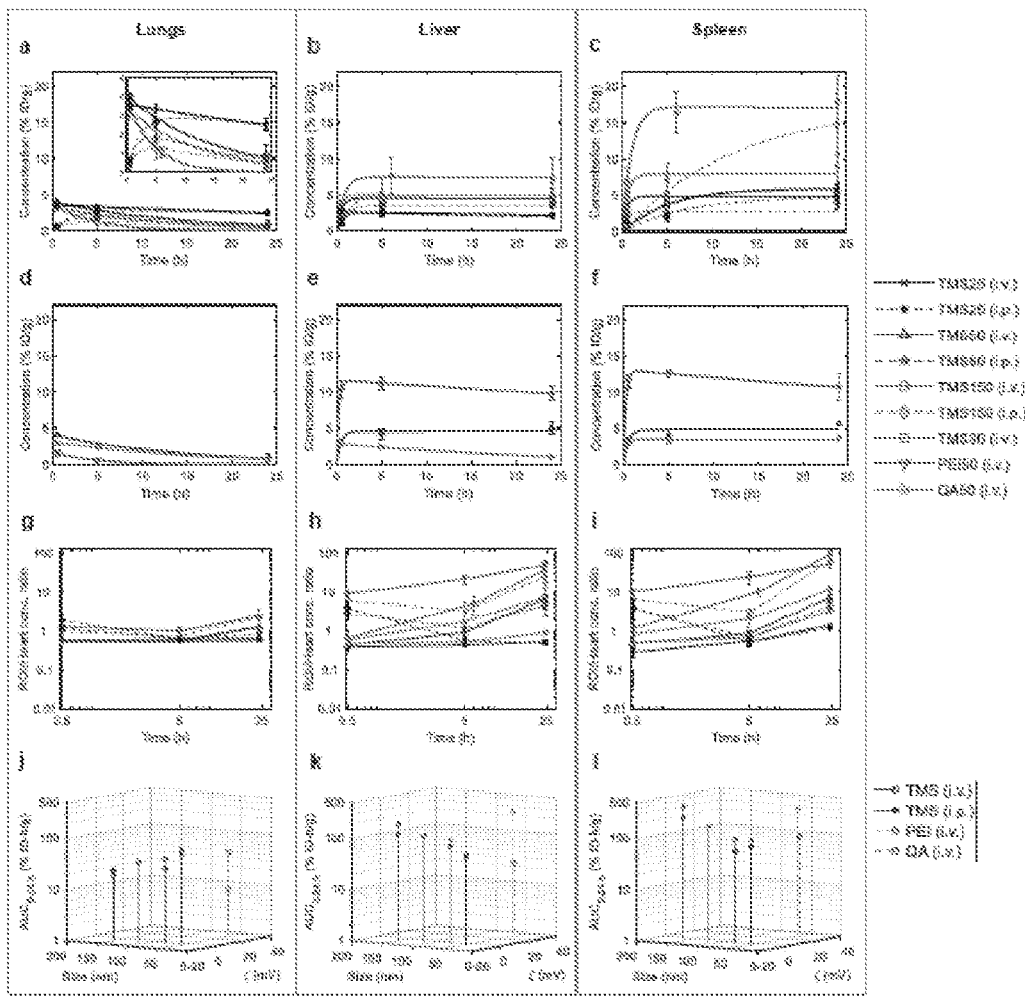
FIGS. 36A-L. Organ kinetics. Panel shows kinetic analysis for lungs, liver, and spleen. A-F) For each ROI, nonlinear regression of equation (1) or its adaptations was performed on the concentration-time data ($R^2 > 0.81$, except PEI50 (i.v.) in lungs and TMS50 (i.p.) in spleen). Solid lines, i.v, cases; dotted lines, i.p, cases. The inset in (a) is a rescaled version of the figure for a clearer view, g-i, Observed concentration of ROIs normalized to concentration of heart (substitute for plasma) is shown over time on a log-log plot. j-1, 3-D stern plots show area under the concentration-time curves ($AUC_{0-24\,h}$), obtained for different MSNs from a-g, in multiparameter space. Data in all plots represents mean±SD, n=4 (except TMS50 (i.p.) and TMS25 (i.p.), where n=3).

As to the effect of MSN size, a larger size of TMS-coated MSNs is associated with a greater $MX_{0-24\ h}$ in sink-like ROIs, irrespective of route of administration, indicating a greater organ exposure to MSNs (see FIGS. 36k,l). The mathematical relations between $AUC_{0-24\ h}$ and particle size (about 32≥size≤~142), $AUC_{0-24\ h} = \lambda \cdot size$ (for i.v.) and $AUC_{0-24\ h} = \lambda \cdot size^{0.5}$ (for i.p.), are consistent across all sink-like ROIs. Comparing the effect of route of administration, i.v. delivered TMS-coated MSNs are associated with a higher $AUC_{0-24\ h}$ value than their i.p. delivered counterparts in spleen (P<0.05), but with comparable values in liver (P>0.05) (see FIGS. 36k,l).

For the PEI50 MSNs with surface exposed amines, spleen and liver are the prime sites of radioactivity, unlike the size- and zeta potential-matched counterpart, QA50, with obstructed amines (see FIGS. 34a and 36e,f). QA50 however shows resemblance in its behavior to TMS50, indicating that surface chemistry plays a bigger role in affecting the hepatic and splenic accumulation of MSNs compared to zeta potential. It is worth mentioning that TMS25 (i.v.) and QA50 (i.v.), show deviation from the norm in liver and show a decline in concentration overtime; hence, the monoexponential decline equation (S5) was fit instead ($R^2 > 0.81$) to their concentration-time course (FIGS. 36b,e). This is also evident from the almost constant liver-to-head concentration ratio for the two MSNs, unlike other MSNs with growing ratio over time (FIG. 5h). Small size of TMS25 seems unfavorable for MSN sequestration in liver[11] and the positive zeta potential of QA50 seems favorable for hepatobiliary elimination[14], hence overall a low sequestration in liver is observed leading to an almost constant liver-to-heart concentration ratio. This information is valuable for MSN design optimization.

Excretion Kinetics

Figure 37:
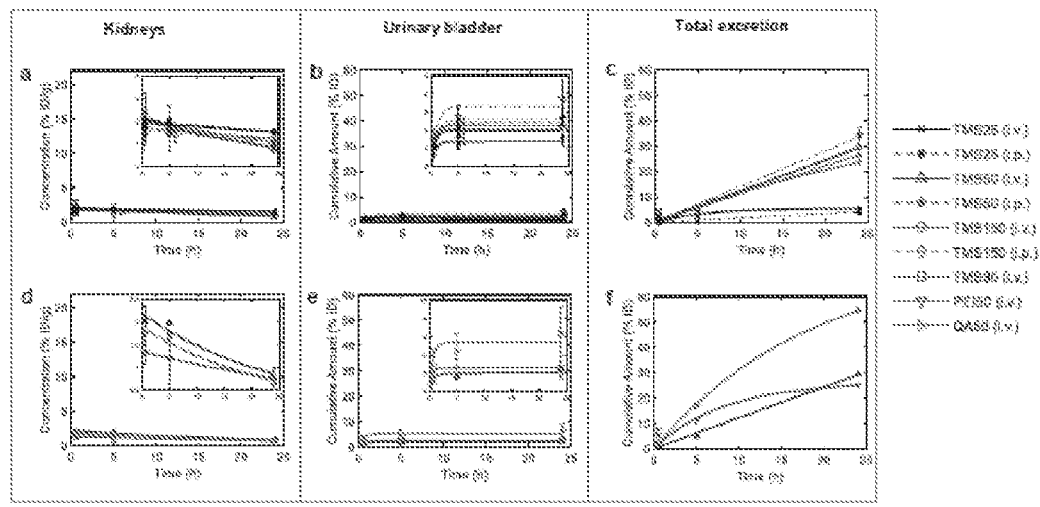
FIGS. 37A-F. Excretion kinetics. Urine and feces were not collected during the in vivo study, we thus examine the kidneys, urinary bladder, and whole-body ROIs to infer excretion kinetics of MSNs. a,d, ROI concentration-time data of kidneys was fit to equation (S5) for iv. cases and equation (1) for i.p. cases, b,c,e,f, To the cumulative urinary bladder and cumulative complement of whole-body (100— whole-body) ROI data, equation (S6) was fit to all cases. ($R^2 > 0.91$, except TMS150 (i.v.) in kidneys. The insets in (a, b, d, e) are a rescaled version of their corresponding figures for a clearer view. Solid lines, i.v, cases; dotted lines, i.p, cases. Cumulative amount, instead of concentration, was used as the measure of excretion. Data represents mean±SD, n=4 (except TMS50 (i.p,) and TMS25 (i.p.), where n=3).

Urine and feces were not collected during the in vivo study; we thus examine kidneys, urinary bladder, and whole-body ROIs (FIGS. 37a-f) to understand the excretion kinetics of MSNs. A monoexponential decay function (equation (S5)) was fit to the concentration-time data in the kidneys following i.v. injection, and equation (1) was fit following i.p. injection. As seen in FIGS. 37a,d, there is a tight overlap between the kidney concentration-time profiles of various MSNs injected i.v. or i.p., with a mean radioactivity concentration of <2.5% ID/g at 30 minutes in all cases, and an overall trend of decline in concentration over time. Because we do not observe a relation between the particle physicochemical properties and behavior in kidneys, and the radioactivity from kidneys may be a result of MSNs in the pre-glomerular vasculature, we refer to the urinary bladder ROI for an understanding of renal clearance of MSNs. Looking at the nonlinear regression of equation (S6) to cumulative amount-time data of various MSNs in urinary bladder (FIGS. 37b,e), the positively charged, QA50 has a greater total amount excreted via urine than other MSNs, consistent with evidence in literature (ANOVA, P<0.0001). TMS-coated MSNs of different sizes injected i.v. or i.p. are excreted to a comparable amount (except TMS25 (i.v.), which has the least amount excreted), consistent with prior studies showing that degradation products of larger MSNs appear in urine faster than smaller MSNs. Thus, a correlation between size or route of administration and urinary excretion was not identified.

Equation (S6) was fit to the total excreted activity (% ID) overtime (FIGS. 37c,f), obtained by subtracting the whole-body activity (% ID) from 100%. The total excreted activity includes excretion by both urinary and fecal routes. The data demonstrates that the total excretion behavior correlates with the cumulative amount behavior in the urinary bladder (FIGS. 37b,e).

Appearance of radioactivity in the urinary bladder defies the established paradigm that solid particles>about 5.5 nm in diameter cannot be efficiently cleared through kidneys. However, previous studies have demonstrated the appearance of intact silica NPs as large as 110 nm in urine, without any apparent damage to the glomerular microarchitecture (Fu et al., 2013; Huang et al., 2011; He et al., 2008). Biochemical indicators of biliary and glomerular function were altered by treatment with MSNs, suggesting that biliary and glomerular function may have been dysregulated, and could help explain the intact excretion of particles without obvious damage (Huang et al., 2011). The onset of clearance from animal models appears to be less than 30 minutes with positively charged particles, and longer (up to several days) with strongly negatively charged particles[14]. This observation is consistent with our study, which shows that strongly positively charged particles, QA50, show higher clearance. However, the other highly positively charged PEI50 shows lesser renal clearance than QA50 because of its greater accumulation in the liver and spleen.

While it is known that MSNs can be broken down into nontoxic silicic acid species, the particles can also be excreted intact or only partially broken down. TEM analysis of urine of mice i.v. injected with PEG-TMS MSNs showed intact MSNs in the urine. While few studies have examined the urine for the presence of particles, the ability of the particles to clear in this manner, potentially without damage, could explain the very rapid appearance of signal in the bladder in both our study and in previous studies, which suggest clearance begins as early as 30 minutes post injection (Souris et al., 2010). The rapid onset of clearance and the potential for intact particle clearance should be investigated further in future experiments. The safety of MSNs is supported by the fact that amorphous silica is Generally Recognized as Safe (GRAS) by the FDA and recently amorphous silica NP 'C-dots' (Cornell Dots) were FDA approved for diagnostic applications in a stage I human clinical trial (Phillips et al., 2014).

Conclusions

A combined mathematical modeling and non-invasive SPECT/CT imaging approach was employed to PK analysis of MSNs. The range of the particles used to test the effect of size, charge, and surface chemistry reveals that in vivo biodistribution and clearance of NPs is significantly affected by these physiochemical properties. The classification of ROIs into source-like and sink-like organs was justified based on their underlying physiological differences and observed NP kinetics, and applied semi-mechanistic models to the concentration-time profiles of NPs in these ROIs to determine relevant PK parameters. The analysis showed that smaller size corresponds with higher systemic bioavailability, irrespective of route of delivery; positive charge favors greater excretion; and importantly surface exposed charged molecules (amines) increase vulnerability to sequestration in liver and spleen. Notably, a consistent mathematical relation between one key PK parameter ($AUC_{0-24\,h}$) and NP size was identified in the form of $AUC_{0-24\,h} = \lambda \cdot size^{-1}$ for systemic circulation and all source-like organs in both i.v. and i.p. cases; however, for sink-like organs, two such relations were identified, i.e., $AUC_{0-24\,h} = \lambda \cdot size$ and $AUC_{0-24\,h} = \lambda \cdot size^{0.5}$, for i.v. and i.p. cases, respectively.

Regarding the predictive power of the semi-mechanistic mathematical model, it operates at a macroscopic scale, i.e. is based on the organ- or tissue-scale concentration-time profiles of NPs, which means that several microscopic mechanisms are lumped into the phenomenological macroscopic constants and variables in the model. The predictive capacity of the model is thus limited in scale. The model can help predict organ exposure of MSNs based on functional relationships (see above) between organ exposure ($AUC_{0-24\,h}$) and MSN size through interpolation within the size range of the study (about 32 nm to about 142 nm). As for extrapolation beyond the studied size range, we expect its accuracy to worsen for NP size below 5.5 nm. Because of predominance of renal clearance below 5.5 nm, systemic circulation and exposure of source-like and sink-like organs to such particles will be drastically reduced, which means that the correlation function for at least systemic circulation and source-like organs, if not for sink-like organs, will be reversed as per Choi et al. (2007). Thus, 5.5 nm was assumed as the safe lower bound for the functions defined in this study. For sizes above 142 nm, the functional relationship disclosed here is expected to apply, as larger sizes of NPs should continue to correlate with even greater hepatic and splenic uptakes (Lundy et al., 2016). Further, as for relationship between $AUC_{0-24\,h}$ and zeta potential, no significant effect of zeta potential was fouond on the systemic circulation and source-like organ exposure of MSNs. However, positive charge, with shielded surface amines, correlates with greater hepatobiliary excretion, hence lower liver accumulation compared to neutral MSNs, or cationic MSNs with surface exposed amines. The same trend holds true for urinary excretion and makes sense given the presence of anionic charge within the glomerular capillary wall[9], but most importantly it highlights the importance of surface exposure of charged molecules in affecting in vivo interactions. Based on these trends, we can extrapolate that anionic MSNs will have reduced hepatobiliary and urinary excretion.[14,40] Furthermore, based on the scope of our study, TMS25 and QA50 are proposed as the choice of MSNs for therapeutic applications, primarily due to their low hepatic and splenic clearance. Because TMS25 stays in circulation about four times longer than QA50, in applications demanding longer circulation times, e.g. tumor delivery, the neutral TMS25 MSN appears to be a better choice over the positive QA50.

EXAMPLE 7

Cholera toxin B (CTB) modified mesoporous silica nanoparticle supported lipid bilayers (CTB-protocells) are a promising, customizable approach for targeting therapeutic cargo to motoneurons. In the present study, the endocytic mechanism and intracellular fate of CTB-protocells in motoneurons was examined to provide information for the development of therapeutic application and cargo delivery. Pharmacological inhibitors elucidated CTB-protocells endocytosis to be dependent on the integrity of lipid rafts and macropinocytosis. Using immunofluorescence techniques, live confocal and transmission electron microscopy, CTB-protocells were primarily found in the cytosol, membrane lipid domains and Golgi. There was no difference in the amount of motoneuron activity dependent uptake of CTB-protocells in neuromuscular junctions, consistent with clathrin activation at the axon terminals during low frequency activity. In conclusion, CTB-protocells uptake is mediated principally by lipid rafts and macropinocytosis. Once internalized, CTB-protocells escape lysosomal degradation, and Background Cholera toxin B (CTB) modified mesoporous silica nanoparticle supported lipid bilayers (CTB-protocells) are a promising, customizable approach for targeting therapeutic cargo to motoneurons (Gonzalez Porras, 2016). Protocells consist of two types of fundamental building blocks, a mesoporous silica nanoparticle core (MSNPs) encapsulated by a supported lipid bilayer (Sun, 2015; Butler, 2016). Protocell modification with CTB allows targeting motoneurons since CTB binds ganglioside GM1 present in neuronal membranes (Sheikh, 1999; Zhang, 1995). The discovery that CTB-protocells can effectively enter motoneurons presents a potential strategy for overcoming the limitations of conventional 'free' drugs, including poor solubility, limited stability, rapid clearing, and, in particular, lack of selectivity, which results in non-specific toxicity to healthy cells. In order to inform selection of appropriate protocell cargo it is imperative to determine the biological mechanism(s) governing cellular uptake and trafficking after CTB-protocell internalization.

Nanoparticle uptake and intracellular trafficking depends on various physicochemical characteristics including particle size, shape, density, and surface chemistry. (Herd, 2013; Xiang, 2012) Nanoparticles can be internalized in cells by endocytosis, which involves the expenditure of metabolic energy, the movement and fusion of membranes and the displacement of cytoplasm in a complex series of events (Silverstein, 1977). Nanoparticles can also translocate through a membrane passively by deformation of membrane lipids (Beddoes, 2015; Le Bihan, 2009). Since CTB internalization is associated with lipid rafts endocytosis because of GM1 binding to rafts (Torgersen, 2001) and the size of raft domains is highly variable, CTB-protocell internalization may be limited to a subset of lipid rafts that include larger transient confinement domains of hundreds of microns (Dietrich, 2002). Macropinocytosis reflects the formation of big endocytic vesicles that sequester a large amount of fluid-phase contents. Among cells and in neurons, macropinocytosis is highly present due to its importance in cell-to-cell communication (Zeineddine, 2015). In various cells, macropinocytosis can be triggered by a variety of factors including nanoparticles (Beddoes, 2015).

Neurons undergo substantial membrane cycling at synapses in an activity-dependent fashion and membrane uptake varies depending on the rate of stimulation such that synaptic membrane recycling during physiological rates of activation primarily reflects clathrin-mediated endocytosis rather than macropinocytosis or other form of bulk membrane retrieval that have been reported during maximal (albeit non-physiological) activation (Royle, 2003; Nicholson-Fish, 2015; Soykan, 2016). It was hypothesized that CTB-protocell uptake in motoneurons is mediated by lipid raft endocytosis and macropinocytosis; and uptake is not affected by activity at the neuromuscular junction (NMJ). These internalization pathways are commonly associated with retrograde intracellular trafficking to the Golgi and endoplasmic reticulum, although transfer to endolysosomal compartments for ultimate degradation is also possible (Xiang, 2012; Xiang, 2012). Accordingly, it was also hypothesized that after internalization CTB-protocells can escape the endo-lysosomal pathway for degradation and become available to the cell.

Methods

Preparation of Mesoporous Silica-Supported Lipid Bilayer Nanoparticles (Protocells)

MSNPs with spherical shape and dendritic 5 nm diameter pore were synthesized via a base-catalyzed solution-based surfactant-directed self-assembly method, adapted from a published biphase synthesis method (Shen, 2014; Wang, 2012; Durfee, 2016). To prepare MSNPs, 193 mg of TEA (Sigma-Aldrich, St. Louis, Mo.) was combined with 36 mL water and 24 mL of 25 wt % CTAC (Sigma-Aldrich). The solution was sealed and stirred at 150 rpm at 55° C., MSNPs were fluorescently modified by dissolving 2.5 mg of Cy3-NHS Ester (Sigma-Aldrich) in 2.5 mL of N,N-dimethyl formamide (Sigma-Aldrich) followed by addition of 2.25 µL 3-aminopropyltriethoxysilane (APTES; Sigma-Aldrich). 20 mL of TEOS (Sigma-Aldrich) was added to the surfactant solution with continued stirring. After 19 hours, the organic phase was removed and 5 v/v % TEOS/cyclohexane was added to the solution. After 21 hours, the particle solution was sealed for hydrothermal treatment and stored at 70° C. for 24 hours. MSNPs were pelleted by centrifugation and surfactant was removed by dissolving MSNPs in 50 mL of 2M acetic acid (Sigma-Aldrich) and stored under static conditions for 2 hours at room-temperature. MSNPs were then transferred to acidic ethanol (20% HCl), sealed, and stirred at 150 rpm for 2 hours at 60° C. MSNPs were washed and stored in ethanol.

Fusion of liposomes to MSNPs (protocell assembly) was based on a method we described previously (Gonzalez Porras, 2016; Durfee, 2016). Briefly, 1,2-distearoyl-sn-glycero-3-phosphocholine (DSPC) phospholipids, cholesterol (Choi) and 1,2-distearoyl-sn-glycero-3-phosphoethanolamine-N-[amino(polyethyleneglycol)-2000] (DSPE-PEG2000-NH2) phospholipids (Avant' Polar Lipids, Birmingham, Ala.) were dried to form lipid films, MSNPs were dissolved in 0.5×PBS, added to lipid films then bath sonicated. Excess liposomes were removed by centrifugation and protocells were re-suspended in PBS (Life Technologies). CTB was conjugated to the protocells using the NeutrAvidin/biotin conjugation strategy described before (Gonzalez Porras, 2016; Durfee, 2016). CTB-biotin (Life Technologies) (50 µg in PBS) was added to NeutrAvidin modified protocells (1 mg in PBS) and incubated at room temperature for 1 hour. The non-conjugated CTB-biotin was removed by centrifugation and resulting targeted protocells were resuspended in PBS.

Cell Culture Conditions

NSC-34 motoneuron-like cells were propagated in 75 cm$^2$ flasks in Dulbecco's Modified Eagle Medium/Nutrient Mixture F-12, with GlutaMAX (ThermoFisher Scientific; Waltham, Mass.) supplemented with 10% fetal bovine serum and 2% Penicillin-Streptomycin.

CTB-Protocells Energy Dependent Uptake

Motoneuron-like cells were differentiated for 24 hours with serum-deprived media. Cells were then incubated with CTB-protocells for 1 hour at 37 or 4° C. After treatment, cells were washed and fixed in 4% paraformaldehyde (PFA). Cells were imaged with a 60× oil immersion lens (NA 1.2) using a Nikon A1 confocal microscope (Nikon Instruments Inc.) equipped with solid state lasers (405, 488, 561 and 640 nm) and appropriate filter combinations. Laser intensity, confocal aperture, and photomultiplier gain were kept constant across samples. NIS-Elements software (Nikon Instruments Inc.) was used for image processing and analysis. Single plane images were acquired in the nuclei midline of differentiated motoneurons (selected based on the expression of dendrites) and the mean protocell fluorescence per cell was quantified. To confirm the energy dependence in the uptake of CTB-protocells, an ATP depletion assay was conducted using 1M sodium azide (NaN$_3$) (Sigma-Aldrich) and 0.6 M of 2-deoxy-D-glucose (Sigma-Aldrich) diluted in glucose free Dulbecco's Modified Eagle Medium for 1 hour, as previously described. (Richard, 2003) ATP depleted media was removed and cells were treated with 50 µg/ml of CTB-protocells diluted in glucose free Dulbecco's Modified Eagle Medium for 1 hour. After washes, cells were imaged using the same procedure explained before.

Mechanism of CTB-Protocell Internalization in Motoneurons

To understand the role of lipid-raft microdomains, differentiated motoneuron-like cells were first incubated with CTB-protocells for 1 hour, rinsed with PBS, and further incubated with Alexa Fluor 488-labeled CTB (8 µg/ml, ThermoFisher Scientific) for 20 minutes at 37° C. followed by fixation in 4% PFA, and confocal imaging to measure the extent of colocalization. To study the different types of endocytosis, cells were pre-incubated with various endocytotic chemical inhibitors for 30 minutes followed by 1 hour of CTB-protocells treatment. 1 mM of methyl-β-cyclodextrin (MβCD) (Sigma-Aldrich) was used to inhibit cholesterol dependent endocytic processes (lipid rafts endocytosis) and 14 µg/ml of amiloride (Sigma-Aldrich) was used to inhibit macropinocytosis. The cellular fluorescence resulting from internalization of CTB-protocells was quantified per cell.

CTB-Protocell Uptake in Endo-Lysosomal Compartments

To examine the position of CTB modified protocells relative to the endo-lysosomal pathway, two approaches were followed. In the first approach antibodies against: early endosome antigen 1 (EEA1; ThermoFisher Scientific) as a marker of early endosomes, and lysosomal-associated membrane protein 1 (LAMP1; Abcam, Cambridge, Mass.) as a marker of lysosomes, were used. Motoneuron-like cells were continuously incubated with CTB-protocells for a set time period: 1 hour, 3 hours, 6 hours and 24 hours; fixed, permeabilized with 0.1% Triton™ X-100 in 0.1 M TBS and blocked with 4% donkey serum. EEA1 or LAMP1 primary antibodies were used followed by secondary antibody Cy5-conjugated anti-rabbit (Jackson lmmunoresearch, West Grove, Pa.). Confocal images were taken (Nikon A1) and quantitative colocalization analysis was performed using the Manders' coefficient plugin in ImageJ software. The secondary approach includes a pulse-chase setup to follow a small window of uptake events. Cells were treated with CTB-protocells for 1 hour only and then placed intro fresh media and imaged at different times (1 hour, 3 hours, 6 hours and 24 hours). For these experiments motoneuron-like cells were plated on glass bottom 35 mm culture dishes (MatTek Corporation; Ashland, Mass.). Cells were incubated with 1) LysoTracker® Blue DND-22 (ThermoFisher Scientific) for 30 minutes before CTB-protocells treatment, to stain acidic vacuoles; or 2) CellLight® Early Endosomes-GFP, BacMam 2.0, (ThermoFisher Scientific) for 24 hours before CTB-protocells treatment, to label early endosomes with green fluorescent protein (GFP) in live cells. Live cells were imaged using an inverted confocal microscope with 60× (NA 1.4) oil-immersion objective. Colocalization with lysosomes or endosomes was quantified using the intersection operation of the Elements software, which permits binarization of the intensity field according to the appropriate filters per channel and subsequent pixel intersection.

Subcellular Localization of CTB-Protocells

To determine if CTB-protocells are taking the retrograde pathway in motoneurons, their colocalization was evaluated with the Endoplasmic Reticulum (ER) and Golgi using the pulse-chase experiment explained before, Motoneuron-like cells were plated on glass bottom 35 mm culture dishes, differentiated and stained with 1) ER-tracker™ Blue-White DPX (ThermoFisher Scientific) to selectively labeled the ER or 2) BODIPY® TR Ceramide (ThermoFisher Scientific) to label the lipid trafficking and Golgi in living cells. After staining, cells were incubated with CTB-protocells for 1 hour followed by confocal live images at 1 hour, 3 hours, 6 hours and 24 hours. In both cases, an inverted confocal microscope was used. To determine how long CTB-protocells stay in motoneurons, motoneuron-like NSC-34 cells were seeded onto a 96-well plate, differentiated to maintain the cell density and treated with CTB-protocells. The fluorescence of rhodamine-labeled protocells was measured at different time points up to 5 days, using a FlexStation 3 microplate reader system (Molecular Devices, Sunnyvale, Calif.).

TEM

Motoneuron-like cells were cultured 24 hours prior to the experiment on 4-chamber Labtek slides, (ThermoFisher Scientific). After motoneuron differentiation, cells were incubated with CTB-protocells for 1 hour, 3 hours, 6 hours or 24 hours and fixed in Trump's fixative (1% glutaraldehyde and 4% formaldehyde in 0.1 M phosphate buffer, pH 7.2). Cells were rinsed in 0.1 M phosphate buffer (pH 7.2), followed by 30 minutes postfix in phosphate-buffered 1% osmium tetroxide ($OSO_4$). After rinsing in distilled water, cells were stained with 2% uranyl acetate for 15 minutes at 60° C., rinsed in distilled water, dehydrated in progressively higher concentrations of ethanol and 100% propylene oxide, and embedded in Spurr's resin. Thin (100 nm) sections were obtained using a Leica EM UC7 ultramicrotome (Buffalo Grove, Ill.), then placed on 200 mesh copper grids, and stained with lead citrate. Micrographs were acquired on a JEOL JEM-1400 TEM (Tokyo, Japan) operating at 80 kv.

Activity Dependent Uptake of CTB-Protocells in Axon Terminals

The uptake of CTB-protocells at NMJs was determined by visualizing changes in CTB-protocell fluorescence intensity in NMJs, with and without phrenic nerve stimulation. Adult male Sprague-Dawley rats (n=3 per group; initial body weight about 300 g) were used in the experiments. All procedures were approved by the Institutional Animal Care and Use Committee at Mayo Clinic.

Diaphragm muscle-phrenic nerve preparation. The midcostal hemidiaphragm and phrenic nerve were rapidly excised and placed in Rees-Simpson solution (of the following composition in mM: $Na^+$135, $K^+$5, $Ca^{2+}$2, $Mg^{2+}$1, $Cl^-$120, $HCO^{3-}$25) while bubbled with 95% $O_2$/5% $CO_2$ at 26° C. Subsequently, the excised hemidiaphragm muscle with phrenic nerve was stretched to optimal length (1.5 times resting length) and mounted on a silico rubber-coated dish (Sylgard DowCorning, Midland, Mich.) for treatment and labeling.

CTB-protocell treatment and NMJ labeling. In order to label recycling synaptic vesicles as they undergo cycles of exo- and endocytosis, the dye FM1-43 (Ex: 510 nm, Em: 626 nm; Molecular Probes, Eugene, Oreg.) was used. Tissue preparations were incubated in Rees-Simpson solution containing 50 µg/ml CTB-protocells and 5 µM of FM1-43. The phrenic nerve was taken into a suction electrode and stimulated using an A-M systems 2100 isolated pulse stimulator at 10 Hz (0.5 ms supramaximal pulses with 67% duty cycle) for 1 hour. Following a 15-minute wash, acetylcholine receptors at motor end-plates were fluorescently labeled with Alexa Fluor 647-conjugated α-bungarotoxin (Ex: 650, Em: 665 nm) (Invitrogen, Carlsbad, Calif.) to facilitate visualization of NMJs. Following sequential rinses in 0.1 M phosphate-buffered saline, preparations were fixed using 4% paraformaldehyde for 2-3 hours.

Fluorescence intensity measurements. Diaphragm NMJs were visualized using a Nikon C1 confocal microscope. Images were obtained using a 40× (NA 0.8) water immersion lens at 3 µm step size. Simultaneous three-channel detection was possible using appropriate dichroic and filter combinations to separate Alexa Fluor 647-bungarotoxin labeled motor end-plates, FM1-43-labeled presynaptic terminals and Cy3-conjugated CTB-protocells. Imaging and acquisition parameters were fixed so that relative changes in fluorescence intensity could be reliably measured across experimental conditions. A region of interest (ROI) outlining the motor end-plate of each NMJ was drawn from the maximum intensity projection in Nikon Elements. Within this ROI, the protocell fluorescence intensity was examined in each plane of the z-stack comprising the NMJ. The mean fluorescence intensity for each motor end-plate (within its defined ROI) was measured and the background subtracted.

Neuromuscular transmission measurements. The extent of neuromuscular transmission failure was assessed using a previously described technique (Mantilla, 2004; Blanco, 2001; Ermilov, 2010). Briefly, midcostal diaphragm-phrenic nerve preparations (3-4 mm wide) were pre-incubated with CTB-protocells (50 µg/ml) or vehicle for 1 hour in bath containing oxygenated Rees-Simpson solution. Subsequently, the central tendon was attached to a force transducer (model 6350; Cambridge Technology, Cambridge, Mass.), while the rib insertion was clamped with a micromanipulator. Isometric twitch force and maximum tetanic force (Po) were measured for each diaphragm segment. To measure the rate of neuromuscular transmission failure (NMTF), the phrenic nerve was stimulated (0.2-ms pulse at supramaximal intensity) using a suction electrode at 40 Hz in 330-ms duration trains repeated each second for a 2-minute period. Every 15 seconds, direct muscle stimulation (via plate electrodes; 1-ms supramaximal pulses at 40 Hz in 330-ms trains) was superimposed. The relative contribution of neuromuscular transmission failure to muscle fatigue, i.e., NMTF, was estimated by the equation: NMTF=(F−MF)/(1−MF), where F is a percent decrement in force during repetitive nerve stimulation, and MF is the percent force decrement during direct muscle stimulation.

Intrapleural Injection of CTB-Protocells (Proof of Concept)

Awake animals were lightly restrained slightly tilted on their side with the help of an assistant, as in previous studies (Alvarez-Argote, 2016; Gransee, 2013; Mantilla, 2013; Mantilla, 2009). While stabilizing the animal's back, the rib cage was palpated in order to identify the fifth intercostal space at the anterior axillary line. Using sterile conditions and appropriate antisepsis, a 50-µl Hamilton syringe was used to inject 50 µl of 1 µg/µl CTB-protocells (for a total of 50 µg of CTB-protocells) or 50 µl of 1 µg/µl unmodified protocells. Injections were performed transcutaneous into the thoracic cavity on the right side (5-7 mm deep, from skin). Animals were monitored closely for any signs of respiratory compromise such as unintentional pneumothorax, but none were evident in this study.

Tissue preparation. Following transcardial fixation, 5-10 mm of the right-phrenic nerve (proximal to the diaphragm) was dissected, the epineurium was removed and immersed in 24% sucrose in PBS for cryoprotection. A subset of nerves was mounted in slides pre-coated with Cell-Tak adhesive (Becton Dickinson Lab Ware, Bedford, Mass.) to perform confocal imaging of the whole nerve. Another subset of nerves was sectioned in 20 µm thick longitudinal sections using a Leica CM1860 cryostat (Leica Biosystems; Wetzlar, Germany) and frozen on Superfrost Plus slides (Thermo Fisher Scientific, Waltham, Mass.). All tissues were treated with graded alcohols and xylene, and coverslipped with DPX mountant (Fluka; Sigma-Aldrich, St. Louis, Mo.). Confocal Microscopy. Whole phrenic nerves and nerve sections were visualized using a Nikon C1 confocal microscope (Nikon Instruments Inc.). Images were obtained using a 20×0.8 NA oil immersion lens at 0.8 µm step size. For the whole nerve imaging, images were stitched to allow better visualization of the dissected nerve.

Statistical Analyses

All statistical evaluations were performed using standard statistical software (JMP 10.0, SAS Institute Inc., Cary, N.C.). Differences between treatment groups were examined using one-way analysis of variance, followed by Tukey-Kramer HSD test when appropriate. Statistical significance was established at the p<0.05 level. All experimental data are presented as mean±SE, unless otherwise specified.

Results

CTB-Protocell Uptake in Motoneurons is Enemy Dependent

Figure 39:
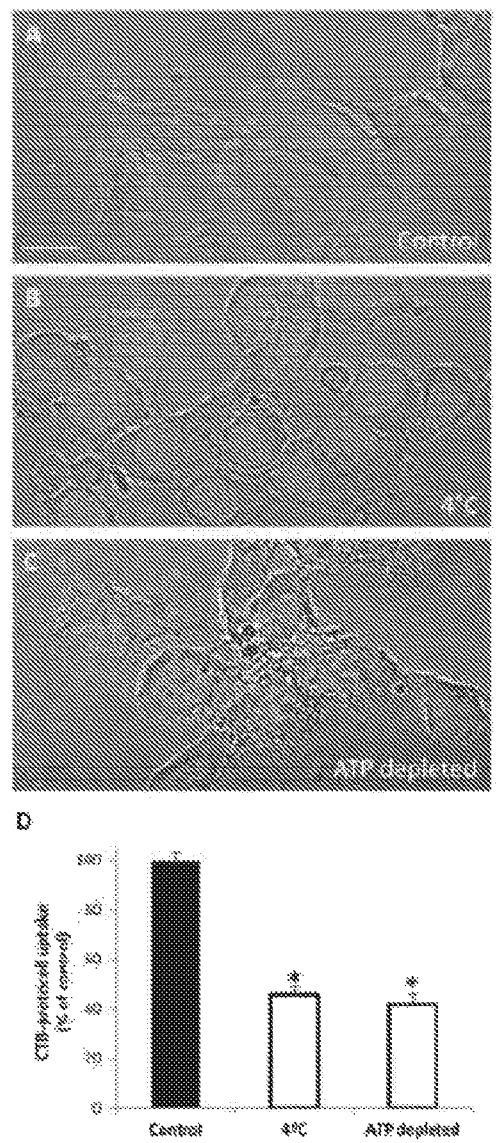
FIGS. 39A-D, Uptake of CTB-protocells in NSC-34 motoneuron-like cells. (A-C) Representative images of NSC-34 cells treated with CTB-protocells for 1 h at 37° C. (A), 4° C. (B) or following ATP depletion with $NaN_3$ (1M) and 2-deoxy-D-glucose (0.6M) (C). Bar, 10 μm. (D) Summary of intracellular CTB-protocell uptake (relative to control; n≥100 cells from three independent experiments). *, p<0.05 (ANOVA, $F_{2,497}$=96.11, p<0.001; post-hoc Tukey-Kramer).

Several proteins and enzymes are sensitive to temperature, thus, active processes are decreased by lowered temperatures. (Iacopetta, 1983; Saraste, 1986) CTB-protocell uptake in motoneurons significantly decreased by 54% at 4° C. compared to 37° C. (FIG. 39).

Energy dependency in the process of CTB-protocell internalization was corroborated by cellular ATP pool depletion. ATP depletion resulted in characteristic cell shape changes observed by confocal images of motoneuron-like cells. These findings are consistent with evidence that $NaN_3$ can disintegrate the actin cytoskeleton and destroy microfilament bundles (Svitkina, 1986). ATP depletion significantly reduced the uptake of CTB-protocells in motoneuron-like cells after 1 hour (59% reduction). Taken together, these results indicate that CTB-protocells are internalized into motoneurons via an energy dependent endocytosis mechanism.

Figure 40:
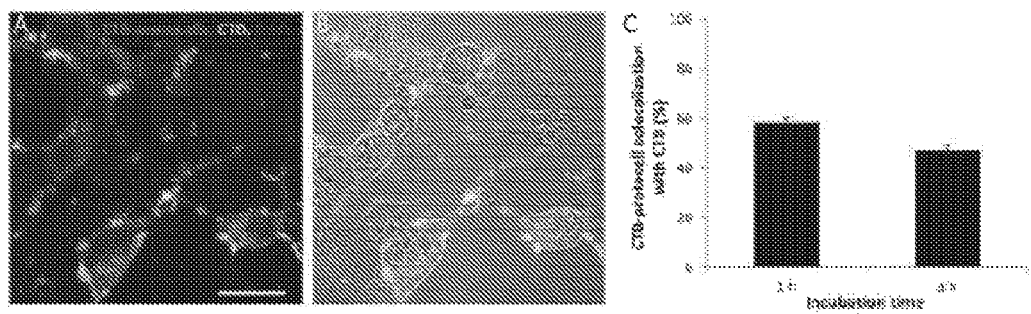
FIGS. 40A-C. Intracellular uptake of CTB or CTB-protocells by NSC-34 motoneuron-like cells. (A-B) Representative confocal image (A) and superimposed brightfield image (B) of CTB-protocells (red), CTB (green), colocalization (yellow) in motoneuron-like cells with nuclear stain (DAPI, blue), Bar, 10 mm. (C) Proportion of intracellular CTB-protocells displaying colocalization with CTB following 1 and 3 h incubation (n≥75 cells from three independent experiments), CTB-protocells show uptake via pathways shared swith CTB (i.e., lipid rafts) but this is limited to 50-60% of total uptake, FIGS. 41A-F, Uptake of CTB-protocells in NSC-34 motoneuron-like cells treated with endocytosis inhibitors. (A-E) Representative images of NSC-34 cells incubated with CTB-protocells and (A) vehicle, (B) amiloride (macropinocytosis inhibitor), (C) MβCD (lipid raft endocytosis inhibitor), (D) both amiloride and MβCD and (E) transferrin plus amiloride and MβCD. Transferrin endocytosis (clathrin-mediated) is evident despite amiloride and MβCD treatment. Bar, 10 μm. (F) Summary of intracellular CTB-protocell uptake (relative to vehicle control; n≥80 cells from three independent experiments). *¥, p<0.05 (ANOVA, $F_{3,395}$=76.48, p<0.001; post hoc Tukey-Kramer).

CTB-Protocell Uptake in Motoneurons is Mediated by Lipid Rafts and Macropinocytosis Confocal microscopy images of motoneuron-like cells were used to quantify the colocalization of CTB-protocells with CTB and confirm that CTB-protocells also follow the lipid raft pathway previously reported for CTB. (Chinnapen, 2007) 50% of CTB-protocells co-localized with CTB at 1 hour and 3 hours of incubation (FIG. 40), suggesting that lipid rafts play a major role in CTB-protocell uptake but it is not the only endocytic mechanism.

Figure 41:
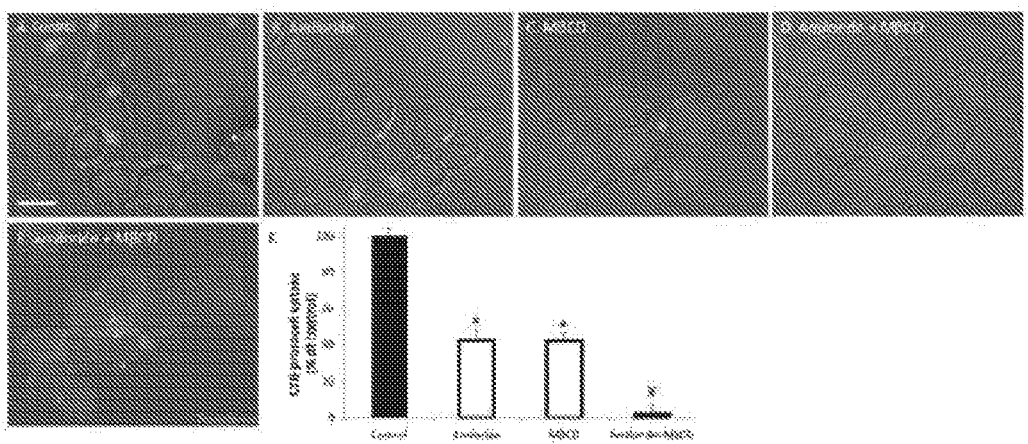

To further test the details of the mechanism of CTB-protocells uptake, motoneuron-like cells were incubated with two different endocytic inhibitors for 30 minutes before treatment with CTB-protocells (FIG. 41). Following pre-treatment with amiloride, (inhibitor of macropinocytosis) (West, 1989), CTB-protocell uptake decreased about 60% after 1 hour of treatment. A similar inhibition was obtained by pre-treatment with MβCD (inhibitor of lipid rafts endocytosis) (Kilsdonk, 1995). In the presence of both amiloride and MβCD, uptake of CTB-protocells was completely abolished, confirming the role of macropinocytosis and lipid raft pathways as the main endocytosis mechanisms in motoneurons. Importantly, uptake of transferrin, one of the best-characterized clathrin-dependent cargoes, (Motley, 2003) was unimpaired after amiloride and MβCD endocytosis inhibitor co-treatment, verifying cell viability and effective endocytosis via a different mechanism.

Figure 42:
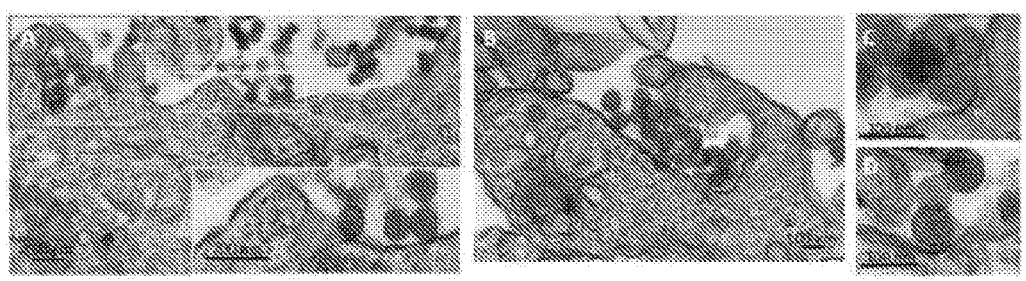
FIGS. 42A-D. TEM images of NSC-34 motoneuron-like cells incubated with CTB-protocells for 3 h. Uptake of CTB-protocells via macropinocytosis is evident by membrane ruffling (membrane extensions) around CTB-protocells (red box in (A), and (B)). Association of CTB-protocells with lipid microdomains (membrane sections with increased electron density, arrows in yellow box, inset in (A) and (C)). Bar, 200 nm in (A), 100 nm in (B) and 50 nm in (C-D).

In TEM images obtained at various times following CTB-protocell treatment, membrane ruffling (extensions) was evident engulfing large amounts of CTB-protocells (FIG. 42), consistent with macropinocytosis (Meier, 2002). Lipid raft microdomains, defined by electron dense staining with $OsO_4$, (Wilson, 2004) displayed higher CTB-protocell association than other membrane portions. These imaging results are consistent with confocal imaging studies indicating endocytosis of CTB-protocells in motoneurons is mainly mediated by two mechanisms: lipid rafts and macropinocytosis.

CTB-Protocells Avoid Endolysosomal Pathways in Motoneurons

Colocalization of CTB-protocells under conditions where cells were continuously incubated (no change in medium) with CTB-protocells (50 µg/ml), was studied. Minimal colocalization (about 10%) of CTB-protocells with the immunofluorescence of protein markers for early endosomes (EEA1) or lysosomes (LAMP1) was evident (Table 2), and this level of colocalization was unchanged up to 24 hours. In addition, a pulse-chase setup was used to investigate whether continuous exposure to CTB-protocells impacted uptake. Motoneuron-like cells were incubated with CTB-protocells for 1 hour at a lower concentration (20 µg/ml) in order to facilitate tracing intracellular CTB-protocells. Single confocal plane images at the mid-nuclear region were superimposed to brightfield images for these analyses (FIG. 43) Colocalization of CTB-protocells with the lysosomal stain LysoTracker was less than 20% at all time points. Colocalization with early endosomes labeled by GFP was also lower than 20% until 6 hours and increased to about 30% at 24 hours. Taken together, these data indicate that the majority of CTB-protocells don't follow the typical endo-lysosomal pathway for degradation.

TABLE 2

Percent colocalization based on Mander's coefficient

| Time | Endosomes | Lysosomes |
|---|---|---|
| 1 h | 6.0 ± 1.5% | 2.7 ± 1.8% |
| 3 h | 10.6 ± 1.2% | 9.3 ± 0.9% |
| 6 h | 9.6 ± 2.1% | 11.3 ± 1.0% |
| 24 h | 9.0 ± 2.06% | 7.1 ± 0.9% | n = ~300 cells from 2 independent experiments.

Figure 44:
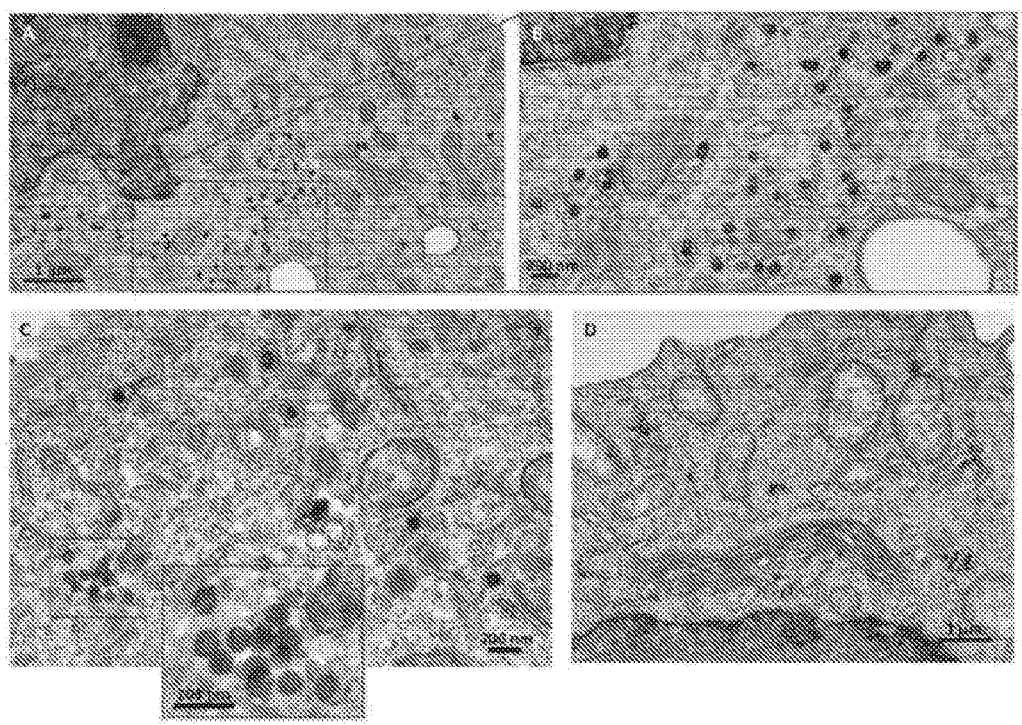
FIGS. 44A-D, TEM images of intracellular CTB-protocells in NSC-34 motoneuron-like cells. Note CTB-protocells are visualized as individual particles in the cytosol (red boxes and inset in A (B) and C) as well as small membrane bound compartments (arrows, consistent with early endosomes or Golgi). Also note lack of localization in larger vesicle compartments (e.g., late endosomes or lysosomes).

The localization of CTB-protocells in TEM images of motoneuron-like cells collected after continuous treatment is consistent with the results of the confocal studies. At all-time points, CTB-protocells were visualized primarily as individual particles in small membrane bound compartments or in the cytosol (FIG. 44). There was scant evidence of CTB-protocells inside larger vesicle compartments such as late endosomes or lysosomes.

Figure 43:
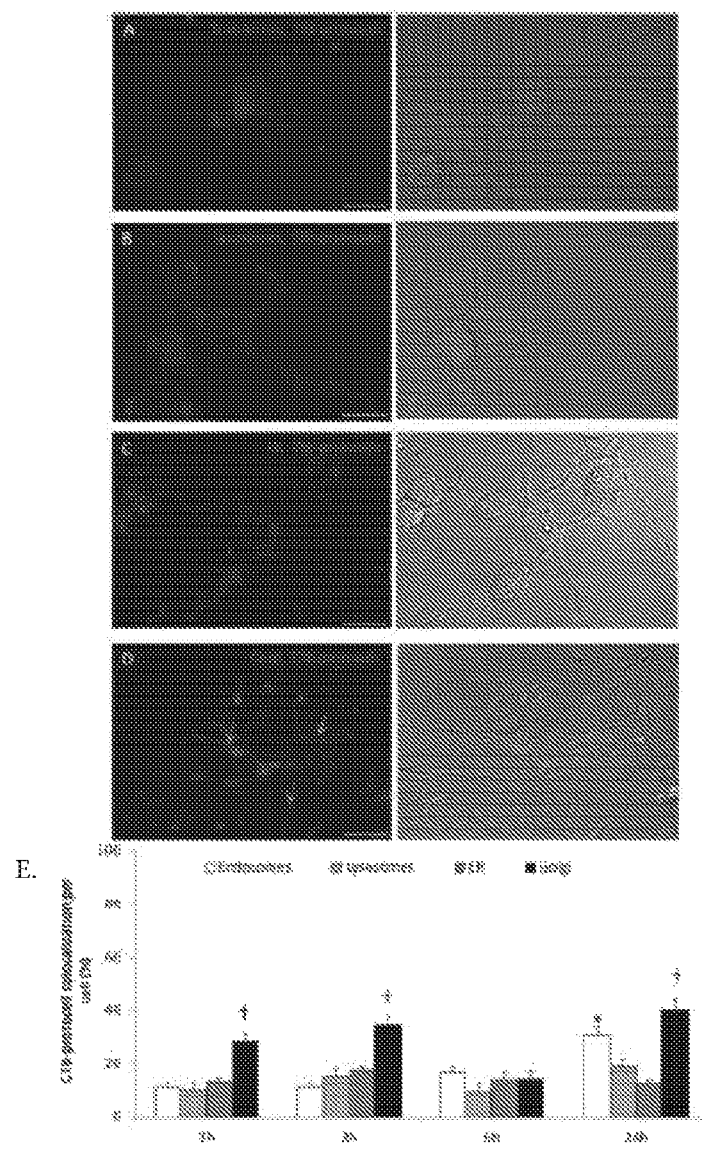
FIGS. 43A-E. Distribution of CTB-protocells across intracellular NSC-34 motoneuron-like cells. (A-D) Representative confocal (left) and superimposed brightfield images (right) after 1 h treatment with CTB-protocells and organelle labeling for lysosomes (A), endosomes (B), ER (C) or Golgi (D). Bar, 200 mm. (E) Summary of CTB-protocell colocalization with different organelles (two-way ANOVA, $F_{15,929}$=10.04, p<0.0001; post hoc Tukey-Kramer, p<0.05; *, different from other time points; †, different from other organelles at same time point). Each bar represents the average of at least 75 cells from three independent experiments.

CTB-Protocells are Primarily Found in the Cytosol and Membranous Lipid Domains in Motoneurons Using a similar pulse-chase setup experiment, colocalization of CTB-protocells with the ER (stained with ErTracker) or lipid-driven membrane domains including the Golgi apparatus (stained with Bodipy) was evaluated (FIG. 43). Colocalization of CTB-protocells differed over time across intracellular organelles with greater CTB-protocell localization in the Golgi across time and increasing in endosomes by 24 hours. These results indicate that CTB-protocells are directed to the Golgi apparatus as a major membrane sorting station, consistent with previous reports for the trafficking of compounds internalized via lipid raft endocytosis (Chinnapen, 2007).

Figure 45:
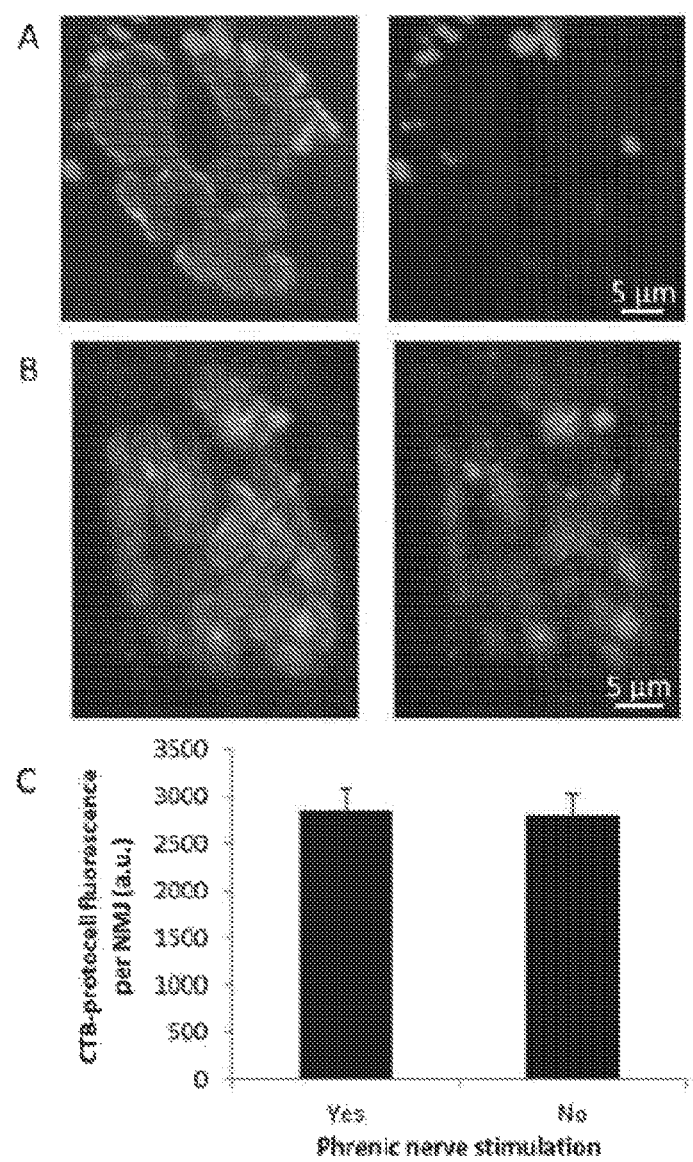
FIGS. 45A-C. Representative maximum intensity projection confocal micrographs of diaphragm NMJs. Diaphragm muscle-phrenic nerve preparations were incubated (A) in the absence of electrical stimulation and (B) with 1 h of repetitive electrical nerve stimulation (10 Hz, 0.1 ms, 300 ms trains repeated every s). (C) Average CTB-protocell fluorescence per NMJ (n=90 NMJs per stimulation group from 3 preparations for each condition).

Intracellular CTB-protocell fluorescence remained mostly unchanged between 1 hour and 24 hours of incubation, with a small decrease in fluorescence by 6 hours. Of note, a similar trend was evident for Golgi colocalization. Results of fluorescence measurements overtime showed that the half-life of CTB-protocells in motoneurons is 3.6 days, indicating a slow exocytosis process consistent with the intracellular pathways followed after lipid raft endocytosis and micropinocytosis (FIG. 44) accompanied potentially by protocell degradation via hydrolysis of the MSN core to form non-toxic silicic acid by-products. TEM images confirmed the confocal imaging data and for up to 24 hours of incubation, CTB-protocells were found inside cisternae structures consistent with Golgi or other lipid-driven membrane domains in proximity to nuclei (FIG. 45).

Figure 46:
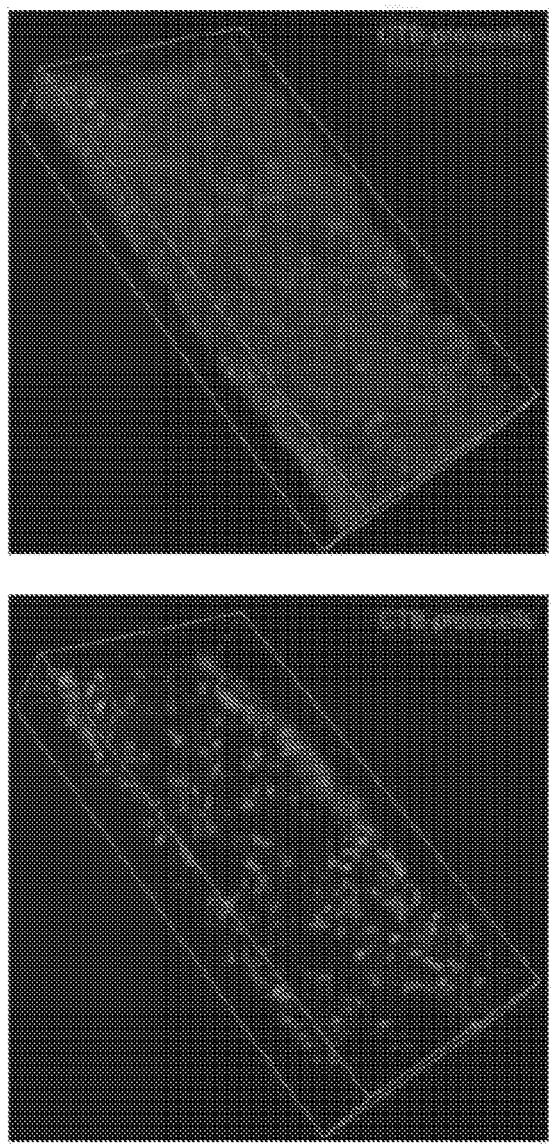
FIG. 46. Evidence of CTB-protocell fluorescence after intrapleural injections. Representative 3D reconstruction of a phrenic nerve section from an animal injected with CTB-protocells (n=3 animals injected).

CTB-Protocell Uptake at the Axon Terminals is not Influenced by Electrical Stimulation In order to determine if motoneuron activity increases the uptake of CTB-protocells, ex vivo diaphragm muscle-phrenic nerve preparations were used. Motor end-plates and presynaptic terminals were labeled using Alexa Fluor 647-conjugated a-bungarotoxin and FM1-43, respectively. Good visualization of both presynaptic and postsynaptic structures was evident (FIG. 46), FM1-43 uptake only occurred with repeated nerve stimulation. In the absence of stimulation, uptake was minimal. CTB-protocell fluorescence showed larger punctate structures, suggesting their presence in structures other than synaptic vesicles such as macropinosomes (Teng, 2007). Indeed, these punctate structures were visualized at NMJs of hemi-diaphragms with and without phrenic nerve stimulation and CTB-protocell uptake didn't change with phrenic nerve stimulation at the low, physiological rate tested (10 Hz).

CTB-Protocell Uptake at the Axon Terminals Doesn't Impair the Synaptic Transmission The effects of CTB-protocells treatment on synaptic transmission, measured as the extent of neuromuscular transmission failure are observed in Table 3. Compared to controls, neuromuscular transmission didn't change following CTB-protocell treatment. Following 2 minutes of repetitive nerve stimulation, the contribution of neuromuscular transmission failure to diaphragm muscle fatigue was 58.4% for controls, 58.3% for CTB-protocell-treated. To evaluate the muscle quality, contractile and fatigue properties of the diaphragm were also evaluated. The Pt and Po generated by the diaphragm were not different between control and CTB-protocells-treated groups. Accordingly, the ratio of twitch to tetanic force was not different across groups.

TABLE 3

Neuromuscular transmission failure (NMTF) and isometric contractile and fatigue properties following CTB-protocell treatment.

| Group | NMTF (%) | Specific $P_t$ (N*cm$^{-2}$) | Specific $P_o$ (N*cm$^{-2}$) | $P_t P_o$ |
|---|---|---|---|---|
| Control | 58.4 ± 8.4 | 5.61 ± 0.46 | 17.1 ± 1.03 | 0.33 ± 0.02 |
| CIB-protocells | 58.3 ± 8.4 | 5.54 ± 0.46 | 17.4 ± 1.03 | 0.32 ± 0.02 |

Diaphragm muscle-phrenic nerve preparations and diaphragm muscle strips were obtained from n = 3 animals per group. Data are mean ± SE.

CTB-Protocells Fluorescence is Evident in the Phrenic Nerve After In Vivo Intrapleural Injection Intrapleural injection of CTB labels phrenic motoneurons within the cervical spinal cord because CTB can be retrogadely transport through the nerve (Alvarez-Argote, 2016; Gransee, 2013; Mantilla, 2013; Mantilla, 2009). As a proof of concept, using the same intrapleural injection technique the presence of CTB-protocells or protocells was evaluated in the phrenic nerve after 24 hours of administration. As showed in FIG. 47, fluorescence of the CTB-protocells was evident in the whole nerve as well as in the 20 μm sections (not shown), indicating uptake and retrograde transport by axons.

Discussion

CTB-protocells represent a novel drug delivery system to motoneurons that can engage biological retrograde pathways not easily reached with untargeted delivery methods. The cytosolic availability of CTB-protocells that avoid lysosomal degradation fulfills an important medical need of targeted vehicles that can load different cargoes for the treatment of neuromuscular disorders, given that current treatments are limited and hindered by bioavailability and off-target effects (Edupuganti, 2012; Lee, 2013), Endocytosis of CTB-Protocells in Motoneurons Endocytosis occurs via various mechanisms and in motoneurons can take place at the dendrites, cell bodies, and axons. We examined endocytosis both in cultured motoneuron-like cells and at NMJs of rat diaphragm muscle-phrenic nerve preparations. The motoneuron-like cells are useful as a model cell line for motoneurons, and share endocytosis mechanisms with motoneurons in vivo (Maier, 2013; Matusica, 2008). These characteristics have permitted their use in understanding receptor trafficking within motoneurons. (Matusica, 2008) Importantly, these cells express GM1 ganglioside as motoneurons in vivo (Gonzalez Porras, 2016) which allow them to be used to study the internalization and intracellular pathway of CTB and CTB-protocells. CTB-modified protocells were previously reported to show uptake by cultured motoneurons and axon terminals in a selective manner, compared to unmodified protocells (Gonzalez Porras, 2016). Consistent with the targeting to motoneurons following modification with CTB, CTB-protocells showed extensive, but not exclusive, colocalization with CTB. Previous studies also support the targeting to motoneurons with systemic CTB administration (Alisky, 2002).

All the pathways involved in endocytosis are energy dependent. Indeed, we found generally similar effects on CTB-protocell uptake in studies conducted at low temperature and following ATP depletion (about 60% decrease). Low levels of residual nanoparticle uptake are still observed at temperatures supporting cell viability (Cartiera, 2009). Also, effects of $NaN_3$ and 2-Deoxy-D-glucose are time and dose dependent (Kang, 2001).The present studies comprised exposures to preserve viability, and after removal of $NaN_3$ and 2-Deoxy-D-glucose, ATP production could have been partially restored.

CTB uptake by cells is known to reflect interactions with lipid domains rich in GM1 gangliosides. (Miller, 2004) Consistent with the CTB internalization pathway, inhibition of lipid rafts endocytosis by MβCD decreased the CTB-protocell uptake in 40%. MβCD is a cyclic oligomer of glucopyranoside that inhibits cholesterol-dependent endocytic processes by reversible extracting the steroid out of the plasma membrane (Rodal, 1999). The colocalization of some CTB-protocells with CTB and the inhibition of half of the CTB-protocell uptake by disruptors of lipid rafts, confirm that indeed some CTB-protocells follow the CTB endocytic pathway, but also implies the existence of another endocytic mechanism, Given that macropinocytosis a highly present process in neurons, it is more likely that other particles such as viruses and nanoparticles, hijack the machinery involved in macropinocytosis to gain cell entry (Hollidge, 2012; Mao, 2017). Macropinocytosis or closely related processes, are thought to regulate growth cone membrane recycling and are an integral part of growth cone collapse, axon retraction and turning during development and injury in neurons (Kolpak, 2009; Tom, 2004). Inhibition of macropinocytosis with amiloride (an inhibitor of Na/H exchange at the cell surface), (Grinstein, 1989) decreased the uptake of CTB-protocells by about 60%. Furthermore, co-incubation of CTB-protocells with both inhibitors (amiloride and MβCD) completely blocked the CTB-protocell uptake, indicating that CTB-protocells are using lipid rafts and macropinocytosis as a primary entry mechanism and its uptake is not occurring by passive mechanisms. Cell viability after chemical inhibitor treatments was confirmed by un-impairment of transferrin endocytosis, a molecule internalized by clathrin endocytosis.

Although the use of chemical inhibitors reveals molecular components required for CTB-protocell internalization, they could have indirect effects that may influence another process in the cell (Vercauteren, 2010; Dutta, 2012). To overcome these limitations, TEM images were used to observe how CTB-protocells interact with motoneuron membranes. Indeed, images showed distinctive characteristics of CTB-protocells being endocytosed by lipid rafts (CTB-protocells interaction with membrane electron dense staining) (Wilson, 2004; Barnakov, 1994) and macropinocytosis (membrane ruffling engulfing a large amount of CTB-protocells).

Intracellular Trafficking Pathways in Motoneurons

Intracellular pathways are dictated by the endocytosis mechanisms (Zhang, 2015). After lipid raft endocytosis, the CTB intracellular distribution is known to follow a retrograde pathway and travels from an early endosome through the trans-Golgi network. (Chinnapen, 2007) The pathway of macropinosomes depends on the cell type. (Meier, 2003; Swanson, 1995) For example in macrophages, macropinosomes become acidified and then completely merge into the lysosomal compartment, (Meier, 2003) while in other cells although the pH decreases, macropinosomes do not fuse into lysosomes and can become "leaky" vesicles (Wadia, 2004). To understand what happens with CTB-protocells after they get internalized by macropinocytosis in motoneuron-like cells, we evaluated whether CTB-protocells can be found in endosomes and lysosomes. In a continuous exposure of CTB-protocells to NSC-34 motoneuron-like cells up to 24 hours, there was minimal colocalization of CTB-protocells with endosomes (EEA1) and lysosomes (LAMP1). Since fluorescent colocalization studies using confocal microscopy have limited spatial resolution, we also used TEM images to confirm intracellular CTB-location. TEM images did not show CTB-protocells in double membrane vesicles, usually recognized as lysosomes or late endosomes. In addition, to analyze a small window of uptake events (1 hour) instead of continuous treatment, we used a pulse-chase setup yielding similar consistent results in terms of CTB-protocell subcellular localization. The general larger colocalization with membranous lipid domains and the Golgi apparatus observed in confocal and TEM images compared to other organelles is consistent with its role as a membrane sorting station of lipid raft microdomains (Diaz-Rohrer, 2014). In neurons, the Golgi is not only important in the trafficking of ion channels, receptors, and other signaling molecules, but also mediates transport of exogenous molecules by retrograde and trans-synaptic pathways (Thayer, 2013). Indeed, lipid raft endocytosis is usually a nonacidic and nondigestive route of internalization, (Ferrari, 2003) and lipid binding toxins, such as CTB, are transported via the Golgi to the endoplasmic reticulum (Chinnapen, 2007). Therefore, it is most likely that the CTB-protocells internalized through lipid raft microdomains would travel to the Golgi complex. Understanding the trafficking of nanoparticles may inform their therapeutic application. For instance, consistent with CTB-protocells taking a retrograde pathway, CTB-protocells show promise as a platform to target the Golgi complex and regulate Golgi fragmentation in motoneurons with neurodegenerative diseases (Liu, 2017). Also, TEM images showed a large portion of CTB-protocells free in the cytosol, thus CTB-protocells could also serve as a delivery platform to target cell membrane impermeable cargoes that will be available when delivered to the cytosol and that don't need to be activated by trafficking to specific organelles (e.g., lysosomes if activated at low pH). Change in incubation time did not influence localization of CTB-protocells which suggests that the binding of CTB-protocells to the plasma membrane is a fast process (<1 hour), but the internalization mechanism is a continuous process that could be regulated by the frequency of the different endocytic pathways. For instance, lipid rafts associated with caveolae (mechanism for cholera endocytosis) are usually small in size and slowly internalized, (Conner, 2003) while macropinosomes are relatively large constituting an efficient route for the nonselective endocytosis of solutes from the extracellular fluid. CTB-protocell exocytosis was shown to be a slow process consistent with the internalization occurring through macropinocytosis and lipid rafts. It is more likely that the CTB-protocells going to the Golgi would be trapped in secretory vesicles for longer times (Sakhtianchi, 2013). Also, it has been demonstrated that nanoparticles that translocate into the cytoplasm have greater difficulty in exocytosis compared to a typical exocytosis process that occurs through the endo-lysosomal pathway (Stayton, 2009).

Activity Dependent Uptake of CTB-Protocells

The dynamic exchange of the neuronal membrane occurs primarily at axon terminals and plays an important role in multiple pathways controlling cellular homeostasis, motility and survival (Deinhardt, 2005). Membrane cycling in motoneurons comprises release of neurotransmitters from synaptic vesicles and replenishment of the synaptic vesicle pool, maintaining membrane homeostasis. Activity-dependent membrane cycling occurs in response to axonal discharge and the endocytic events following synaptic vesicle release depend on stimulation frequency (Royle, 2003; Nicholson-Fish, 2015; Soykan, 2016). Under low, physiological stimulation frequencies, synaptic vesicle pools are recycled back by clathrin mediated endocytosis (Clayton, 2009; Royle, 2003). The lack of activity-dependent uptake of CTB-protocells at NMJs is consistent with clathrin-mediated endocytosis not participating in CTB-protocell uptake. This finding has important implications in future applications where unstimulated motoneurons (e.g., after spinal cord injury) or disease motoneurons (e.g., amyotrophic lateral sclerosis) will be targeted.

The nature and molecular components of other modes of synaptic vesicle recycling and the underlying mechanisms remain a matter of debate (Soykan, 2016). However, some studies suggest that sustained stimulations will elicit activity-dependent bulk endocytosis of extensive membrane patches (Clayton, 2009; Nicholson-Fish, 2015). The possible impact of such stimulation on CTB-protocell uptake remains undetermined. Importantly, after CTB-protocell uptake at the axon terminals, the synaptic transmission was not impaired, suggesting that the CTB-protocell intracellular pathway don't interfere with motoneuron activity.

Despite the importance of motoneurons in human health and disease, the precise control of their membrane dynamics and the molecular basis of the coordination of specific endocytic events with retrograde transport pathways remain largely unknown. As a proof of concept, we demonstrated evidence of CTB-protocells retrograde transport in the phrenic nerve after intrapleural injection. Carriers for toxins in neurons, including CTB, share retrograde transport endosomes with neurotrophins characterized by lack of acidification during the process (Wang, 2016; Lalli, 2002; Butowt, 2003). It is possible that CTB-protocells hijack this transport machinery to travel along the axon. Future studies will explore the retrograde transport of CTB-protocells to the cell soma of motoneurons in the spinal cord. Mechanisms that link biological efficacy to subcellular nanocarrier performance, including the fate of carrier constituents, drug bioavailability and cell integrity, represent important information to understand cell physiological properties and mechanisms by which motoneurons interact with nanoparticles that will allow improving the design of drug targeting therapy. The intracellular drug-delivery processes will depend on both nanocarrier intrinsic properties (Rejman, 2004) and the endocytic pathways in a given cell type (Zauner, 2001). Mechanisms of CTB-protocell endocytosis (lipid raft and macropinocytosis) and the subsequent intracellular trafficking pathways are dictated by the surface motoneuron targeting ligand CTB, the size of CTB-protocells and the main endocytic pathways present in motoneurons. The localization of CTB-protocells in the cytosol and in the Golgi apparatus, suggest that CTB-protocells can effectively deliver cargo intracellularly and take a "retrograde" trafficking pathway. These studies support the utility of CTB-protocells as a motoneuron targeting therapeutic platform to engage biological pathways not readily accessible with untargeted delivery methods.

REFERENCES

Albanese et al., *Annu. Rev. Biomed. Eng.*, 14:1, (2012).
Alisky et al., *Ever. Neurol.*, 178:139 (2002).
Ashley et al., *ACS Nano.*, 6:2174 (2012).
Ashley et al., *Nat. Mater.*, 10:389 (2011).
Baeza et al., *Adv. Funct. Mater.*, 24:4625 (2014).
Barnakov, *J. Microsc.-Oxford* 175:171 (1994).
Beddoes et al., *Adv. Colloid Interface Sci.*, 218:48 (2015).
Bello et al., *Microsc. Microanal.* 16:456 (2010).
Berger et al., *J. Pathol.*, 152:297 (1987).
Bozzuto et al., *Int. J. Nanomedicine*, 10:975 (2015).
Butler et al. *Small*, 12:2173 (2016).
Cartiera et al., *Biomaterials*, 30:2790 (2009).
Child et al., *ACS Nano*, 5:7910 (2011).
Chinnapen et al., *FEMS Microbiol. Lett.* 266:129 (2007).
Chung et al., *Biomaterials.*, 28:2059 (2007).
Clayton and Cousin, *J. Neurosci. Meth.*, 185:76 (2009).
Conner and Schmid, *Nature*, 422:37 (2003).
Dacarro et al., *Dalton Trans.*, 41:2456 (2012).
Deinhardt and Schiavo, *Biochem. Soc. Symp.*, 72:139 (2005).
Diaz-Rohrer et al., *Bba-Biomembranes*, 1838:3003 (2014).
Dietrich et al., *Biophys. J.*, 82:274 (2002).
Dobrovolskaia et al., *Mol. Pharmaceut.*, 5:487 (2008).
Drummond et al., *J. Control. Release*, 141:13 (2010).
Durfee et al., *ACS Nano*. 10:8325 (2016).
Ediriwickrema et al., *ACS Biomater. Sci. Eng.*, 1:64 2015.
Edupuganti et al., *FEBS J.*, 279:2555 (2012).
Ferrari et al., *Mol. Ther.*, 8:284 (2003).
Florence, *J. Control. Release*. 164:115 (2012).
Fournier et al., *Neurosc. Lett.*, 125:34 (1991).
Gonzalez Porras et al., *J. Neurosc, Meth.*, 273:160 (2016),
Grinstein et al., *Biochem. Biophs. Acta*, 988:73 (1989),
Hanahan et al., *Cell*, 144:646 (2011).
He et al., *Biomaterials*, 31:1085 (2010),
Herben et al., *Clin. Pharmacokinet.*, 31:85 (1996),
Herd et al., *ACS Nano.*, 7:1961 (2013),
Hollidge et al., *J. Virol.*, 86:7988 (2012).
Kang et al., *Am. J. Physiol.-Endoc. M.*, 280:E428 (2001).
Karakoti et al., *Angew, Chemie Int. Ed.*, 50:1980 2011.
Kilsdonk et al., *J. Biol. Chem.*, 270:17250 (1995).
Kolpak et al., *J. Neurosci.*, 29:10488 (2009).
Lai et al., *J. Am. Chem, Soc.*, 125:4451 (2003).
Lee et al., *PloS One*, 8:e78724 (2013).
Leong et al., *Nat. Protoc.*, 5:1406 (2010).
Lin et al., *J. Am. Chem. Soc.*, 132:4834 (2010).
Lin et al., *J. Am. Chem. Soc.*, 133:20444 (2011).
Lin et al., *J. Phys. Chem. Lett.*, 3:364 (2012).
Liu et al., *J. Control. Release*, 219:632 (2015).
Liu et al., *Proc. Nat. Acad. Sci. USA*, 114:346 (2017).
Maeda, *Adv. Drug Deliv. Rev.*, 91:3 (2015).
Maier et al., *Neurochem. Int.*, 62:1029 (2013).
Mantilla et al., *J. Neurosc. Meth.*, 182:244 (2009).
Mantilla et al., *Muscle & Nerve*, 29:381 (2004),
Mao et al., *Mol. Ther.*, 25:803 (2017).
Matsumura et al., *Cancer Res.*, 46:6387 (1986),
Matusica et al., *J. Neurosci. Res.*, 86:553 (2008).

McKee et al., *Cancer Res.*, 66:2509 (2006),
Meier and Greber, *J. Gene Med.*, 5:451 (2003).
Meier et al., *J. Cell. Biol.*, 158:1119 (2002).
Miller et al., *Biophys. J.*, 86:3700 (2004).
Motley et al., *J. Cell. Biol.*, 162:909 (2003).
Mura et al., *Nat. Mater.*,12:99 (2013).
Nel et al., *Nat. Mater,* 8:543 (2009).
Nett et al., *Cancer Res.*, 60:2497 (2000).
Nguyen *Acc. Chem. Res.*, 48:3016 (2015).
Noh et al., *Biomaterials*, 45:81 (2015).
Nussbaumer et al., *Talanta*, 85:2265 (2011).
Parodi et al., *ACS Nano.*, 8:9874 (2014).
Richard et al., *J. Biol. Chem.*, 278:585 (2003).
Rodal et al., *Mol. Biol. Cell.*, 10:961 (1999).
Rosenholm et al., *ACS Nano.*, 3:197 (2009).
Royle and Lagnado, *J. Physio.* (*London*), 553:345 (2003).
Sakhtianchi et al., *Adv. Colloid. Interf. Sci.*, 201-202:18 (2013).
Saraste et al., *Proc. Natl. Acad. Sci. USA,* 83:6425 (1986).
Shen et al., *Nano. Left.*, 14:923 (2014).
Shin et al., *Nanoscale.*, 5:5879 (2013).
Siegel et al., *CA Cancer J. Clin.*, 66:7 (2016).
Silverstein et al., *Annu. Rev. Biochem.*, 46:669 (1977).
Simmchen et al., *Nanoscale*, 6:8907 (2014).
Slowing et al., *J. Am. Chem. Soc.*, 128:14792 (2006).
Soykan et al., *Curr. Obin. Neurobiol.*, 39:17 (2016).
Stayton et al., *Anal. Bioanal. Chem.*, 394:1595 (2009).
Sun et al., *Biomaterials*. 35, 836 (2014).
Sun et al., *Life* (*Basel*), 5:214 (2015).
Svitkina et al., *J. Cell. Sci.*, 82:235 (1986).
Tarn et al., *Acc. Chem. Res.*, 46:792 (2013).
Teng et al., *J. Physiol.* (*London*), 582:243 (2007).
Thayer et al., *Proc. Natl. Acad. Sci. USA.* 110:1482 (2013).
Vallet-Regi et al., *Angew. Chemie-International Ed.*, 46:7548 (2007).
Vallet-Regi et al., *Chem. Mater.*, 13:308 (2001).
Vercauteren et al., *Mol, Ther.*, 18:561 (2010).
Villegas et al., *ACS Appl. Mater. Interfaces*, 7:24075 (2015).
Wadia et al., *Nat. Med.*, 10:310 (2004).
Wang et al., *J. Colloid. Interf. Sci.*, 385:41 (2012).
Wang et al., *Small*, 14:1919 (2011).
West et al., *J. Cell. Biol.*, 109:2731 (1989).
Wilhelm *Nat. Rev. Mater.*, 1:16014 (2016).
Wilson et al., *Mol. Biol. Cell*, 15:2580 (2004).
Xiang et al., *J. Control Release*, 158:371 (2012).
Xu et al., *Trends Mol. Med.*, 21:223 (2015).
Zeineddine and Yerbury, *Front. Physiol.* 6: (2015).
Zhang et al., *ACS Nano.*, 9:8655 (2015).
Zhang et al., *J. Am. Chem. Soc.*, 134:15790 (2012).
Zhang et al., *Small.* 7:271 (2011).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A population of protocells comprising a cargo and a lipid bi- or multi-layer coating monodisperse mesoporous silica nanoparticles (MSNPs), wherein the lipid bi- or multi-layer comprises a plurality of lipid molecules comprising polyethylene glycol (PEG) and a CD19 targeting ligand or an EGFR targeting ligand and a plurality of lipid molecules covalently attached to nanocapsules comprising a proteolytic enzyme that degrades extracellular matrix, wherein the MSNPs have a diameter ranging from about 1 nm to about 300 nm.

2. The population of claim I wherei :he targeting ligand is an antibody, an antibody fragment or a scFv.

3. The population of claim 1 wherein the lipid bi- or multi-layer is PEGylated.

4. The population of claim 1 wherein the cargo comprises peptides, proteins, antibodies, nucleic acids, or drugs.

5. The population of claim 4 wherein the drug comprises vincristine, daunorubicin, doxorubicin, cytarabine, L-asparaginase, PEG-L-asparaginase, etoposide, teniposide, 6-mercaptopurine, methotrexate, cyclophosphamide, predisone, dexamethasone, imatinib, dasatinib, nilotinib, ponatinib, nelarabine, rituximab, blinatumumab, or inotuzumab.

6. The population of claim 1 wherein the lipid bi- or multi-layer comprises DSPC, cholesterol, PEG-DSPC, or a combination thereof.

7. The population of claim 6 wherein the amount of DSPC is about 45 mol % to about 80 mol % or about 50 mol % to about 78 mol %.

8. The population of claim 6 wherein the amount of cholesterol is about 10 mol % to about 50 mol % or about 17 mol % to about 25 mol %.

9. The population of claim 8 wherein the amount of PEG-DSPC is about 1 mol % to about 3 mol % or about 2 mol % to about 2.7 mol %.

10. The population of claim 1 wherein said MSNPs have an average diameter of less than about 200 nm or greater than about 20 nm.

11. The population of claim 1 wherein the CD19 targeting ligand comprises blinatumomab or a portion thereof, coltuxmiabravtasine or a portion thereof, MOR208 or a portion thereof, MEDI-551 or a portion thereof, denintuzumabmafodotin or a portion thereof, B4 or a portion thereof, DI-B4 or a portion thereof, taplitumomapaptox or a portion thereof, XmAb 5871 or a portion thereof, MDX-1342 or a portion thereof, or AFM 11 or a portion thereof.

12. The population of claim 1 wherein the EGFR targeting ligand comprises cetuximab, panitumumab, IMC-225, CR62, ABX-EGF, necitumumab, EMD72000, matuzumab, zalutumumab, or nemotuzmumab, a fragment thereof, or a scFv thereof.

13. A pharmaceutical composition comprising the population of claim 1, in combination with a pharmaceutically acceptable carrier, additive and/or excipient.

14. A population of protocells comprising MSNPs, and a lipid bi-layer comprising lipid molecules comprising PEG and an EGFR targeting ligand and lipid molecules comprising covalently linked nanocapsules comprising an enzyme that degrades extracellular matrix, wherein the MSNPs have a diameter ranging from about 1 nm to about 300 nm, and wherein the protocells optionally comprise a chemotherapeutic drug.

15. A method of treating cancer, comprising administering to a subject in need thereof the pharmaceutical composition of claim 13 which comprises a CD19 targeting ligand or an EGFR targeting ligand.

16. The method of claim 15 wherein the composition is systemically administered.

17. The method of claim 15 wherein the subject has ALL.

18. The method of claim 15 wherein the targeting ligand is an antibody, an antibody fragment or a scFv.

19. The method of claim 15 wherein the cargo comprises peptides, proteins, antibodies, nucleic acids, or a drug.

20. The method of claim 15 wherein the CD19 targeting ligand comprises blinatumomab or a portion thereof, coltuxmiabravtasine or a portion thereof, MOR208 or a portion thereof, MEDI-551 or a portion thereof, denintuzumabmafodotin or a portion thereof, B4 or a portion thereof, DI-B4 or a portion thereof, taplitumomapaptox or a portion thereof, XmAb 5871 or a portion thereof, MDX-1342 or a portion thereof, or AFM 11 or a portion thereof or wherein the EGFR targeting ligand comprises cetuximab, panitumumab, IMC-225, CR62, ABX-EGF, necitumumab, EMD72000, matuzumab, zalutumumab, or nemotuzmumab, a fragment htereof, or a scFv thereof.

\* \* \* \* \*

UNITED STATES PATENT AND TRADEMARK OFFICE
CERTIFICATE OF CORRECTION

PATENT NO. : 11,344,629 B2
APPLICATION NO. : 16/490280
DATED : May 31, 2022
INVENTOR(S) : Brinker et al.

It is certified that error appears in the above-identified patent and that said Letters Patent is hereby corrected as shown below:

On the Title Page

On page 2, in Column 1, under "U.S. Patent Documents", Line 63, delete "2014/0023421" and insert --2014/0234210-- therefor On page 5, in Column 2, under "Other Publications", Line 23, delete "t" and insert --to-- therefor On page 6, in Column 2, under "Other Publications", Line 56, delete "Appiication" and insert --Application-- therefor On page 7, in Column 1, under "Other Publications", Line 3, delete ""international" and insert --"International-- therefor On page 9, in Column 2, under "Other Publications", Line 44, delete "3CG-CWS" and insert --BCG-CWS-- therefor In the Claims In Column 74, Line 6, in Claim 2, delete "claim I wherei :he" and insert --claim 1 wherein the-- therefor In Column 74, Line 27, in Claim 9, delete "claim 8" and insert --claim 6-- therefor In Column 74, Line 55, in Claim 14, after "protocells", delete "optionally"

In Column 74, Line 67, in Claim 19, delete "or a drug." and insert --vincristine, daunorubicin, doxorubicin, cytarabine, L-asparaginase, PEG-L-asparaginase, etoposide, teniposide, 6-mercaptopurine, methotrexate, cyclophosphamide, predisone, dexamethasone, imatinib, Signed and Sealed this
Twenty-fourth Day of January, 2023

Katherine Kelly Vidal
*Director of the United States Patent and Trademark Office* dasatinib, nilotinib, ponatinib, nelarabine, rituximab, blinatumumab, or inotuzumabor.-- therefor In Column 75, Line 12, in Claim 20, delete "htereof," and insert --thereof,-- therefor